US011560388B2

(12) United States Patent
Long et al.

(10) Patent No.: US 11,560,388 B2
(45) Date of Patent: Jan. 24, 2023

(54) ANTHELMINTIC AZA-BENZOTHIOPHENE AND AZA-BENZOFURAN COMPOUNDS

(71) Applicants: Boehringer Ingelheim Vetmedica GmbH, Ingelheim am Rhein (DE); BOEHRINGER INGELHEIM PHARMA GMBH & CO. KG, Ingelheim am Rhein (DE)

(72) Inventors: Alan Long, Flowery Branch, GA (US); Hannes Fiepko Koolman, Biberach an der Riss (DE); Hyoung Ik Lee, Alpharetta, GA (US)

(73) Assignees: Boehringer Ingelheim Vetmedica GmbH; Boehringer Ingelheim Pharma GmbH & Co. KG

( * ) Notice: Subject to any disclaimer, the term of this patent is extended or adjusted under 35 U.S.C. 154(b) by 52 days.

(21) Appl. No.: 16/823,138

(22) Filed: Mar. 18, 2020

(65) Prior Publication Data

US 2020/0299304 A1      Sep. 24, 2020

Related U.S. Application Data

(60) Provisional application No. 62/820,352, filed on Mar. 19, 2019.

(51) Int. Cl.
| | | |
|---|---|---|
| *C07D 495/04* | (2006.01) | |
| *C07D 307/85* | (2006.01) | |
| *C07D 407/12* | (2006.01) | |
| *C07D 409/12* | (2006.01) | |
| *C07D 413/14* | (2006.01) | |
| *C07D 519/00* | (2006.01) | |
| *A61P 33/10* | (2006.01) | |
| *A61K 45/06* | (2006.01) | |

(52) U.S. Cl.
CPC ............ *C07D 495/04* (2013.01); *A61P 33/10* (2018.01); *C07D 307/85* (2013.01); *C07D 407/12* (2013.01); *C07D 409/12* (2013.01); *C07D 413/14* (2013.01); *C07D 519/00* (2013.01); *A61K 45/06* (2013.01)

(58) Field of Classification Search
CPC .. C07D 495/04; C07D 307/85; C07D 407/12; C07D 409/12; C07D 413/14; C07D 519/00
See application file for complete search history.

(56) References Cited

U.S. PATENT DOCUMENTS

| | | | |
|---|---|---|---|
| 4,464,372 A | 8/1984 | Bristol et al. | |
| 5,434,150 A | 7/1995 | Austel et al. | |
| 6,900,208 B2 | 5/2005 | Salvati et al. | |
| 6,911,543 B2 | 6/2005 | Walker et al. | |
| 7,030,112 B2 | 4/2006 | Salvati et al. | |
| 7,153,854 B2 | 12/2006 | Abe et al. | |
| 7,300,932 B2 | 11/2007 | Fox et al. | |
| 7,306,631 B2 | 12/2007 | Glenn, Jr. et al. | |
| 7,420,056 B2 | 9/2008 | Kuehnert et al. | |
| 7,456,192 B2 | 11/2008 | Imbert et al. | |
| 7,723,336 B2 | 5/2010 | Vaccaro et al. | |
| 7,893,085 B2 | 2/2011 | Savy et al. | |
| 7,919,628 B2 | 4/2011 | Hachtel et al. | |
| 7,956,068 B2 | 6/2011 | Carson et al. | |
| 7,964,204 B2 | 6/2011 | Lahm et al. | |
| 8,030,327 B2 | 10/2011 | Sato et al. | |
| 8,252,795 B2 | 8/2012 | Fink et al. | |
| 8,431,593 B2 | 4/2013 | Hutchison et al. | |
| 8,450,354 B2 | 5/2013 | Mjalli et al. | |
| 8,772,301 B2 | 7/2014 | Hardy et al. | |
| 9,023,850 B2 | 5/2015 | Lahm et al. | |
| 9,556,169 B2 | 1/2017 | Chatterjee et al. | |
| 9,718,816 B2 | 8/2017 | Chesworth et al. | |
| 9,802,961 B2 | 10/2017 | Clark et al. | |
| 9,868,749 B2 | 1/2018 | Alexander et al. | |
| 9,873,703 B2 | 1/2018 | Ali et al. | |
| 10,138,248 B2 | 11/2018 | Buesking et al. | |

(Continued)

FOREIGN PATENT DOCUMENTS

| | | |
|---|---|---|
| CL | 202100033 | 7/2021 |
| EP | 1277754 B1 | 7/2005 |

(Continued)

OTHER PUBLICATIONS

CAS Registry Entry for Registry No. 2134947-60-5, which entered STN on Oct. 15, 2017 (Year: 2017).*
CAS Registry Entry for Registry No. 1953874-77-5, which entered STN on Jul. 17, 2016 (Year: 2016).*
CAS Registry Entry for Registry No. 1318005-39-8, which entered STN on Aug. 15, 2011 (Year: 2011).*
CAS Registry Entry for Registry No. 1835595-46-4, which entered STN on Dec. 23, 2015 (Year: 2015).*
CAS Registry Entry for Registry No. 2249355-47-1, which entered STN on Nov. 18, 2018 (Year: 2018).*
CAS Registry Entry for Registry No. 1944784-28-4, which entered STN on Jul. 4, 2016 (Year: 2016).*

(Continued)

*Primary Examiner* — Matthew P Coughlin
(74) *Attorney, Agent, or Firm* — John Esteban Ezcurra

(57) ABSTRACT

This invention provides for compounds of the formula:

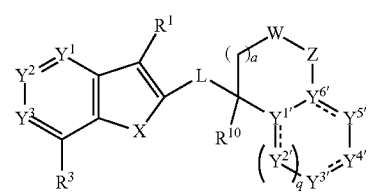

wherein the variables are defined herein, or a stereoisomer, tautomer, N-oxide, hydrate, solvate, or salt thereof, compositions comprising these compounds, and method for the treatment, control or prevention of a parasitic infestation or infection in an animal in need thereof by administering an effective amount of these compounds to said animal.

27 Claims, No Drawings

(56) References Cited

U.S. PATENT DOCUMENTS

| | | |
|---|---|---|
| 2004/0242587 A1 | 12/2004 | Fu |
| 2006/0074102 A1 | 4/2006 | Cusack et al. |
| 2007/0027093 A1 | 2/2007 | Ogawa et al. |
| 2007/0275962 A1 | 11/2007 | Koul et al. |
| 2011/0105457 A1 | 5/2011 | Taniyama et al. |
| 2011/0195933 A1 | 8/2011 | Katz et al. |
| 2011/0206607 A1 | 8/2011 | Olsson et al. |
| 2011/0245274 A1 | 10/2011 | Nanchen et al. |
| 2012/0065200 A1 | 3/2012 | Barbosa et al. |
| 2012/0083476 A1 | 4/2012 | Breitenbucher et al. |
| 2012/0219500 A1 | 8/2012 | Sakurai et al. |
| 2013/0071415 A1 | 3/2013 | Babu et al. |
| 2013/0203692 A1 | 8/2013 | Soll et al. |
| 2014/0045826 A1 | 2/2014 | Shakespeare et al. |
| 2014/0066434 A1 | 3/2014 | Shakespeare |
| 2015/0126523 A1 | 5/2015 | Meng |
| 2016/0106102 A1 | 4/2016 | Kuebbeler et al. |
| 2016/0333012 A1 | 11/2016 | Chatterjee et al. |
| 2017/0369486 A1 | 12/2017 | Acharya et al. |
| 2018/0230157 A1 | 8/2018 | Bacon et al. |
| 2019/0071447 A1 | 3/2019 | Kohler et al. |
| 2019/0233425 A1 | 8/2019 | Bayly et al. |
| 2019/0352275 A1 | 11/2019 | Meldrum et al. |
| 2020/0024264 A1 | 1/2020 | Hubsch et al. |
| 2020/0237771 A1 | 7/2020 | Hallur et al. |
| 2022/0047569 A1 | 2/2022 | Kazmi et al. |

FOREIGN PATENT DOCUMENTS

| | | | |
|---|---|---|---|
| EP | 3078664 A1 | 10/2016 | |
| EP | 3643711 A1 | 4/2020 | |
| JP | 2009203214 A | 9/2009 | |
| JP | 2011140452 A | 7/2011 | |
| JP | 2012012299 A | 1/2012 | |
| JP | 2016505529 A | 2/2016 | |
| WO | 2000053602 A1 | 9/2000 | |
| WO | 2005066177 A1 | 7/2005 | |
| WO | 2006004191 A1 | 1/2006 | |
| WO | 2007123855 A2 | 11/2007 | |
| WO | 2008019309 A1 | 2/2008 | |
| WO | 2010017046 A1 | 2/2010 | |
| WO | 2011058109 A1 | 5/2011 | |
| WO | 2011075591 A1 | 6/2011 | |
| WO | 2011137587 A1 | 11/2011 | |
| WO | 2011146401 A1 | 11/2011 | |
| WO | 2012100342 A1 | 8/2012 | |
| WO | 2012107533 A1 | 8/2012 | |
| WO | 2015066277 A1 | 5/2015 | |
| WO | 2017093180 A1 | 6/2017 | |
| WO | 2017125898 A1 | 7/2017 | |
| WO | 2017/178416 A1 | 10/2017 | |
| WO | 2017178416 A1 | 10/2017 | |
| WO | 2018/087036 A1 | 5/2018 | |
| WO | 2018/197401 A1 | 11/2018 | |
| WO | 2019/002132 A1 | 1/2019 | |
| WO | 2019002132 A1 | 1/2019 | |
| WO | 2019/025341 A1 | 2/2019 | |
| WO | 2019/115768 A1 | 6/2019 | |
| WO | 2019/215182 A1 | 11/2019 | |
| WO | 2020002124 A1 | 1/2020 | |
| WO | 2020012336 A1 | 1/2020 | |
| WO | 2020014068 A1 | 1/2020 | |
| WO | 2020/083971 A1 | 4/2020 | |
| WO | WO-2020083971 A2 * | 4/2020 | ........... C07D 471/04 |
| WO | 2020/131629 A1 | 6/2020 | |
| WO | 2020/131631 A1 | 6/2020 | |
| WO | 2020191091 A1 | 9/2020 | |
| WO | 2020247747 A1 | 12/2020 | |
| WO | 2021018839 A1 | 2/2021 | |
| WO | 2021030379 A1 | 2/2021 | |
| WO | 2021032934 A1 | 2/2021 | |
| WO | 2021122906 A1 | 6/2021 | |
| WO | 2021122911 A1 | 6/2021 | |
| WO | 2021204930 A1 | 10/2021 | |
| WO | 2021231571 A1 | 11/2021 | |
| WO | 2022106469 A2 | 5/2022 | |
| WO | 2022117783 A1 | 6/2022 | |
| WO | 2022122987 A1 | 6/2022 | |
| WO | 2022122988 A1 | 6/2022 | |
| WO | 2022152918 A1 | 7/2022 | |

OTHER PUBLICATIONS

Database Registry (Online) Chemical Abstracts Service, Columbus, Ohio, US; Jul. 17, 2016, XP002799055, Database accession No. 1953874-77-5, 2-Benzofurancarboxamide,3,4,7-trimethyl-N-(octahydro-4-benzofuranyl).

Database Registry (Online) Chemical Abstracts Service, Columbus, Ohio, US; Oct. 15, 2017, XP002799056, Database accession No. 2134947-60-5, 2-Benzofurancarboxamide,3,4,7-trimethyl-N-(4,5,6,7-tetrahydro-1-methyl-1H-indazol-4-yl).

Database Registry (Online) Chemical Abstracts Service, Columbus, Ohio, US; Aug. 15, 2011, XP002799057, Database accession No. 1318005-39-8, 2-Benzofurancarboxamide, N-(6-bromo-3,4-dihydro-2H-1-benzopyran-4-yl)-3,7-dimethyl.

Database Registry (Online) Chemical Abstracts Service, Columbus, Ohio, US; Dec. 23, 2015, XP002799058, Database accession No. 1835595-46-4, 2-Benzofurancarboxamide, N-(6-amino-1,2,3,4-tetrahydro-1-naphthalenyl)-3,4,7-trimethyl-, hydrochloride (1:1).

Database Registry (Online) Chemical Abstracts Service, Columbus, Ohio, US; Nov. 18, 2018, XP002799059, Database accession No. 2249355-47-1, 2-Benzofurancarboxamide, N-(6,7-dihydro-5H-pyrrolo[1,2-a]imidazol-7-yl)-3,7-dimethyl.

Database Registry (Online) Chemical Abstracts Service, Columbus, Ohio, US; Jul. 4, 2016, XP002799060, Database accession No. 1944784-28-4, 2-Benzofurancarboxamide, 5-bromo-7-methyl-N-(4,5,6,7-tetrahydro-2-methyl-2H-indazol-4-yl).

Database Registry [Online], May 1, 2020 (May 1, 2020), Life Chemicals Inc.: "Imidazo[1,2-b]pyridazine-6-carboxamide, N-(1,2,3,4-tetrahydro-1-naphthalenyl)-", XP055837558, Database accession No. 2415490-08-1 compound with the Registry No. 2415490-08-1.

* cited by examiner

ANTHELMINTIC AZA-BENZOTHIOPHENE AND AZA-BENZOFURAN COMPOUNDS

CROSS REFERENCE TO RELATED APPLICATIONS

This application claims the benefit of priority to U.S. Provisional Application No. 62/820,352 filed Mar. 19, 2019, which is incorporated herein by reference in its entirety.

FIELD OF THE INVENTION

This patent application relates to new antiparasitic compounds, compositions comprising the compounds, processes for their preparation, and methods of using the compounds to control parasites that harm animals.

BACKGROUND OF THE INVENTION

Animals, such as mammals and birds, are often susceptible to parasite infestations. These parasites may be ectoparasites, such as fleas and ticks. Animals and humans also suffer from endoparasitic infections including, for example, helminthiasis which is most frequently caused by a group of parasitic worms described as nematodes or roundworms. These parasites cause severe economic losses in pigs, sheep, horses, and cattle as well as affecting companion animals (e.g. cats and dogs) and poultry. Other parasites include those which occur in the gastrointestinal tract of animals and humans such as *Ancylostoma*, *Necator*, *Ascaris*, *Strongyloides*, *Trichinella*, *Capillaria*, *Toxocara*, *Toxascaris*, *Trichuris* and *Enterobius*. Other parasites which are found in the blood or other tissues and organs include filarial worms and the extra intestinal stages of *Strongyloides* and *Trichinella*.

One type of endoparasite which seriously harms mammals is *Dirofilaria immitis*, also known as Heartworm. Other filarial endoparasites include *Dirofilaria repens* and *Dirofilaria honkongensis*, which can also infect humans. The most common hosts are dogs and cats but other mammals such as ferrets and raccoons may also be infected. Heartworms go through several life stages before they become adults infecting the pulmonary artery of the host mammal. The worms require the mosquito as an intermediate host to complete their life cycle. The period between the initial infection when the dog is bitten by a mosquito and the maturation of the worms into adults living in the heart and pulmonary arteries is six to seven months in dogs and is known as the "prepatent period." L3 larvae migrate during blood feeding of the mosquito to the tip of the mosquito's mouth parts (labium), leave the mosquito and are deposited on the skin of the dog where they then migrate through the bite wound into the host. Most L3 larvae molt to fourth-stage larvae (L4s) in canine subcutaneous tissues within 1-3 days after infection. Then, they migrate to the muscles of the chest and abdomen, and 45 to 60 days after infection, molt to the fifth stage (L5, immature adult). Between 75 and 120 days after infection, these immature heartworms then enter the bloodstream and are carried through the heart to reside in the pulmonary artery. Around seven months after infection, *Dirofilaria immitis* adults reach maturity and sexually reproduce in the pulmonary arteries and right ventricle. Adult males are around 15 cm in length, and females are around 25 cm in length and their normal life span as adults is calculated to be about 5 years.

Heartworm infection is a severe and life-threatening disease. Canine heartworm infection is preventable and prophylaxis treatment is a priority in heartworm endemic areas. Treatment of mature heartworm infection with an adulticide (e.g. melarsomine dihydrochloride) is costly and can cause serious side effects, thus prevention by monthly administration of drugs that interrupt larvae development is widely used. The goal of marketed heartworm preventive therapies in dogs is to prevent the development of the parasite to adult heartworms by interrupting the *Dirofilaria immitis* life cycle post-infection.

The macrocyclic lactones (MLs, e.g. ivermectin, eprinomectin, milbemycin oxime, moxidectin, and selamectin) are the most commonly used chemoprophylaxis agents and are administered at monthly or six-month intervals. These drugs have been effective against *Dirofilaria immitis* infective third-stage larvae (L3) deposited by the mosquito as well as maturing fourth-stage larvae (L4). When administered monthly, MLs kill L3 and L4 larvae acquired within the previous 30 days, and thus prevent disease caused by adult worms. MLs can also be used monthly in infected dogs to suppress reproduction in adult worms and remove microfilariae, thereby reducing transmission and gradually causing the attrition of adult worms (*Vet. Parasitol*. 2005 Oct. 24 133(2-3) 197-206).

In recent years, an increased number of lack of efficacy (LOE) cases have been reported, in which dogs develop mature heartworm infections despite receiving monthly prophylactic doses of macrocyclic lactones drugs. For example, Atkins et al., (*Vet. Parasitol*. 206 (2014) 106-113) recently reported that an increasing number of cases of dogs that tested heartworm antigen positive while receiving heartworm preventive medication which suggests that some populations of *Dirofilaria immitis* have developed selectional resistance to heartworm preventives (American Heartworm Society, 2010. Heartworm Preventive Resistance. Is it Possible, vol. 37. Bulletin of the American Heartworm Society, pp. 5.). Thus, there is an ongoing need to develop new anthelmintic agents with improved activity against *Dirofilaria immitis* and other endoparasites.

WO 2017/178416 A1 provides pyrazolopyrimidine derivatives for the control, treatment and/or prevention of helminths. WO 2018/197401 A1 provides bicyclic pyrazole derivatives for the control, treatment and/or prevention of helminths. WO 2018/087036 A1 provides quinolone-3-carboxamide derivatives for the control, treatment and/or prevention of helminths. WO 2019/025341 provides quinoline compounds for the treatment, control and/or prevention of helminth infections and WO 2019/002132 A1 azaquinone derivatives for the control, treatment and/or prevention of helminths. All these publications are to Bayer Animal Health GmbH and are incorporated herein by reference in their entirety.

More recently WO 2020/014068 A1 (incorporated herein by reference) describes anthelmintic heterocyclic compounds that were found to be active against *Dirofilaria immitis*.

It is expressly noted that citation or identification of any document in this application is not an admission that such document is available as prior art to the present description. Any foregoing applications, and all documents cited therein or during their prosecution ("application cited documents") and all documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the description.

SUMMARY OF THE INVENTION

The present application provides for novel anthelmintic and antiparasitic heterocyclic compounds with improved activity against endoparasites and ectoparasites. The application is also directed to compositions comprising the compounds, methods and uses of the compounds for eradicating, controlling, and preventing a parasitic infestation and/or infection in animals including humans. The compounds may be administered to animals, particularly mammals, fish and birds, to prevent or treat parasitic infections.

An aspect of the present invention includes a compound of Formula (I):

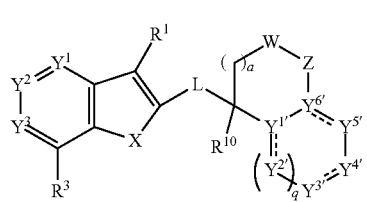

a stereoisomer, tautomer, N-oxide, hydrate, solvate, or salt thereof, wherein variables $R^1$, $R^3$, $R^{10}$, $Y^1$, $Y^2$, $Y^3$, X, L, W, Z, $Y^{1'}$, $Y^{2'}$, $Y^{3'}$, $Y^{4'}$, $Y^{5'}$, $Y^{6'}$, a and q are defined herein, and the dashed bonds ( ---- ) signifies a single or double bond.

The invention also includes a veterinarily acceptable composition comprising a compound of Formula (I) and a veterinarily acceptable carrier and a method of controlling parasites, including helminths, comprising administering the compound, or the veterinarily acceptable composition thereof, to an animal in need thereof. An embodiment of the invention also includes the use of the compound of Formula (I) for eradicating, controlling, and preventing a parasitic infestation and/or infection in animals. The compounds of the invention may be administered to animals, particularly mammals, fish and birds, to prevent or treat parasitic infections.

The compound and compositions comprising the compound are highly effective for the treatment and prophylaxis of internal parasites in mammals, fish and birds, and in particular, cats, dogs, horses, chickens, pigs, sheep and cattle, with the aim of substantially ridding these hosts of endoparasites.

In an embodiment, compounds of Formula (I) and compositions comprising said compounds are substantially effective against endoparasites, such as filariae (e.g. heartworm), hookworms, whipworms and roundworms of the digestive tract of animals and humans. In certain embodiments, compounds of Formula (I) and compositions comprising said compounds are effective against *Dirofilaria immitis* (heartworm) isolates that are less sensitive to treatment with macrocyclic lactones. In another embodiment, the compounds and compositions of the invention are effective for treating and preventing infections of animals with nematodes that are less sensitive to treatment with commercially available or known active agents.

In an embodiment, the description includes a combination of a compound of Formula (I) with at least a second active agent, which may broaden the scope of protection afforded to animals against endoparasites and/or ectoparasites.

Another embodiment includes a method for the treatment and/or prevention of a parasitic infection and/or infestation in an animal comprising administering a compound of Formula (I) to the animal. Another embodiment includes a use of a compound of Formula (I) for the treatment and/or prevention of a parasitic infections and/or infestations in animals and the use of the compound of Formula (I) in the preparation of a medicament for the treatment and/or prevention of a parasitic infection in an animal.

Thus, the invention includes the following non-limiting embodiments:

(a) a compound of Formula (I) or a pharmaceutically or a veterinarily acceptable salt thereof, which is an active endoparasiticide and in some cases also active against ectoparasites;

(b) a veterinary composition comprising a parasiticidally effective amount of a compound of Formula (I), or a pharmaceutically or veterinarily acceptable salt thereof, in combination with a pharmaceutically or veterinarily acceptable carrier or diluent;

(c) a veterinary composition comprising a parasiticidally effective amount of a compound of Formula (I), or a pharmaceutically or veterinarily acceptable salt thereof, in combination with one or more additional active agents (i.e., active ingredient not encompassed by Formula (I)) and a pharmaceutically or veterinarily acceptable carrier or diluent;

(d) a method for treating a parasitic infestation/infection in or on an animal comprising administering a parasiticidally effective amount a compound of Formula (I), or a pharmaceutically or veterinarily acceptable salt thereof, optionally with one or more additional active agents (i.e., active ingredient not encompassed by Formula (I)), to the animal in need thereof;

(e) a method for the prevention of a parasitic infestation/infection of an animal, which comprises administering a parasiticidally effective amount of a compound of Formula (I), or a pharmaceutically or a veterinarily acceptable salt thereof, optionally with one or more additional active agents (i.e., active ingredient not encompassed by Formula (I)), to the animal in need thereof;

(f) a use of a compound of Formula (I), or a pharmaceutically or a veterinarily acceptable salt thereof, for the treatment or prevention of a parasitic infection and possibly also a parasitic infestation in an animal;

(g) a use of a compound of Formula (I), or a pharmaceutically or veterinarily acceptable salt thereof, for the manufacture of a veterinary medicament for the treatment or prevention of a parasitic infection in an animal; and (h) a process for the preparation of a compound of Formula (I).

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved. Nothing herein is to be construed as a promise.

The term "compound of Formula (I)" includes any a stereoisomer, tautomer, N-oxide, hydrate, solvate, or salt thereof.

These and other embodiments are disclosed or are obvious from and encompassed by, the following Detailed Description.

Definitions

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

Terms used herein will have their customary meanings in the art unless otherwise specified. The organic moieties mentioned in the definitions of the variables of the compounds e.g, the compound of formula (I) are like the term halogen—i.e., collective terms for individual listings of the individual group members—fluoro, chloro, bromo and iodo with respect to halogen. The prefix $C_n$-$C_m$ indicates in each case the possible number of carbon atoms in the group from an integer n to another integer m.

In the present specification and claims the term "including but not limited to" is equivalent to "included".

By the term "optionally substituted" is meant a radical that is optionally substituted by one or more of the following moieties: halogen, hydroxyl, carboxyl, acyl, acyloxy, amino, alkyl- or dialkylamino, amido, arylamino, alkoxy, aryloxy, nitro, cyano, azido, thiol, imino, sulfonic acid, sulfate, sulfonyl, sulfanyl, sulfinyl, sulfamoyl, ester, phosphonyl, phosphinyl, phosphoryl, phosphine, thioester, thioether, acid halide, anhydride, oxime, hydrazine, carbamate, phosphonic acid, phosphate, phosphonate, aryl, and heteroaryl, or any other viable functional group that does not inhibit the biological activity of the compounds of the description, either unprotected, or protected as necessary, as known to those skilled in the art, for example, as taught in Greene and Wuts, Protective Groups in Organic Synthesis, John Wiley and Sons, Third Edition, 1999, hereby incorporated by reference. For avoidance of doubt, "optionally substituted alkyl" includes haloalkyl.

Unless otherwise stated, "alkyl" means, either alone or in combination with a heteroatom, e.g., alkoxy, thioalkyl, alkylamino, and the like, saturated straight, branched, primary, secondary or tertiary hydrocarbons, including those having 1 to 12 atoms. In some embodiments, alkyl groups will include $C_1$-$C_{10}$, $C_1$-$C_8$, $C_1$-$C_6$, $C_1$-$C_4$ or $C_1$-$C_3$ alkyl groups. Examples of $C_1$-$C_{10}$ alkyl include, but are not limited to, methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, octyl, 2-ethylhexyl, nonyl and decyl and their isomers. C1-C4-alkyl means for example methyl, ethyl, propyl, 1-methylethyl, butyl, 1-methylpropyl, 2-methylpropyl or 1,1-dimethylethyl.

Cyclic alkyl groups, may be referred to as "cycloalkyl" and include those with 3 to 10 carbon atoms having single or multiple fused rings. Non-limiting examples of cycloalkyl groups include adamantyl, cyclopropyl, cyclobutyl, cyclopentyl, cyclohexyl, cycloheptyl, cyclooctyl and the like.

Carbocyclic groups are cyclic groups composed exclusively of carbon. The carbocyclic groups include both aromatic rings such as phenyl and non-aromatic rings such as cycloalkyl rings including cyclopropyl, cyclobutyl, cyclopentyl, cyclohexyl, and the like, and include those with 3 to 14 carbon atoms having single or multiple fused rings.

The term "alkenyl" refers to both straight and branched carbon chains which have at least one carbon-carbon double bond. In some embodiments, alkenyl groups may include $C_2$-$C_{12}$ alkenyl groups. In other embodiments, alkenyl includes $C_2$-$C_{10}$, $C_2$-$C_8$, $C_2$-$C_6$, $C_2$-$C_4$, or $C_3$-$C_4$ alkenyl groups. In one embodiment of alkenyl, the number of double bonds is 1-3; in another embodiment of alkenyl, the number of double bonds is one. Other ranges of carbon-carbon double bonds and carbon numbers are also contemplated depending on the location of the alkenyl moiety on the molecule. "alkenyl" groups may include more than one double bond in the chain. Examples of alkenyl or a specific range thereof include, but are not limited to, ethenyl, 1-propenyl, 2-propenyl, 1-methyl-ethenyl, 1-butenyl, 2-butenyl, 3-butenyl, 1-methyl-1-propenyl, 2-methyl-1-propenyl, 1-methyl-2-propenyl, 2-methyl-2-propenyl; 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl.

"Alkynyl" refers to both straight and branched carbon chains which have at least one carbon-carbon triple bond. In one embodiment of alkynyl, the number of triple bonds is 1-3; in another embodiment of alkynyl, the number of triple bonds is one. In some embodiments, alkynyl groups include from 2 to 12 carbon atoms. In other embodiments, alkynyl groups may include $C_2$-$C_{10}$, $C_2$-$C_8$, $C_2$-$C_6$ or $C_2$-$C_4$ alkynyl groups. Other ranges of carbon-carbon triple bonds and carbon numbers are also contemplated depending on the location of the alkenyl moiety on the molecule. For example, the term "$C_2$-$C_{10}$-alkynyl" as used herein refers to a straight-chain or branched unsaturated hydrocarbon group having 2 to 10 carbon atoms and containing at least one triple bond, such as ethynyl, prop-1-yn-1-yl, prop-2-yn-1-yl, n-but-1-yn-1-yl, n-but-1-yn-3-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl or 4-methylpent-2-yn-5-yl and the like.

The term "haloalkyl" refers to an alkyl group, as defined herein, which is substituted by one or more halogen atoms. For example $C_1$-$C_4$-haloalkyl includes, but is not limited to, chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and the like. The term "fluoroalkyl" as used herein refers to an alkyl in which one or more of the hydrogen atoms is replaced with fluorine atoms, for example difluoromethyl, trifluoromethyl, 1-fluoroethyl, 2-fluoroethyl, 2,2-difluoroethyl, 2,2,2-trifluoroethyl, 1,1,2,2-tetrafluoroethyl or pentafluoroethyl.

The term "haloalkenyl" refers to an alkenyl group, as defined herein, which is substituted by one or more halogen atoms.

The term "haloalkynyl" refers to an alkynyl group, as defined herein, which is substituted by one or more halogen atoms.

The term "alkoxy" refers to alkyl-O—, wherein alkyl is as defined above. Similarly, the terms "alkenyloxy," "alkynyloxy," "haloalkoxy," "haloalkenyloxy," "haloalkynyloxy," "cycloalkoxy," "cycloalkenyloxy," "halocycloalkoxy," and "halocycloalkenyloxy" refer to the groups alkenyl-O—, alkynyl-O—, haloalkyl-O—, haloalkenyl-O—, haloalkynyl-O—, cycloalkyl-O—, cycloalkenyl-O—, halocycloalkyl-O—, and halocycloalkenyl-O—, respectively, wherein alkenyl, alkynyl, haloalkyl, haloalkenyl, haloalkynyl, cycloalkyl, cycloalkenyl, halocycloalkyl, and halocycloalkenyl are as defined above. Examples of $C_1$-$C_6$-alkoxy include, but are not limited to, methoxy, ethoxy, $OCH_2$—$C_2H_5$, $OCH(CH_3)_2$, n-butoxy, $OCH(CH_3)$—$C_2H_5$, $OCH_2$—$CH(CH_3)_2$, $OC(CH_3)_3$, n-pentoxy, 1-methylbutoxy, 2-methylbutoxy, 3-methylbutoxy, 1,1-dimethylpropoxy, 1,2-dimethylpropoxy, 2,2-dimethyl-propoxy, 1-ethylpropoxy, n-hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy, 1-ethyl-2-methylpropoxy and the like.

The term "aryl" refers to a monovalent aromatic carbocyclic group of from 6 to 14 carbon atoms having a single ring or multiple fused rings. Aryl groups include, but are not limited to, phenyl, biphenyl, and naphthyl. In some embodiments aryl includes tetrahydronaphthyl, phenylcyclopropyl and indanyl. Aryl groups may be unsubstituted or substituted by one or more moieties selected from halogen, cyano, nitro, hydroxy, mercapto, amino, alkyl, alkenyl, alkynyl, cycloalkyl, cycloalkenyl, haloalkyl, haloalkenyl, haloalkynyl, halocycloalkyl, halocycloalkenyl, alkoxy, alkenyloxy, alkynyloxy, haloalkoxy, haloalkenyloxy, haloalkynyloxy, cycloalkoxy, cycloalkenyloxy, halocycloalkoxy, halocycloalkenyloxy, alkylthio, haloalkylthio, cycloalkylthio, halocycloalkylthio, alkylsulfinyl, alkenylsulfinyl, alkynylsulfinyl, haloalkylsulfinyl, haloalkenylsulfinyl, haloalkynylsulfinyl, alkylsulfonyl, alkenylsulfonyl, alkynylsulfonyl, haloalkyl-sulfonyl, haloalkenylsulfonyl, haloalkynylsulfonyl, —$SF_5$, alkylamino, alkenylamino, alkynylamino, di(alkyl)amino, di(alkenyl)-amino, di(alkynyl)amino, or trialkylsilyl.

The term "aralkyl" refers to an aryl group that is bonded to the parent compound through a diradical alkylene bridge, (—$CH_2$—)$_n$, where n is 1-12 and where "aryl" is as defined above.

The term "heteroaryl" refers to a monovalent aromatic group of from 1 to 15 carbon atoms, preferably from 1 to 10 carbon atoms, having one or more oxygen, nitrogen, and sulfur heteroatoms within the ring, preferably 1 to 4 heteroatoms, or 1 to 3 heteroatoms. The nitrogen and sulfur heteroatoms may optionally be oxidized. Heteroaryl groups will typically include a 5- or 6-membered aromatic ring. Such heteroaryl groups can have a single ring (e.g., pyridyl or furyl) or multiple fused rings provided that the point of attachment is through a heteroaryl ring atom. Examples of heteroaryls include pyridyl, pyridazinyl, pyrimidinyl, pyrazinyl, triazinyl, pyrrolyl, indolyl, quinolinyl, isoquinolinyl, quinazolinyl, quinoxalinnyl, furanyl, thiophenyl, furyl, pyrrolyl, imidazolyl, oxazolyl, isoxazolyl, isothiazolyl, pyrazolyl benzofuranyl, benzothiophenyl, imidazopyridyl, imidazopyrimidyl, or pyrrolopyrimidyl. Heteroaryl rings may be unsubstituted or substituted by one or more moieties as described for aryl above.

The term "heterocyclyl," "heterocyclic" or "heterocyclo" refers to fully saturated or unsaturated, cyclic groups, for example, 3 to 7 membered monocyclic, 7 to 11 membered bicyclic, or 10 to 15 membered tricyclic ring systems, which have one or more oxygen, sulfur or nitrogen heteroatoms in ring, preferably 1 to 4 or 1 to 3 heteroatoms. The nitrogen and sulfur heteroatoms may optionally be oxidized and the nitrogen heteroatoms may optionally be quaternized. The heterocyclic group may be attached at any heteroatom or carbon atom of the ring or ring system and may be unsubstituted or substituted by one or more moieties as described for aryl groups above.

Exemplary monocyclic heterocyclic groups include, but are not limited to, aziridinyl, azetidinyl, oxetanyl, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridinyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, triazolyl, triazinyl, and the like.

Exemplary bicyclic heterocyclic groups include, but are not limited to, indolyl, benzothiazolyl, benzoxazolyl, benzodioxolyl, benzothienyl, quinuclidinyl, quinolinyl, tetrahydroisoquinolinyl, isoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxo-quinazolinyl), tetrahydroquinolinyl and the like.

Bicyclic and tricyclic carbocyclic or heterocyclic ring systems include spirocyclic systems in which at least two of the rings in the system are connected through a single carbon atom. The spirocyclic ring systems will include a combination of from 3- to 8-membered carbocyclic and/or heterocyclic ring systems joined at a common carbon atom. Thus, the spirocyclic ring systems may include a 3-membered ring bonded to another 3-membered ring (either carbocyclic or heterocyclic) to an 8-membered ring bonded to another 8-membered ring and all the combinations of different ring sizes between. The heterocyclic ring component of a spirocyclic ring system will include one or two heteroatoms selected from N, O or S.

The term "alkylthio" refers to alkyl-S—, where "alkyl" is as defined above. In some embodiments, the alkyl component of the alkylthio group will include $C_1$-$C_{10}$, $C_1$-$C_8$, $C_1$-$C_6$ $C_1$-$C_4$ or $C_1$-$C_3$ alkyl groups. For example, $C_1$-$C_4$-alkylthio include, but are not limited to, methylthio, ethylthio, propylthio, 1-methylethylthio, butylthio, 1-methylpropylthio, 2-methylpropylthio or 1,1-dimethylethylthio.

Similarly, the terms "haloalkylthio," "cycloalkylthio," "halocycloalkylthio" refer to the groups —S-haloalkyl, —S-cycloalkyl, and —S-halocycloalkyl, respectively, where the terms "haloalkyl," "cycloalkyl," and "halocycloalkyl" are as defined above.

The term "alkylsulfinyl" refers to the group alkyl-S(=O)—, where "alkyl" is as defined above. In some embodiments, the alkyl component in alkylsulfinyl groups will include $C_1$-$C_{12}$, $C_1$-$C_{10}$, $C_1$-$C_8$, $C_1$-$C_6$, $C_1$-$C_4$ or $C_1$-$C_3$ alkyl groups. Examples include, but are not limited to, —SO—$CH_3$, —SO—$C_2H_5$, n-propylsulfinyl, 1-methylethyl sulfinyl, n-butylsulfinyl, 1-methylpropylsulfinyl, 2-methylpropylsulfinyl, 1,1-dimethylethylsulfinyl, n-pentylsulfinyl, 1-methylbutylsulfinyl, 2-methylbutylsulfinyl, 3-methylbutylsulfinyl, 1,1-dimethylpropyl sulfinyl, 1,2-dimethylpropylsulfinyl, 2,2-dimethylpropylsulfinyl, 1-ethylpropylsulfinyl, n-hexylsulfinyl, 1-methylpentylsulfinyl, 2-methylpentylsulfinyl, 3-methylpentylsulfinyl, 4-methylpentylsulfinyl, 1,1-dimethylbutyl sulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropylsulfinyl or 1-ethyl-2-methylpropylsulfinyl.

Similarly, the terms "alkenylsulfinyl," "alkynylsulfinyl," "haloalkylsulfinyl," "haloalkenylsulfinyl," and "haloalkynylsulfinyl" refer to the groups alkenyl-S(=O)—, alkynyl-S(=O)—, and haloalkyl-S(=O)—, haloalkenyl-S(=O)—, and haloalkynyl-S(=O)—, where the terms "alkenyl," "alkynyl," "haloalkyl," "haloalkenyl," and "haloalkynyl" are as defined above.

The term "alkylsulfonyl" refers to the group alkyl-S(=O)$_2$—, where the term "alkyl" is as defined above. In some embodiments, the alkyl component in alkylsulfonyl groups will include $C_1$-$C_{12}$, $C_1$-$C_{10}$, $C_1$-$C_8$, $C_1$-$C_6$ or $C_1$-$C_4$ alkyl groups. Examples include, but are not limited to, —$SO_2$—$CH_3$, —$SO_2$—$C_2H_5$, n-propylsulfonyl, —$SO_2$—$CH(CH_3)_2$, n-butylsulfonyl, 1-methylpropylsulfonyl, 2-methylpropylsulfonyl, —$SO_2$—$C(CH_3)_3$, n-pentylsulfonyl, 1-methylbutylsulfonyl, 2-methylbutylsulfonyl, 3-methylbutylsulfonyl, 1,1-dimethylpropylsulfonyl, 1,2-dimethylpropylsulfonyl, 2,2-dimethylpropylsulfonyl, 1-ethylpropylsulfonyl, n-hexylsulfonyl, 1-methylpentylsulfonyl, 2-methylpentylsulfonyl, 3-methylpentylsulfonyl, 4-methylpentylsulfonyl, 1,1-dimethylbutyl sulfonyl, 1,2-dimethylbutylsulfonyl, 1,3-dimethylbutylsulfonyl, 2,2-dimethylbutyl sulfonyl, 2,3-dimethylbutylsulfonyl, 3,3-dimethylbutylsulfonyl, 1-ethylbutylsulfonyl, 2-ethylbutyl sulfonyl, 1,1,2-trimethylpropylsulfonyl, 1,2,2-trimethylpropylsulfonyl, 1-ethyl-1-methylpropylsulfonyl or 1-ethyl-2-methylpropylsulfonyl and the like.

The terms "alkenylfulfonyl," "alkynylsulfonyl," "haloalkylsulfonyl," "haloalkenylsulfonyl," and "haloalkynylsulfonyl" refer to the groups alkenyl-S(=O)$_2$—, alkynyl-S(=O)$_2$—, and haloalkyl-S(=O)$_2$—, haloalkenyl-S(=O)$_2$—, and haloalkynyl-S(=O)$_2$—, where the terms "alkenyl," "alkynyl," "haloalkyl," "haloalkenyl," and "haloalkynyl" are as defined above.

The terms "alkylamino," "dialkylamino," "alkenylamino," "alkynylamino," "di(alkenyl)amino," and "di(alkynyl)amino" refer to the groups —NH(alkyl), —N(alkyl)$_2$, —NH(alkenyl), —NH(alkynyl), —N(alkenyl)$_2$ and —N(alkynyl)$_2$, where the terms "alkyl," "alkenyl," and "alkynyl" are as defined above. In some embodiments, the alkyl component in alkylamino or dialkylamino groups will include $C_1$-$C_{12}$, $C_1$-$C_{10}$, $C_1$-$C_8$, $C_1$-$C_6$ or $C_1$-$C_4$ alkyl groups.

The terms "alkylcarbonyl", "alkoxycarbonyl", "alkylaminocarbonyl", and "dialkylaminocarbonyl" refer to alkyl-C(O)—, alkoxy-C(O)—, alkylamino-C(O)— and dialkylamino-C(O)— where alkyl, alkoxy, alkylamino and dialkylamino are as defined above. Similarly, the terms "haloalkylcarbonyl," "haloalkoxycarbonyl", "haloalkylaminocarbonyl", and "dihaloalkylaminocarbonyl" refer to the groups haloalkyl-C(O)—, haloalkoxy-C(O)—, haloalkylamino-C(O)— and dihaloalkylamino-C(O)— where haloalkyl, haloalkoxy, haloalkylamino and dihaloalkylamino are as defined above.

DETAILED DESCRIPTION

An embodiment of the present invention includes a compound of Formula (I):

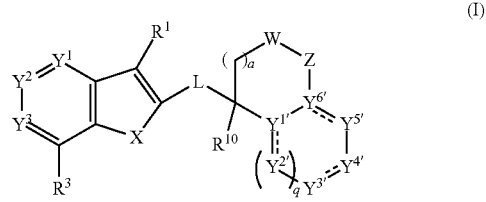

wherein:
L is L1 or L2:

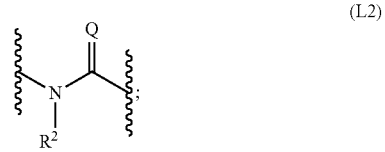

$R^1$ is hydrogen, cyano, halo, hydroxyl, optionally substituted alkyl, optionally substituted alkoxy, optionally substituted alkenyl, optionally substituted alkynyl, optionally substituted aryl, optionally substituted aryloxy, optionally substituted heteroaryl, optionally substituted cycloalkyl, optionally substituted cycloalkyloxy, optionally substituted heterocyclyl, optionally substituted alkylcarbonyl, optionally substituted alkoxycarbonyl, aminocarbonyl, optionally substituted alkylaminocarbonyl, optionally substituted dialkylaminocarbonyl, —SO$_p$(optionally substituted alkyl or haloalkyl), —SF$_5$, or —NR$^a$R$^b$ wherein R$^a$ and R$^b$ are independently H or optionally substituted alkyl; or R$^a$ and R$^b$ may form, with the nitrogen to which they are attached, a 3-, 4-, 5-, 6-, 7-, or 8-membered-heterocyclyl group, which may include one to three additional heteroatoms selected from the group consisting of N, O and S and may be optionally substituted;

$R^2$ is hydrogen, optionally substituted alkyl, optionally substituted cycloalkyl, or optionally substituted aryl;

$R^{2'}$ is optionally substituted alkyl, optionally substituted cycloalkyl, or optionally substituted aryl;

$R^3$ is optionally substituted alkyl, optionally substituted cycloalkyl, optionally substituted alkylcarbonyl, optionally substituted alkoxycarbonyl, aminocarbonyl, optionally substituted alkylaminocarbonyl, optionally substituted dialkylaminocarbonyl, —S(O)$_p$(optionally substituted alkyl), —SF$_5$, optionally substituted heterocyclyl, optionally substituted 6- to 10-membered aryl, optionally substituted 5- to 10-membered heteroaryl, a spirocyclic heterocyclyl-carbocyclyl group, a spirocyclic heterocyclyl-heterocyclyl group, a spirocyclic carbocyclyl-carbocyclyl group, a spirocyclic carbocyclyl-heterocyclyl group or —NR$^a$R$^b$ wherein R$^a$ and R$^b$ are independently H or optionally substituted alkyl; or R$^a$ and R$^b$ may form, with the nitrogen to which they are attached, a 3-, 4-, 5-, 6-, 7-, or 8-membered-heterocyclyl group, which may include one to three additional heteroatoms selected from the group consisting of N, O and S and may be optionally substituted;

$R^4$ is independently in each occurrence hydrogen, cyano, hydrogen, halo, hydroxyl, optionally substituted alkyl, optionally substituted alkoxy, optionally substituted alkenyl, optionally substituted alkynyl, optionally substituted aryl; optionally substituted aryloxy, optionally substituted heteroaryl, optionally substituted cycloalkyl, optionally substituted cycloalkyloxy, optionally substiapted heterocyclyl, optionally substituted alkylcarbonyl, optionally substituted alkoxycarbonyl, optionally substituted aminocarbonyl, optionally substituted alkylaminocarbonyl, optionally substituted dialkylaminocarbonyl, —SO$_p$(optionally substituted alkyl or haloalkyl), —SF$_5$, or —NR$^a$R$^b$ wherein R$^a$ and R$^b$ are independently H or optionally substituted alkyl; or R$^a$ and R$^b$ may form, with the nitrogen to which they are attached, a 3-, 4-, 5-, 6-, 7-, or 8-membered-heterocyclyl group, which may include one to three additional heteroatoms selected from the group consisting of N, O and S and may be optionally substituted $R^5$ and $R^{5'}$ are independently in each occurrence, hydrogen, halogen, cyano, nitro, hydroxyl, optionally substituted alkyl, optionally substituted alkoxy, optionally substituted cycloalkyl, optionally substituted cycloalkyloxy, optionally substituted aryl, optionally substituted heteraryl, —SF$_5$, —SO$_p$(optionally substituted alkyl or haloalkyl), or —NR$^c$R$^d$ wherein R$^c$ and R$^d$ are independently H or optionally substituted alkyl; or R and R$^d$ may form, with the nitrogen to which they are attached, a 3-, 4-, 5-, 6-, 7-, or 8-membered-heterocyclyl group, which may include one to three additional heteroatoms selected from the group consisting of N, O and S and may be optionally substituted;

$R^{10}$ is hydrogen, halogen, alkyl, haloalkyl, cycloalkyl, alkenyl or alkynyl;

X is O or S;

Q is O, S or N—R$^{2'}$;

$Y^1$, $Y^2$ and $Y^3$ are each independently N or —CR$^4$—;

$Y^{1'}$ and $Y^{6'}$ are each independently N, C, or —CR$^5$—;

$Y^{2'}$, $Y^{3'}$, $Y^{4'}$ and $Y^{5'}$ are each independently N, NR$^2$, S, O, —CR$^5$— or CR$^5$R$^{5'}$;

W is CR$^6$R$^7$, O, S, or N—R$^8$,

Z is CR$^6$R$^7$, O, S, or N—R$^8$, wherein

R$^6$ and R$^7$ are independently in each occurrence hydrogen, halo, C$_1$-C$_4$-alkyl, C$_1$-C$_4$-haloalkyl, C$_1$-C$_4$-alkoxy, C$_1$-C$_4$-haloalkoxy or cycloalkoxy;

R$^8$ is hydrogen or C$_1$-C$_4$-alkyl; and wherein at most three of $Y^{1'}$, $Y^{2'}$, $Y^{3'}$, $Y^{4'}$, $Y^{5'}$ and $Y^{6'}$ are heteroatoms;

a is 0 or 1;

q is 0 or 1;

p is independently in each occurrence is 0, 1, or 2; and the dashed bonds ( - - - - ) signifies a single or double bond;

a stereoisomer, tautomer, N-oxide, hydrate, solvate, or salt thereof.

In another embodiment, the invention provides a compound of Formula (I)

wherein:

$R^1$ is hydrogen, cyano, halo, hydroxyl, C$_1$-C$_6$-alkyl, C$_1$-C$_6$-haloalkyl, hydroxy-C$_1$-C$_6$-alkyl, hydroxy-C$_1$-C$_6$-haloalkyl, C$_1$-C$_6$-alkoxy-C$_1$-C$_6$-alkyl, C$_1$-C$_6$-haloalkoxy-C$_1$-C$_6$-alkyl, amino-C$_1$-C$_6$-alkyl, C$_1$-C$_6$-alkoxy, C$_1$-C$_6$-haloalkoxy, C$_2$-C$_6$-alkenyl, C$_2$-C$_6$-haloalkenyl, C$_2$-C$_6$-alkynyl, C$_2$-C$_6$-haloalkynyl, C$_1$-C$_6$-alkylcarbonyl, C$_1$-C$_6$-haloalkylcarbonyl, C$_1$-C$_6$-alkoxycarbonyl, C$_1$-C$_6$-haloalkoxycarbonyl, aminocarbonyl, C$_1$-C$_6$-alkylaminocarbonyl, C$_1$-C$_6$-haloalkylaminocarbonyl, di-C$_1$-C$_6$-alkylaminocarbonyl, di-C$_1$-C$_6$-haloalkylaminocarbonyl, optionally substituted aryl, optionally substituted aryloxy, optionally substituted heteroaryl, optionally substituted C$_3$-C$_8$-cycloalkyl, optionally substituted C$_3$-C$_8$-cycloalkyloxy, optionally substituted 3- to 7-membered heterocyclyl, —SF$_5$, —SO$_p$(optionally substituted C$_1$-C$_6$-alkyl or C$_1$-C$_6$-haloalkyl), or —NR$^a$R$^b$ wherein R$^a$ and R$^b$ are independently H or optionally substituted C$_1$-C$_6$-alkyl; or R$^a$ and R$^b$ may form, with the nitrogen to which they are attached, a 3-, 4-, 5-, 6-, 7-, or 8-membered-heterocyclyl group, which may include one to three additional heteroatoms selected from the group consisting of N, O and S and may be optionally substituted;

$R^2$ is hydrogen, C$_1$-C$_6$-alkyl, C$_1$-C$_6$-haloalkyl, optionally substituted C$_3$-C$_8$-cycloalkyl, or optionally substituted phenyl;

$R^{2'}$ is C$_1$-C$_6$-alkyl, C$_1$-C$_6$-haloalkyl, optionally substituted C$_3$-C$_8$-cycloalkyl, or optionally substituted phenyl;

$R^3$ is C$_1$-C$_6$-alkyl, C$_1$-C$_6$-haloalkyl, C$_1$-C$_6$-alkoxy-C$_1$-C$_6$-alkyl, C$_1$-C$_6$-haloalkoxy-C$_1$-C$_6$-alkyl, optionally substituted C$_3$-C$_8$-cycloalkyl, C$_1$-C$_6$-alkylcarbonyl, C$_1$-C$_6$-haloalkylcarbonyl, C$_1$-C$_6$-alkoxycarbonyl, C$_1$-C$_6$-haloalkoxycarbonyl, aminocarbonyl, C$_1$-C$_6$-alkylaminocarbonyl, C$_1$-C$_6$-haloalkylaminocarbonyl, di-C$_1$-C$_6$-alkylaminocarbonyl, di-C$_1$-C$_6$-haloalkylaminocarbonyl, —SF$_5$, —S(O)$_p$(C$_1$-C$_6$-alkyl or C$_1$-C$_6$-haloalkyl), optionally substituted 3- to 7-membered heterocyclyl containing from one to three heteroatoms selected from the group consisting of N, O and S; optionally substituted phenyl, optionally substituted 5- to 10-membered heteroaryl, a 5- to 11-membered spirocyclic heterocyclyl-carbocyclyl group, a 5- to 11-membered spirocyclic heterocyclyl-heterocyclyl group, a 5-to 11-membered spirocyclic carbocyclyl-carbocyclyl group, a 5- to 11-membered spirocyclic carbocyclyl-heterocyclyl group, or —NR$^a$R$^b$ wherein R$^a$ and R$^b$ are independently H, C$_1$-C$_6$-alkyl or C$_1$-C$_6$-haloalkyl; or R$^a$ and R$^b$ may form, with the nitrogen to which they are attached, a 3-, 4-, 5-, 6-, 7-, or 8-membered-heterocyclyl group, which may include one to three additional heteroatoms selected from the group consisting of N, O and S and may be optionally substituted;

R$^4$ is independently in each occurrence hydrogen, cyano, halo, hydroxyl, C$_1$-C$_6$-alkyl, C$_1$-C$_6$-haloalkyl, C$_1$-C$_6$-alkoxy, C$_1$-C$_6$-haloalkoxy, C$_2$-C$_6$-alkenyl, C$_2$-C$_6$-haloalkenyl, C$_2$-C$_6$-alkynyl, C$_2$-C$_6$-haloalkynyl, C$_1$-C$_6$-alkoxy-C$_1$-C$_6$-alkyl, C$_1$-C$_6$-haloalkoxy-C$_1$-C$_6$-alkyl, optionally substituted phenyl; optionally substituted phenyloxy, optionally substituted 5- or 6-membered heteroaryl, optionally substituted C$_3$-C$_8$-cycloalkyl, optionally substituted C$_3$-C$_8$-cycloalkyloxy, optionally substituted 3- to 7-membered heterocyclyl containing from one to three heteroatoms selected from the group consisting of N, O and S, C$_1$-C$_6$-alkylcarbonyl, C$_1$-C$_6$-haloalkylcarbonyl, C$_1$-C$_6$-alkoxycarbonyl, C$_1$-C$_6$-haloalkoxycarbonyl, aminocarbonyl, C$_1$-C$_6$-alkylaminocarbonyl, C$_1$-C$_6$-haloalkylaminocarbonyl, di-C$_1$-C$_6$-alkylaminocarbonyl, di-C$_1$-C$_6$-haloalkylaminocarbonyl, —SO$_p$(optionally substituted C$_1$-C$_6$-alkyl or C$_1$-C$_6$-haloalkyl), SF$_5$, or —NR$^a$R$^b$ wherein R$^a$ and R$^b$ are independently H, C$_1$-C$_6$-alkyl or C$_1$-C$_6$-haloalkyl; or R$^a$ and R$^b$ may form, with the nitrogen to which they are attached, a 3-, 4-, 5-, 6-, 7-, or 8-membered-heterocyclyl group, which may include one to three additional heteroatoms selected from the group consisting of N, O and S and may be optionally substituted;

R$^5$ and R$^{5'}$ are independently in each occurrence, hydrogen, halogen, cyano, nitro, hydroxyl, C$_1$-C$_6$-alkyl, C$_1$-C$_6$-haloalkyl, C$_1$-C$_6$-alkoxy, C$_1$-C$_6$-haloalkoxy, C$_1$-C$_6$-alkoxy-C$_1$-C$_6$-alkyl, C$_1$-C$_6$-haloalkoxy-C$_1$-C$_6$-alkyl, optionally substituted C$_3$-C$_8$-cycloalkyloxy, optionally substituted phenyl, optionally substituted 5- or 6-membered heteroaryl, —SF$_5$, —SO$_p$(optionally substituted C$_1$-C$_6$-alkyl or C$_1$-C$_6$-haloalkyl), or —NR$^c$R$^d$ wherein R$^c$ and R$^d$ are independently H, C$_1$-C$_6$-alkyl or C$_1$-C$_6$-haloalkyl; or R$^c$ and R$^d$ may form, with the nitrogen to which they are attached, a 3-, 4-, 5-, 6-, 7-, or 8-membered-heterocyclyl group, which may include one to three additional heteroatoms selected from the group consisting of N, O and S and may be optionally substituted;

R$^{10}$ is hydrogen, halogen, C$_1$-C$_6$-alkyl, C$_1$-C$_6$-haloalkyl, C$_3$-C$_8$-cycloalkyl, C$_2$-C$_6$-alkenyl or C$_2$-C$_6$-alkynyl; and L, X, Q, Y$^1$, Y$^2$, Y$^3$, Y$^{1'}$, Y$^{2'}$, Y$^3$, Y$^4$, Y$^5$, Y$^6$, W, Z, R$^6$, R$^7$, R$^8$, a, q, p and the dashed bonds ( ----- ) are as defined above for the compound of Formula (I).

In one embodiment, L is L1. In another embodiment, L is L2. In some embodiments:

R$^1$ is hydrogen, cyano, optionally substituted C$_1$-C$_4$-alkyl, optionally substituted C$_1$-C$_4$-alkoxy, optionally substituted C$_1$-C$_4$-alkenyl, optionally substituted C$_1$-C$_4$-alkynyl, optionally substituted C$_3$-C$_8$-cycloalkyl, optionally substituted, saturated or unsaturated 5-, 6-, or 7-membered heterocycle group, optionally substituted aryl, optionally substituted heteroaryl, optionally substituted aryloxy, optionally substituted C$_1$-C$_4$-alkylcarbonyl, optionally substituted C$_1$-C$_4$-alkoxycarbonyl, optionally substituted aminocarbonyl, optionally substituted C$_1$-C$_4$-alkylaminocarbonyl, optionally substituted C$_1$-C$_4$-dialkylaminocarbonyl, optionally substituted alkyl-SO$_p$—, haloalkyl-SO$_p$—, amino, —NH-optionally substituted C$_1$-C$_4$-alkyl, or —NR$^a$R$^b$ wherein R$^a$ and R$^b$ are independently optionally substituted alkyl; or R$^a$ and R$^b$ may form, with the nitrogen to which they are attached, a 3-, 4-5-, 6-, 7-, or 8-membered-heterocyclyl group, which may include one to three additional heteroatoms selected from the group consisting of N, O and S and may be optionally substituted;

R$^2$ is hydrogen or C$_1$-C$_4$-alkyl;

R$^3$ is C$_1$-C$_4$-alkyl, C$_3$-C$_6$-cycloalkyl, 4- to 6-membered-heterocyclyl, 6- to 10-membered aryl, 5- to 10-membered heteroaryl, each of which may be optionally substituted with 1, 2, or 3 substituents;

Each R$^4$ is independently hydrogen, halogen, cyano, nitro, —OH, optionally substituted C$_1$-C$_4$-alkyl, optionally substituted C$_1$-C$_4$-alkoxy, optionally substituted C$_3$-C$_8$-cycloalkyl, -amino, NH-optionally substituted C$_1$-C$_4$-alkyl, —SF$_5$, or —NR$^a$R$^b$ wherein R$^c$ and R$^a$ are independently optionally substituted C$_1$-C$_4$-alkyl; or R$^a$ and R$^b$ may form, with the nitrogen to which they are attached, a 3, 4, 5, 6, 7, or 8 membered-heterocyclyl group, which may be optionally substituted, SO$_p$(optionally substituted C$_1$-C$_4$-alkyl or haloalkyl).

Each R$^5$ is independently hydrogen, halogen, cyano, nitro, —OH, optionally substituted C$_1$-C$_4$-alkyl, optionally substituted C$_1$-C$_4$-alkoxy, optionally substituted C$_3$-C$_8$-cycloalkyl, -amino, NH-optionally substituted C$_1$-C$_4$-alkyl, —SF$_5$, or —NR$^c$R$^d$ wherein R$^c$ and R$^d$ are independently optionally substituted C$_1$-C$_4$-alkyl; or R$^c$ and R$^d$ may form, with the nitrogen to which they are attached, a 3, 4, 5, 6, 7, or 8 membered-heterocyclyl group, which may be optionally substituted, SO$_p$(optionally substituted C$_1$-C$_4$-alkyl or haloalkyl.

In some embodiments, R$^1$ is hydrogen.

In some embodiments, R$^1$ is C$_1$-C$_4$-alkyl, C$_1$-C$_4$-haloalkyl, amino, C$_1$-C$_4$-alkylamino, or di-(C$_1$-C$_4$-alkyl) amino.

In another embodiment, R$^1$ is halogen.

In another embodiment, R$^1$ is C$_1$-C$_4$-alkyl-SO$_p$—, C$_1$-C$_4$-haloalkyl-SO$_p$— or —SF$_5$.

In other embodiments, R$^1$ is hydroxy-C$_1$-C$_4$-alkyl, C$_1$-C$_4$-alkoxy-C$_1$-C$_4$-alkyl, C$_1$-C$_4$-haloalkoxy-C$_1$-C$_4$-alkyl or C$_1$-C$_4$-haloalkoxy-C$_1$-C$_4$-haloalkyl.

In another embodiment, R$^1$ is methyl, ethyl, propyl, butyl, pentyl, isopropyl (i-Pr), tert-butyl (t-butyl), prop-1-en-2-yl, 2-fluoroprop-2-yl or 2-hydroxyprop-2-yl.

In another embodiment, R$^1$ is CF$_3$, —CH$_2$CF$_3$, —CHFCF$_3$ or —CF$_2$CF$_3$.

In some embodiments, R$^1$ is C$_2$-C$_4$-alkenyl or C$_2$-C$_4$-haloalkenyl In some embodiments, R$^1$ is optionally substituted cyclopentyl or optionally substituted cyclohexyl.

In some embodiments, R$^1$ is an optionally substituted, saturated or unsaturated 6-membered heterocyclyl group.

In one embodiment, R$^1$ is —NR$^a$R$^b$ wherein R$^a$ and R$^b$ are independently hydrogen or C$_1$-C$_6$ alkyl. In another embodiment R$^1$ is —NR$^a$R$^b$ wherein R$^a$ and R$^b$ may form, with the nitrogen to which they are attached, a 3-, 4-, 5-, 6-, 7-, or 8-membered-heterocyclyl group, which may include one to three additional heteroatoms selected from the group consisting of N, O and S and may be optionally substituted.

In another embodiment, R$^1$ is C$_1$-C$_6$-alkylcarbonyl, C$_1$-C$_6$-haloalkylcarbonyl, C$_1$-C$_6$-alkoxycarbonyl, C$_1$-C$_6$-haloalkoxycarbonyl, aminocarbonyl, $C_1$-$C_6$-alkylaminocarbonyl, $C_1$-$C_6$-haloalkylaminocarbonyl, di-$C_1$-$C_6$-alkylaminocarbonyl, di-$C_1$-$C_6$-haloalkylaminocarbonyl.

In some embodiments, $R^1$ is optionally substituted tetrahydrofuryl, dihydrofuryl, morpholino, pyranyl, dihydropyranyl, piperidinyl, dihydropiperidinyl, dihydrothiophene, or tetrahydrothiophene.

In some embodiments, $R^1$ is optionally substituted phenyl.

In some embodiments, $R^1$ is aziridinyl, azetidinyl, oxetanyl, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridinyl, pyrazinyl, pyrimidinyl, pyridazinyl, pyranyl, dihydropyranyl, tetrahydropyranyl, thiopyranyl, dihydrothiopyranyl, tetrahydrothiopyranyl, morpholinyl, thiamorpholinyl, thiamorpholinyl sulfoxide, thiamorpholinyl sulfone, 1,3-dioxolane and tetrahydro-1,1-dioxothienyl, triazolyl or triazinyl.

In some embodiments, $R^1$ is aziridinyl, azetidinyl, oxetanyl, pyrrolidinyl, pyrrolyl, or morpholinyl, all of which are optionally substituted by one or more halogen.

In some embodiments, $R^3$ is 6- to 10-membered aryl optionally substituted with 1, 2, 3, 4 or 5 substituents.

In some embodiments, $R^3$ is $C_1$-$C_4$-alkyl or $C_1$-$C_4$-haloalkyl.

In some embodiments, $R^3$ is methyl, ethyl, n-propyl, n-butyl, iso-propyl, tert-butyl, sec-butyl or iso-butyl.

In other embodiments, $R^3$ is $CF_3$, —$CH_2CF_3$, —$CHFCF_3$ or —$CF_2CF_3$.

In some embodiments, $R^3$ is optionally substituted $C_3$-$C_8$-cycloalkyl. In yet other embodiments, $R^3$ is optionally substituted $C_3$-$C_6$-cycloalkyl. In yet other embodiments, $R^3$ is optionally substituted $C_3$-$C_8$-cycloalkenyl or $C_3$-$C_6$-cycloalkenyl. In some embodiments, $R^3$ is optionally substituted cyclopentyl or cyclohexyl.

In one embodiment, $R^3$ is cyclohexyl optionally substituted by one or more halo, $C_1$-$C_3$-alkyl or $C_1$-$C_3$-haloalkyl. In another embodiment, $R^3$ is cyclohexyl substituted by 1 or 2 fluoro, chloro or $CF_3$.

In some embodiments, $R^3$ is optionally substituted piperidinyl, morpholinyl, tetahydrofuranyl or dihydrofuranyl. In some embodiments, $R^3$ is piperidinyl, morpholinyl, tetahydrofuranyl or dihydrofuranyl substituted with one or more halo, $C_1$-$C_6$-alkyl or $C_1$-$C_6$-haloalkyl. In another embodiment, $R^3$ is piperidinyl, morpholinyl, tetrahydrofuranyl or dihydrofuranyl substituted with one or more methyl, chloro or fluoro.

In some embodiments, $R^3$ is 5- to 10-membered heteroaryl optionally substituted with 1, 2, 3, 4 or 5 substituents. In one embodiment, the 5- to 10-membered heteroaryl is pyridyl, pyridazinyl, pyrimidinyl, pyrazinyl, triazinyl, pyrrolyl, indolyl, quinolinyl, isoquinolinyl, quinazolinyl, quinoxalinnyl, furanyl, thiophenyl, furyl, pyrrolyl, imidazolyl, oxazolyl, isoxazolyl, isothiazolyl, pyrazolyl benzofuranyl, benzothiophenyl, imidazopyridyl, imidazopyrimidyl or pyrrolopyrimidyl.

In other embodiments, $R^3$ is an optionally substituted spirocyclic heterocyclyl-carbocyclyl group, an optionally substituted spirocyclic heterocyclyl-heterocyclyl group, an optionally substituted spirocyclic carbocyclyl-carbocyclyl group or an optionally substituted spirocyclic carbocyclyl-heterocyclyl group. In other embodiments, $R^3$ is a 5- to 11-membered optionally substitued spirocyclic heterocyclyl-carbocyclyl group, a 5- to 11-membered optionally substitued spirocyclic heterocyclyl-heterocyclyl group, a 5- to 11-membered optionally substitued spirocyclic carbocyclyl-carbocyclyl group or a 5- to 11-membered optionally substitued spirocyclic carbocyclyl-heterocyclyl group. Non-limiting examples of spirocyclic carbocyclyl-carbocyclyl, spiroclycic carbocyclyl-heterocyclyl and spirocyclyl heterocyclyl-heterocyclyl groups are shown below for illustration.

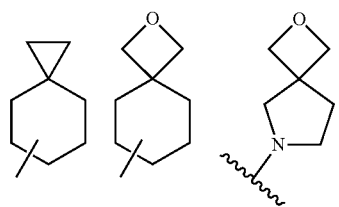

However, it will be apparent to persons skilled in the art that the second ring of the spirocyclic group may be joined at any available carbon of the first ring. It will also be understood that the first ring of the spirocyclic group may be bonded to the molecule at any available atom. Thus, the present invention includes 3-, 4-, 5-, 6- and 7-membered carbocyclic or heterocyclic rings as defined herein joined to a second 3-, 4-, 5-, 6- and 7-membered carbocyclic or heterocyclic ring at any available carbon atom of the first ring.

In some embodiments, $R^3$ is phenyl substituted with 1 to 4 substituents. In another embodiment, $R^3$ is phenyl substituted by 1 to 3 substituents. In yet another embodiment, $R^3$ is phenyl substituted by 1 or 2 substituents. In some embodiments, $R^3$ is phenyl substituted by 1, 2, 3 or 4 substituents which are independently halo, cyano, nitro, alkylsulfonyl, haloalkylsulfonyl, alkyl, alkenyl, alkynyl, cycloalkyl, cycloalkenyl, phenyl, substituted phenyl, haloalkyl, haloalkenyl, haloalkynyl, halocycloalkyl, halocycloalkenyl, alkoxy, alkenyloxy, alkynyloxy, haloalkoxy or haloalkenyloxy.

In some embodiments, $R^3$ is para-substituted phenyl.
In some embodiments, $R^3$ is meta-substituted phenyl.
In some embodiments, $R^3$ is ortho-substituted phenyl.
In some embodiments, $R^3$ is halophenyl. In some embodiments $R^3$ is haloalkylphenyl.
In some embodiments, $R^3$ is haloalkoxyphenyl.

In some embodiments, $R^3$ is phenyl substituted with 2 substituents which are independently halo, cyano, nitro, alkylsulfonyl, haloalkylsulfonyl, alkyl, alkenyl, alkynyl, cycloalkyl, cycloalkenyl, haloalkyl, haloalkenyl, haloalkynyl, halocycloalkyl, halocycloalkenyl, alkoxy, alkenyloxy, alkynyloxy, haloalkoxy or haloalkenyloxy.

In some embodiments, $R^3$ is 2,3-disubstituted phenyl.
In some embodiments, $R^3$ is 2,4-disubstituted phenyl.
In some embodiments, $R^3$ is 2,5-disubstituted phenyl.
In some embodiments, $R^3$ is a 2-, 6-disubstituted phenyl.
In some embodiments, $R^3$ is a 3-, 5-disubstituted phenyl.
In other embodiments, $R^3$ is a 3-, 4-disubstituted phenyl.
In other embodiments, $R^3$ is a 3-, 6-disubstituted phenyl.
In some embodiments, $R^3$ is dihalophenyl, e.g., dichloro; difluoro; or chloro, fluoro.
In some embodiments, $R^3$ is 2,3-dihalophenyl.

In some embodiments, $R^3$ is chlorophenyl. In another embodiment, $R^3$ is fluorophenyl. In another embodiment, $R^3$ dichlorophenyl. In another embodiment, $R^3$ is difluorophenyl. In yet another embodiment, $R^3$ is 3,5-dichlorophenyl. In another embodiment, $R^3$ is 3,5-difluorophenyl. In another embodiment, $R^3$ is 2,6-dichlorophenyl. In another embodiment, $R^3$ is 2,6-difluorophenyl.

In some embodiments $R^3$ is phenyl substituted with halo and haloalkyl.

In some embodiments $R^3$ is phenyl substituted with halo and haloalkoxy.

In some embodiments $R^3$ is phenyl substituted with haloalkyl and haloalkoxy.

In some embodiments, $R^3$ is phenyl substituted with 3 substituents which are independently halo, cyano, nitro, alkylsulfonyl, haloalkylsulfonyl, alkyl, alkenyl, alkynyl, cycloalkyl, cycloalkenyl, haloalkyl, haloalkenyl, haloalkynyl, halocycloalkyl, halocycloalkenyl, alkoxy, alkenyloxy, alkynyloxy, haloalkoxy or haloalkenyloxy.

In some embodiments, $R^3$ is trihalophenyl, e.g., trichloro; trifluoro; or chloro, chloro, fluoro, or fluoro, fluoro, chloro.

In some embodiments $R^3$ is phenyl substituted with 2 halo and haloalkyl.

In some embodiments $R^3$ is phenyl substituted with 2 halo and haloalkoxy.

In some embodiments $R^3$ is phenyl substituted with 1 haloalkyl, 1 halo, and 1 haloalkoxy.

In some embodiments $R^3$ is phenyl substituted with 1 halo and 2 haloalkyl.

In some embodiments, $R^3$ is 5-membered heteroaryl optionally substituted with 1 or 2 substituents which are independently halo, cyano, nitro, alkylsulfonyl, haloalkylsulfonyl, alkyl, alkenyl, alkynyl, cycloalkyl, cycloalkenyl, haloalkyl, haloalkenyl, haloalkynyl, halocycloalkyl, halocycloalkenyl, alkoxy, alkenyloxy, alkynyloxy, haloalkoxy or haloalkenyloxy.

In some embodiments, $R^3$ is 6-membered heteroaryl optionally substituted with 1 or 2 substituents which are independently halo, cyano, nitro, alkylsulfonyl, haloalkylsulfonyl, alkyl, alkenyl, alkynyl, cycloalkyl, cycloalkenyl, haloalkyl, haloalkenyl, haloalkynyl, halocycloalkyl, halocycloalkenyl, alkoxy, alkenyloxy, alkynyloxy, haloalkoxy or haloalkenyloxy.

In some embodiments, $R^3$ is 2-pyridyl optionally substituted with 1 or 2 substituents which are independently halo, cyano, nitro, alkylsulfonyl, haloalkylsulfonyl, alkyl, alkenyl, alkynyl, cycloalkyl, cycloalkenyl, haloalkyl, haloalkenyl, haloalkynyl, halocycloalkyl, halocycloalkenyl, alkoxy, alkenyloxy, alkynyloxy, haloalkoxy or haloalkenyloxy.

In some embodiments, $R^3$ is 3-pyridyl optionally substituted with 1 or 2 substituents which are independently halo, cyano, nitro, alkylsulfonyl, haloalkylsulfonyl, alkyl, alkenyl, alkynyl, cycloalkyl, cycloalkenyl, haloalkyl, haloalkenyl, haloalkynyl, halocycloalkyl, halocycloalkenyl, alkoxy, alkenyloxy, alkynyloxy, haloalkoxy or haloalkenyloxy.

In some embodiments, $R^3$ is 4-pyridyl optionally substituted with 1 or 2 substituents which are independently halo, cyano, nitro, alkylsulfonyl, haloalkylsulfonyl, alkyl, alkenyl, alkynyl, cycloalkyl, cycloalkenyl, haloalkyl, haloalkenyl, haloalkynyl, halocycloalkyl, halocycloalkenyl, alkoxy, alkenyloxy, alkynyloxy, haloalkoxy or haloalkenyloxy.

In another embodiment, $R^3$ is 4-pyridyl which is unsubstituted or substituted with 1 or 2 chloro or fluoro. In yet another embodiment $R^3$ is 3-pyridyl which is unsubstituted or substituted with 1 or 2 chloro or fluoro.

In other embodiments, $R^3$ is an optionally substituted 3- to 7-membered heterocycle. In some embodiments $R^3$ is optionally substituted aziridinyl, azetidinyl, oxetanyl, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridinyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, triazolyl or triazinyl.

In another embodiment, $R^3$ may be a heterocyclic, bridged bicyclic group, which may be optionally substituted.

In some embodiments, each $R^4$ is independently hydrogen, $C_1$-$C_4$-alkyl, $C_1$-$C_4$-haloalkyl, amino, $C_1$-$C_4$-alkylamino, or di-($C_1$-$C_4$alkyl) amino.

In another embodiment, each $R^4$ is independently hydrogen, methyl, ethyl, n-propyl, iso-propyl, n-butyl, sec-butyl, iso-butyl or tert-butyl.

In another embodiment, each $R^4$ is independently hydrogen, $CF_3$, —$CH_2CF_3$, —$CHFCF_3$ or —$CF_2CF_3$.

In some embodiments, $R^4$ is hydrogen.

In some embodiments, $R^4$ is halogen.

In another embodiment, $R^4$ is fluoro or chloro.

In another embodiment, each $R^4$ is independently hydrogen, $C_1$-$C_4$-alkoxy, $C_1$-$C_4$-haloalkoxy or $S(O)_p$($C_1$-$C_4$-alkyl or $C_1$-$C_4$-haloalkyl) where p is 0, 1 or 2.

In another embodiment, $R_4$ is methoxy, ethoxy, propoxy or butoxy.

In another embodiment, $R_4$ is methylthio, ethylthio, propylthio or butylthio.

In another embodiment, $R_4$ is —$OCF_3$ or —$SCF_3$.

In some embodiments, $R^4$ is $C_1$-$C_4$-alkenyl or $C_1$-$C_4$-haloalkenyl.

In some embodiments, $R^4$ is optionally substituted cyclopentyl or optionally substituted cyclohexyl.

In some embodiments, $R^4$ is an optionally substituted, saturated or unsaturated 6-membered heterocyclyl group.

In some embodiments, $R^4$ is optionally substituted tetrahydrofuryl, dihydrofuryl, morpholino, pyranyl, dihydropyranyl, piperidinyl, dihydropiperidinyl, dihydrothiophene, or tetrahydrothiophene.

In some embodiments, $R^4$ is optionally substituted phenyl.

In other embodiments, $R^4$ is phenyl substituted with 1, 2, or 3 substituents, which are independently halo, cyano, nitro, alkylsulfonyl, haloalkylsulfonyl, alkyl, alkenyl, alkynyl, cycloalkyl, cycloalkoxy, cycloalkenyl, haloalkyl, haloalkenyl, haloalkynyl, halocycloalkyl, halocycloalkenyl, alkoxy, alkenyloxy, alkynyloxy, haloalkoxy or haloalkenyloxy.

In another embodiment, $R^4$ is a 5- or 6-membered heteroaryl with 1 or 2 substituents which are independently halo, cyano, nitro, alkylsulfonyl, haloalkylsulfonyl, alkyl, alkenyl, alkynyl, cycloalkyl, cycloalkenyl, haloalkyl, haloalkenyl, haloalkynyl, halocycloalkyl, halocycloalkenyl, alkoxy, alkenyloxy, alkynyloxy, haloalkoxy or haloalkenyloxy.

In some embodiments, $R^4$ is optionally substituted aziridinyl, azetidinyl, oxetanyl, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridinyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, triazolyl or triazinyl.

In some embodiments, $R^4$ is aziridinyl, azetidinyl, oxetanyl, pyrrolidinyl, pyrrolyl, or morpholinyl, all of which are optionally substituted by one or more halogen.

In some embodiments, $R^5$ is hydrogen.

In some embodiments, each $R^5$ is independently hydrogen, $C_1$-$C_4$-alkyl, $C_1$-$C_4$-haloalkyl, amino, $C_1$-$C_4$-alkylamino, or di-($C_1$-$C_4$alkyl) amino.

In another embodiment, each $R^5$ is methyl, ethyl, n-propyl, iso-propyl, n-butyl, sec-butyl, iso-butyl or tert-butyl.

In another embodiment, $R^5$ is $CF_3$, —$CH_2CF_3$, —$CHFCF_3$ or —$CF_2CF_3$.

In some embodiments, $R^5$ is halogen.

In another embodiment, $R^5$ is fluoro or chloro.

In another embodiment, $R^5$ is $C_1$-$C_4$-alkoxy, $C_1$-$C_4$-haloalkoxy or $S(O)_p$($C_1$-$C_4$-alkyl or $C_1$-$C_4$-haloalkyl) where p is 0, 1 or 2.

In another embodiment, $R_5$ is methoxy, ethoxy, propoxy or butoxy.

In another embodiment, $R_5$ is methylthio, ethylthio, propylthio or butylthio.

In another embodiment, $R_5$ is —$OCF_3$ or —$SCF_3$.

In some embodiments, $R^5$ is $C_1$-$C_4$-alkenyl or $C_1$-$C_4$-haloalkenyl

In some embodiments, $R^5$ is optionally substituted cyclopentyl or optionally substituted cyclohexyl.

In some embodiments, $R^5$ is optionally substituted tetrahydrofuryl, dihydrofuryl, morpholino, pyranyl, dihydropyranyl, piperidinyl, dihydropiperidinyl, dihydrothiophene, or tetrahydrothiophene.

In some embodiments, $R^5$ is optionally substituted phenyl.

In other embodiments, $R^5$ is phenyl substituted with 1, 2, or 3 substituents, which are independently halo, cyano, nitro, alkylsulfonyl, haloalkylsulfonyl, alkyl, alkenyl, alkynyl, cycloalkyl, cycloalkoxy, cycloalkenyl, haloalkyl, haloalkenyl, haloalkynyl, halocycloalkyl, halocycloalkenyl, alkoxy, alkenyloxy, alkynyloxy, haloalkoxy or haloalkenyloxy.

In other embodiments, $R^5$ is a 5- or 6-membered heteroaryl with 1 or 2 substituents which are independently halo, cyano, nitro, alkylsulfonyl, haloalkylsulfonyl, alkyl, alkenyl, alkynyl, cycloalkyl, cycloalkenyl, haloalkyl, haloalkenyl, haloalkynyl, halocycloalkyl, halocycloalkenyl, alkoxy, alkenyloxy, alkynyloxy, haloalkoxy or haloalkenyloxy.

In some embodiments, $R^5$ is optionally substituted aziridinyl, azetidinyl, oxetanyl, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridinyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, triazolyl or triazinyl.

In some embodiments, $R^5$ is aziridinyl, azetidinyl, oxetanyl, pyrrolidinyl, pyrrolyl, or morpholinyl, all of which are optionally substituted by one or more halogen.

In some embodiments, a is 0.
In some embodiments, a is 1.
In some embodiments, X is O.
In some embodiments, X is S.
In some embodiments, Q is O.
In some embodiments, Q is S.
In some embodiments, Q is $NR^{2'}$.
In some embodiments, W is $CH_2$ In some embodiments, Z is $CH_2$.
In some embodiments, Z is O.
In some embodiments, Z is S.
In some embodiments, Z is NH.

In some embodiments, the compound of Formula (I) is the compound of Formula (I-1):

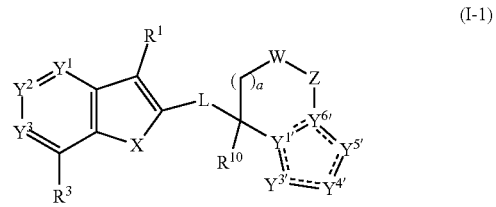

(I-1)

wherein variables L, $R^1$, $R^3$, $Y^1$, $Y^2$, $Y^3$, $Y^{1'}$, $Y^{3'}$, $Y^{4'}$, $Y^{5'}$, $Y^{6'}$, X, W, Z, $R^{10}$ and a are as defined for formula (I).

In some embodiments, the compound of Formula (I) is the compound of formula (I-2):

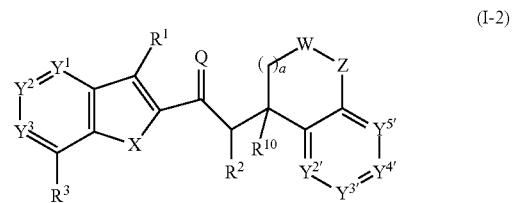

(I-2)

wherein variables $R^1$, $R^2$, $R^3$, $Y^1$, $Y^2$, $Y^3$, $Y^{2'}$, $Y^{3'}$, $Y^{4'}$, $Y^{5'}$, X, Q, W, Z, $R^{10}$ and a are as defined for formula (I).

In other embodiments, the compound of Formula (I) is the compound of Formula (I-3) below:

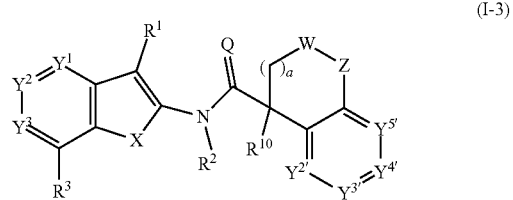

(I-3)

wherein variables $R^1$, $R^2$, $R^3$, $Y^1$, $Y^2$, $Y^3$, $Y^{2'}$, $Y^{3'}$, $Y^{4'}$, $Y^{5'}$, X, Q, W, Z, $R^{10}$ and a are as defined for formula (I).

In other embodiments, the compound of Formula (I) is the compound of Formula (I-4):

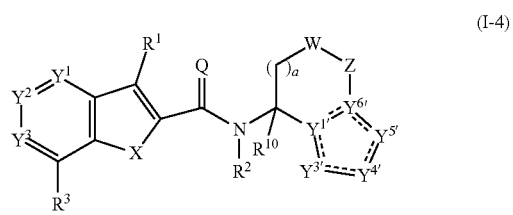

(I-4)

wherein variables $R^1$, $R^2$, $R^3$, $Y^1$, $Y^{2'}$, $Y^{3'}$, $Y^{1'}$, $Y^{3'}$, $Y^{4'}$, $Y^{5'}$, $Y^{6'}$, X, Q, W, Z, R and a are as defined for formula (I).

In another embodiment, the compound of Formula (I) is the compound of Formula (I-5):

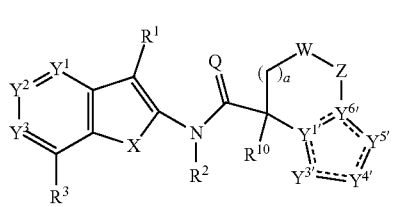
(I-5)

wherein variables $R^1$, $R^2$, $R^3$, $Y^1$, $Y^2$, $Y^3$, $Y^{1'}$, $Y^{3'}$, $Y^{4'}$, $Y^{5'}$, $Y^{6'}$, X, Q, W, Z, $R^{10}$ and a are as defined for formula (I).

In some embodiments, the compound of formula (I) is the compound of formula (Ia):

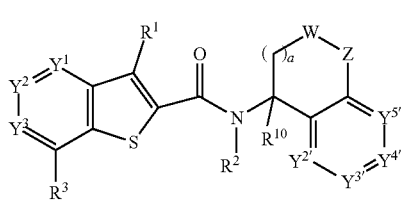
(Ia)

wherein variables $Y^1$, $Y^2$, $Y^3$, $R^1$, $R^2$, $R^3$, W, Z, $Y^{2'}$, $Y^{3'}$, $Y^{4'}$, $Y^{5'}$, $R^{10}$ and a are as defined for formula (I).

In some embodiments, the compound of formula (I) is the compound of formula (Ib):

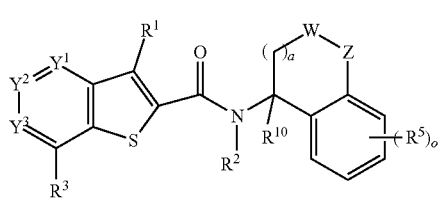
(Ib)

wherein variables $Y^1$, $Y^2$, $Y^3$, $R^1$, $R^2$, $R^3$, $R^5$, W, Z, $R^{10}$ and a are as defined for formula (I), and o is 0, 1, 2, 3 or 4.

In some embodiments, the compound of formula (I) is the compound of formula (Ic):

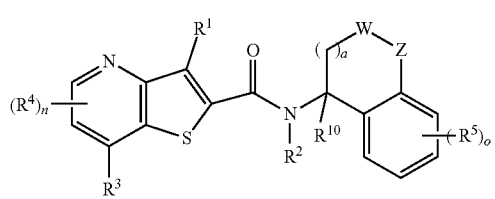
(Ic)

wherein variables $R^1$, $R^2$, $R^3$, $R^4$, $R^5$, W, Z, $R^{10}$ and a are as defined for formula (I); n is 0, 1 or 2; and o is 0, 1, 2, 3 or 4.

In other embodiments, the compound of formula (I) is the compound of formula (Id):

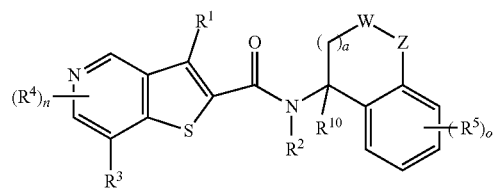
(Id)

wherein variables $R^1$, $R^2$, $R^3$, $R^4$, $R^5$, W, Z, $R^{10}$ and a are as defined for formula (I); n is 0, 1 or 2; and o is 0, 1, 2, 3 or 4.

In some embodiments, the compound of formula (I) is the compound of formula (Ie):

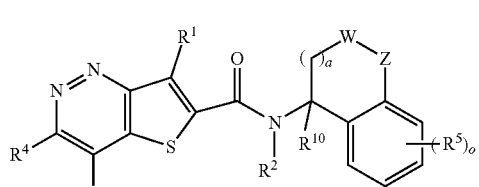
(Ie)

wherein variables $R^1$, $R^2$, $R^3$, $R^4$, $R^5$, W, Z, $R^{10}$ and a are as defined for formula (I); and o is 0, 1, 2, 3 or 4.

In some embodiments, the compound of formula (I) is the compound of formula (If):

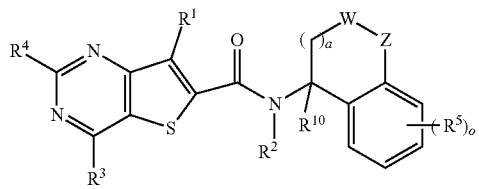
(If)

wherein variables R, $R^2$, $R^3$, $R^4$, $R^5$, W, Z, $R^{10}$ and a are as defined for formula (I); and o is 0, 1, 2, 3 or 4.

In some embodiments, the compound of formula (I) is the compound of formula (Ig):

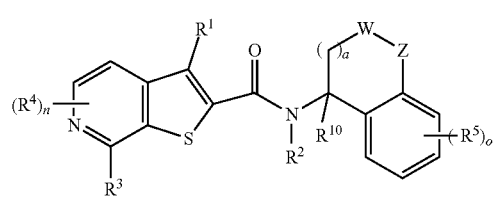
(Ig)

wherein variables $R^1$, $R^2$, $R^3$, $R^4$, $R^5$, W, Z, $R^{10}$ and a are as defined for formula (I); n is 0, 1 or 2; and o is 0, 1, 2, 3 or 4.

In other embodiments, the compound of formula (I) is the compound of formula (Ih):

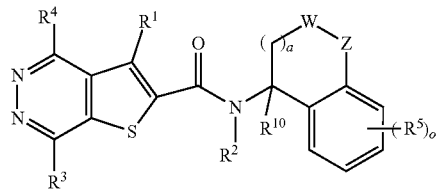

wherein variables $R^1$, $R^2$, $R^3$, $R^4$, $R^5$, W, Z, R and a are as defined for formula (I); and o is 0, 1, 2, 3 or 4.

In some embodiments, the compound of formula (I) is the compound of formula (Ii):

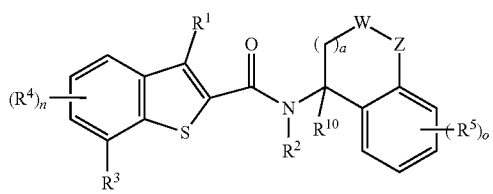

wherein variables $R^1$, $R^2$, $R^3$, $R^4$, $R^5$, W, Z, $R^{10}$ and a are as defined for formula (I); n is 0, 1, 2 or 3; and o is 0, 1, 2, 3 or 4.

It will be appreciated by persons of skill in the art that in any of Formulae (Ib) to (Ii) where variables $R^4$ and $R^5$ are indicated to be present as substituents on the aromatic rings (e.g. as $(R^4)_n$ and $(R^5)_o$ groups where n is 0, 1, 2 or 3 and o is 0, 1, 2, 3 or 4), they will represent non-hydrogen substituents since in embodiments where n and o are 0, $R^4$ and $R^5$ will not be present.

In other embodiments, the present invention includes compounds of formula (I) which have the structures of formulae (Ia) to (Ii) shown above but wherein the sulfur atom corresponding to variable X in formula (I) is replaced with an oxygen atom. Thus, the present invention provides compounds of formulae (Ia'), (Ib'), (Ic'), (Id'), (Ie'), (If'), (Ig'), (Ih') and (Ii') corresponding to formulae (Ia), (Ib), (Ic), (Id), (Ie), (If), (Ig), (Ih) and (Ii) but wherein the sulfur atom in formulae (Ia) to (Ii), corresponding to variable X in formula (I), is replaced with an oxygen.

In other embodiments, the invention provides compounds of formula (IA) wherein variables $R^1$, $R^2$, $R^3$, $R^4$, $R^5$, X, W, Z, $R^{10}$ and a are as defined for formula (I) above, and $Y^1$, $Y^2$, $Y^3$, $Y^{2'}$, $Y^{3'}$, $Y^{4'}$ and $Y^{5'}$ are as shown in Table 1:

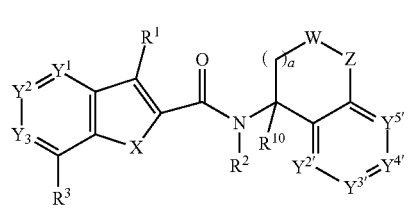

TABLE 1

| Formula | $Y^1$ | $Y^2$ | $Y^3$ | $Y^{2'}$ | $Y^{3'}$ | $Y^{4'}$ | $Y^{5'}$ |
|---|---|---|---|---|---|---|---|
| IA-1 | $CR^4$ | $CR^4$ | $CR^4$ | $CR^5$ | $CR^5$ | $CR^5$ | $CR^5$ |
| IA-2 | $CR^4$ | $CR^4$ | $CR^4$ | N | $CR^5$ | $CR^5$ | $CR^5$ |
| IA-3 | $CR^4$ | $CR^4$ | $CR^4$ | $CR^5$ | N | $CR^5$ | $CR^5$ |
| IA-4 | $CR^4$ | $CR^4$ | $CR^4$ | $CR^5$ | $CR^5$ | N | $CR^5$ |
| IA-5 | $CR^4$ | $CR^4$ | $CR^4$ | $CR^5$ | $CR^5$ | $CR^5$ | N |
| IA-6 | $CR^4$ | $CR^4$ | $CR^4$ | N | N | $CR^5$ | $CR^5$ |
| IA-7 | $CR^4$ | $CR^4$ | $CR^4$ | $CR^5$ | N | N | $CR^5$ |
| IA-8 | $CR^4$ | $CR^4$ | $CR^4$ | $CR^5$ | $CR^5$ | N | N |
| IA-9 | N | $CR^4$ | $CR^4$ | $CR^5$ | $CR^5$ | $CR^5$ | $CR^5$ |
| IA-10 | N | $CR^4$ | $CR^4$ | N | $CR^5$ | $CR^5$ | $CR^5$ |
| IA-11 | N | $CR^4$ | $CR^4$ | $CR^5$ | N | $CR^5$ | $CR^5$ |
| IA-12 | N | $CR^4$ | $CR^4$ | $CR^5$ | $CR^5$ | N | $CR^5$ |
| IA-13 | N | $CR^4$ | $CR^4$ | $CR^5$ | $CR^5$ | $CR^5$ | N |
| IA-14 | N | $CR^4$ | $CR^4$ | N | N | $CR^5$ | $CR^5$ |
| IA-15 | N | $CR^4$ | $CR^4$ | $CR^5$ | N | N | $CR^5$ |
| IA-16 | N | $CR^4$ | $CR^4$ | $CR^5$ | $CR^5$ | N | N |
| IA-17 | $CR^4$ | N | $CR^4$ | $CR^5$ | $CR^5$ | $CR^5$ | $CR^5$ |
| IA-18 | $CR^4$ | N | $CR^4$ | N | $CR^5$ | $CR^5$ | $CR^5$ |
| IA-19 | $CR^4$ | N | $CR^4$ | $CR^5$ | N | $CR^5$ | $CR^5$ |
| IA-20 | $CR^4$ | N | $CR^4$ | $CR^5$ | $CR^5$ | N | $CR^5$ |
| IA-21 | $CR^4$ | N | $CR^4$ | $CR^5$ | $CR^5$ | $CR^5$ | N |
| IA-22 | $CR^4$ | N | $CR^4$ | N | N | $CR^5$ | $CR^5$ |
| IA-23 | $CR^4$ | N | $CR^4$ | $CR^5$ | N | N | $CR^5$ |
| IA-24 | $CR^4$ | N | $CR^4$ | $CR^5$ | $CR^5$ | N | N |
| IA-25 | $CR^4$ | $CR^4$ | N | $CR^5$ | $CR^5$ | $CR^5$ | $CR^5$ |
| IA-26 | $CR^4$ | $CR^4$ | N | N | $CR^5$ | $CR^5$ | $CR^5$ |
| IA-27 | $CR^4$ | $CR^4$ | N | $CR^5$ | N | $CR^5$ | $CR^5$ |
| IA-28 | $CR^4$ | $CR^4$ | N | $CR^5$ | CH | N | $CR^5$ |
| IA-29 | $CR^4$ | $CR^4$ | N | $CR^5$ | $CR^5$ | $CR^5$ | N |
| IA-30 | $CR^4$ | $CR^4$ | N | N | N | $CR^5$ | $CR^5$ |
| IA-31 | $CR^4$ | $CR^4$ | N | $CR^5$ | N | N | $CR^5$ |
| IA-32 | $CR^4$ | $CR^4$ | N | $CR^5$ | $CR^5$ | N | N |
| IA-33 | N | N | $CR^4$ | $CR^5$ | $CR^5$ | $CR^5$ | $CR^5$ |
| IA-34 | N | N | $CR^4$ | N | $CR^5$ | $CR^5$ | $CR^5$ |
| IA-35 | N | N | $CR^4$ | $CR^5$ | N | $CR^5$ | $CR^5$ |
| IA-36 | N | N | $CR^4$ | $CR^5$ | $CR^5$ | N | $CR^5$ |
| IA-37 | N | N | $CR^4$ | $CR^5$ | $CR^5$ | $CR^5$ | N |
| IA-38 | N | N | $CR^4$ | N | N | $CR^5$ | $CR^5$ |
| IA-39 | N | N | $CR^4$ | $CR^4$ | N | N | $CR^5$ |
| IA-40 | N | N | $CR^4$ | $CR^5$ | $CR^5$ | N | N |
| IA-41 | $CR^4$ | N | N | $CR^5$ | $CR^5$ | $CR^5$ | $CR^5$ |
| IA-42 | $CR^4$ | N | N | N | $CR^5$ | $CR^5$ | $CR^5$ |
| IA-43 | $CR^4$ | N | N | $CR^5$ | N | $CR^5$ | $CR^5$ |
| IA-44 | $CR^4$ | N | N | $CR^5$ | $CR^5$ | N | $CR^5$ |
| IA-45 | $CR^4$ | N | N | $CR^5$ | $CR^5$ | $CR^5$ | N |
| IA-46 | $CR^4$ | N | N | N | N | $CR^5$ | $CR^5$ |
| IA-47 | $CR^4$ | N | N | $CR^5$ | N | N | $CR^5$ |
| IA-48 | $CR^4$ | N | N | $CR^5$ | $CR^5$ | N | N |
| IA-49 | N | $CR^4$ | N | $CR^5$ | $CR^5$ | $CR^5$ | $CR^5$ |
| IA-50 | N | $CR^4$ | N | N | $CR^5$ | $CR^5$ | $CR^5$ |
| IA-51 | N | $CR^4$ | N | $CR^5$ | N | $CR^5$ | $CR^5$ |
| IA-52 | N | $CR^4$ | N | $CR^5$ | $CR^5$ | N | $CR^5$ |
| IA-53 | N | $CR^4$ | N | $CR^5$ | $CR^5$ | $CR^5$ | N |
| IA-54 | N | $CR^4$ | N | N | N | $CR^5$ | $CR^5$ |
| IA-55 | N | $CR^4$ | N | $CR^5$ | N | N | $CR^5$ |
| IA-56 | N | $CR^4$ | N | $CR^5$ | $CR^5$ | N | N |

In some embodiment, the present invention provides compounds of formulae IA-1 to IA-56 wherein X is S.

In some embodiment, the present invention provides compounds of formulae IA-1 to IA-56 wherein X is O.

In some embodiment, the present invention provides compounds of formulae IA-1 to IA-56 wherein each $R^4$ is independently H, halo, $C_1$-$C_4$-alkyl, $C_1$-$C_4$-haloalkyl, $C_1$-$C_4$-alkoxy, $C_1$-$C_4$-haloaloxy or $S(O)_p$($C_1$-$C_4$-alkyl or $C_1$-$C_4$-haloalkyl).

In some embodiment, the present invention provides compounds of formulae IA-1 to IA-56 wherein each $R^4$ is independently H, chloro, fluoro, methyl, ethyl, n-propyl, iso-propyl, n-butyl, sec-butyl, iso-butyl or tert-butyl.

In some embodiment, the present invention provides compounds of formulae IA-1 to IA-56 wherein each $R^4$ is independently H, $CF_3$, —$CH_2CF_3$, —$CHFCF_3$ or —$CF_2CF_3$.

In some embodiment, the present invention provides compounds of formulae IA-1 to IA-56 wherein each $R^4$ is independently H, methoxy, ethoxy, propoxy or butoxy.

In some embodiment, the present invention provides compounds of formulae IA-1 to IA-56 wherein each $R^4$ is independently H, —$OCF_3$ or —$SCF_3$.

In some embodiment, the present invention provides compounds of formulae IA-1 to IA-56 wherein each $R^5$ is independently H, halo, $C_1$-$C_4$-alkyl, $C_1$-$C_4$-haloalkyl, $C_1$-$C_4$-alkoxy, $C_1$-$C_4$-haloaloxy or $S(O)_p$($C_1$-$C_4$-alkyl or $C_1$-$C_4$-haloalkyl).

In some embodiment, the present invention provides compounds of formulae IA-1 to IA-56 wherein each $R^5$ is independently H, chloro, fluoro, methyl, ethyl, n-propyl, iso-propyl, n-butyl, sec-butyl, iso-butyl or tert-butyl.

In some embodiment, the present invention provides compounds of formulae IA-1 to IA-56 wherein each $R^5$ is independently H, $CF_3$, —$CH_2CF_3$, —$CHFCF_3$ or —$CF_2CF_3$.

In some embodiment, the present invention provides compounds of formulae IA-1 to IA-56 wherein each $R^5$ is independently H, methoxy, ethoxy, propoxy or butoxy.

In some embodiment, the present invention provides compounds of formulae IA-1 to IA-56 wherein each $R^5$ is independently H, —$OCF_3$ or —$SCF_3$.

In other embodiments, the invention provides compounds of formulae IA-1 to IA-56, wherein $R^2$ and $R^{10}$ are independently H or $C_1$-$C_3$-alkyl.

In other embodiments, the invention provides compounds of formulae IA-1 to IA-56 wherein a is 1, W is $CH_2$ and Z is O.

In other embodiments, the invention provides compounds of formulae IA-1 to IA-56 wherein $R^1$ is $C_1$-$C_6$-alkyl, $C_1$-$C_6$-haloalkyl, hydroxy-$C_1$-$C_6$-alkyl, $C_1$-$C_6$-alkoxy-$C_1$-$C_6$-alkyl, $C_1$-$C_6$-haloalkoxy-$C_1$-$C_6$-alkyl, amino-$C_1$-$C_6$-alkyl, $C_1$-$C_6$-alkoxy, $C_1$-$C_6$-haloalkoxy, $C_2$-$C_6$-alkenyl, $C_2$-$C_6$-haloalkenyl, optionally substituted $C_3$-$C_8$-cycloalkyl, optionally substituted 3- to 7-membered heterocyclyl, or —$NR^aR^b$ wherein $R^a$ and $R^b$ are independently H or optionally substituted $C_1$-$C_6$-alkyl; or $R^a$ and $R^b$ may form, with the nitrogen to which they are attached, a 3-, 4-, 5- or 6-membered-heterocyclyl group, which may include one to three additional heteroatoms selected from the group consisting of N, O and S and may be optionally substituted.

In other embodiments, the invention provides compounds of formulae IA-1 to IA-56 wherein $R^3$ is $C_1$-$C_6$-alkyl, $C_1$-$C_6$-haloalkyl, optionally substituted $C_3$-$C_8$-cycloalkyl, optionally substituted 3- to 7-membered heterocyclyl containing from one to three heteroatoms selected from the group consisting of N, O and S; optionally substituted phenyl, optionally substituted 5- to 10-membered heteroaryl, a 5- to 11-membered spirocyclic heterocyclyl-carbocyclyl group, a 5- to 11-membered spirocyclic heterocyclyl-heterocyclyl group, a 5- to 11-membered spirocyclic carbocyclyl-carbocyclyl group, a 5- to 11-membered spirocyclic carbocyclyl-heterocyclyl group, or —$NR^aR^b$ wherein $R^a$ and $R^b$ are independently H, $C_1$-$C_6$-alkyl or $C_1$-$C_6$-haloalkyl; or $R^a$ and $R^b$ may form, with the nitrogen to which they are attached, a 3-, 4-, 5- or 6-membered-heterocyclyl group, which may include one to three additional heteroatoms selected from the group consisting of N, O and S and may be optionally substituted.

In other embodiments, the invention provides compounds of formulae IA-1 to IA-56 wherein X is S, $R^2$ and $R^{10}$ are independently H or $C_1$-$C_3$-alkyl; W is $CH_2$, Z is O and a is 1.

In other embodiments, the invention provides a compound of Formula IA-1 above, wherein X is S; $R^1$ is optionally substituted $C_1$-$C_3$-alkyl; $R^3$ is phenyl optionally independently substituted by 1 to 3 halo; each $R^4$ is independently H or halo; each $R^5$ is independently H or halo; and $R^2$ is H or $C_1$-$C_3$-alkyl.

In other embodiments, the invention provides a compound of Formula IA-1 above, wherein X is O; $R^1$ is optionally substituted $C_1$-$C_3$-alkyl; $R^3$ is phenyl optionally independently substituted by 1 to 3 halo; each $R^4$ is independently H or halo; each $R^5$ is independently H or halo; and $R^2$ is H or $C_1$-$C_3$-alkyl.

In other embodiments, the invention provides a compound of Formula IA-9 above, wherein X is S; $R^1$ is optionally substituted $C_1$-$C_3$-alkyl; $R^3$ is phenyl optionally independently substituted by 1 to 3 halo; each $R^4$ is independently H or halo; each $R^5$ is independently H or halo; and $R^2$ is H or $C_1$-$C_3$-alkyl.

In other embodiments, the invention provides a compound of Formula IA-9 above, wherein X is O; $R^1$ is optionally substituted $C_1$-$C_3$-alkyl; $R^3$ is phenyl optionally independently substituted by 1 to 3 halo; each $R^4$ is independently H or halo; each $R^5$ is independently H or halo; and $R^2$ is H or $C_1$-$C_3$-alkyl.

In other embodiments, the invention provides a compound of Formula IA-17 above, wherein X is S; $R^1$ is optionally substituted $C_1$-$C_3$-alkyl; $R^3$ is phenyl optionally independently substituted by 1 to 3 halo; each $R^4$ is independently H or halo; each $R^5$ is independently H or halo; and $R^2$ is H or $C_1$-$C_3$-alkyl.

In other embodiments, the invention provides a compound of Formula IA-17 above, wherein X is O; $R^1$ is optionally substituted $C_1$-$C_3$-alkyl; $R^3$ is phenyl optionally independently substituted by 1 to 3 halo; each $R^4$ is independently H or halo; each $R^5$ is independently H or halo; and $R^2$ is H or $C_1$-$C_3$-alkyl.

In other embodiments, the invention provides a compound of Formula IA-25 above, wherein X is S; $R^1$ is optionally substituted $C_1$-$C_3$-alkyl; $R^3$ is phenyl optionally independently substituted by 1 to 3 halo; each $R^4$ is independently H or halo; each $R^5$ is independently H or halo; and $R^2$ is H or $C_1$-$C_3$-alkyl.

In other embodiments, the invention provides a compound of Formula IA-25 above, wherein X is O; $R^1$ is optionally substituted $C_1$-$C_3$-alkyl; $R^3$ is phenyl optionally independently substituted by 1 to 3 halo; each $R^4$ is independently H or halo; each $R^5$ is independently H or halo; and $R^2$ is H or $C_1$-$C_3$-alkyl.

In other embodiments, the invention provides a compound of Formula IA-49 above, wherein X is S; $R^1$ is optionally substituted $C_1$-$C_3$-alkyl; $R^3$ is phenyl optionally independently substituted by 1 to 3 halo; each $R^4$ is independently H or halo; each $R^5$ is independently H or halo; and $R^2$ is H or $C_1$-$C_3$-alkyl.

In other embodiments, the invention provides a compound of Formula IA-49 above, wherein X is O; $R^1$ is optionally substituted $C_1$-$C_3$-alkyl; $R^3$ is phenyl optionally independently substituted by 1 to 3 halo; each $R^4$ is independently H or halo; each $R^5$ is independently H or halo; and $R^2$ is H or $C_1$-$C_3$-alkyl.

In other embodiments, the invention provides compounds of formula (IB) shown below wherein variables $R^1$, $R^2$, $R^4$, $R^5$, X, W, Z, $R^{10}$ and a are as defined for formula (I) above; each $R^9$ is cyano, halo, hydroxyl, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkoxy-$C_1$-$C_6$-alkyl, $C_1$-$C_6$-haloalkoxy-$C_1$-$C_6$-alkyl, optionally substituted phenyl; optionally substituted phenyloxy, optionally substituted 5- or 6-membered heteroaryl, optionally substituted $C_3$-$C_8$-cycloalkyl, optionally substituted $C_3$-$C_8$-cycloalkyloxy, optionally substituted 3- to 7-membered heterocyclyl containing from one to three heteroatoms selected from the group consisting of N, O and S, $C_1$-$C_6$-alkylcarbonyl, $C_1$-$C_6$-haloalkylcarbonyl, $C_1$-$C_6$-alkoxycarbonyl, $C_1$-$C_6$-haloalkoxycarbonyl, aminocarbonyl, $C_1$-$C_6$-alkylaminocarbonyl, $C_1$-$C_6$-haloalkylaminocarbonyl, di-$C_1$-$C_6$-alkylaminocarbonyl, di-$C_1$-$C_6$-haloalkylaminocarbonyl, —$SO_p$(optionally substituted $C_1$-$C_6$-alkyl or $C_1$-$C_6$-haloalkyl) where p is 0, 1 or 2, $SF_5$, or —$NR^aR^b$ wherein $R^a$ and $R^b$ are independently H, $C_1$-$C_6$-alkyl or $C_1$-$C_6$-haloalkyl; or $R^a$ and $R^b$ may form, with the nitrogen to which they are attached, a 3-, 4-, 5-, 6-, 7-, or 8-membered-heterocyclyl group, which may include one to three additional heteroatoms selected from the group consisting of N, O and S and may be optionally substituted;

m is 0, 1, 2, 3 or 4; and $Y^1$, $Y^2$, $Y^3$, $Y^{2'}$, $Y^{3'}$, $Y^{4'}$ and $Y^{5'}$ are as shown in Table 2:

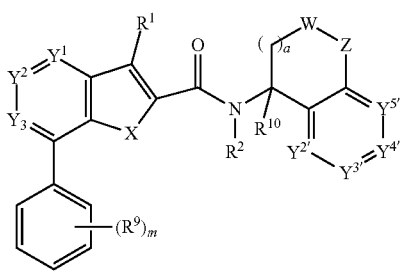

(IB)

TABLE 2

| Formula | $Y^1$ | $Y^2$ | $Y^3$ | $Y^{2'}$ | $Y^{3'}$ | $Y^{4'}$ | $Y^{5'}$ |
|---|---|---|---|---|---|---|---|
| IB-1 | $CR^4$ | $CR^4$ | $CR^4$ | $CR^5$ | $CR^5$ | $CR^5$ | $CR^5$ |
| IB-2 | $CR^4$ | $CR^4$ | $CR^4$ | N | $CR^5$ | $CR^5$ | $CR^5$ |
| IB-3 | $CR^4$ | $CR^4$ | $CR^4$ | $CR^5$ | N | $CR^5$ | $CR^5$ |
| IB-4 | $CR^4$ | $CR^4$ | $CR^4$ | $CR^5$ | $CR^5$ | N | $CR^5$ |
| IB-5 | $CR^4$ | $CR^4$ | $CR^4$ | $CR^5$ | $CR^5$ | $CR^5$ | N |
| IB-6 | $CR^4$ | $CR^4$ | $CR^4$ | N | N | $CR^5$ | $CR^5$ |
| IB-7 | $CR^4$ | $CR^4$ | $CR^4$ | $CR^5$ | N | N | $CR^5$ |
| IB-8 | $CR^4$ | $CR^4$ | $CR^4$ | $CR^5$ | $CR^5$ | N | N |
| IB-9 | N | $CR^4$ | $CR^4$ | $CR^5$ | $CR^5$ | $CR^5$ | $CR^5$ |
| IB-10 | N | $CR^4$ | $CR^4$ | N | $CR^5$ | $CR^5$ | $CR^5$ |
| IB-11 | N | $CR^4$ | $CR^4$ | $CR^5$ | N | $CR^5$ | $CR^5$ |
| IB-12 | N | $CR^4$ | $CR^4$ | $CR^5$ | $CR5$ | N | $CR^5$ |
| IB-13 | N | $CR^4$ | $CR^4$ | $CR^5$ | $CR^5$ | $CR^5$ | N |
| IB-14 | N | $CR^4$ | $CR^4$ | N | N | $CR^5$ | $CR^5$ |
| IB-15 | N | $CR^4$ | $CR^4$ | $CR^5$ | N | N | $CR^5$ |
| IB-16 | N | $CR^4$ | $CR^4$ | $CR^5$ | $CR^5$ | N | N |
| IB-17 | $CR^4$ | N | $CR^4$ | $CR^5$ | $CR^5$ | $CR^5$ | $CR^5$ |
| IB-18 | $CR^4$ | N | $CR^4$ | N | $CR^5$ | $CR^5$ | $CR^5$ |
| IB-19 | $CR^4$ | N | $CR^4$ | $CR^5$ | N | $CR^5$ | $CR^5$ |
| IB-20 | $CR^4$ | N | $CR^4$ | $CR^5$ | $CR^5$ | N | $CR^5$ |
| IB-21 | $CR^4$ | N | $CR^4$ | $CR^5$ | $CR^5$ | $CR^5$ | N |
| IB-22 | $CR^4$ | N | $CR^4$ | N | N | $CR^5$ | $CR^5$ |
| IB-23 | $CR^4$ | N | $CR^4$ | $CR^5$ | N | N | $CR^5$ |
| IB-24 | $CR^4$ | N | $CR^4$ | $CR^5$ | $CR^5$ | N | N |
| IB-25 | $CR^4$ | $CR^4$ | N | $CR^5$ | $CR^5$ | $CR^5$ | $CR^5$ |
| IB-26 | $CR^4$ | $CR^4$ | N | N | $CR^5$ | $CR^5$ | $CR^5$ |
| IB-27 | $CR^4$ | $CR^4$ | N | $CR^5$ | N | $CR^5$ | $CR^5$ |
| IB-28 | $CR^4$ | $CR^4$ | N | $CR^5$ | CH | N | $CR^5$ |
| IB-29 | $CR^4$ | $CR^4$ | N | $CR^5$ | $CR^5$ | $CR^5$ | N |
| IB-30 | $CR^4$ | $CR^4$ | N | N | N | $CR^5$ | $CR^5$ |
| IB-31 | $CR^4$ | $CR^4$ | N | $CR^5$ | N | N | $CR^5$ |
| IB-32 | $CR^4$ | $CR^4$ | N | $CR^5$ | $CR^5$ | N | N |
| IB-33 | N | N | $CR^4$ | $CR^5$ | $CR^5$ | $CR^5$ | $CR^5$ |
| IB-34 | N | N | $CR^4$ | N | $CR^5$ | $CR^5$ | $CR^5$ |
| IB-35 | N | N | $CR^4$ | $CR^5$ | N | $CR^5$ | $CR^5$ |
| IB-36 | N | N | $CR^4$ | $CR^5$ | $CR^5$ | N | $CR^5$ |
| IB-37 | N | N | $CR^4$ | $CR^5$ | $CR^5$ | $CR^5$ | N |
| IB-38 | N | N | $CR^4$ | N | N | $CR^5$ | $CR^5$ |
| IB-39 | N | N | $CR^4$ | $CR^4$ | N | N | $CR^5$ |
| IB-40 | N | N | $CR^4$ | $CR^5$ | $CR^5$ | N | N |
| IB-41 | $CR^4$ | N | N | $CR^5$ | $CR^5$ | $CR^5$ | $CR^5$ |
| IB-42 | $CR^4$ | N | N | N | $CR^5$ | $CR^5$ | $CR^5$ |
| IB-43 | $CR^4$ | N | N | $CR^5$ | N | $CR^5$ | $CR^5$ |
| IB-44 | $CR^4$ | N | N | $CR^5$ | $CR^5$ | N | $CR^5$ |
| IB-45 | $CR^4$ | N | N | $CR^5$ | $CR^5$ | $CR^5$ | N |
| IB-46 | $CR^4$ | N | N | N | N | $CR^5$ | $CR^5$ |
| IB-47 | $CR^4$ | N | N | $CR^5$ | N | N | $CR^5$ |
| IB-48 | $CR^4$ | N | N | $CR^5$ | $CR^5$ | N | N |
| IB-49 | N | $CR^4$ | N | $CR^5$ | $CR^5$ | $CR^5$ | $CR^5$ |
| IB-50 | N | $CR^4$ | N | N | $CR^5$ | $CR^5$ | $CR^5$ |
| IB-51 | N | $CR^4$ | N | $CR^5$ | N | $CR^5$ | $CR^5$ |
| IB-52 | N | $CR^4$ | N | $CR^5$ | $CR^5$ | N | $CR^5$ |
| IB-53 | N | $CR^4$ | N | $CR^5$ | $CR^5$ | $CR^5$ | N |
| IB-54 | N | $CR^4$ | N | N | N | $CR^5$ | $CR^5$ |
| IB-55 | N | $CR^4$ | N | $CR^5$ | N | N | $CR^5$ |
| IB-56 | N | $CR^4$ | N | $CR^5$ | $CR^5$ | N | N |

In some embodiment, the present invention provides compounds of formulae IB-1 to IB-56 wherein X is S.

In some embodiment, the present invention provides compounds of formulae IB-1 to IB-56 wherein X is O.

In some embodiment, the present invention provides compounds of formulae IB-1 to IB-56 wherein each $R^4$ is independently H, halo, $C_1$-$C_4$-alkyl, $C_1$-$C_4$-haloalkyl, $C_1$-$C_4$-alkoxy, $C_1$-$C_4$-haloaloxy or $S(O)_p$($C_1$-$C_4$-alkyl or $C_1$-$C_4$-haloalkyl).

In some embodiment, the present invention provides compounds of formulae IB-1 to IB-56 wherein each $R^4$ is independently H, chloro, fluoro, methyl, ethyl, n-propyl, iso-propyl, n-butyl, sec-butyl, iso-butyl or tert-butyl.

In some embodiment, the present invention provides compounds of formulae IB-1 to IB-56 wherein each $R^4$ is independently H, $CF_3$, —$CH_2CF_3$, —$CHFCF_3$ or —$CF_2CF_3$.

In some embodiment, the present invention provides compounds of formulae IB-1 to IB-56 wherein each $R^4$ is independently H, methoxy, ethoxy, propoxy or butoxy.

In some embodiment, the present invention provides compounds of formulae IB-1 to IB-56 wherein each $R^4$ is independently H, —$OCF_3$ or —$SCF_3$.

In some embodiment, the present invention provides compounds of formulae IB-1 to IB-56 wherein each $R^5$ is independently H, halo, $C_1$-$C_4$-alkyl, $C_1$-$C_4$-haloalkyl, $C_1$-$C_4$-alkoxy, $C_1$-$C_4$-haloaloxy or $S(O)_p$($C_1$-$C_4$-alkyl or $C_1$-$C_4$-haloalkyl).

In some embodiment, the present invention provides compounds of formulae IB-1 to IB-56 wherein each $R^5$ is independently H, chloro, fluoro, methyl, ethyl, n-propyl, iso-propyl, n-butyl, sec-butyl, iso-butyl or tert-butyl.

In some embodiment, the present invention provides compounds of formulae IB-1 to IB-56 wherein each $R^5$ is independently H, $CF_3$, —$CH_2CF_3$, —$CHFCF_3$ or —$CF_2CF_3$.

In some embodiment, the present invention provides compounds of formulae IB-1 to IB-56 wherein each $R^5$ is independently H, methoxy, ethoxy, propoxy or butoxy.

In some embodiment, the present invention provides compounds of formulae IB-1 to IB-56 wherein each $R^5$ is independently H, —$OCF_3$ or —$SCF_3$.

In other embodiments, the invention provides compounds of formulae IB-1 to IB-56, wherein $R^2$ and $R^{10}$ are independently H or $C_1$-$C_3$-alkyl.

In other embodiments, the invention provides compounds of formulae IB-1 to IB-56 wherein $R^1$ is $C_1$-$C_6$-alkyl, $C_1$-$C_6$-haloalkyl, hydroxy-$C_1$-$C_6$-alkyl, $C_1$-$C_6$-alkoxy-$C_1$-$C_6$-alkyl, $C_1$-$C_6$-haloalkoxy-$C_1$-$C_6$-alkyl, amino-$C_1$-$C_6$-alkyl, $C_1$-$C_6$-alkoxy, $C_1$-$C_6$-haloalkoxy, $C_2$-$C_6$-alkenyl, $C_2$-$C_6$-haloalkenyl, optionally substituted $C_3$-$C_8$-cycloalkyl, optionally substituted 3- to 7-membered heterocyclyl, or —$NR^aR^b$ wherein $R^a$ and $R^b$ are independently H or optionally substituted $C_1$-$C_6$-alkyl; or $R^a$ and $R^b$ may form, with the nitrogen to which they are attached, a 3-, 4-, 5- or 6-membered-heterocyclyl group, which may include one to three additional heteroatoms selected from the group consisting of N, O and S and may be optionally substituted.

In other embodiments, the invention provides compounds of formulae IB-1 to IB-56 wherein $R^3$ is $C_1$-$C_6$-alkyl, $C_1$-$C_6$-haloalkyl, optionally substituted $C_3$-$C_8$-cycloalkyl, optionally substituted 3- to 7-membered heterocyclyl containing from one to three heteroatoms selected from the group consisting of N, O and S; optionally substituted phenyl, optionally substituted 5- to 10-membered heteroaryl, a 5- to 11-membered spirocyclic heterocyclyl-carbocyclyl group, a 5- to 11-membered spirocyclic heterocyclyl-heterocyclyl group, a 5- to 11-membered spirocyclic carbocyclyl-carbocyclyl group, a 5- to 11-membered spirocyclic carbocyclyl-heterocyclyl group, or —$NR^aR^b$ wherein $R^a$ and $R^b$ are independently H, $C_1$-$C_6$-alkyl or $C_1$-$C_6$-haloalkyl; or $R^a$ and $R^b$ may form, with the nitrogen to which they are attached, a 3-, 4-, 5- or 6-membered-heterocyclyl group, which may include one to three additional heteroatoms selected from the group consisting of N, O and S and may be optionally substituted.

In other embodiments, the invention provides compounds of formulae IB-1 to IB-56 wherein a is 1, W is $CH_2$ and Z is O.

In other embodiments, the invention provides compounds of formulae IB-1 to IB-56 wherein $R^9$ is independently halo, cyano, nitro, $C_3$-$C_6$-cycloalkyl, $C_1$-$C_6$-haloalkyl, $C_3$-$C_6$-halocycloalkyl, $C_1$-$C_6$-alkoxy, $C_1$-$C_6$-haloalkoxy or $S(O)_p(C_1$-$C_6$-alkyl or $C_1$-$C_6$-haloalkyl), and m is 0, 1, 2, or 3.

In other embodiments, the invention provides compounds of formulae IB-1 to IB-56 wherein $R^9$ is independently halo and m is 1, 2 or 3.

In other embodiments, the invention provides compounds of formulae IB-1 to IB-56 wherein $R^9$ is independently fluoro or chloro and m is 1, 2 or 3.

In other embodiments, the invention provides compounds of formulae IB-1 to IB-56 wherein X is S, $R^9$ is independently halo and m is 1, 2 or 3, $R^2$ and $R^{10}$ are independently H or $C_1$-$C_3$-alkyl; W is $CH_2$, Z is O and a is 1.

In other embodiments, the invention provides compounds of formulae IB-1 to IB-56 wherein X is S, $R^9$ is independently chloro or fluoro and m is 1, 2 or 3, $R^2$ and $R^{10}$ are independently H or $C_1$-$C_3$-alkyl; W is $CH_2$, Z is O and a is 1.

In other embodiments, the invention provides a compound of Formula IB-1 above, wherein X is S; $R^1$ is optionally substituted $C_1$-$C_3$-alkyl; $R^3$ is phenyl optionally independently substituted by 1 to 3 halo; each $R^4$ is independently H or halo; each $R^5$ is independently H or halo; $R^2$ is H or $C_1$-$C_3$-alkyl; $R^9$ is independently halo, cyano, nitro, cycloalkyl, haloalkyl, halocycloalkyl, alkoxy or haloalkoxy and m is 0, 1, 2 or 3.

In other embodiments, the invention provides a compound of Formula IB-1 above, wherein X is O; $R^1$ is optionally substituted $C_1$-$C_3$-alkyl; $R^3$ is phenyl optionally independently substituted by 1 to 3 halo; each $R^4$ is independently H or halo; each $R^5$ is independently H or halo; $R^2$ is H or $C_1$-$C_3$-alkyl; $R^9$ is independently halo, cyano, nitro, cycloalkyl, haloalkyl, halocycloalkyl, alkoxy or haloalkoxy and m is 0, 1, 2 or 3.

In other embodiments, the invention provides a compound of Formula IB-9 above, wherein X is S; $R^1$ is optionally substituted $C_1$-$C_3$-alkyl; $R^3$ is phenyl optionally independently substituted by 1 to 3 halo; each $R^4$ is independently H or halo; each $R^5$ is independently H or halo; $R^2$ is H or $C_1$-$C_3$-alkyl; $R^9$ is independently halo, cyano, nitro, cycloalkyl, haloalkyl, halocycloalkyl, alkoxy or haloalkoxy and m is 0, 1, 2 or 3.

In other embodiments, the invention provides a compound of Formula IB-9 above, wherein X is O; $R^1$ is optionally substituted $C_1$-$C_3$-alkyl; $R^3$ is phenyl optionally independently substituted by 1 to 3 halo; each $R^4$ is independently H or halo; each $R^5$ is independently H or halo; $R^2$ is H or $C_1$-$C_3$-alkyl; $R^9$ is independently halo, cyano, nitro, cycloalkyl, haloalkyl, halocycloalkyl, alkoxy or haloalkoxy and m is 0, 1, 2 or 3.

In other embodiments, the invention provides a compound of Formula IB-17 above, wherein X is S; $R^1$ is optionally substituted $C_1$-$C_3$-alkyl; $R^3$ is phenyl optionally independently substituted by 1 to 3 halo; each $R^4$ is independently H or halo; each $R^5$ is independently H or halo; $R^2$ is H or $C_1$-$C_3$-alkyl; $R^9$ is independently halo, cyano, nitro, cycloalkyl, haloalkyl, halocycloalkyl, alkoxy or haloalkoxy and m is 0, 1, 2 or 3.

In other embodiments, the invention provides a compound of Formula IB-17 above, wherein X is O; $R^1$ is optionally substituted $C_1$-$C_3$-alkyl; $R^3$ is phenyl optionally independently substituted by 1 to 3 halo; each $R^4$ is independently H or halo; each $R^5$ is independently H or halo; $R^2$ is H or $C_1$-$C_3$-alkyl; $R^9$ is independently halo, cyano, nitro, cycloalkyl, haloalkyl, halocycloalkyl, alkoxy or haloalkoxy and m is 0, 1, 2 or 3.

In other embodiments, the invention provides a compound of Formula IB-25 above, wherein X is S; $R^1$ is optionally substituted $C_1$-$C_3$-alkyl; $R^3$ is phenyl optionally independently substituted by 1 to 3 halo; each $R^4$ is independently H or halo; each $R^5$ is independently H or halo; $R^2$ is H or $C_1$-$C_3$-alkyl; $R^9$ is independently halo, cyano, nitro, cycloalkyl, haloalkyl, halocycloalkyl, alkoxy or haloalkoxy and m is 0, 1, 2 or 3.

In other embodiments, the invention provides a compound of Formula IB-25 above, wherein X is O; $R^1$ is optionally substituted $C_1$-$C_3$-alkyl; $R^3$ is phenyl optionally independently substituted by 1 to 3 halo; each $R^4$ is independently H or halo; each $R^5$ is independently H or halo; $R^2$ is H or $C_1$-$C_3$-alkyl; $R^9$ is independently halo, cyano, nitro, cycloalkyl, haloalkyl, halocycloalkyl, alkoxy or haloalkoxy and m is 0, 1, 2 or 3.

In other embodiments, the invention provides a compound of Formula IB-49 above, wherein X is S; $R^1$ is optionally substituted $C_1$-$C_3$-alkyl; $R^3$ is phenyl optionally independently substituted by 1 to 3 halo; each $R^4$ is independently H or halo; each $R^5$ is independently H or halo; $R^2$ is H or $C_1$-$C_3$-alkyl; $R^9$ is independently halo, cyano, nitro, cycloalkyl, haloalkyl, halocycloalkyl, alkoxy or haloalkoxy and m is 0, 1, 2 or 3.

In other embodiments, the invention provides a compound of Formula (I)B-49 above, wherein X is O; $R^1$ is optionally substituted $C_1$-$C_3$-alkyl; $R^3$ is phenyl optionally independently substituted by 1 to 3 halo; each $R^4$ is independently H or halo; each $R^5$ is independently H or halo; $R^2$ is H or $C_1$-$C_3$-alkyl; $R^9$ is independently halo, cyano, nitro, cycloalkyl, haloalkyl, halocycloalkyl, 5 alkoxy or haloalkoxy and m is 0, 1, 2 or 3.

In other embodiments, the invention provides compounds of formula (IC) wherein variables $R^1$, $R^2$, $R^4$, $R^5$, W and X are as defined for formula (I) above; $R^9$ and m are as defined for Formula IB above; o is 0, 1, 2, 3 or 4; and $Y^1$, $Y^2$ and $Y^3$ are as shown in Table 3:

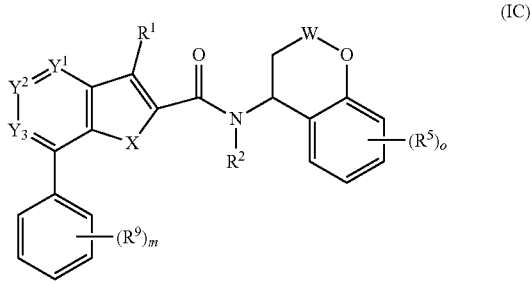

(IC)

TABLE 3

| Formula | $Y^1$ | $Y^2$ | $Y^3$ |
|---|---|---|---|
| IC-1 | $CR^4$ | $CR^4$ | $CR^4$ |
| IC-2 | N | $CR^4$ | $CR^4$ |
| IC-3 | $CR^4$ | N | $CR^4$ |
| IC-4 | $CR^4$ | $CR^4$ | N |
| IC-5 | N | N | $CR^4$ |
| IC-6 | $CR^4$ | N | N |
| IC-7 | N | $CR^4$ | N |

In some embodiment, the present invention provides compounds of formulae IC-1 to IC-7 wherein X is S.

In some embodiment, the present invention provides compounds of formulae IC-1 to IC-7 wherein X is O.

In some embodiment, the present invention provides compounds of formulae IC-1 to IC-7 wherein each $R^4$ is independently H, halo, $C_1$-$C_4$-alkyl, $C_1$-$C_4$-haloalkyl, $C_1$-$C_4$-alkoxy, $C_1$-$C_4$-haloaloxy or $S(O)_p(C_1$-$C_4$-alkyl or $C_1$-$C_4$-haloalkyl).

In some embodiment, the present invention provides compounds of formulae IC-1 to IC-7 wherein each $R^4$ is independently H, chloro, fluoro, methyl, ethyl, n-propyl, iso-propyl, n-butyl, sec-butyl, iso-butyl, tert-butyl.

In some embodiment, the present invention provides compounds of formulae IC-1 to IC-7 wherein each $R^4$ is independently H, $CF_3$, —$CH_2CF_3$, —$CHFCF_3$, —$CF_2CF_3$.

In some embodiment, the present invention provides compounds of formulae IC-1 to IC-7 wherein each $R^4$ is independently H, methoxy, ethoxy, propoxy or butoxy.

In some embodiment, the present invention provides compounds of formulae IC-1 to IC-7 wherein each $R^4$ is independently H, —$OCF_3$ or —$SCF_3$.

In some embodiment, the present invention provides compounds of formulae IC-1 to IC-7 wherein each $R^5$ is independently halo, $C_1$-$C_4$-alkyl, $C_1$-$C_4$-haloalkyl, $C_1$-$C_4$-alkoxy, $C_1$-$C_4$-haloaloxy or $S(O)_p(C_1$-$C_4$-alkyl or $C_1$-$C_4$-haloalkyl); and o is 0, 1, 2 or 3.

In some embodiment, the present invention provides compounds of formulae IC-1 to IC-7 wherein each $R^5$ is independently chloro, fluoro, methyl, ethyl, n-propyl, iso-propyl, n-butyl, sec-butyl, iso-butyl or tert-butyl; and o is 0, 1, 2 or 3.

In some embodiment, the present invention provides compounds of formulae IC-1 to IC-7 wherein each $R^5$ is independently $CF_3$, —$CH_2CF_3$, —$CHFCF_3$ or —$CF_2CF_3$; and o is 0, 1, 2 or 3.

In some embodiment, the present invention provides compounds of formulae IC-1 to IC-7 wherein each $R^5$ is independently methoxy, ethoxy, propoxy or butoxy; and o is 0, 1, 2 or 3.

In some embodiment, the present invention provides compounds of formulae IC-1 to IC-7 wherein each $R^5$ is independently —$OCF_3$ or —$SCF_3$; and o is 0, 1, 2 or 3.

In other embodiments, the invention provides compounds of formulae IC-1 to IC-7, wherein $R^2$ is H or $C_1$-$C_3$-alkyl.

In other embodiments, the invention provides compounds of formulae IC-1 to IC-7 wherein $R^1$ is $C_1$-$C_6$-alkyl, $C_1$-$C_6$-haloalkyl, hydroxy-$C_1$-$C_6$-alkyl, $C_1$-$C_6$-alkoxy-$C_1$-$C_6$-alkyl, $C_1$-$C_6$-haloalkoxy-$C_1$-$C_6$-alkyl, amino-$C_1$-$C_6$-alkyl, $C_1$-$C_6$-alkoxy, $C_1$-$C_6$-haloalkoxy, $C_2$-$C_6$-alkenyl, $C_2$-$C_6$-haloalkenyl, optionally substituted $C_3$-$C_8$-cycloalkyl, optionally substituted 3- to 7-membered heterocyclyl, or —$NR^aR^b$ wherein $R^a$ and $R^b$ are independently H or optionally substituted $C_1$-$C_6$-alkyl; or $R^a$ and $R^b$ may form, with the nitrogen to which they are attached, a 3-, 4-, 5- or 6-membered-heterocyclyl group, which may include one to three additional heteroatoms selected from the group consisting of N, O and S and may be optionally substituted.

In other embodiments, the invention provides compounds of formulae IC-1 to IC-7 wherein $R^3$ is $C_1$-$C_6$-alkyl, $C_1$-$C_6$-haloalkyl, optionally substituted $C_3$-$C_8$-cycloalkyl, optionally substituted 3- to 7-membered heterocyclyl containing from one to three heteroatoms selected from the group consisting of N, O and S; optionally substituted phenyl, optionally substituted 5- to 10-membered heteroaryl, a 5- to 11-membered spirocyclic heterocyclyl-carbocyclyl group, a 5- to 11-membered spirocyclic heterocyclyl-heterocyclyl group, a 5- to 11-membered spirocyclic carbocyclyl-carbocyclyl group, a 5- to 11-membered spirocyclic carbocyclyl-heterocyclyl group, or —$NR^aR^b$ wherein $R^a$ and $R^b$ are independently H, $C_1$-$C_6$-alkyl or $C_1$-$C_6$-haloalkyl; or $R^a$ and $R^b$ may form, with the nitrogen to which they are attached, a 3-, 4-, 5- or 6-membered-heterocyclyl group, which may include one to three additional heteroatoms selected from the group consisting of N, O and S and may be optionally substituted.

In other embodiments, the invention provides compounds of formulae IC-1 to IC-7 wherein $R^9$ is independently halo, cyano, nitro, cycloalkyl, haloalkyl, halocycloalkyl, alkoxy, or haloalkoxy, and m is 0, 1, 2, or 3.

In other embodiments, the invention provides compounds of formulae IC-1 to IC-7 wherein $R^9$ is independently halo and m is 1, 2 or 3.

In other embodiments, the invention provides compounds of formulae IC-1 to IC-7 wherein $R^9$ is independently fluoro or chloro and m is 1, 2 or 3.

In other embodiments, the invention provides compounds of formulae IC-1 to IC-7 wherein X is S, $R^9$ is independently halo and m is 1, 2 or 3, and $R^2$ is H or $C_1$-$C_3$-alkyl.

In other embodiments, the invention provides compounds of formulae IC-1 to IC-7 wherein X is S, $R^9$ is independently chloro or fluoro and m is 1, 2 or 3, and $R^2$ is H or $C_1$-$C_3$-alkyl.

In other embodiments, the invention provides a compound of Formula IC-1 above, wherein $R^9$ is independently halo, cyano, nitro, cycloalkyl, haloalkyl, halocycloalkyl, alkoxy or haloalkoxy, and m is 0, 1, 2 or 3.

In other embodiments, the invention provides a compound of Formula IC-2 above, wherein $R^9$ is independently halo, cyano, nitro, cycloalkyl, haloalkyl, halocycloalkyl, alkoxy or haloalkoxy, and m is 0, 1, 2 or 3.

In other embodiments, the invention provides a compound of Formula IC-3 above, wherein $R^9$ is independently halo, cyano, nitro, cycloalkyl, haloalkyl, halocycloalkyl, alkoxy or haloalkoxy, and m is 0, 1, 2 or 3.

In other embodiments, the invention provides a compound of Formula IC-7 above, wherein $R^9$ is independently halo, cyano, nitro, cycloalkyl, haloalkyl, halocycloalkyl, alkoxy or haloalkoxy, and m is 0, 1, 2 or 3.

In other embodiments, the invention provides a compound of Formula IC-1 above, wherein X is S; $R^1$ is optionally substituted $C_1$-$C_3$-alkyl; $R^3$ is phenyl optionally independently substituted by 1 to 3 halo; each $R^4$ is independently H or halo; each $R^5$ is independently halo and o is 0, 1 or 2; $R^2$ is H or $C_1$-$C_3$-alkyl; $R^9$ is independently halo, cyano, nitro, cycloalkyl, haloalkyl, halocycloalkyl, alkoxy or haloalkoxy and m is 0, 1, 2 or 3.

In other embodiments, the invention provides a compound of Formula IC-1 above, wherein X is O; $R^1$ is optionally substituted $C_1$-$C_3$-alkyl; $R^3$ is phenyl optionally independently substituted by 1 to 3 halo; each $R^4$ is independently H or halo; each $R^5$ is independently halo and o is 0, 1 or 2; $R^2$ is H or $C_1$-$C_3$-alkyl; $R^9$ is independently halo, cyano, nitro, cycloalkyl, haloalkyl, halocycloalkyl, alkoxy or haloalkoxy and m is 0, 1, 2 or 3.

In other embodiments, the invention provides a compound of Formula IC-2 above, wherein X is S; $R^1$ is optionally substituted $C_1$-$C_3$-alkyl; $R^3$ is phenyl optionally independently substituted by 1 to 3 halo; each $R^4$ is independently H or halo; each $R^5$ is independently halo and o is 0, 1 or 2; $R^2$ is H or $C_1$-$C_3$-alkyl; $R^9$ is independently halo, cyano, nitro, cycloalkyl, haloalkyl, halocycloalkyl, alkoxy or haloalkoxy and m is 0, 1, 2 or 3.

In other embodiments, the invention provides a compound of Formula IC-2 above, wherein X is O; $R^1$ is optionally substituted $C_1$-$C_3$-alkyl; $R^3$ is phenyl optionally independently substituted by 1 to 3 halo; each $R^4$ is independently H or halo; $R^5$ is halo and o is 0, 1 or 2; $R^2$ is H or $C_1$-$C_3$-alkyl; $R^9$ is independently halo, cyano, nitro, cycloalkyl, haloalkyl, halocycloalkyl, alkoxy or haloalkoxy and m is 0, 1, 2 or 3.

In other embodiments, the invention provides a compound of Formula IC-3 above, wherein X is S; $R^1$ is optionally substituted $C_1$-$C_3$-alkyl; $R^3$ is phenyl optionally independently substituted by 1 to 3 halo; each $R^4$ is independently H or halo; each $R^5$ is independently halo and o is 0, 1 or 2; $R^2$ is H or $C_1$-$C_3$-alkyl; $R^9$ is independently halo, cyano, nitro, cycloalkyl, haloalkyl, halocycloalkyl, alkoxy or haloalkoxy and m is 0, 1, 2 or 3.

In other embodiments, the invention provides a compound of Formula IC-3 above, wherein X is O; $R^1$ is optionally substituted $C_1$-$C_3$-alkyl; $R^3$ is phenyl optionally independently substituted by 1 to 3 halo; each $R^4$ is independently H or halo; each $R^5$ is independently halo and o is 0, 1 or 2; $R^2$ is H or $C_1$-$C_3$-alkyl; $R^9$ is independently halo, cyano, nitro, cycloalkyl, haloalkyl, halocycloalkyl, alkoxy or haloalkoxy and m is 0, 1, 2 or 3.

In other embodiments, the invention provides a compound of Formula IC-7 above, wherein X is S; $R^1$ is optionally substituted $C_1$-$C_3$-alkyl; $R^3$ is phenyl optionally independently substituted by 1 to 3 halo; each $R^4$ is independently H or halo; each $R^5$ is independently halo and o is 0, 1 or 2; $R^2$ is H or $C_1$-$C_3$-alkyl; $R^9$ is independently halo, cyano, nitro, cycloalkyl, haloalkyl, halocycloalkyl, alkoxy or haloalkoxy and m is 0, 1, 2 or 3.

In other embodiments, the invention provides a compound of Formula IC-7 above, wherein X is O; $R^1$ is optionally substituted $C_1$-$C_3$-alkyl; $R^3$ is phenyl optionally independently substituted by 1 to 3 halo; each $R^4$ is independently H or halo; each $R^5$ is independently halo and o is 0, 1 or 2; $R^2$ is H or $C_1$-$C_3$-alkyl; $R^9$ is independently halo, cyano, nitro, cycloalkyl, haloalkyl, halocycloalkyl, alkoxy or haloalkoxy and m is 0, 1, 2 or 3.

In other embodiments, the invention provides compounds of formula (ID) wherein variables $R^1$, $R^2$, $R^4$, $R^5$, $R^{10}$, X, W, Z and a as defined for formula (I) above; $R^9$ and m are as defined for Formula IB above; b is 0 or 1; the dashed bond ( - - - - ) is either a single or double bond; D is N, C or C—$R^4$; $D^1$ is N, O, —$CR^4R^5$, $S(O)_p$ where p is 0, 1 or 2, or $D^1$ is $CR^4R^5$ wherein $R^4$ and $R^5$ together form a 2- to 5-membered chain optionally with one heteroatom in the chain to form a spirocyclic group; and $Y^1$, $Y^2$, $Y^3$, $Y^{2'}$, $Y^{3'}$, $Y^{4'}$ and $Y^{5'}$ are as shown in Table 4:

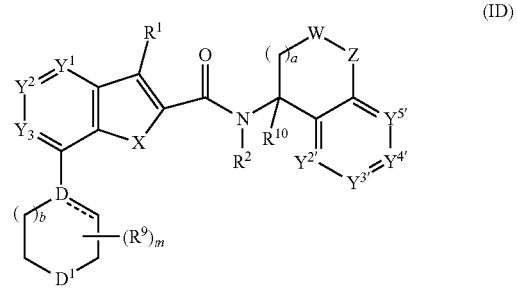

(ID)

TABLE 4

| Formula | $Y^1$ | $Y^2$ | $Y^3$ | $Y^{2'}$ | $Y^{3'}$ | $Y^{4'}$ | $Y^{5'}$ |
|---|---|---|---|---|---|---|---|
| ID-1 | $CR^4$ | $CR^4$ | $CR^4$ | $CR^5$ | $CR^5$ | $CR^5$ | $CR^5$ |
| ID-2 | $CR^4$ | $CR^4$ | $CR^4$ | N | $CR^5$ | $CR^5$ | $CR^5$ |
| ID-3 | $CR^4$ | $CR^4$ | $CR^4$ | $CR^5$ | N | $CR^5$ | $CR^5$ |
| ID-4 | $CR^4$ | $CR^4$ | $CR^4$ | $CR^5$ | $CR^5$ | N | $CR^5$ |
| ID-5 | $CR^4$ | $CR^4$ | $CR^4$ | $CR^5$ | $CR^5$ | $CR^5$ | N |
| ID-6 | $CR^4$ | $CR^4$ | $CR^4$ | N | N | $CR^5$ | $CR^5$ |
| ID-7 | $CR^4$ | $CR^4$ | $CR^4$ | $CR^5$ | N | N | $CR^5$ |
| ID-8 | $CR^4$ | $CR^4$ | $CR^4$ | $CR^5$ | $CR^5$ | N | N |
| ID-9 | N | $CR^4$ | $CR^4$ | $CR^5$ | $CR^5$ | $CR^5$ | $CR^5$ |
| ID-10 | N | $CR^4$ | $CR^4$ | N | $CR^5$ | $CR^5$ | $CR^5$ |
| ID-11 | N | $CR^4$ | $CR^4$ | $CR^5$ | N | $CR^5$ | $CR^5$ |
| ID-12 | N | $CR^4$ | $CR^4$ | $CR^5$ | $CR^5$ | N | $CR^5$ |
| ID-13 | N | $CR^4$ | $CR^4$ | $CR^5$ | $CR^5$ | $CR^5$ | N |
| ID-14 | N | $CR^4$ | $CR^4$ | N | N | $CR^5$ | $CR^5$ |
| ID-15 | N | $CR^4$ | $CR^4$ | $CR^5$ | N | N | $CR^5$ |
| ID-16 | N | $CR^4$ | $CR^4$ | $CR^5$ | $CR^5$ | N | N |
| ID-17 | $CR^4$ | N | $CR^4$ | $CR^5$ | $CR^5$ | $CR^5$ | $CR^5$ |
| ID-18 | $CR^4$ | N | $CR^4$ | N | $CR^5$ | $CR^5$ | $CR^5$ |
| ID-19 | $CR^4$ | N | $CR^4$ | $CR^5$ | N | $CR^5$ | $CR^5$ |
| ID-20 | $CR^4$ | N | $CR^4$ | $CR^5$ | $CR^5$ | N | $CR^5$ |
| ID-21 | $CR^4$ | N | $CR^4$ | $CR^5$ | $CR^5$ | $CR^5$ | N |
| ID-22 | $CR^4$ | N | $CR^4$ | N | N | $CR^5$ | $CR^5$ |
| ID-23 | $CR^4$ | N | $CR^4$ | $CR^5$ | N | N | $CR^5$ |
| ID-24 | $CR^4$ | N | $CR^4$ | $CR^5$ | $CR^5$ | N | N |
| ID-25 | $CR^4$ | $CR^4$ | N | $CR^5$ | $CR^5$ | $CR^5$ | $CR^5$ |
| ID-26 | $CR^4$ | $CR^4$ | N | N | $CR^5$ | $CR^5$ | $CR^5$ |
| ID-27 | $CR^4$ | $CR^4$ | N | $CR^5$ | N | $CR^5$ | $CR^5$ |
| ID-28 | $CR^4$ | $CR^4$ | N | $CR^5$ | CH | N | $CR^5$ |
| ID-29 | $CR^4$ | $CR^4$ | N | $CR^5$ | $CR^5$ | $CR^5$ | N |
| ID-30 | $CR^4$ | $CR^4$ | N | N | N | $CR^5$ | $CR^5$ |
| ID-31 | $CR^4$ | $CR^4$ | N | $CR^5$ | N | N | $CR^5$ |
| ID-32 | $CR^4$ | $CR^4$ | N | $CR^5$ | $CR^5$ | N | N |
| ID-33 | N | N | $CR^4$ | $CR^5$ | $CR^5$ | $CR^5$ | $CR^5$ |
| ID-34 | N | N | $CR^4$ | N | $CR^5$ | $CR^5$ | $CR^5$ |
| ID-35 | N | N | $CR^4$ | $CR^5$ | N | $CR^5$ | $CR^5$ |
| ID-36 | N | N | $CR^4$ | $CR^5$ | $CR^5$ | N | $CR^5$ |
| ID-37 | N | N | $CR^4$ | $CR^5$ | $CR^5$ | $CR^5$ | N |
| ID-38 | N | N | $CR^4$ | N | N | $CR^5$ | $CR^5$ |
| ID-39 | N | N | $CR^4$ | $CR^4$ | N | N | $CR^5$ |
| ID-40 | N | N | $CR^4$ | $CR^5$ | $CR^5$ | N | N |
| ID-41 | $CR^4$ | N | N | $CR^5$ | $CR^5$ | $CR^5$ | $CR^5$ |
| ID-42 | $CR^4$ | N | N | N | $CR^5$ | $CR^5$ | $CR^5$ |

TABLE 4-continued

| Formula | $Y^1$ | $Y^2$ | $Y^3$ | $Y^{2'}$ | $Y^{3'}$ | $Y^{4'}$ | $Y^{5'}$ |
|---|---|---|---|---|---|---|---|
| ID-43 | $CR^4$ | N | N | $CR^5$ | N | $CR^5$ | $CR^5$ |
| ID-44 | $CR^4$ | N | N | $CR^5$ | $CR^5$ | N | $CR^5$ |
| ID-45 | $CR^4$ | N | N | $CR^5$ | $CR^5$ | $CR^5$ | N |
| ID-46 | $CR^4$ | N | N | N | N | $CR^5$ | $CR^5$ |
| ID-47 | $CR^4$ | N | N | $CR^5$ | N | N | $CR^5$ |
| ID-48 | $CR^4$ | N | N | $CR^5$ | $CR^5$ | N | N |
| ID-49 | N | $CR^4$ | N | $CR^5$ | $CR^5$ | $CR^5$ | N |
| ID-50 | N | $CR^4$ | N | N | $CR^5$ | $CR^5$ | $CR^5$ |
| ID-51 | N | $CR^4$ | N | $CR^5$ | N | $CR^5$ | $CR^5$ |
| ID-52 | N | $CR^4$ | N | $CR^5$ | $CR^5$ | N | $CR^5$ |
| ID-53 | N | $CR^4$ | N | $CR^5$ | $CR^5$ | $CR^5$ | N |
| ID-54 | N | $CR^4$ | N | N | N | $CR^5$ | $CR^5$ |
| ID-55 | N | $CR^4$ | N | $CR^5$ | N | N | $CR^5$ |
| ID-56 | N | $CR^4$ | N | $CR^5$ | $CR^5$ | N | N |

In some embodiment, the present invention provides compounds of formulae ID-1 to ID-56 wherein X is S.

In some embodiment, the present invention provides compounds of formulae ID-1 to ID-56 wherein X is O.

In some embodiments, the present invention provides compounds of formulae ID-1 to ID-56 wherein the dashed bond is a single bond.

In some embodiments, the present invention provides compounds of formulae ID-1 to ID-56 wherein the dashed bond is a double bond.

In some embodiments, the present invention provides compounds of formulae ID-1 to ID-56 wherein D is CH, C-halo or N.

In some embodiments, the present invention provides compounds of formulae ID-1 to ID-56 wherein D is C, CH, C—F or N.

In some embodiments, the present invention provides compounds of formulae ID-1 to ID-56 wherein $D^1$ is $CR^4R^5$ wherein $R^4$ and $R^5$ together form a 2- to 5-membered chain optionally with one heteroatom in the chain to form a spirocyclic group.

In some embodiments, the present invention provides compounds of formulae ID-1 to ID-56 wherein $D^1$ is $CH_2$, independently C-(halo)$_2$, CH($C_1$-$C_3$-alkyl) or CH($C_1$-$C_3$-haloalkyl).

In some embodiments, the present invention provides compounds of formulae ID-1 to ID-56 wherein $D^1$ is $CH_2$, independently $CF_2$, $CH(CH_3)$ or $CH(CF_3)$.

In some embodiments, the present invention provides compounds of formulae ID-1 to ID-56 wherein $D^1$ is O, S, S(O) or $S(O)_2$.

In some embodiments, the present invention provides compounds of formulae ID-1 to ID-56 wherein D is CH or C-halo; and $D^1$ is $CH_2$.

In some embodiments, the present invention provides compounds of formulae ID-1 to ID-56 wherein D is N; and $D^1$ is $CH_2$, O or S.

In some embodiments, the present invention provides compounds of formulae ID-1 to ID-56 wherein the dashed line is a double bond; D is C; and $D^1$ is $CH_2$, $CF_2$, O or S.

In some embodiments, the present invention provides compounds of formulae ID-1 to ID-56 wherein D is N; and $D^1$ is $CR^4R^5$ wherein $R^4$ and $R^5$ together form a 2- to 4-membered chain optionally with one oxygen in the chain to form a spirocyclic group.

In some embodiments, the present invention provides compounds of formulae ID-1 to ID-56 wherein D is CH; and $D^1$ is $CR^4R^5$ wherein $R^4$ and $R^5$ together form a 2- to 4-membered chain optionally with one oxygen in the chain to form a spirocyclic group.

In some embodiments, the present invention provides compounds of formulae ID-1 to ID-56 wherein D is C and the dashed bond signify a double bond; and $D^1$ is $CR^4R^5$ wherein $R^4$ and $R^5$ together form a 2- to 4-membered chain optionally with one oxygen in the chain to form a spirocyclic group.

In some embodiment, the present invention provides compounds of formulae ID-1 to ID-56 wherein $R^4$ is independently H, halo, $C_1$-$C_4$-alkyl, $C_1$-$C_4$-haloalkyl, $C_1$-$C_4$-alkoxy, $C_1$-$C_4$-haloaloxy or $S(O)_p$($C_1$-$C_4$-alkyl or $C_1$-$C_4$-haloalkyl).

In some embodiment, the present invention provides compounds of formulae ID-1 to ID-56 wherein $R^4$ is independently H, chloro, fluoro, methyl, ethyl, n-propyl, iso-propyl, n-butyl, sec-butyl, iso-butyl, tert-butyl.

In some embodiment, the present invention provides compounds of formulae ID-1 to ID-56 wherein $R^4$ is independently H, $CF_3$, —$CH_2CF_3$, —$CHFCF_3$, —$CF_2CF_3$.

In some embodiment, the present invention provides compounds of formulae ID-1 to ID-56 wherein $R^4$ is independently H, methoxy, ethoxy, propoxy or butoxy.

In some embodiment, the present invention provides compounds of formulae ID-1 to ID-56 wherein $R^4$ is independently H, —$OCF_3$ or —$SCF_3$.

In some embodiment, the present invention provides compounds of formulae ID-1 to ID-56 wherein $R^5$ is independently H, halo, $C_1$-$C_4$-alkyl, $C_1$-$C_4$-haloalkyl, $C_1$-$C_4$-alkoxy, $C_1$-$C_4$-haloaloxy or $S(O)_p$($C_1$-$C_4$-alkyl or $C_1$-$C_4$-haloalkyl).

In some embodiment, the present invention provides compounds of formulae ID-1 to ID-56 wherein $R^5$ is independently H, chloro, fluoro, methyl, ethyl, n-propyl, iso-propyl, n-butyl, sec-butyl, iso-butyl, tert-butyl.

In some embodiment, the present invention provides compounds of formulae ID-1 to ID-56 wherein $R^5$ is independently H, $CF_3$, —$CH_2CF_3$, —$CHFCF_3$, —$CF_2CF_3$.

In some embodiment, the present invention provides compounds of formulae ID-1 to ID-56 wherein $R^5$ is independently H, methoxy, ethoxy, propoxy or butoxy.

In some embodiment, the present invention provides compounds of formulae ID-1 to ID-56 wherein $R^5$ is independently H, —$OCF_3$ or —$SCF_3$.

In other embodiments, the invention provides compounds of formulae ID-1 to ID-56, wherein $R^2$ is H or $C_1$-$C_3$-alkyl.

In other embodiments, the invention provides compounds of formulae ID-1 to ID-56 wherein $R^1$ is $C_1$-$C_6$-alkyl, $C_1$-$C_6$-haloalkyl, hydroxy-$C_1$-$C_6$-alkyl, $C_1$-$C_6$-alkoxy-$C_1$-$C_6$-alkyl, $C_1$-$C_6$-haloalkoxy-$C_1$-$C_6$-alkyl, amino-$C_1$-$C_6$-alkyl, $C_1$-$C_6$-alkoxy, $C_1$-$C_6$-haloalkoxy, $C_2$-$C_6$-alkenyl, $C_2$-$C_6$-haloalkenyl, optionally substituted $C_3$-$C_8$-cycloalkyl, optionally substituted 3- to 7-membered heterocyclyl, or —$NR^aR^b$ wherein $R^a$ and $R^b$ are independently H or optionally substituted $C_1$-$C_6$-alkyl; or $R^a$ and $R^b$ may form, with the nitrogen to which they are attached, a 3-, 4-, 5- or 6-membered-heterocyclyl group, which may include one to three additional heteroatoms selected from the group consisting of N, O and S and may be optionally substituted.

In other embodiments, the invention provides compounds of formulae ID-1 to ID-56 wherein $R^9$ is independently halo, cyano, nitro, cycloalkyl, haloalkyl, halocycloalkyl, alkoxy, or haloalkoxy, m is 0, 1, 2, or 3, and b is 0 or 1.

In other embodiments, the invention provides compounds of formulae ID-1 to ID-56 wherein $R^9$ is independently halo and m is 1, 2 or 3.

In other embodiments, the invention provides compounds of formulae ID-1 to ID-56 wherein $R^9$ is independently fluoro or chloro and m is 1, 2 or 3.

In other embodiments, the invention provides compounds of formulae ID-1 to ID-56 wherein X is S, $R^9$ is independently halo and m is 1, 2 or 3, and $R^2$ is H or $C_1$-$C_3$-alkyl.

In other embodiments, the invention provides compounds of formulae ID-1 to ID-56 wherein X is S, $R^9$ is independently chloro or fluoro and m is 1, 2 or 3, and $R^2$ is H or $C_1$-$C_3$-alkyl.

In other embodiments, the invention provides compounds of formulae ID-1 to ID-56 wherein X is S, $R^9$ is independently halo, cyano, nitro, cycloalkyl, haloalkyl, halocycloalkyl, alkoxy or haloalkoxy; D is N or CH; $D^1$ is NH, O or $CH_2$; b is 0 or 1; and m is 0, 1, 2 or 3.

In other embodiments, the invention provides a compound of Formula ID-1 above, wherein X is S; $R^1$ is optionally substituted $C_1$-$C_3$-alkyl; $R^3$ is phenyl optionally independently substituted by 1 to 3 halo; each $R^4$ is independently H or halo; each $R^5$ is independently H or halo; $R^2$ is H or $C_1$-$C_3$-alkyl; $R^9$ is independently halo, cyano, nitro, cycloalkyl, haloalkyl, halocycloalkyl, alkoxy or haloalkoxy and m is 0, 1, 2 or 3.

In other embodiments, the invention provides a compound of Formula ID-1 above, wherein X is O; $R^1$ is optionally substituted $C_1$-$C_3$-alkyl; $R^3$ is phenyl optionally independently substituted by 1 to 3 halo; each $R^4$ is independently H or halo; each $R^5$ is independently H or halo; $R^2$ is H or $C_1$-$C_3$-alkyl; $R^9$ is independently halo, cyano, nitro, cycloalkyl, haloalkyl, halocycloalkyl, alkoxy or haloalkoxy and m is 0, 1, 2 or 3.

In other embodiments, the invention provides a compound of Formula ID-9 above, wherein X is S; $R^1$ is optionally substituted $C_1$-$C_3$-alkyl; $R^3$ is phenyl optionally independently substituted by 1 to 3 halo; each $R^4$ is independently H or halo; each $R^5$ is independently H or halo; $R^2$ is H or $C_1$-$C_3$-alkyl; $R^9$ is independently halo, cyano, nitro, cycloalkyl, haloalkyl, halocycloalkyl, alkoxy or haloalkoxy and m is 0, 1, 2 or 3.

In other embodiments, the invention provides a compound of Formula ID-9 above, wherein X is O; $R^1$ is optionally substituted $C_1$-$C_3$-alkyl; $R^3$ is phenyl optionally independently substituted by 1 to 3 halo; each $R^4$ is independently H or halo; each $R^5$ is independently H or halo; $R^2$ is H or $C_1$-$C_3$-alkyl; $R^9$ is independently halo, cyano, nitro, cycloalkyl, haloalkyl, halocycloalkyl, alkoxy or haloalkoxy and m is 0, 1, 2 or 3.

In other embodiments, the invention provides a compound of Formula ID-17 above, wherein X is S; $R^1$ is optionally substituted $C_1$-$C_3$-alkyl; $R^3$ is phenyl optionally independently substituted by 1 to 3 halo; each $R^4$ is independently H or halo; each $R^5$ is independently H or halo; $R^2$ is H or $C_1$-$C_3$-alkyl; $R^9$ is independently halo, cyano, nitro, cycloalkyl, haloalkyl, halocycloalkyl, alkoxy or haloalkoxy and m is 0, 1, 2 or 3.

In other embodiments, the invention provides a compound of Formula ID-17 above, wherein X is O; $R^1$ is optionally substituted $C_1$-$C_3$-alkyl; $R^3$ is phenyl optionally independently substituted by 1 to 3 halo; each $R^4$ is independently H or halo; each $R^5$ is independently H or halo; $R^2$ is H or $C_1$-$C_3$-alkyl; $R^9$ is independently halo, cyano, nitro, cycloalkyl, haloalkyl, halocycloalkyl, alkoxy or haloalkoxy and m is 0, 1, 2 or 3.

In other embodiments, the invention provides a compound of Formula ID-25 above, wherein X is S; $R^1$ is optionally substituted $C_1$-$C_3$-alkyl; $R^3$ is phenyl optionally independently substituted by 1 to 3 halo; each $R^4$ is independently H or halo; each $R^5$ is independently H or halo; $R^2$ is H or $C_1$-$C_3$-alkyl; $R^9$ is independently halo, cyano, nitro, cycloalkyl, haloalkyl, halocycloalkyl, alkoxy or haloalkoxy and m is 0, 1, 2 or 3.

In other embodiments, the invention provides a compound of Formula ID-25 above, wherein X is O; $R^1$ is optionally substituted $C_1$-$C_3$-alkyl; $R^3$ is phenyl optionally independently substituted by 1 to 3 halo; each $R^4$ is independently H or halo; each $R^5$ is independently H or halo; $R^2$ is H or $C_1$-$C_3$-alkyl; $R^9$ is independently halo, cyano, nitro, cycloalkyl, haloalkyl, halocycloalkyl, alkoxy or haloalkoxy and m is 0, 1, 2 or 3.

In other embodiments, the invention provides a compound of Formula ID-49 above, wherein X is S; $R^1$ is optionally substituted $C_1$-$C_3$-alkyl; $R^3$ is phenyl optionally independently substituted by 1 to 3 halo; each $R^4$ is independently H or halo; each $R^5$ is independently H or halo; $R^2$ is H or $C_1$-$C_3$-alkyl; $R^9$ is independently halo, cyano, nitro, cycloalkyl, haloalkyl, halocycloalkyl, alkoxy or haloalkoxy and m is 0, 1, 2 or 3.

In other embodiments, the invention provides a compound of Formula ID-49 above, wherein X is O; $R^1$ is optionally substituted $C_1$-$C_3$-alkyl; $R^3$ is phenyl optionally independently substituted by 1 to 3 halo; each $R^4$ is independently H or halo; each $R^5$ is independently H or halo; $R^2$ is H or $C_1$-$C_3$-alkyl; $R^9$ is independently halo, cyano, nitro, cycloalkyl, haloalkyl, halocycloalkyl, alkoxy or haloalkoxy and m is 0, 1, 2 or 3.

In any of the embodiments in Tables 1, 2 or 4 above, each of $Y^{2'}$, $Y^{3'}$, $Y^{4'}$, $Y^{5'}$ are CH.

In any of the embodiments in Tables 1, 2 or 4 above, one of $Y^{2'}$, $Y^{3'}$, $Y^{4'}$ and $Y^{5'}$ is $CR^5$ where $R^5$ is a non-hydrogen substituent.

In any of the embodiments in Tables 1, 2 or 4 above, two of $Y^{2'}$, $Y^{3'}$, $Y^{4'}$ and $Y^{5'}$ are $CR^5$ where each $R^5$ are independently a non-hydrogen substituent.

In any of the embodiments in Tables 1, 2 or 4 above, three of $Y^{2'}$, $Y^{3'}$, $Y^{4'}$ and $Y^{5'}$ are $CR^5$ where each $R^5$ are independently a non-hydrogen substituent.

In any of the embodiments in Tables 1, 2 or 4 above, all four of $Y^{2'}$, $Y^{3'}$, $Y^{4'}$ and $Y^{5'}$ are $CR^5$ where each $R^5$ are independently non-hydrogen substituents.

In any of the embodiments in Tables 1 to 4 above, each of $Y^1$, $Y^2$ and $Y^3$ are CH.

In any of the embodiments in Tables 1 to 4 above, one of $Y^1$, $Y^2$ and $Y^3$ $CR^4$ where $R^4$ is a non-hydrogen substituent.

In any of the embodiments in Tables 1 to 4 above, two of $Y^1$, $Y^2$ and $Y^3$ are $CR^4$ where each $R^4$ are independently a non-hydrogen substituent.

In any of the embodiments in Tables 1 to 4 above, three of $Y^1$, $Y^2$ and $Y^3$ are $CR^4$ where each $R^4$ are independently non-hydrogen substituents.

In any of the embodiments in Tables 1, 2 or 4 above, one of $Y^{2'}$, $Y^{3'}$, $Y^{4'}$ and $Y^{5'}$ is C-halogen.

In any of the embodiments in Tables 1, 2 or 4 above, two of $Y^{2'}$, $Y^{3'}$, $Y^{4'}$ and $Y^{5'}$ are C-halogen.

In any of the embodiments in Tables 1, 2 or 4 above, three of $Y^{2'}$, $Y^{3'}$, $Y^{4'}$ and $Y^{5'}$ are C-halogen.

In any of the embodiments in Tables 1 to 4 above, one of $Y^1$, $Y^2$ and $Y^3$ is C-halogen.

In any of the embodiments in Tables 1 to 4 above, two of $Y^1$, $Y^2$ and $Y^3$ are C-halogen.

In any of the embodiments in Tables 1 to 4 above, three of $Y^1$, $Y^2$ and $Y^3$ are C-halogen.

In any of the embodiments in Tables 1, 2 or 4 above, one of $Y^{2'}$, $Y^{3'}$, $Y^{4'}$ and $Y^{5'}$ is C—Cl or C—F.

In any of the embodiments in Tables 1, 2 or 4 above, two of $Y^{2'}$, $Y^{3'}$, $Y^{4'}$ and $Y^{5'}$ are independently C—Cl or C—F.

In any of the embodiments in Tables 1, 2 or 4 above, three of $Y^{2'}$, $Y^{3'}$, $Y^{4'}$ and $Y^{5'}$ are independently C—Cl or C—F.

In any of the embodiments in Tables 1 to 4 above, one of $Y^1$, $Y^2$ and $Y^3$ is C—Cl or C—F.

In any of the embodiments in Tables 1 to 4 above, two of $Y^1$, $Y^2$ and $Y^3$ are independently C—Cl or C—F.

In any of the embodiments in Tables 1 to 4 above, three of $Y^1$, $Y^2$ and $Y^3$ are independently C—Cl or C—F.

In any of the embodiments in Tables 1, 2 or 4 above, a is 1, W is —CH$_2$—, and Z is O.

In any of the embodiments in Tables 1 to 4 above, $R^1$ is $C_1$-$C_4$-alkyl, $C_1$-$C_4$ alkenyl, $C_1$-$C_4$-cycloalkyl, amino, $C_1$-$C_4$-alkylamino, di($C_1$-$C_4$-alkyl)amino, morpholino, pyranyl, tetrahydropyranyl, or dihydropyranyl.

In any of the embodiments in Tables 1 to 4 above, one, two or three $R^4$s are hydrogen.

In any of the embodiments in Tables 1 to 4 above, an $R^4$ is, independently of other $R^4$, a halogen, cyano, $C_1$-$C_4$-alkyl, $C_1$-$C_4$ haloalkyl, $C_1$-$C_4$-cycloalkyl, amino, $C_1$-$C_4$-alkylamino, di($C_1$-$C_4$-alkyl)amino, or phenyl optionally substituted 1 or 2 times by halo or $C_1$-$C_4$-alkyl.

In any of the embodiments in Tables 1 to 4 above, an $R^5$ is, independently of other $R^5$, a halogen, cyano, $C_1$-$C_4$-alkyl, $C_1$-$C_4$ haloalkyl, $C_1$-$C_4$-cycloalkyl, amino, $C_1$-$C_4$-alkylamino, di($C_1$-$C_4$-alkyl)amino, or phenyl optionally substituted 1 or 2 times by halo or $C_1$-$C_4$-alkyl.

In other embodiments, the present invention includes the compounds of Formula (I) shown in Table 5 below, wherein Y1, Y2, Y3, L, X, R1 and R3 are shown in the table; $R^2$ and $R^{2'}$ are both hydrogen; Q is oxygen; and the group:

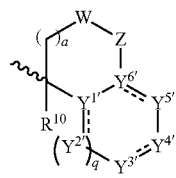

is abbreviated as "Ring System" in the table and represents the following groups:

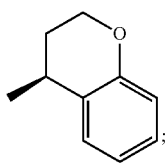
Ring System A

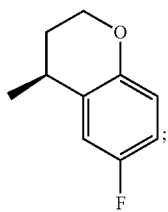
Ring System B

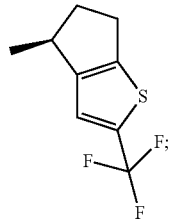
Ring System C

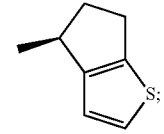
Ring System D

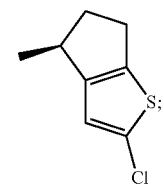
Ring System E

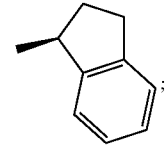
Ring System F

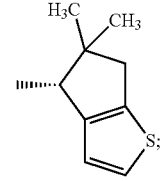
Ring System G

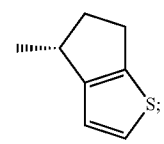
Ring System H

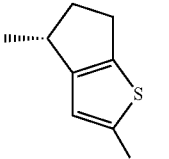
Ring System I

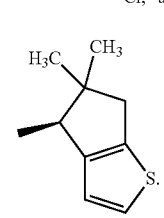
Ring System K

In Table 5, the expression "3,5-di-F-Ph" represents the 3,5-difluorophenyl group; "3,5-di-Cl-Ph" represents 3,5-dichlorophenyl; "2,3,5-tri-F-Ph" represents 2,3,5-trifluorophenyl; "3-F-Ph" represents 3-fluorophenyl; "2,6-di-F-Ph" represents 2,6-difluorophenyl; "2,3-di-$C_1$-Ph" represents 2,3-dichlorophenyl; "2,3,6-tri-F-Ph" represents 2,3,6-trifluorophenyl; "4-F-2,6-di-Me-Ph" represents 4-fluoro-2,6- dimethylphenyl; "2-Cl-6-F-Ph" represents 2-chloro-6-fluorophenyl; "3-Cl-5-(3,5-di-Cl-Ph)-Ph represents 3-chloro-5-(3,5-dichlorophenyl)phenyl; and so on;

prop-1-en-2-yl represents the group

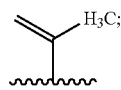

2-OH-prop-2-yl represents the group

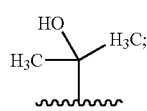

and

2-F-prop-2-yl represents the group

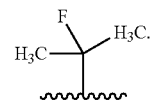

Formula (I)

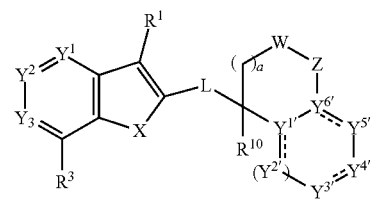

TABLE 5

| Cmpd. # | $Y^1$ | $Y^2$ | $Y^3$ | L | X | $R^1$ | $R^3$ | Ring System |
|---|---|---|---|---|---|---|---|---|
| 309 | N | CH | CF | L1 | S | i-Pr | 3,5-di-Cl-Ph | A |
| 264-0 | CH | N | CH | L1 | S | 2-OH-prop-2-yl | 3,5-di-Cl-Ph | A |
| 310 | N | CH | CCl | L1 | S | i-Pr | 3,5-di-F-Ph | A |
| 347 | N | CH | CH | L1 | S | i-Pr | 2,3,5-tri-F-Ph | A |
| 348 | N | CH | CH | L1 | S | i-Pr | 2,3,5-tri-F-Ph | B |
| 338 | N | CH | CF | L1 | S | t-Bu | 3,5-di-Cl-Ph | B |
| 336 | N | CH | CF | L1 | S | t-Bu | 3,5-di-Cl-Ph | B |
| 122 | N | CH | CH | L1 | S | ![morpholine] | 3,5-di-F-Ph | B |
| 263-8 | N | CH | CF | L1 | S | 2-OH-prop-2-yl | 3,5-di-Cl-Ph | A |
| 263 | N | CH | CF | L1 | S | 2-F-prop-2-yl | 3,5-di-Cl-Ph | A |
| 210 | N | CH | CH | L1 | S | t-Bu | 3,5-di-F-Ph | A |
| 204 | N | CH | CF | L1 | S | i-Pr | 3,5-di-F-Ph | A |
| 211 | N | CH | CH | L1 | S | i-Pr | 3,5-di-Cl-Ph | B |
| 311 | N | CH | CH | L1 | S | 2-F-prop-2-yl | 3,5-di-F-Ph | A |
| 259-5 | N | CH | CH | L1 | S | 2-OH-prop-2-yl | 3,5-di-Cl-Ph | B |
| 257 | N | CH | CH | L1 | S | i-Pr | 3,5-di-F-Ph | B |
| 300 | N | CH | CF | L1 | S | 2-F-prop-2-yl | 3,5-di-F-Ph | B |
| 264 | CH | N | CH | L1 | S | 2-F-prop-2-yl | 3,5-di-Cl-Ph | A |
| 309 | N | CH | CF | L1 | S | i-Pr | 3,5-di-Cl-Ph | A |
| 259 | N | CH | CH | L1 | S | 2-F-prop-2-yl | 3,5-di-Cl-Ph | B |
| 285 | N | CH | CH | L1 | S | prop-1-en-2-yl | 3,5-di-Cl-Ph | A |
| 260 | N | CH | CF | L1 | S | i-Pr | 3,5-di-F-Ph | B |
| 102 | CH | CH | CH | L1 | S | ![tetrahydropyran] | 3,5-di-F-Ph | A |
| 212 | N | CH | CH | L1 | S | 2-F-prop-2-yl | 3,5-di-Cl-Ph | A |
| 119 | N | CH | CH | L1 | S | prop-1-en-2-yl | 3,5-di-F-Ph | A |
| 120 | N | CH | CH | L1 | S | i-Pr | 3,5-di-F-Ph | A |
| 207 | N | CH | CH | L1 | S | i-Pr | 3-F-Ph | A |
| 258 | N | CH | CH | L1 | S | i-Pr | 3,5-di-Cl-Ph | B |
| 212-0 | N | CH | CH | L1 | S | 2-OH-prop-2-yl | 3,5-di-Cl-Ph | A |
| 128 | CH | N | CH | L1 | S | i-Pr | 3,5-di-F-Ph | A |
| 337 | N | CH | CF | L1 | S | t-Bu | 3,5-di-F-Ph | B |

TABLE 5-continued
| Cmpd. # | Y¹ | Y² | Y³ | L | X | R¹ | R³ | Ring System |
|---|---|---|---|---|---|---|---|---|
| 268-4 | N | CH | CH | L1 | S | 2-OH-prop-2-yl | 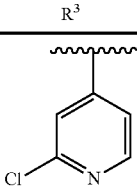 | A |
| 234 | N | CH | C—OMe | L1 | S | i-Pr | 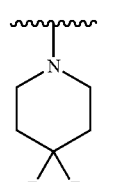 | A |
| 254 | N | CH | CH | L1 | S | i-Pr | 3,5-di-F-Ph | C |
| 268 | N | CH | CH | L1 | S | 2-F-prop-2-yl | 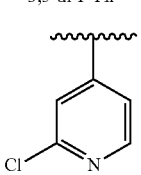 | A |
| 218 | CH | N | CH | L1 | S | i-Pr | 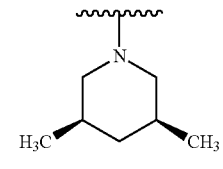 | A |
| 220 | N | CH | CH | L1 | S | i-Pr | 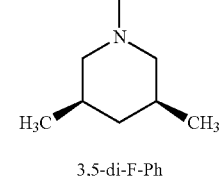 | A |
| 252 | N | CH | CH | L1 | S | i-Pr | 3,5-di-F-Ph | D |
| 209 | N | CH | CH | L1 | S | i-Pr | 2,6-di-F-Ph | A |
| 253 | N | CH | CH | L1 | S | i-Pr | 3,5-di-F-Ph | E |
| 246 | N | CH | CH | L1 | S | i-Pr | 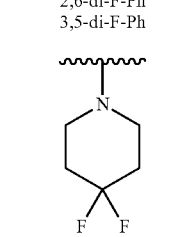 | A |
| 222 | N | CH | CH | L1 | S | i-Pr | Cyclopentyl | A |
| 206 | N | CH | CH | L1 | S | i-Pr | 2,3-di-Cl-Ph | A |
| 255 | N | CH | CH | L1 | S | i-Pr | 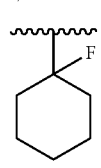 | A |
| 255-0 | N | CH | CH | L1 | S | i-Pr | 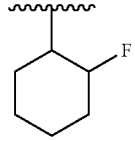 | A |
| 203 | N | CH | CH | L1 | S | i-Pr | 2,3,6-tri-F-Ph | A |
| 256 | N | CH | CH | L1 | S | prop-1-en-2-yl | 3,5-di-F-Ph | B |

TABLE 5-continued

| Cmpd. # | Y¹ | Y² | Y³ | L | X | R¹ | R³ | Ring System |
|---|---|---|---|---|---|---|---|---|
| 302 | N | CH | CH | L1 | S | i-Pr | —CF₃ | A |
| 301 | N | CH | CH | L1 | S | i-Pr | t-Bu | A |
| 238 | N | CH | CH | L1 | S | —CF₂CF₃ | 3,5-di-F-Ph | A |
| 243 | N | CH | CH | L1 | S | i-Pr | 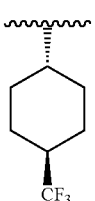 | A |
| 213 | N | CH | CH | L1 | S | i-Pr | 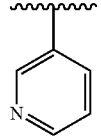 | A |
| 236 | N | CH | CH | L1 | S | —CF₃ | 3,5-di-F-Ph | A |
| 201 | N | CH | CH | L1 | S | i-Pr | 4-F-2,6-di-Me-Ph | A |
| 199 | N | CH | CH | L1 | S | 2-OH-prop-2-yl | 3,5-di-F-Ph | A |
| 205 | N | CH | CH | L1 | S | —CHF₂ | 3,5-di-F-Ph | A |
| 229 | N | CH | CH | L1 | S | i-Pr | 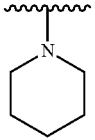 | A |
| 223 | N | CH | CH | L1 | S | i-Pr | cyclohexyl | A |
| 224 | N | CH | CH | L1 | S | —N(CH₃)₂ | cyclohexyl | A |
| 115 | N | CH | N | L1 | S | prop-1-en-2-yl | 3,5-di-F-Ph | A |
| 116 | N | CH | N | L1 | S | i-Pr | 3,5-di-F-Ph | A |
| 126 | CH | CH | N | L1 | S | 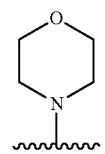 | 3,5-di-F-Ph | A |
| 125 | CH | CH | N | L1 | S | —N(CH₃)₂ | 3,5-di-F-Ph | A |
| 127 | CH | N | CH | L1 | S | prop-1-en-2-yl | 3,5-di-F-Ph | A |
| 129 | CH | N | CH | L1 | S | —N(CH₃)₂ | 3,5-di-F-Ph | A |
| 102-1 | CH | CH | CH | L1 | S | 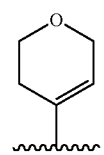 [SMILES: *C1=CCOCC1] | 3,5-di-F-Ph | A |
| 101 | CH | CH | CH | L1 | S | 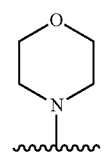 | 3,5-di-F-Ph | A |
| 090 | CH | CH | CH | L1 | S | i-Pr | 3,5-di-F-Ph | A |
| 130 | CH | N | CH | L1 | S | 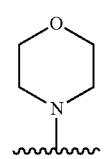 | 3,5-di-F-Ph | A |

TABLE 5-continued

| Cmpd. # | Y¹ | Y² | Y³ | L | X | R¹ | R³ | Ring System |
|---|---|---|---|---|---|---|---|---|
| 121 | N | CH | CH | L1 | S | —N(CH$_3$)$_2$ | 3,5-di-F-Ph | A |
| 026 | CH | CH | CH | L1 | O | i-Pr | 3,5-di-Cl-Ph | A |
| 029 | CH | CH | CH | L1 | O | i-Pr | 2,6-di-F-Ph | A |
| 030 | C-i-Pr | CH | CH | L1 | O | H | 3,5-di-Cl-Ph | A |
| 027 | CH | CH | CH | L1 | O | 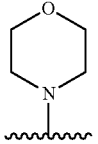 | 3,5-di-Cl-Ph | A |
| 098 | CH | CH | C(3,5-di-F-Ph) | L1 | S | prop-1-en-2-yl | H | A |
| 100 | CH | CH | C(3,5-di-F-Ph) | L1 | S | —N(CH$_3$)$_2$ | H | A |
| 099 | CH | CH | C(3,5-di-F-Ph) | L1 | S | i-Pr | H | A |
| 28 | CH | CH | CH | L1 | O | i-Pr | 3,5-di-Cl-Ph | F |
| 92 | CH | CH | CH | L1 | S | prop-1-en-2-yl | 3,5-di-F-Ph | A |
| 83 | CH | CH | CH | L1 | S | —N(CH$_3$)$_2$ | 3,5-di-F-Ph | A |
| 239-INT | N | N | CH | L1 | S | prop-1-en-2-yl | 3,5-di-F-Ph | A |
| 239 | N | N | CH | L1 | S | i-Pr | 3,5-di-F-Ph | A |
| 117 | N | CH | N | L1 | S | —N(CH$_3$)$_2$ | 3,5-di-F-Ph | A |
| 226-3 | N | CH | CH | L1 | S | —N(CH$_3$)$_2$ | —C(O)CH$_3$ | A |
| 259-4 | N | CH | CH | L1 | S | —C(O)CH$_3$ | 3,5-di-Cl-Ph | B |
| 221 | N | CH | CH | L1 | S | i-Pr | —CH(CH$_3$)CH$_2$—CH(CH$_3$)$_2$ | A |
| 319 | N | CH | CF | L1 | S | i-Pr | 3,5-di-Cl-Ph | A |
| 309 | N | CH | CF | L1 | S | i-Pr | 3,5-di-Cl-Ph | A |
| 115-INT-3 | N | CH | N | L1 | S | Br | 3,5-di-F-Ph | A |
| 237 | N | C—CF$_3$ | N | L1 | S | i-Pr | 3,5-di-F-Ph | A |
| 225-0 | N | CH | CH | L1 | S | —N(CH$_3$)$_2$ | 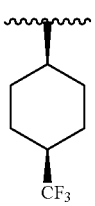 | A |
| 226 | N | CH | CH | L1 | S | —N(CH$_3$)$_2$ | —CH(CH$_3$)CH$_2$—CH(CH$_3$)$_2$ | A |
| 240 | N | CH | CH | L1 | S | i-Pr | 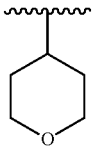 | A |
| 241 | N | CH | CH | L1 | S | i-Pr | 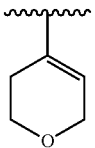 | A |
| 216 | N | CH | CH | L1 | S | 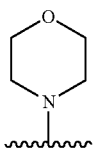 | 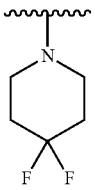 | A |
| 208 | N | CH | CH | L1 | S | i-Pr | 2-Cl-6-F-Ph | A |

TABLE 5-continued

| Cmpd. # | Y¹ | Y² | Y³ | L | X | R¹ | R³ | Ring System |
|---|---|---|---|---|---|---|---|---|
| 230 | N | CH | CH | L1 | S | —N(CH$_3$)$_2$ | 4,4-difluoropiperidin-1-yl | A |
| 232 | N | CH | CH | L1 | S | i-Pr | 2-oxa-6-azaspiro[3.4]octan-6-yl | A |
| 228 | N | CH | CH | L1 | S | —N(CH$_3$)$_2$ | piperidin-1-yl | A |
| 250 | N | CH | CH | L1 | S | i-Pr | 1,1-dioxidotetrahydro-2H-thiopyran-4-yl | A |
| 219 | CH | CH | CH | L1 | S | i-Pr | 4,4-difluoropiperidin-1-yl | A |
| 262 | N | CH | CH | L1 | S | i-Pr | 3,5-di-F-Ph | G |
| 249 | N | CH | CH | L1 | S | i-Pr | 3,6-dihydro-2H-thiopyran-4-yl | A |
| 247 | N | CH | CH | L1 | S | i-Pr | spiro[2.5]oct-5-en-6-yl | A |
| 237 | N | C—CF$_3$ | N | L1 | S | prop-1-en-2-yl | 3,5-di-F-Ph | A |
| 251 | N | CH | CH | L1 | S | i-Pr | 3,5-di-F-Ph | H |
| 215 | N | C—CF$_3$ | CH | L1 | S | i-Pr | 3,5-di-Cl-Ph | A |
| 231 | N | CH | CH | L1 | S | i-Pr | 2-oxa-5-azabicyclo[2.2.1]heptan-5-yl | A |

TABLE 5-continued
| Cmpd. # | Y¹ | Y² | Y³ | L | X | R¹ | R³ | Ring System |
|---|---|---|---|---|---|---|---|---|
| 225 | N | CH | CH | L1 | S | —N(CH₃)₂ | 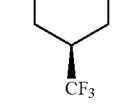 | A |
| 253-0 | N | CH | CH | L1 | S | i-Pr | 3,5-di-F-Ph | I |
| 245 | N | CH | CH | L1 | S | i-Pr | 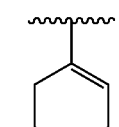 | A |
| 214 | N | CH | CH | L1 | S | i-Pr | 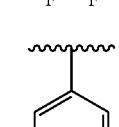 | A |
| 211-0 | N | CH | CH | L1 | S | i-Pr | 3-Cl-5-(3,5-di-Cl-Ph)-Ph | A |
| 248 | N | CH | CH | L1 | S | i-Pr | 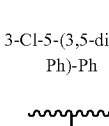 | A |
| 118 | N | CH | N | L1 | S |  | 3,5-di-F-Ph | A |
| 202 | N | CH | CH | L1 | S | i-Pr | 4-F-Ph | A |
| 242 | N | CH | CH | L1 | S | i-Pr |  | A |
| 261 | N | CH | CH | L1 | S | i-Pr | 3,5-di-F-Ph | K |
| 217 | N | CH | CH | L1 | S |  | 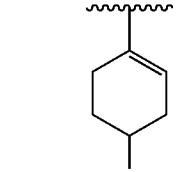 | A |

TABLE 5-continued

| Cmpd. # | Y¹ | Y² | Y³ | L | X | R¹ | R³ | Ring System |
|---|---|---|---|---|---|---|---|---|
| 227 | N | CH | CH | L1 | S | —N(CH$_3$)$_2$ | 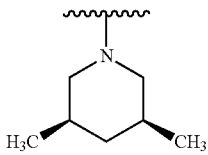 | A |
| 124 | CH | CH | N | L1 | S | i-Pr | 3,5-di-F-Ph | A |
| 123 | CH | CH | N | L1 | S | prop-1-en-2-yl | 3,5-di-F-Ph | A |

For avoidance of doubt, each of the compounds presented in Table 5 have been prepared and tested.

Stereoisomers and Polymorphic Forms

It will be appreciated by those of skill in the art that the compound may exist and be isolated in optically active and racemic forms. Compounds having one or more chiral centers, including that at a sulfur atom, may be present as single enantiomers or diastereomers or as mixtures of enantiomers and/or diastereomers. For example, it is well known in the art that sulfoxide compounds may be optically active and may exist as single enantiomers or racemic mixtures. In addition, compounds of the description may include one or more chiral centers, which results in a theoretical number of optically active isomers. In the present case, the compounds of formula (I) include at least one chiral center, the carbon atom bearing variable $R^{10}$. Where compounds of the description include n chiral centers, the compounds may comprise up to $2^n$ optical isomers. Thus, the compounds of the present invention include at least 2 enantiomers which are encompassed by the invention. The description encompasses the specific enantiomers or diastereomers of each compound as well as mixtures of different enantiomers and/or diastereomers of the compounds that possess the useful properties described herein. The optically active forms can be prepared by, for example, resolution of the racemic forms by selective crystallization techniques, by synthesis from optically active precursors, by chiral synthesis, by chromatographic separation using a chiral stationary phase or by enzymatic resolution.

The compound may also be present in different solid forms such as different crystalline forms or in the form of an amorphous solid. The description includes different crystalline forms as well as amorphous forms of the compound.

In addition, the compound may exist as hydrates or solvates, in which a certain stoichiometric amount of water or a solvent is associated with the molecule in the crystalline form. The hydrates and solvates of the compound are also the subject of the description.

Salts

In addition to the neutral compound, salt forms of the compound are also active against endoparasites. The term "veterinarily acceptable salt" is used throughout the specification to describe any salts of the compounds that are acceptable for administration for veterinary applications, and which provides an active compound upon administration.

In cases where compounds are sufficiently basic or acidic to form stable non-toxic acid or base salts, the compound may be in the form of a veterinarily or agriculturally acceptable salt. Veterinarily acceptable salts include those derived from veterinarily or agriculturally acceptable inorganic or organic bases and acids. Suitable salts include those comprising alkali metals such as lithium, sodium or potassium, alkaline earth metals such as calcium, magnesium and barium. Salts comprising transition metals including, but not limited to, manganese, copper, zinc and iron are also suitable. In addition, salts comprising ammonium cations ($NH_4^+$) as well as substituted ammonium cations, in which one or more of the hydrogen atoms are replaced by alkyl or aryl groups are encompassed by the description.

Salts derived from inorganic acids including, but not limited to, hydrohalide acids (HCl, HBr, HF, HI), sulfuric acid, nitric acid, phosphoric acid, and the like are particularly suitable. Suitable inorganic salts also include, but not limited to, bicarbonate, and carbonate salts. In some embodiments, examples of veterinarily and agriculturally acceptable salts are organic acid addition salts formed with organic acids including, but not limited to, maleate, dimaleate, fumarate, tosylate, methanesulfonate, acetate, citrate, malonate, tartarate, succinate, benzoate, ascorbate, α-ketoglutarate, and α-glycerophosphate. Of course, other acceptable organic acids may be used.

Alkali metal (for example, sodium, potassium or lithium) or alkaline earth metal (for example calcium) salts of the compound can also be made by reacting a sufficiently acidic residue on the compounds with a hydroxide of the alkali metal or alkaline earth metal.

Veterinarily acceptable salts may be obtained using standard procedures well known in the art, for example by reacting a sufficiently basic compound such as an amine with a suitably acid functional group present in the compound, or by reacting a suitable acid with a suitably basic functional group on the compound of the description.

Processes for the Preparation of the Compounds

The compounds of Formula (I) or pharmaceutically or a veterinarily acceptable salts thereof may be prepared by adopting one of schemes 1 to 4 below or schemes 5 to 12 and the procedures in the examples:

Scheme 1

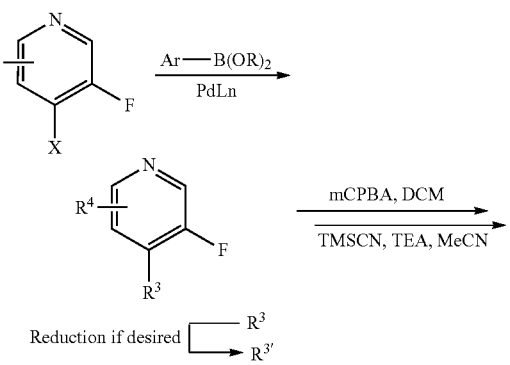

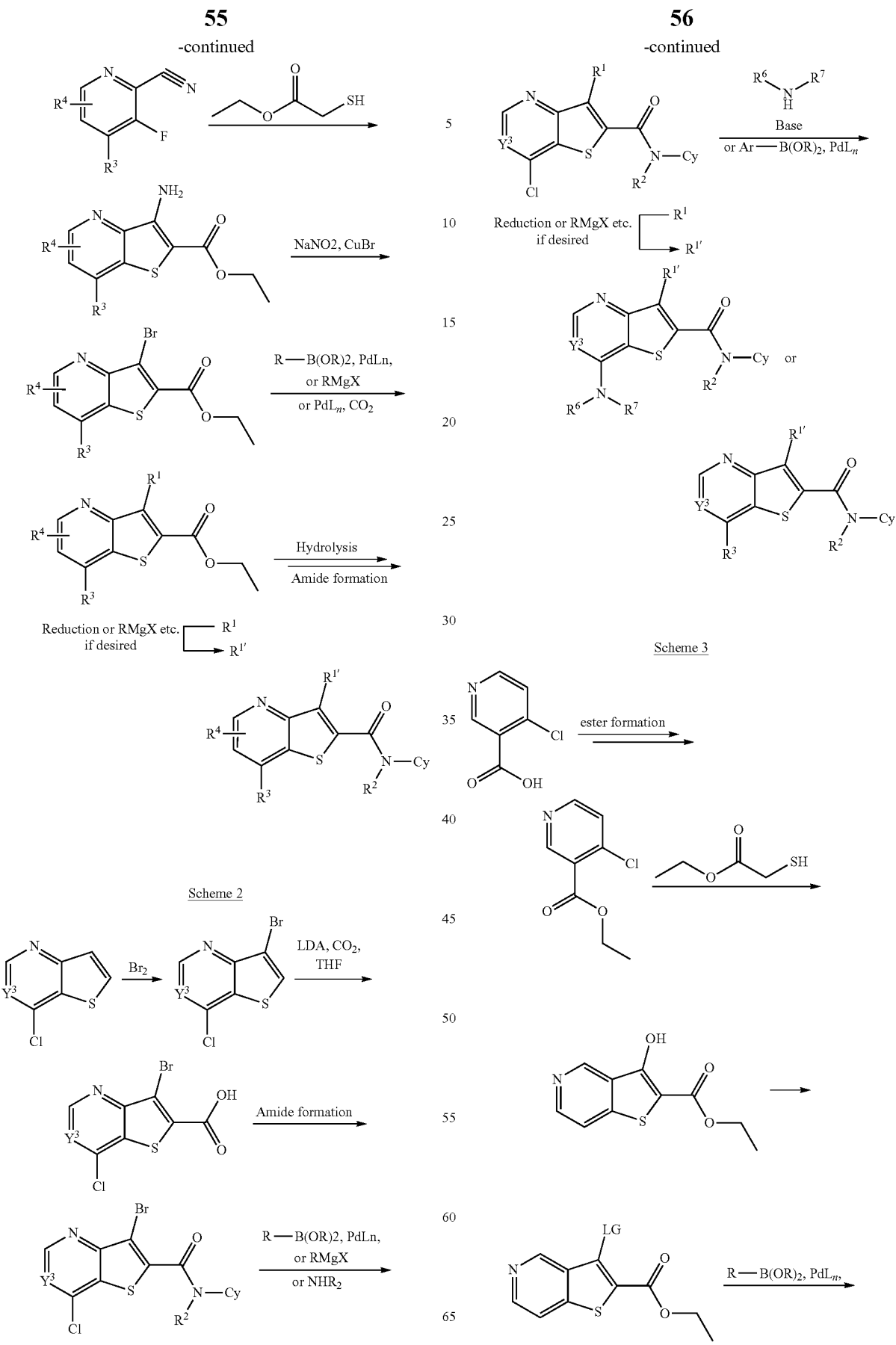

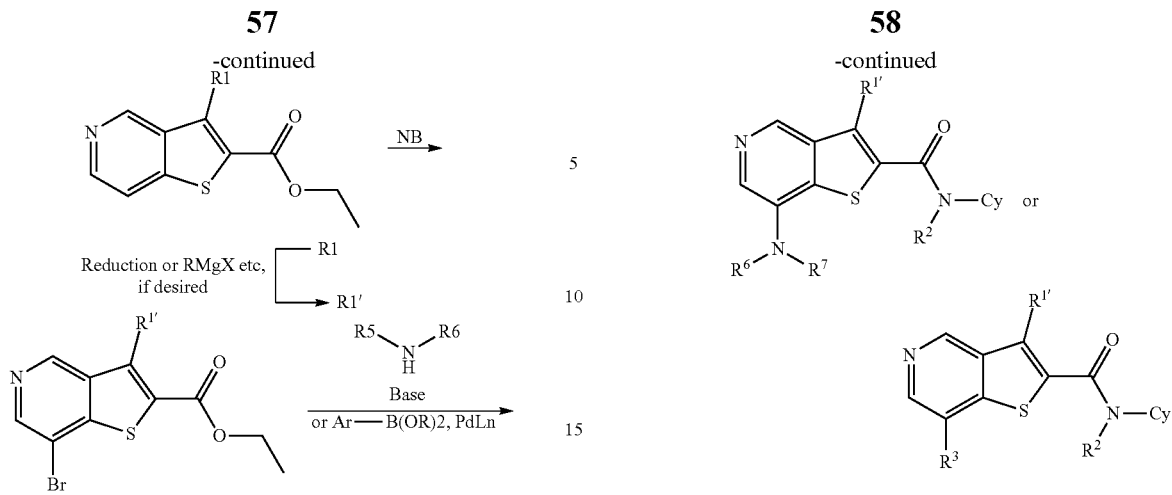
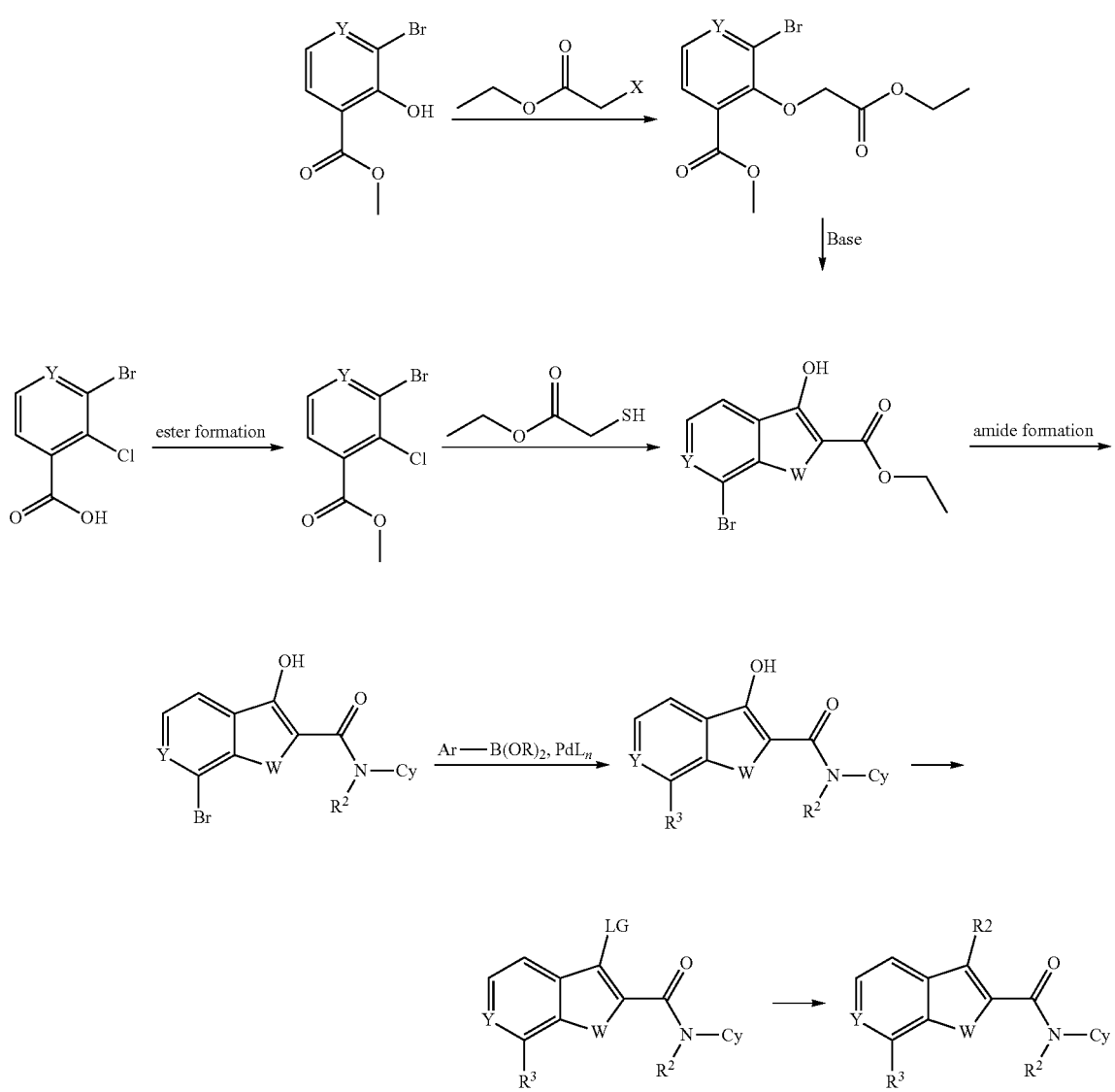
Y = N or C—R⁴ as defined herein
W = O or S

It is well within the skill level of a person of ordinary skill in the art to adapt these schemes to synthesize a specific compound of the invention. Moreover, the starting materials are either readily available or can be made via known procedures.

Veterinary Compositions

The compound and compositions comprising the compound are useful for the prevention and treatment of parasitic infestations/infections in animals. The compositions of the description comprise an effective amount of a compound or a veterinarily acceptable salt thereof, in combination with a veterinarily acceptable carrier or diluent and optionally a non-active excipient. The compositions may be in a variety of solid and liquid forms which are suitable for various forms of application or administration to an animal. For example, the veterinary compositions comprising the compound may be in compositions suitable for oral administration, injectable administration, including subcutaneous and parenteral administration, and topical administration (e.g. spot-on or pour-on), dermal or subdermal administration. The compositions are intended to be administered to an animal including, but not limited to, mammals, birds and fish. Examples of mammals include but are not limited to humans, cattle, sheep, goats, llamas, alpacas, pigs, horses, donkeys, dogs, cats and other livestock or domestic mammals. Examples of birds include turkeys, chickens, ostriches and other livestock or domestic birds. The use of the compound to protect companion animals such as dogs and cats from endoparasites is particularly useful.

As discussed above, the compositions of the description may be in a form suitable for oral use (see, e.g., U.S. Pat. No. 4,564,631, which is hereby incorporated by reference in its entirety), dietary supplements, troches, lozenges, chewables, tablets, hard or soft capsules, bolus, emulsions, aqueous or oily suspensions, aqueous or oily solutions, oral drench compositions, dispersible powders or granules, premixes, syrups or elixirs, enteric compositions or pastes. Compositions intended for oral use may be prepared according to any method known in the art for the manufacture of pharmaceutical compositions and such compositions may contain one or more sweetening agents, bittering agents, flavoring agents, coloring agents and preserving agents in order to provide pharmaceutically elegant and palatable preparations.

Tablets may contain the active ingredient in admixture with non-toxic, pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in U.S. Pat. Nos. 4,256,108; 4,166,452; and 4,265,874 (all incorporated herein by reference in their entirety) to form osmotic therapeutic tablets for controlled release.

Oral compositions include hard gelatin capsules, wherein the active ingredient is mixed with an inert solid diluent, for example, calcium carbonate, calcium phosphate or kaolin. Capsules may also be soft gelatin capsules, wherein the active ingredient is mixed with water or miscible solvents such as propylene glycol, PEGs and ethanol, or an oil medium, for example peanut oil, liquid paraffin, or olive oil.

In one embodiment, the compound may be administered in chewable tablet compositions or soft chewable compositions such as those described in US 2013/0203692 A1, US 2010/0087492, US 2006/0222684, US 2004/0151759, U.S. Pat. No. 7,955,632, all incorporated herein by reference. The veterinary compositions may be in the form of a soft chewable composition ("soft chew") which is palatable and acceptable to the animal. In addition to the active ingredient (s), the soft chews of the description may include one or more of the following components: a solvent or mixture of solvents, one or more fillers, one or more binders, one or more surfactants, one or more humectants, one or more lubricants, one or more disintegrants, one or more colorants, one or more antimicrobial agents, one or more antioxidants, one or more pH modifiers and one or more flavoring agents.

Solvents that may be used in the compositions of the description include, but are not limited to, various grades of liquid polyethylene glycol (PEG) including PEG 200, PEG 300, PEG 400 and PEG 540; propylene carbonate; propylene glycol; triglycerides including, but not limited to caprylic/capric triglyceride, caprylic/capric/linoleic triglyceride (e.g. MIGLYOL® 810 and 812, caprylic/capric/succinic triglyceride, propylene glycol dicaprylate/dicaprate, and the like; water, sorbitol solution, glycerol caprylate/caprate and polyglycolized glycerides (e.g. GELUCIRE®), or a combination thereof.

Various fillers known in the art may be used in the soft chewable compositions of the description. Fillers include, but are not limited to, corn starch, pre-gelatinized corn starch, soy protein fines, corn cob, and corn gluten meal, and the like. In some embodiments, a combination of two or more fillers may be used in the compositions.

Binders that may be used in the compositions of the description include, but are not limited to, polyvinylpyrrolidone (e.g. Povidone), cross-linked polyvinylpyrrolidone (Crospovidone), polyethylene glycols of various grades including PEG 3350, PEG 4000, PEG 6000, PEG 8000 and even PEG 20,000, and the like; co-polymers of vinylpyrrolidone and vinyl acetate (e.g. Copovidone) such as the product sold by BASF by the tradename Kollidon® VA 64 and the like; starch such as potato starch, tapioca starch or corn starch; molasses, corn syrup, honey, maple syrup and sugars of various types; or a combination of two or more binders.

Humectants that may be used in the compositions include, but are not limited to, glycerol (also referred to herein as glycerin), propylene glycol, cetyl alcohol and glycerol monostearate, and the like. Polyethylene glycols of various grades may also be used as humectants.

Surfactants may be present in the composition to improve their solubility and absorption after ingestion. Surfactants are typically present in a concentration of about 1 to 10% (w/w), more typically about 1 to about 5% (w/w). Examples of surfactants that may be used in the compositions include, but are not limited to, glyceryl monooleate, polyoxyethylene sorbitan fatty acid esters, sorbitan esters including sorbitan monooleate (Span® 20), polyvinyl alcohol, polysorbates including polysorbate 20 and polysorbate 80, d-α-tocopheryl polyethylene glycol 1000 succinate (TPGS), sodium lauryl sulfate, co-polymers of ethylene oxide and propylene oxide (e.g. poloxamers such as LUTROL® F87 and the like), polyethylene glycol castor oil derivatives including polyoxyl 35 castor oil (Cremophor® EL), polyoxyl 40 hydrogenated castor oil (Cremophor® RH 40), polyoxyl 60 hydrogenated castor oil (Cremophor® RH60); propylene glycol monolaurate (LAUROGLYCOL®); glyceride esters including glycerol caprylate/caprate (CAPMUL® MCM), polyglycolized glycerides (GELUCIRE®), PEG 300 caprylic/capric glycerides (Softigen® 767), PEG 400 caprylic/capric glycerides (Labrasol®), PEG 300 oleic glycerides (Labrafil® M-1944CS), PEG 300 linoleic glycerides (Labrafil® M-2125CS); polyethylene glycol stearates and polyethylene glycol hydroxy stearates including polyoxyl 8 stearate (PEG 400 monostearate), polyoxyl 40 stearate (PEG 1750 monostearate, and the like.

The compositions may contain other inert ingredients such as antioxidants, preservatives, or pH stabilizers. These compounds are well known in the composition art. Antioxidants may be added to the compositions of the description to inhibit degradation of the active agents. Suitable antioxidants include, but are not limited to, alpha tocopherol, ascorbic acid, ascrobyl palmitate, fumaric acid, malic acid, sodium ascorbate, sodium metabisulfate, n-propyl gallate, BHA (butylated hydroxy anisole), BHT (butylated hydroxy toluene) monothioglycerol and the like.

The compositions of the description may also include one or more lubricants and/or processing aids. In some cases, the lubricant/processing aid may also behave as a solvent, and accordingly, there some of the components of the inventive compositions may have dual functions. Lubricants/processing aids include, but are not limited to polyethylene glycols of various molecular weight ranges including PEG 3350 (Dow Chemical) and PEG 4000, corn oil, mineral oil, hydrogenated vegetable oils (STEROTEX or LUBRITAB), peanut oil and/or castor oil.

Many flavoring agents may be used in the compositions of the description to improve the palatability of the oral veterinary compositions. Preferred flavoring agents are those that are not derived from animal sources. In various embodiments, flavoring components derived from fruit, meat (including, but not limited to pork, beef, chicken, fish, poultry, and the like), vegetable, cheese, bacon, cheese-bacon and/or artificial flavorings may be used. A flavoring component is typically chosen based upon consideration related to the organism that will be ingesting the soft chew. For example, a horse may prefer an apple flavoring component, while a dog may prefer a meat flavoring component. Although flavoring components derived from non-animal sources are preferred, in some embodiments, natural flavors containing beef or liver extracts, etc., may be used such as braised beef flavor artificial powdered beef flavor, roast beef flavor and corned beef flavor among others.

In another embodiment of the description, the active composition may be administered via a drench, and may be administered either topically or orally. Drench compositions are those in which the liquid-containing compositions of the description are administered to the mouth or throat of the animal, or poured onto the skin or coat of the animal.

The compositions of the description may also be in the form of oil-in-water or water-in-oil emulsions. The oily phase maybe a vegetable oil, for example, olive oil or *arachis* oil, or a mineral oil, for example, liquid paraffin or mixtures of these. Suitable emulsifying agents include naturally-occurring phosphatides, for example, soy bean, lecithin, and esters or partial esters derived from fatty acids and hexitol anhydrides, for example, sorbitan monoleate, and condensation products of the said partial esters with ethylene oxide, for example, polyoxyethylene sorbitan monooleate. The emulsions may also contain sweetening agents, bittering agents, flavoring agents, and/or preservatives.

In one embodiment, the composition of the description may be in the form of a microemulsion. Microemulsions are well suited as the liquid carrier vehicle. Microemulsions are quaternary systems comprising an aqueous phase, an oily phase, a surfactant and a cosurfactant. They are translucent and isotropic liquids.

Microemulsions are composed of stable dispersions of microdroplets of the aqueous phase in the oily phase or conversely of microdroplets of the oily phase in the aqueous phase. The size of these microdroplets may be less than 200 nm (1000 to 100,000 nm for emulsions). The interfacial film may be composed of an alternation of surface-active (SA) and co-surface-active (Co-SA) molecules which, by lowering the interfacial tension, allows the microemulsion to be formed spontaneously.

In one embodiment of the oily phase, the oily phase may be formed from mineral or vegetable oils, from unsaturated polyglycosylated glycerides or from triglycerides, or alternatively from mixtures of such compounds. In one embodiment of the oily phase, the oily phase may be comprised of triglycerides; in another embodiment of the oily phase, the triglycerides are medium-chain triglycerides, for example $C_8$-$C_{10}$ caprylic/capric triglyceride. In another embodiment of the oily phase may represent a % v/v range of about 2 to about 15%; about 7 to about 10%; and about 8 to about 9% v/v of the microemulsion.

The aqueous phase may include, for example water or glycol derivatives, such as propylene glycol, glycol ethers, polyethylene glycols or glycerol. In one embodiment, the glycol may be propylene glycol, diethylene glycol monoethyl ether, dipropylene glycol monoethyl ether or mixtures thereof. Generally, the aqueous phase will represent a proportion from about 1 to about 4% v/v in the microemulsion.

Surfactants for the microemulsion may include diethylene glycol monoethyl ether, dipropyelene glycol monomethyl ether, polyglycolyzed $C_8$-$C_{10}$ glycerides or polyglyceryl-6 dioleate. In addition to these surfactants, the cosurfactants may include short-chain alcohols, such as ethanol and propanol.

Some compounds are common to the three components discussed above, i.e., aqueous phase, surfactant and cosurfactant. However, it is well within the skill level of the practitioner to use different compounds for each component of the same composition. In one embodiment for the amount of surfactant/cosurfactant, the cosurfactant to surfactant ratio will be from about ⅐ to about ½. In another embodiment for the amount of cosurfactant, there will be from about 25 to about 75% v/v of surfactant and from about 10 to about 55% v/v of cosurfactant in the microemulsion.

Oily suspensions may be formulated by suspending the active ingredient in a vegetable oil, for example, atachis oil, olive oil, sesame oil or coconut oil, or in mineral oil such as liquid paraffin. The oily suspensions may contain a thickening agent, for example, beeswax, hard paraffin or cetyl alcohol. Sweetening agents such as sucrose, saccharin or aspartame, bittering agents, and flavoring agents may be added to provide a palatable oral preparation. These compositions may be preserved by the addition of an anti-oxidant such as ascorbic acid, or other known preservatives.

Aqueous suspensions may contain the active material in admixture with excipients suitable for the manufacture of aqueous suspensions. Such excipients include suspending agents, for example, sodium carboxymethylcellulose, methylcellulose, hydroxy-propylmethylcellulose, sodium alginate, polvinylpyrrolidone, gum tragacanth and gum acacia; dispersing or wetting agents include naturally-occurring phosphatide, for example lecithin, or condensation products of an alkylene oxide with fatty acids, for example polyoxyethylene stearate, or condensation products of ethylene oxide with long chain aliphatic alcohols, for example, heptadecaethyleneoxycetanol, or condensation products of ethylene oxide with partial esters derived from fatty acids and a hexitol such as polyoxyethylene sorbitol monooleate, or condensation products of ethylene oxide, with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents and/or bittering agents, such as those set forth above.

Dispersible powders and granules suitable for preparation of an aqueous suspension by the addition of water may provide the active ingredient in admixture with a dispersing or wetting agent, suspending agent and one or more preservatives. Suitable dispersing or wetting agents and suspending agents are exemplified by those already mentioned above. Additional excipients, for example, sweetening, bittering, flavoring and coloring agents, may also be present.

Syrups and elixirs may be formulated with sweetening agents, for example, glycerol, propylene glycol, sorbitol or sucrose. Such compositions may also contain a demulcent, a preservative, flavoring agent(s) and/or coloring agent(s).

In another embodiment of the description, the composition may be in paste form. Examples of embodiments in a paste form include, but are not limited to, those described in U.S. Pat. Nos. 6,787,342 and 7,001,889 (each of which are incorporated herein by reference). In addition to the compounds of the description, the paste may further contain fumed silica; a viscosity modifier; a carrier; optionally, an absorbent; and optionally, a colorant, stabilizer, surfactant, or preservative.

In one embodiment of the composition, the composition may be a paste containing the compounds of the description, fumed silica, a viscosity modifier, an absorbent, a colorant; and a hydrophilic carrier which is triacetin, a monoglyceride, a diglyceride, or a triglyceride.

The paste may also include a viscosity modifier. Suitable viscosity modifiers include, but are not limited to, polyethylene glycols (PEG) including, but not limited to, PEG 200, PEG 300, PEG 400, PEG 600; monoethanolamine, triethanolamine, glycerol, propylene glycol, polyoxyethylene (20) sorbitan mono-oleate (polysorbate 80 or Tween 80), or poloxamers (e.g., Pluronic L 81); an absorbent such as magnesium carbonate, calcium carbonate, starch, and cellulose and its derivatives; and a colorant including, but not limited to, titanium dioxide iron oxide, or FD&C Blue #1 Aluminum Lake.

In some embodiments, the compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example, as a solution in 1,3-butane diol. Among the acceptable vehicles and solvents that may be employed are water, Ringer's solution and isotonic sodium chloride solution. Cosolvents such as ethanol, propylene glycol, glycerol formal or polyethylene glycols may also be used. Preservatives, such as phenol or benzyl alcohol, may be used.

In addition, sterile, fixed oils may be conventionally employed as a solvent or suspending medium. For this purpose any bland fixed oil may be employed including synthetic mono- or diglycerides. In addition, fatty acids such as oleic acid find use in the preparation of injectables.

Topical, dermal and subdermal compositions may include, by way of non-limiting example, emulsions, creams, ointments, gels, pastes, powders, shampoos, pour-on compositions, ready-to-use compositions, spot-on solutions and suspensions, dips and sprays. Topical application of an inventive compound or of a composition including at least one inventive compound among active agent(s) therein, in the form of a spot-on, spray-on or pour-on composition, may allow for the inventive composition to be absorbed through the skin to achieve systemic levels, distributed through the sebaceous glands or on the surface of the skin achieving levels throughout the coat. When the compound is distributed through the sebaceous glands, they may act as a reservoir, whereby there may be a long-lasting effect (up to several months) effect. Spot-on compositions are typically applied in a localized region which refers to an area other than the entire animal. In one embodiment, the location may be between the shoulders. In another embodiment it may be a stripe, e.g. a stripe from head to tail of the animal.

Pour-on compositions are described in U.S. Pat. No. 6,010,710, also incorporated herein by reference. Pour-on compositions may be advantageously oily, and generally comprise a diluent or vehicle and also a solvent (e.g. an organic solvent) for the active ingredient if the latter is not soluble in the diluent.

Organic solvents that can be used in the description include, but are not limited to, acetyltributyl citrate, fatty acid esters such as the dimethyl ester, diisobutyl adipate, acetone, acetonitrile, benzyl alcohol, ethyl alcohol, butyl diglycol, dimethylacetamide, dimethylformamide, dimethyl sulfoxide, dipropylene glycol n-butyl ether, ethanol, isopropanol, methanol, ethylene glycol monoethyl ether, ethylene glycol monomethyl ether, monomethylacetamide, dipropylene glycol monomethyl ether, liquid polyoxyethylene glycols, propylene glycol, 2-pyrrolidone (e.g. N-methylpyrrolidone), diethylene glycol monoethyl ether, ethylene glycol, triacetin, $C_1$-$C_{10}$ esters of carboxylic acids such as butyl or octyl acetate, and diethyl phthalate, or a mixture of at least two of these solvents.

The solvent will be used in proportion with the concentration of the active agent compound and its solubility in this solvent. It will be sought to have the lowest possible volume. The vehicle makes up the difference to 100%.

A vehicle or diluent for the compositions may include dimethyl sulfoxide (DMSO), glycol derivatives such as, for example, propylene glycol, glycol ethers, polyethylene glycols or glycerol. As vehicle or diluent, mention may also be made of plant oils such as, but not limited to soybean oil, groundnut oil, castor oil, corn oil, cotton oil, olive oil, grape seed oil, sunflower oil, etc.; mineral oils such as, but not limited to, petrolatum, paraffin, silicone, etc.; aliphatic or cyclic hydrocarbons or alternatively, for example, medium-chain (such as $C_8$ to $C_{12}$) triglycerides.

In another embodiment of the description, an emollient and/or spreading and/or film-forming agent may be added. In one embodiment, the emollient and/or spreading and/or film-forming agent may be:

(a) polyvinylpyrrolidone, polyvinyl alcohols, copolymers of vinyl acetate and vinylpyrrolidone, polyethylene glycols, benzyl alcohol, mannitol, glycerol, sorbitol, polyoxyethylenated sorbitan esters; lecithin, sodium carboxymethylcellulose, silicone oils, polydiorganosiloxane oils (such as polydimethylsiloxane (PDMS) oils), for example those containing silanol functionalities, or a 45V2 oil, (b) anionic surfactants such as alkaline stearates, sodium, potassium or ammonium stearates; calcium stearate, triethanolamine stearate; sodium abietate; alkyl sulphates (e.g. sodium lauryl sulphate and sodium cetyl sulphate); sodium dodecylbenzenesulphonate, sodium dioctylsulphosuccinate; fatty acids (e.g. those derived from coconut oil), (c) cationic surfactants include water-soluble quaternary ammonium salts of formula N+R'R"R'"R"", Y⁻ in which the radicals R are optionally hydroxylated hydrocarbon radicals and Y⁻ is an anion of a strong acid such as the halide, sulphate and sulphonate anions; cetyltrimethylammonium bromide is among the cationic surfactants which can be used, (d) amine salts of formula N⁺ HR'R"R'" in which the radicals R are optionally hydroxylated hydrocarbon radicals; octadecylamine hydrochloride is among the cationic surfactants which can be used, (e) nonionic surfactants such as sorbitan esters, which are optionally polyoxyethylenated (e.g. polysorbate 80), polyoxyethylenated alkyl ethers; polyoxypropylated fatty alcohols such as polyoxypropylene-styrol ether; polyethylene glycol stearate, polyoxyethylenated derivatives of castor oil, polyglycerol esters, polyoxyethylenated fatty alcohols, polyoxyethylenated fatty acids, copolymers of ethylene oxide and propylene oxide, (f) amphoteric surfactants such as the substituted lauryl compounds ofbetaine; or (g) a mixture of at least two of these agents.

In one embodiment of the amount of emollient, the emollient used may be in a proportion of from about 0.1 to 50% or 0.25 to 5%, by volume. In another embodiment, the emollient used may be in a proportion of from about 0.1% to about 30%, about 1% to about 30%, about 1% to about 20%, or about 5% to about 20% by volume.

In another embodiment of the description, the composition may be in ready-to-use solution form as is described in U.S. Pat. No. 6,395,765, incorporated herein by reference. In addition to the compounds of the description, the ready-to-use solution may contain a crystallization inhibitor and an organic solvent or a mixture of organic solvents. In some embodiments, water may be included with the organic solvent.

In various embodiments of the description, the compositions may include a crystallization inhibitor in an amount of about 1 to about 50% (w/v) or about 5 to about 40% (w/v) based on the total weight of the composition. In other embodiments, the amount of crystallization inhibitor in the inventive compositions may be about 1% to about 30%, about 5% to about 20%, about 1% to about 15%, or about 1% to about 10% (w/w). The type of crystallization inhibitor used in the inventive compositions is not limited as long as it functions to inhibit crystallization of the active or inactive agents from the composition. For example, in certain embodiments of the description, a solvent or co-solvent of the composition may also function as a crystallization inhibitor if it sufficiently inhibits the formation of crystals from forming over time when the composition is administered.

Crystallization inhibitors which are useful for the description include, but are not limited to:

(a) polyvinylpyrrolidone, polyvinyl alcohols, copolymers of vinyl acetate and vinylpyrrolidone, polyethylene glycols, benzyl alcohol, dimethylformamide, dimethylacetamide, dimethylsulfoxide, 2-pyrrolidone, N-methylpyrrolidone, mannitol, glycerol, sorbitol or polyoxyethylenated esters of sorbitan; lecithin or sodium carboxymethylcellulose; or acrylic derivatives, such as acrylates or methacrylates or polymers or copolymers thereof, polyethyleneglycols (PEG) or polymers containing polyethyleneglycols, such as glycofurol and the like, and others;

(b) anionic surfactants, such as alkaline stearates (e.g. sodium, potassium or ammonium stearate); calcium stearate or triethanolamine stearate; sodium abietate; alkyl sulphates, which include but are not limited to sodium lauryl sulphate and sodium cetyl sulphate; sodium dodecylbenzenesulphonate or sodium dioctyl sulphosuccinate; or fatty acids (e.g. coconut oil);

(c) cationic surfactants, such as water-soluble quaternary ammonium salts of formula N+R'R"R'"R""Y⁻, in which the R radicals are identical or different optionally hydroxylated hydrocarbon radicals and Y⁻ is an anion of a strong acid, such as halide, sulphate and sulphonate anions; cetyltrimethylammonium bromide is one of the cationic surfactants which can be used;

(d) amine salts of formula N+HR'R"R'", in which the R radicals are identical or different optionally hydroxylated hydrocarbon radicals; octadecylamine hydrochloride is one of the cationic surfactants which can be used;

(e) non-ionic surfactants, such as optionally polyoxyethylenated esters of sorbitan, e.g. Polysorbate 80, or polyoxyethylenated alkyl ethers; polyethylene glycol stearate, polyoxyethylenated derivatives of castor oil, polyglycerol esters, polyoxyethylenated fatty alcohols, polyoxyethylenated fatty acids or copolymers of ethylene oxide and of propylene oxide;

(f) amphoteric surfactants, such as substituted lauryl compounds of betaine;

(g) a mixture of at least two of the compounds listed in (a)-(f) above; or (h) an organic solvent or mixture of solvents which inhibit the formation of crystals or amorphous solid after the composition is administered.

In one embodiment of the crystallization inhibitor, a crystallization inhibitor pair will be used. Such pairs include, for example, the combination of a film-forming agent of polymeric type and of a surface-active agent. These agents will be selected from the compounds mentioned above as crystallization inhibitor.

In some embodiments, the organic solvent(s) may have a dielectric constant of between about 10 and about 35 or between about 20 and about 30. In other embodiments, the organic solvent may have a dielectric constant of between about 10 and about 40 or between about 20 and about 30. The content of this organic solvent or mixture of solvents in the overall composition is not limited and will be present in an amount sufficient to dissolve the desired components to a desired concentration. As discussed above, the organic solvent may also function as a crystallization inhibitor in the composition.

In some embodiments, one or more of the organic solvent(s) may have a boiling point of below about 100° C., or below about 80° C. In other embodiments, the organic solvent(s) may have a boiling point of below about 300° C., below about 250° C., below about 230° C., below about 210° C. or below about 200° C.

In some embodiments where there is a mixture of solvents, i.e. a solvent and a co-solvent, the solvents may be present in the composition in a weight/weight (W/W) ratio of about 1/50 to about 1/1. Typically the solvents will be in a ratio of about 1/30 to about 1/1, about 1/20 to about 1/1, or about 1/15 to about 1/1 by weight. Preferably, the two solvents will be present in a weight/weight ratio of about 1/15 to about 1/2. In some embodiments, at least one of the solvents present may act as to improve solubility of the active agent or as a drying promoter. In particular embodiments, at least one of the solvents will be miscible with water.

The composition may also comprise an antioxidizing agent intended to inhibit oxidation in air, this agent may be present in a proportion of about 0.005 to about 1% (w/v), about 0.01 to about 0.1%, or about 0.01 to about 0.05%.

In one embodiment of the film-forming agent, the agents are of the polymeric type which include but are not limited to the various grades of polyvinylpyrrolidone, polyvinyl alcohols, and copolymers of vinyl acetate and of vinylpyrrolidone.

In one embodiment of the surface-active agents, the agents include but are not limited to those made of non-ionic surfactants; in another embodiment of the surface active agents, the agent is a polyoxyethylenated esters of sorbitan and in yet another embodiment of the surface-active agent, the agents include the various grades of polysorbate, for example Polysorbate 80.

In another embodiment of the description, the film-forming agent and the surface-active agent may be incorporated in similar or identical amounts within the limit of the total amounts of crystallization inhibitor mentioned elsewhere.

The crystallization inhibitor inhibits the formation of crystals on the coat, and improves the maintenance of the cosmetic appearance of the skin or fur; that is to say without a tendency towards sticking or towards a sticky appearance, despite the high concentration of active material. Substances other than those mentioned herein may be used as crystallization inhibitors in the present description. In one embodiment, the effectiveness of the crystallization inhibitor may be demonstrated by a test according to which 0.3 mL of a solution comprising 10% (w/v) of the active agent in an appropriate solvent as defined above, and 10% (w/v) of the compound acting as a crystallization inhibitor are placed on a glass slide at 20° C. for 24 hours, after which fewer than 10 crystals, preferably 0 crystals, are seen with the naked eye on the glass slide.

In one embodiment of the antioxidizing agents, the agents are those conventional in the art and include but are not limited to butylated hydroxyanisole, butylated hydroxytoluene, ascorbic acid, sodium metabisulphite, propyl gallate, sodium thiosulphate or a mixture of at least two compounds with antioxidant properties.

The composition adjuvants discussed above are well known to the practitioner in this art and may be obtained commercially or through known techniques. These concentrated compositions are generally prepared by simple mixing of the constituents as defined above; advantageously, the starting point is to mix the active material in the main solvent and then the other ingredients or adjuvants are added.

The volume of the composition applied will depend on the type of animal and the size of the animal as well as the strength of the composition and the potency of the active agents. In one embodiment, an amount of about 0.1 to about 20 ml of the composition may be applied to the animal. In other embodiment for the volume, the volume may be about 0.1 to about 10 ml, about 0.1 to about 5 ml, about 0.5 ml to about 10 ml, or about 0.3 to about 3 ml.

In another embodiment of the description, application of a spot-on composition according to the present description may also provide long-lasting and broad-spectrum efficacy when the solution is applied to the mammal or bird. The spot-on compositions provide for topical administration of a concentrated solution, suspension, microemulsion or emulsion for intermittent application to a spot on the animal, generally between the two shoulders (solution of spot-on type).

For spot-on compositions, the carrier may be a liquid carrier vehicle as described in U.S. Pat. No. 6,426,333 (incorporated herein by reference), which in one embodiment of the spot-on composition may comprise a solvent or mixture of solvents including, but not limited to, acetone, an aliphatic alcohol such as methanol, ethanol, propanol, butanol, isopropanol, pentanol, hexanol, heptanol, octanol, nonanol, cyclopentanol, cyclohexanol, ethylene glycol, propylene glycol and the like; an aromatic alcohol such as phenol, cresol, naphthol, benzyl alcohol and the like; acetonitrile, butyl diglycol, an organic amide such as dimethylacetamide, dimethylformamide, monomethylacetamide, 2-pyrrolidone, N-methylpyrrolidone, vinylpyrrolidone and the like; propylene or ethylene carbonate, dimethylsulfoxide (DMSO), a glycol polymer or an ether thereof, such as polyethylene glycol (PEG) of various grades, polypropylene glycols of various grades, dipropylene glycol n-butyl ether, ethylene glycol monoethyl ether, ethylene glycol monomethyl ether, dipropylene glycol monomethyl ether, diethylene glycol monoethyl ether, ethylene glycol, diethyl phthalate fatty acid esters, such as the diethyl ester or diisobutyl adipate, or a mixture of at least two of these solvents.

The liquid carrier vehicle may optionally contain a crystallization inhibitor including, but not limited to, those described in (a) to (h) above, or a compound that may act both as a solvent and a crystallization inhibitor (as defined above), or a mixture of these crystallization inhibitors.

Spot-on compositions may be prepared by dissolving the active ingredients into the pharmaceutically or veterinary acceptable vehicle. Alternatively, the spot-on composition may be prepared by encapsulation of the active ingredient to leave a residue of the therapeutic agent on the surface of the animal. These compositions will vary with regard to the weight of the therapeutic agent in the combination depending on the species of host animal to be treated, the severity and type of infection and the body weight of the host.

Dosage forms may typically contain from about 0.1 mg to about 5 g. In other embodiments, the dosage form may contain about 0.5 mg to about 5 g of an active agent. In one embodiment of the dosage form, the dosage may contain from about 1 mg to about 500 mg of an active agent, typically about 25 mg, about 50 mg, about 100 mg, about 200 mg, about 300 mg, about 400 mg, about 500 mg, about 600 mg, about 800 mg, or about 1000 mg.

In one embodiment of the description, the compound of Formula (I) may be present in the composition at a concentration of about 0.05 to about 50% weight/weight. In other embodiments, the compound of Formula (I) may be present in a concentration of about 0.1 to about 30% (w/w).

In other embodiments, the compound of Formula (I) may be present in a concentration of about 0.5 to about 30% (w/w), about 1 to about 20% (w/w) or about 0.05 to about 10% (w/w). In other embodiments, the compound of Formula (I) may be present in a concentration of about 10 to about 50% (w/w), about 10 to about 30% (w/w), about 10 to about 20% (w/w). In yet another embodiment, the compound of Formula (I) may be present in a concentration of about 1 to 10% (w/w) or about 5 to about 15% (w/w). In another embodiment of the description, the active agent may be present in the composition as a concentration from about 0.1 to about 2% w/w. In yet another embodiment of the description, the active agent may be present in the composition as a concentration from about 0.25 to about 1.5% w/w.

In still another embodiment of the description, the active agent may be present in the composition as a concentration about 1% w/w.

Methods of Treatment

As discussed above, the compound of Formula (I) are effective against endoparasites and may be used to treat and prevent parasitic infections in animals. In one embodiment, the present description provides a method of treating or preventing an endoparasite infection in or on an animal (e.g. a mammal or bird) comprising administering an endoparasiticidally effective amount of a compound of formula (I), or veterinarily acceptable salts thereof, or a composition of the description, to the animal.

In certain embodiments, the compound of Formula (I) may also effective against ectoparasites and may be used to treat and prevent ectoparasitic infestations on animals. In another embodiment, the present description provides a method of treating or preventing an ectoparasitic infestation on an animal (e.g. a mammal or bird) comprising administering an ectoparasiticidally effective amount of a compound of formula (I), or veterinarily acceptable salts thereof, or a composition of the description, to the animal.

In another embodiment, the description provides a method for treating or preventing an endoparasitic infection and an ectoparasitic infestation in and on an animal, comprising administering a composition comprising an effective amount of a compound of formula (I) in combination with an effective amount of at least a second active agent, or veterinarily acceptable salts thereof, to the animal.

In still another embodiment of the description, a method is provided for the treatment or prevention of a parasitic infestation at a locus, which comprises administering or applying a parasiticidally effective amount of a compound of formula (I), or veterinarily acceptable salts thereof, to the locus. With respect to animal health applications, "locus" is intended to mean a habitat, breeding ground, area, material or environment in which a parasite is growing or may grow, excluding in or on an animal.

In another embodiment, the description provides methods and uses of the compound for controlling pests in plants and crops or for protecting wood-containing structures.

Mammals which can be treated include but are not limited to humans, cats, dogs, cattle, chickens, cows, bison, deer, goats, horses, llamas, camels, pigs, sheep and yaks. In one embodiment of the description, the mammals treated are humans, cats or dogs.

In one embodiment of the description, the compounds of Formula (I) have been found to have superior efficacy against endoparasites, and in particular against endoparasites that are resistant to active agents of the macrocyclic lactone class. In one embodiment, the compounds and compositions of the description are effective for controlling *Haemonchus contortus*, *Ostertagia circumcincta* and *Trichostrongylus colubriformis* in mammals or birds.

In another embodiment, the description provides a method for treating an parasitic infestation or infection in an animal, comprising administering an effective amount of an anthelmintic compound of the description in combination with an effective amount of activators of invertebrate GABA receptors including an avermectin or milbemycin to the animal in need thereof. Avermectins that may be used in combination with the compounds of the description include, but are not limited to abamectin, dimadectin, doramectin, emamectin, eprinomectin, ivermectin, latidectin, lepimectin, and selamectin Milbemycins compounds that may be used in combination with the compounds of the description include, but are not limited to, milbemectin, milbemycin D, moxidectin and nemadectin. Also included are the 5-oxo and 5-oxime derivatives of said avermectins and milbemycins.

In one embodiment, the compounds and compositions of the description may be used for treating or preventing an endoparasitic infection of the following parasite: *Anaplocephala* (*Anoplocephala*), *Ancylostoma*, *Necator*, *Ascaris*, *Brugia*, *Bunostomum*, *Capillaria*, *Chabertia*, *Cooperia*, *Cyathostomum*, *Cylicocyclus*, *Cylicodontophorus*, *Cylicostephanus*, *Craterostomum*, *Dictyocaulus*, *Dipetalonema*, *Dipylidium*, *Dirofilaria*, *Dracunculus*, *Echinococcus*, *Enterobius*, *Fasciola*, *Filaroides*, *Habronema*, *Haemonchus*, *Metastrongylus*, *Moniezia*, *Necator*, *Nematodirus*, *Nippostrongylus*, *Oesophagostomum*, *Onchocerca*, *Ostertagia*, *Oxyuris*, *Parascaris*, *Schistosoma*, *Strongylus*, *Taenia*, *Toxocara*, *Strongyloides*, *Toxascaris*, *Trichinella*, *Trichuris*, *Trichostrongylus*, *Triodontophorus*, *Uncinaria*, *Wuchereria*, and combinations thereof.

In a particularly preferred embodiment of the description, the compounds and compositions of the description are used to treat or prevent an infection by *Dirofilaria immitis*. The compounds have been found to be highly effective against *D. immitis* microfilaria and L4 larvae. Thus, the compounds may be used to protect animals from developing heartworm disease by killing the immature stages of *D. immitis* before they can develop into adult worms. In one embodiment, the compound and compositions comprising the compounds may be used to prevent the development of heartworm disease by killing immature stages of *D. immitis* that are resistant to macrocyclic lactones. In another embodiment the compounds and compositions of the description are used to treat or prevent an infection by *Dirofilaria repens* or *Dirofilaria hongkongensis*.

In another embodiment of the description, the parasite is *Haemonchus contortus*, *Ostertagia circumcincta*, *Trichostrongylus axei*, *Trichostrongylus colubriformis*, *Cooperia curticei*, *Nematodirus battus* and combinations thereof.

In another embodiment for treatment against both endoparasites and ectoparasites when combined with ectoparasiticidal agents, the ectoparasite is one or more insect or arachnid including those of the genera *Ctenocephalides*, *Rhipicephalus*, *Dermacentor*, *Ixodes*, *Boophilus*, *Amblyomma*, *Haemaphysalis*, *Hyalomma*, *Sarcoptes*, *Psoroptes*, *Otodectes*, *Chorioptes*, *Hypoderma*, *Damalinia*, *Linognathus*, *Haematopinus*, *Solenoptes*, *Trichodectes*, and *Felicola*.

In another embodiment for the treatment against ectoparasites, the ectoparasite is from the genera *Ctenocephalides*, *Rhipicephalus*, *Dermacentor*, *Ixodes* and/or *Boophilus*. The ectoparasites treated include but are not limited to fleas, ticks, mites, mosquitoes, flies, lice, blowfly and combinations thereof. Specific examples include but are not limited to cat and dog fleas (*Ctenocephalides felis*, *Ctenocephalides* spp. and the like), ticks (*Rhipicephalus* spp., *Ixodes* spp., *Dermacentor* spp., *Amblyomma* spp. and the like), and mites (*Demodex* spp., *Sarcoptes* spp., *Otodectes* spp. and the like), lice (*Trichodectes* spp., *Cheyletiella* spp., *Linognathus* spp., and the like), mosquitoes (*Aedes* spp., *Culex* spp., *Anopheles* spp., and the like) and flies (*Haematobia* spp., *Musca* spp., *Stomoxys* spp., *Dermatobia* spp., *Cochliomyia* spp., and the like). In yet another embodiment for the treatment against ectoparasites, the ectoparasite is a flea and/or tick.

Additional examples of ectoparasites include but are not limited to the tick genus *Boophilus*, especially those of the species *microplus* (cattle tick), *decoloratus* and *annulatus*; myiasis such as *Dermatobia hominis* (known as Berne in Brazil) and *Cochliomyia hominivorax* (greenbottle); sheep myiasis such as *Lucilia sericata*, *Lucilia cuprina* (known as blowfly strike in Australia, New Zealand and South Africa). Flies proper, namely those whose adult constitutes the parasite, such as *Haematobia irritans* (horn fly); lice such as *Linognathus vitulorum*, etc.; and mites such as *Sarcoptes scabiei* and *Psoroptes ovis*. The above list is not exhaustive and other ectoparasites are well known in the art to be harmful to animals and humans. These include, for example migrating dipterous larvae.

In another embodiment of the description, the compounds and compositions of the description are suitable for controlling pests such as insects selected from the group consisting of *Blatella germanica, Heliothis virescens, Leptinotarsa decemlineata, Tetramorium caespitum* and combinations thereof.

The phytoparasitic nematodes include, for example, *Anguina* spp., *Aphelenchoides* spp., *Belonoaimus* spp., *Bursaphelenchus* spp., *Ditylenchus dipsaci, Globodera* spp., *Heliocotylenchus* spp., *Heterodera* spp., *Longidorus* spp., *Meloidogyne* spp., *Pratylenchus* spp., *Radopholus similis, Rotylenchus* spp., *Trichodorus* spp., *Tylenchorhynchus* spp., *Tylenchulus* spp., *Tylenchulus semipenetrans, Xiphinema* spp.

In addition, with or without the other pesticidal agents added to the composition, the description can also be used to treat other pests which include but are not limited to pests:

(1) from the order of Isopoda, for example *Oniscus asellus, Armadillidium vulgare* and *Porcellio scaber;*

(2) from the order of Diplopoda, for example *Blaniulus guttulatus;*

(3) from the order of Chilopoda, for example *Geophilus carpophagus* and *Scutigera* spp.;

(4) from the order of Symphyla, for example *Scutigerella immaculata;*

(5) from the order of Thysanura, for example *Lepisma saccharina;*

(6) from the order of Collembola, for example *Onychiurus armatus;*

(7) from the order of Blattaria, for example *Blatta orientalis, Periplaneta americana, Leucophaea maderae* and *Blattella germanica;*

(8) from the order of Hymenoptera, for example *Diprion* spp., *Hoplocampa* spp., *Lasius* spp., *Monomorium pharaonis* and *Vespa* spp.;

(9) from the order of Siphonaptera, for example *Xenopsylla cheopis* and *Ceratophyllus* spp.;

(10) from the order of Anoplura (Phthiraptera), for example, *Damalinia* spp., *Haematopinus* spp., *Linognathus* spp., *Pediculus* spp., *Trichodectes* spp.;

(11) from the class of Arachnida, for example, *Acarus siro, Aceria sheldoni, Aculops* spp., *Aculus* spp., *Amblyomma* spp., *Argas* spp., *Boophilus* spp., *Brevipalpus* spp., *Bryobia praetiosa, Chorioptes* spp., *Dermanyssus gallinae, Eotetranychus* spp., *Epitrimerus pyri, Eutetranychus* spp., *Eriophyes* spp., *Hemitarsonemus* spp., *Hyalomma* spp., *Ixodes* spp., *Latrodectus mactans, Metatetranychus* spp., *Oligonychus* spp., *Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vasates lycopersici.;*

(12) from the class of Bivalva, for example, *Dreissena* spp.;

(13) from the order of Coleoptera, for example, *Acanthoscelides obtectus, Adoretus* spp., *Agelastica alni, Agriotes* spp., *Amphimallon solstitialis, Anobium punctatum, Anoplophora* spp., *Anthonomus* spp., *Anthrenus* spp., *Apogonia* spp., *Atomaria* spp., *Attagenus* spp., *Bruchidius obtectus, Bruchus* spp., *Ceuthorhynchus* spp., *Cleonus mendicus, Conoderus* spp., *Cosmopolites* spp., *Costelytra zealandica, Curculio* spp., *Cryptorhynchus lapathi, Dermestes* spp., *Diabrotica* spp., *Epilachna* spp., *Faustinus cubae, Gibbium psylloides, Heteronychus arator, Hylamorpha elegans, Hylotrupes bajulus, Hypera postica, Hypothenemus* spp., *Lachnosterna consanguinea, Leptinotarsa decemlineata, Lissorhoptrus oryzophilus, Lixus* spp., *Lyctus* spp., *Meligethes aeneus, Melolontha, Migdolus* spp., *Monochamus* spp., *Naupactus xanthographus, Niptus hololeucus, Oryctes rhinoceros, Oryzaephilus surinamensis, Otiorrhynchus sulcatus, Oxycetonia jucunda, Phaedon cochleariae, Phyllophaga* spp., *Popillia japonica, Premnotrypes* spp., *Psylliodes chrysocephala, Ptinus* spp., *Rhizobius ventralis, Rhizopertha dominica, Sitophilus* spp., *Sphenophorus* spp., *Sternechus* spp., *Symphyletes* spp., *Tenebrio molitor, Tribolium* spp., *Trogoderma* spp., *Tychius* spp., *Xylotrechus* spp., *Zabrus* spp.;

(14) from the order of Diptera, for example, *Aedes* spp., *Anopheles* spp., *Bibio hortulanus, Calliphora erythrocephala, Ceratitis capitata, Chrysomyia* spp., *Cochliomyia* spp., *Cordylobia anthropophaga, Culex* spp., *Cuterebra* spp., *Dacus oleae, Dermatobia hominis, Drosophila* spp., *Fannia* spp., *Gastrophilus* spp., *Hylemyia* spp., *Hyppobosca* spp., *Hypoderma* spp., *Liriomyza* spp., *Lucilia* spp., *Musca* spp., *Nezara* spp., *Oestrus* spp., *Oscinella* fit, *Pegomyia hyoscyami, Phorbia* spp., *Stomoxys* spp., *Tabanus* spp., *Tannia* spp., *Tipulapaludosa, Wohlfahrtia* spp.;

(15) from the class of Gastropoda, for example, *Arion* spp., *Biomphalaria* spp., *Bulinus* spp., *Deroceras* spp., *Galba* spp., *Lymnaea* spp., *Oncomelania* spp., *Succinea* spp.;

(16) from the class of helminths, for example, *Ancylostoma duodenale, Ancylostoma ceylanicum, Ancylostoma braziliensis, Ancylostoma* spp., *Ascaris lumbricoides, Ascaris* spp., *Brugia malayi, Brugia timori, Bunostomum* spp., *Chabertia* spp., *Clonorchis* spp., *Cooperia* spp., *Dicrocoelium* spp, *Dictyocaulus filaria, Diphyllobothrium latum, Dracunculus medinensis, Echinococcus granulosus, Echinococcus multilocularis, Enterobius vermicularis, Faciola* spp., *Haemonchus* spp., *Heterakis* spp., *Hymenolepis nana, Hyostrongulus* spp., *Loa, Nematodirus* spp., *Oesophagostomum* spp., *Opisthorchis* spp., *Onchocerca volvulus, Ostertagia* spp., *Paragonimus* spp., *Schistosomen* spp., *Strongyloides fuelleborni, Strongyloides stercoralis, Strongyloides* spp., *Taenia saginata, Taenia solium, Trichinella spiralis, Trichinella nativa, Trichinella britovi, Trichinella nelsoni, Trichinella pseudopsiralis, Trichostrongulus* spp., *Trichuris trichiura, Wuchereria bancrofti.;*

(17) from the order of Heteroptera, for example, *Anasa tristis, Antestiopsis* spp., *Blissus* spp., *Calocoris* spp., *Campylomma livida, Cavelerius* spp., *Cimex* spp., *Creontiades dilutus, Dasynus piperis, Dichelops furcatus, Diconocoris hewetti, Dysdercus* spp., *Euschistus* spp., *Eurygaster* spp., *Heliopeltis* spp., *Horcias nobilellus, Leptocorisa* spp., *Leptoglossus phyllopus, Lygus* spp., *Macropes excavatus, Miridae, Nezara* spp., *Oebalus* spp., *Pentomidae, Piesma quadrata, Piezodorus* spp., *Psallus seriatus, Pseudacysta persea, Rhodnius* spp., *Sahlbergella singularis, Scotinophora* spp., *Stephanitis nashi, Tibraca* spp., *Triatoma* spp.;

(18) from the order of Homoptera, for example, *Acyrthosipon* spp., *Aeneolamia* spp., *Agonoscena* spp., *Aleurodes* spp., *Aleurolobus barodensis, Aleurothrixus* spp., *Amrasca* spp., *Anuraphis cardui, Aonidiella* spp., *Aphanostigma piri, Aphis* spp., *Arboridia apicalis, Aspidiella* spp., *Aspidiotus* spp., *Atanus* spp., *Aulacorthum solani, Bemisia* spp., *Brachycaudus helichrysii, Brachycolus* spp., *Brevicoryne*

*brassicae, Calligypona marginata, Carneocephala fulgida, Ceratovacuna lanigera, Cercopidae, Ceroplastes* spp., *Chaetosiphon fragaefolii, Chionaspis tegalensis, Chlorita onukii, Chromaphis juglandicola, Chrysomphalus ficus, Cicadulina mbila, Coccomytilus halli, Coccus* spp., *Cryptomyzus ribis, Dalbulus* spp., *Dialeurodes* spp., *Diaphorina* spp., *Diaspis* spp., *Doralis* spp., *Drosicha* spp., *Dysaphis* spp., *Dysmicoccus* spp., *Empoasca* spp., *Eriosoma* spp., *Erythroneura* spp., *Euscelis bilobatus, Geococcus coffeae, Homalodisca coagulata, Hyalopterus arundinis, Icerya* spp., *Idiocerus* spp., *Idioscopus* spp., *Laodelphax striatellus, Lecanium* spp., *Lepidosaphes* spp., *Lipaphis erysimi, Macrosiphum* spp., *Mahanarva fimbriolata, Melanaphis sacchari, Metcaljiella* spp., *Metopolophium dirhodum, Monellia costalis, Monelliopsis pecanis, Myzus* spp., *Nasonovia ribisnigri, Nephotettix* spp., *Nilaparvata lugens, Oncometopia* spp., *Orthezia praelonga, Parabemisia myricae, Paratrioza* spp., *Parlatoria* spp., *Pemphigus* spp., *Peregrinus maidis, Phenacoccus* spp., *Phloeomyzus passerinii, Phorodon humuli, Phylloxera* spp., *Pinnaspis aspidistrae, Planococcus* spp., *Protopulvinaria pyriformis, Pseudaulacaspis pentagona, Pseudococcus* spp., *Psylla* spp., *Pteromalus* spp., *Pyrilla* spp., *Quadraspidiotus* spp., *Quesada gigas, Rastrococcus* spp., *Rhopalosiphum* spp., *Saissetia* spp., *Scaphoides titanus, Schizaphis graminum, Selenaspidus articulatus, Sogata* spp., *Sogatella furcifera, Sogatodes* spp., *Stictocephala festina, Tenalaphara malayensis, Tinocallis caryaefoliae, Tomaspis* spp., *Toxoptera* spp., *Trialeurodes vaporariorum, Trioza* spp., *Typhlocyba* spp., *Unaspis* spp., *Viteus vitifolii.;*

(19) from the order of Isoptera, for example, *Reticulitermes* spp., *Odontotermes* spp.;

(20) from the order of Lepidoptera, for example, *Acronicta major, Aedia leucomelas, Agrotis* spp., *Alabama argillacea, Anticarsia* spp., *Barathra brassicae, Bucculatrix thurberiella, Bupalus piniarius, Cacoecia podana, Capua reticulana, Carpocapsa pomonella, Cheimatobia brumata, Chilo* spp., *Choristoneura fumiferana, Clysia ambiguella, Cnaphalocerus* spp., *Earias insulana, Ephestia kuehniella, Euproctis chrysorrhoea, Euxoa* spp., *Feltia* spp., *Galleria mellonella, Helicoverpa* spp., *Heliothis* spp., *Hofmannophila pseudospretella, Homona magnanima, Hyponomeuta padella, Laphygma* spp., *Lithocolletis blancardella, Lithophane antennata, Loxagrotis albicosta, Lymantria* spp., *Malacosoma neustria, Mamestra brassicae, Mocis repanda, Mythimna separata, Oria* spp., *Oulema oryzae, Panolis flammea, Pectinophora gossypiella, Phyllocnistis citrella, Pieris* spp., *Plutella xylostella, Prodenia* spp., *Pseudaletia* spp., *Pseudoplusia includens, Pyrausta nubilalis, Spodoptera* spp., *Thermesia gemmatalis, Tinea pellionella, Tineola bisselliella, Tortrix viridana, Trichoplusia* spp.;

(21) from the order of Orthoptera, for example, *Acheta domesticus, Blatta orientalis, Blattella germanica, Gryllotalpa* spp., *Leucophaea maderae, Locusta* spp., *Melanoplus* spp., *Periplaneta americana, Schistocerca gregaria.;*

(22) from the order of Thysanoptera, for example, *Baliothrips biformis, Enneothrips flavens, Frankliniella* spp., *Heliothrips* spp., *Hercinothrips femoralis, Kakothrips* spp., *Rhipiphorothrips cruentatus, Scirtothrips* spp., *Taeniothrips cardamoni, Thrips* spp.;

(23) from the class of Protozoa, for example, *Eimeria* spp.

In each aspect of the description, the compounds and compositions of the description can be applied against a single pest or combinations thereof.

Mixtures with Other Active Agents

In another embodiment, the compositions comprising the compounds of Formula (I) may also include other veterinary therapeutic agents. Veterinary pharmaceutical agents that may be included in the compositions of the description are well-known in the art (see e.g. *Plumb' Veterinary Drug Handbook*, 5$^{th}$ Edition, ed. Donald C. Plumb, Blackwell Publishing, (2005) or *The Merck Veterinary Manual*, 9$^{th}$ Edition, (January 2005)) and include but are not limited to acarbose, acepromazine maleate, acetaminophen, acetazolamide, acetazolamide sodium, acetic acid, acetohydroxamic acid, acetylcysteine, acitretin, acyclovir, albendazole, albuterol sulfate, alfentanil, allopurinol, alprazolam, altrenogest, amantadine, amikacin sulfate, aminocaproic acid, aminopentamide hydrogen sulfate, aminophylline/theophylline, amiodarone, amitriptyline, amlodipine besylate, ammonium chloride, ammonium molybdenate, amoxicillin, clavulanate potassium, amphotericin B desoxycholate, amphotericin B lipid-based, ampicillin, amprolium, antacids (oral), antivenin, apomorphione, apramycin sulfate, ascorbic acid, asparaginase, aspiring, atenolol, atipamezole, atracurium besylate, atropine sulfate, aurnofin, aurothioglucose, azaperone, azathioprine, azithromycin, baclofen, barbiturates, benazepril, betamethasone, bethanechol chloride, bisacodyl, bismuth subsalicylate, bleomycin sulfate, boldenone undecylenate, bromides, bromocriptine mesylate, budenoside, buprenorphine, buspirone, busulfan, butorphanol tartrate, cabergoline, calcitonin salmon, calcitrol, calcium salts, captopril, carbenicillin indanyl sodium, carbimazole, carboplatin, carnitine, carprofen, carvedilol, cefadroxil, cefazolin sodium, cefixime, clorsulon, cefoperazone sodium, cefotaxime sodium, cefotetan disodium, cefoxitin sodium, cefpodoxime proxetil, ceftazidime, ceftiofur sodium, ceftiofur, ceftriaxone sodium, cephalexin, cephalosporins, cephapirin, charcoal (activated), chlorambucil, chloramphenicol, chlordiazepoxide, chlordiazepoxide+/−clidinium bromide, chlorothiazide, chlorpheniramine maleate, chlorpromazine, chlorpropamide, chlortetracycline, chorionic gonadotropin (HCG), chromium, cimetidine, ciprofloxacin, cisapride, cisplatin, citrate salts, clarithromycin, clemastine fumarate, clenbuterol, clindamycin, clofazimine, clomipramine, claonazepam, clonidine, cloprostenol sodium, clorazepate dipotassium, clorsulon, cloxacillin, codeine phosphate, colchicine, corticotropin (ACTH), cosyntropin, cyclophosphamide, cyclosporine, cyproheptadine, cytarabine, dacarbazine, dactinomycin/actinomycin D, dalteparin sodium, danazol, dantrolene sodium, dapsone, decoquinate, deferoxamine mesylate, deracoxib, deslorelin acetate, desmopressin acetate, desoxycorticosterone pivalate, detomidine, dexamethasone, dexpanthenol, dexraazoxane, dextran, diazepam, diazoxide (oral), dichlorphenamide, diclofenac sodium, dicloxacillin, diethylcarbamazine citrate, diethylstilbestrol (DES), difloxacin, digoxin, dihydrotachysterol (DHT), diltiazem, dimenhydrinate, dimercaprol/BAL, dimethyl sulfoxide, dinoprost tromethamine, diphenylhydramine, disopyramide phosphate, dobutamine, docusate/DSS, dolasetron mesylate, domperidone, dopamine, doramectin, doxapram, doxepin, doxorubicin, doxycycline, edetate calcium disodium calcium EDTA, edrophonium chloride, enalapril/enalaprilat, enoxaparin sodium, enrofloxacin, ephedrine sulfate, epinephrine, epoetin/erythropoietin, eprinomectin, epsiprantel, erythromycin, esmolol, estradiol cypionate, ethacrynic acid/ethacrynate sodium, ethanol (alcohol), etidronate sodium, etodolac, etomidate, euthanasia agents w/pentobarbital, famotidine, fatty acids (essential/omega), felbamate, fentanyl, ferrous sulfate, filgrastim, finasteride, fipronil, florfenicol, fluconazole, flucytosine, fludrocortisone acetate, flumazenil, flumethasone, flunixin meglumine, fluorouracil (5-FU), fluoxetine, fluticasone propionate, fluvoxamine maleate, fomepizole (4-MP), furazolidone, furosemide, gabapentin, gemcitabine, gentamicin sulfate, glimepiride, glipizide, glucagon, glucocorticoid agents, glucosamine/chondroitin sulfate, glutamine, glyburide, glycerine (oral), glycopyrrolate, gonadorelin, grisseofulvin, guaifenesin, halothane, hemoglobin glutamer-200 (OXYGLOBIN®®), heparin, hetastarch, hyaluronate sodium, hydrazaline, hydrochlorothiazide, hydrocodone bitartrate, hydrocortisone, hydromorphone, hydroxyurea, hydroxyzine, ifosfamide, imidacloprid, imidocarb dipropinate, impenem-cilastatin sodium, imipramine, inamrinone lactate, insulin, interferon alfa-2a (human recombinant), iodide (sodium/potassium), ipecac (syrup), ipodate sodium, iron dextran, isoflurane, isoproterenol, isotretinoin, isoxsuprine, itraconazole, ivermectin, kaolin/pectin, ketamine, ketoconazole, ketoprofen, ketorolac tromethamine, lactulose, leuprolide, levamisole, levetiracetam, levothyroxine sodium, lidocaine, lincomycin, liothyronine sodium, lisinopril, lomustine (CCNU), lufenuron, lysine, magnesium, mannitol, marbofloxacin, mechlorethamine, meclizine, meclofenamic acid, medetomidine, medium chain triglycerides, medroxyprogesterone acetate, megestrol acetate, melarsomine, melatonin, meloxican, melphalan, meperidine, mercaptopurine, meropenem, metformin, methadone, methazolamide, methenamine mandelate/hippurate, methimazole, methionine, methocarbamol, methohexital sodium, methotrexate, methoxyflurane, methylene blue, methylphenidate, methylprednisolone, metoclopramide, metoprolol, metronidaxole, mexiletine, mibolerlone, midazolam milbemycin oxime, mineral oil, minocycline, misoprostol, mitotane, mitoxantrone, morphine sulfate, moxidectin, naloxone, mandrolone decanoate, naproxen, narcotic (opiate) agonist analgesics, neomycin sulfate, neostigmine, niacinamide, nitazoxanide, nitenpyram, nitrofurantoin, nitroglycerin, nitroprusside sodium, nizatidine, novobiocin sodium, nystatin, octreotide acetate, olsalazine sodium, omeprazole, ondansetron, opiate antidiarrheals, orbifloxacin, oxacillin sodium, oxazepam, oxibutynin chloride, oxymorphone, oxytretracycline, oxytocin, pamidronate disodium, pancreplipase, pancuronium bromide, paromomycin sulfate, parozetine, pencillamine, general information penicillins, penicillin G, penicillin V potassium, pentazocine, pentobarbital sodium, pentosan polysulfate sodium, pentoxifylline, pergolide mesylate, phenobarbital, phenoxybenzamine, pheylbutazone, phenylephrine, phenypropanolamine, phenytoin sodium, pheromones, parenteral phosphate, phytonadione/vitamin K-1, pimobendan, piperazine, pirlimycin, piroxicam, polysulfated glycosaminoglycan, ponazuril, potassium chloride, pralidoxime chloride, prazosin, prednisolone/prednisone, primidone, procainamide, procarbazine, prochlorperazine, propantheline bromide, *Propionibacterium acnes* injection, propofol, propranolol, protamine sulfate, pseudoephedrine, *psyllium* hydrophilic mucilloid, pyridostigmine bromide, pyrilamine maleate, pyrimethamine, quinacrine, quinidine, ranitidine, rifampin, s-adenosyl-methionine (SAMe), saline/hyperosmotic laxative, selamectin, selegiline/1-deprenyl, sertraline, sevelamer, sevoflurane, silymarin/milk thistle, sodium bicarbonate, sodium polystyrene sulfonate, sodium stibogluconate, sodium sulfate, sodum thiosulfate, somatotropin, sotalol, spectinomycin, spironolactone, stanozolol, streptokinase, streptozocin, succimer, succinylcholine chloride, sucralfate, sufentanil citrate, sulfachlorpyridazine sodium, sulfadiazine/trimethroprim, sulfamethoxazole/trimethoprim, sulfadimetoxine, sulfadimethoxine/ormetoprim, sulfasalazine, taurine, tepoxaline, terbinafline, terbutaline sulfate, testosterone, tetracycline, thiacetarsamide sodium, thiamine, thioguanine, thiopental sodium, thiotepa, thyrotropin, tiamulin, ticarcilin disodium, tiletamine/zolazepam, tilmocsin, tiopronin, tobramycin sulfate, tocainide, tolazoline, telfenamic acid, topiramate, tramadol, trimcinolone acetonide, trientine, trilostane, trimepraxine tartrate w/prednisolone, tripelennamine, tylosin, urdosiol, valproic acid, vanadium, vancomycin, vasopressin, vecuronium bromide, verapamil, vinblastine sulfate, vincristine sulfate, vitamin E/selenium, warfarin sodium, xylazine, yohimbine, zafirlukast, zidovudine (AZT), zinc acetate/zinc sulfate, zonisamide and mixtures thereof.

In one embodiment of the description, arylpyrazole compounds such as phenylpyrazoles may be included in the veterinary compositions of the description. Arylpyrazoles are known in the art and may be suitable for combination with the compound of Formula (I) in the compositions of the description. Examples of such arylpyrazole compounds include but are not limited to those described in U.S. Pat. Nos. 6,001,384; 6,010,710; 6,083,519; 6,096,329; 6,174,540; 6,685,954, 6,998,131 and 7,759,381 (all of which are incorporated herein by reference). A particularly preferred arylpyrazole active agent is fipronil.

In another embodiment of the description, one or more macrocyclic lactones, which act as an acaricide, an anthelmintic agent and/or an insecticide, can be included in the compositions of the description in combination with the compound. For the avoidance of doubt, the term "macrocyclic lactone" as used herein includes both naturally occurring and synthetic or semi-synthetic avermectin and milbemycin compounds.

The macrocyclic lactones that may be used in the compositions of the description include, but are not limited to, the naturally produced avermectins (e.g. including the components designated as Ala, Alb, A2a, A2b, Bia, Bib, B2a and B2b) and milbemycin compounds, semisynthetic avermectins and milbemycins, avermectin monosaccharide compounds and avermectin aglycone compounds. Examples of macrocyclic lactone compounds that may be used in the compositions include, but are not limited to, abamectin, dimadectin, doramectin, emamectin, eprinomectin, ivermectin, latidectin, lepimectin, selamectin, ML-1,694,554 and milbemycins including, but not limited to, milbemectin, milbemycin D, milbemycin A3, milbemycin A4, milbemycin oxime, moxidectin and nemadectin. Also included are the 5-oxo and 5-oxime derivatives of said avermectins and milbemycins.

The macrocyclic lactone compounds are known in the art and can easily be obtained commercially or through synthesis techniques known in the art. Reference is made to the widely available technical and commercial literature. For avermectins, ivermectin and abamectin, reference may be made, for example, to the work "Ivermectin and Abamectin", 1989, by M. H. Fischer and H. Mrozik, William C. Campbell, published by Springer Verlag., or Albers-Schönberg et al. (1981), "Avermectins Structure Determination", J. Am. Chem. Soc., 103, 4216-4221. For doramectin, "Veterinary Parasitology", vol. 49, No. 1, July 1993, 5-15 may be consulted. For milbemycins, reference may be made, inter alia, to Davies H. G. et al., 1986, "Avermectins and Milbemycins", Nat. Prod. Rep., 3, 87-121, Mrozik H. et al., 1983, Synthesis of Milbemycins from Avermectins, Tetrahedron Lett., 24, 5333-5336, U.S. Pat. No. 4,134,973 and EP 0 677 054, both incorporated herein by reference.

The structure of the avermectins and milbemycins are closely related, e.g., by sharing a complex 16-membered macrocyclic lactone ring. The natural product avermectins are disclosed in U.S. Pat. No. 4,310,519 and the 22,23-dihydro avermectin compounds are disclosed in U.S. Pat. No. 4,199,569. Mention is also made of U.S. Pat. Nos.

4,468,390, 5,824,653, EP 0 007 812 A1, U.K. Patent Specification 1 390 336, EP 0 002 916, and New Zealand Patent No. 237 086, inter alia. Naturally occurring milbemycins are described in U.S. Pat. No. 3,950,360 as well as in the various references cited in "The Merck Index" 12$^{th}$ ed., S. Budavari, Ed., Merck & Co., Inc. Whitehouse Station, N.J. (1996). Latidectin is described in the "International Nonproprietary Names for Pharmaceutical Substances (INN)", *WHO Drug Information*, vol. 17, no. 4, pp. 263-286, (2003). Semisynthetic derivatives of these classes of compounds are well known in the art and are described, for example, in U.S. Pat. Nos. 5,077,308, 4,859,657, 4,963,582, 4,855,317, 4,871,719, 4,874,749, 4,427,663, 4,310,519, 4,199,569, 5,055,596, 4,973,711, 4,978,677, 4,920,148 and EP 0 667 054, all incorporated herein by reference.

In one embodiment, the veterinary compositions of the description comprise an effective amount of at least one of abamectin, dimadectin, doramectin, emamectin, eprinomectin, ivermectin, latidectin, lepimectin, selamectin, milbemectin, milbemycin D, milbemycin A3, milbemycin A4, milbemycin oxime, moxidectin or nemadectin, or a combination thereof. In another embodiment, the description provides a veterinary composition comprising an effective amount of at least one of abamectin, emamectin, eprinomectin, ivermectin, doramectin or selamectin, or a combination thereof. In still another embodiment, the veterinary compositions of the description comprise an effective amount of at least one of ivermectin, milbemectin, milbemycin oxime or moxidectin, or a combination thereof.

In another embodiment of the description, a composition comprising a compound of Formula (I) in combination with a class of acaricide or insecticides known as insect growth regulators (IGRs) are provided. Compounds belonging to this group are well known to the practitioner and represent a wide range of different chemical classes. These compounds all act by interfering with the development or growth of the insect pests. Insect growth regulators are described, for example, in U.S. Pat. Nos. 3,748,356, 3,818,047, 4,225,598, 4,798,837, 4,751,225, EP 0 179 022 or U.K. 2 140 010 as well as U.S. Pat. Nos. 6,096,329 and 6,685,954 (all incorporated herein by reference).

In one embodiment the compositions of the description may include an IGR compound that mimics juvenile hormone or that modulates levels of juvenile hormones in insects. Examples of juvenile hormone mimics include azadirachtin, diofenolan, fenoxycarb, hydroprene, kinoprene, methoprene, pyriproxyfen, tetrahydroazadirachtin and 4-chloro-2(2-chloro-2-methyl-propyl)-5-(6-iodo-3-pyridylmethoxy)pyridazine-3 (2H)-one. In another embodiment, the compositions of the description comprise a compound of formula (I) in combination with methoprene or pyriproxyfen and a pharmaceutically acceptable carrier.

In another embodiment, the compositions of the description include an IGR compound that is a chitin synthesis inhibitor. Chitin synthesis inhibitors include chlorofluazuron, cyromazine, diflubenzuron, fluazuron, flucycloxuron, flufenoxuron, hexaflumoron, lufenuron, tebufenozide, teflubenzuron, triflumoron, 1-(2,6-difluorobenzoyl)-3-(2-fluoro-4-(trifluoromethyl)phenylurea, 1-(2,6-difluoro-benzoyl)-3-(2-fluoro-4-(1,1,2,2-tetrafluoroethoxy)-phenylurea and 1-(2,6-difluorobenzoyl)-3-(2-fluoro-4-trifluoromethyl) phenylurea.

In some embodiments, the compositions of the description may include one or more antinematodal agents including, but not limited to, active agents in the benzimidazoles, imidazothiazoles, tetrahydropyrimidines and the organophosphate class of compounds. In some embodiments, benzimidazoles including, but not limited to, thiabendazole, cambendazole, parbendazole, oxibendazole, mebendazole, flubendazole, fenbendazole, oxfendazole, albendazole, cyclobendazole, febantel, thiophanate and its o,o-dimethyl analogue may be included in the compositions.

In other embodiments, the compositions of the description may include an imidazothiazole compounds including, but not limited to, tetramisole, levamisole and butamisole.

In still other embodiments, the compositions of the description may include tetrahydropyrimidine active agents including, but not limited to, pyrantel, oxantel, and morantel.

Suitable organophosphate active agents include, but are not limited to, coumaphos, trichlorfon, haloxon, naftalofos and dichlorvos, heptenophos, mevinphos, monocrotophos, TEPP, and tetrachlorvinphos.

In other embodiments, the compositions may include the antinematodal compounds phenothiazine, piperazine as the neutral compound and in various salt forms, diethylcarbamazine, phenols such as disophenol, arsenicals such as arsenamide, ethanolamines such as bephenium, thenium closylate, and methyridine; cyanine dyes including pyrvinium chloride, pyrvinium pamoate and dithiazanine iodide; isothiocyanates including bitoscanate, suramin sodium, phthalofyne, and various natural products including, but not limited to, hygromycin B, ca-santonin and kainic acid.

In other embodiments, the compositions of the description may include antitrematodal agents. Suitable antitrematodal agents include, but are not limited to, the miracils such as miracil D and mirasan; praziquantel, clonazepam and its 3-methyl derivative, oltipraz, lucanthone, hycanthone, oxamniquine, amoscanate, niridazole, nitroxynil, various bisphenol compounds known in the art including hexachlorophene, bithionol, bithionol sulfoxide and menichlopholan; various salicylanilide compounds including tribromsalan, oxyclozanide, clioxanide, rafoxanide, nitroxynil, brotianide, bromoxanide and closantel; triclabendazole, diamfenetide, clorsulon, hetolin and emetine.

Anticestodal compounds may also be advantageously used in the compositions of the description including, but not limited to, arecoline in various salt forms, bunamidine, niclosamide, nitroscanate, paromomycin, paromomycin II, praziquantel and epsiprantel.

In yet other embodiments, the compositions of the description may include other active agents that are effective against arthropod parasites. Suitable active agents include, but are not limited to, bromocyclen, chlordane, DDT, endosulfan, lindane, methoxychlor, toxaphene, bromophos, bromophos-ethyl, carbophenothion, chlorfenvinphos, chlorpyrifos, crotoxyphos, cythioate, diazinon, dichlorenthion, diemthoate, dioxathion, ethion, famphur, fenitrothion, fenthion, fospirate, iodofenphos, malathion, naled, phosalone, phosmet, phoxim, propetamphos, ronnel, stirofos, allethrin, cyhalothrin, cypermethrin, deltamethrin, fenvalerate, flucythrinate, permethrin, phenothrin, pyrethrins, resmethrin, benzyl benzoate, carbon disulfide, crotamiton, difluben-zuron, diphenylamine, disulfiram, isobornyl thiocyanato acetate, methoprene, monosulfiram, pirenonylbutoxide, rotenone, triphenyltin acetate, triphenyltin hydroxide, deet, dimethyl phthalate, and the compounds 1,5a,6,9,9a,9b-hexahydro-4a(4H)-dibenzofurancarboxaldehyde (MGK-11), 2-(2-ethylhexyl)-3a,4,7,7a-tetrahydro-4,7-methano-1H-isoindole-1,3(2H)dione (MGK-264), dipropyl-2,5-pyridinedicarboxylate (MGK-326) and 2-(octylthio)ethanol (MGK-874).

In another embodiment, an antiparasitic agent that can be included in the veterinary composition containing a compound of formula (I) can be a biologically active peptide or protein including, but not limited to, depsipeptides other than the compound. These include PF 1022A or analogs thereof and emodepside. Other cyclic depsipeptide compounds that may be included in the compositions comprising a compound of Formula (I) are those described in WO 2016/187534 A1 and WO 2017/116702 A1, both incorporated herein by reference. These compounds act at the neuromuscular junction by stimulating presynaptic receptors belonging to the secretin receptor family resulting in the paralysis and death of parasites. In one embodiment of the depsipeptide, the depsipeptide is emodepside (see Wilson et al., Parasitology, January 2003, 126(Pt 1):79-86).

In another embodiment, the compositions of the description may comprise an active agent from the neonicotinoid class of parasiticides. The neonicotinoids bind and inhibit insect specific nicotinic acetylcholine receptors. In one embodiment, the neonicotinoid insecticidal agent that can be combined with a compound of Formula (I) in a composition of the description is imidacloprid. Agents of this class are described, for example, in U.S. Pat. No. 4,742,060 or in EP 0 892 060 (both incorporated herein by reference). In another embodiment, the compositions of the description may comprise nitenpyram, another active agent of the neonicotinoid class of pesticides. The use of nitenpyram for controlling fleas is described in U.S. Pat. No. 5,750,548, which is incorporated herein by reference in its entirety.

In certain other embodiments of the description, the compound of Formula (I) can be combined with the compositions of the description is a semicarbazone, such as metaflumizone.

In another embodiment, the compositions of the description may advantageously include one or more isoxazoline compounds known in the art. Isoxazoline active agents are highly effective against a variety of ectoparasites and combination with the compound of Formula (I) would expand the scope of efficacy against these parasites. Particularly useful isoxazoline active agents that can be combined with the compound include afoxolaner (including substantially pure active enantiomer), sarolaner, fluralaner (including substantially pure active enantiomer) and lotilaner. These active agents are described in U.S. Pat. No. 7,964,204, US 2010/0254960 A1, US2011/0159107, US2012/0309620, US2012/0030841, US2010/0069247, WO 2007/125984, WO 2012/086462, U.S. Pat. Nos. 8,318,757, 8,466,115, 8,618,126, 8,822,466, 8,383,659, 8,853,186, 9,221,835, US 2011/0144349, U.S. Pat. No. 8,053,452; US 2010/0137612, U.S. Pat. No. 8,410,153, US 2011/152081, WO 2012/089623, WO 2012/089622, U.S. Pat. Nos. 8,119,671; 7,947, 715; WO 2102/120135, WO 2012/107533, WO 2011/157748, US 2011/0245274, US 2011/0245239, US 2012/0232026, US 2012/0077765, US 2012/0035122, US 2011/0251247, WO 2011/154433, WO 2011/154434, US 2012/0238517, US 2011/0166193, WO 2011/104088, WO 2011/104087, WO 2011/104089, US 2012/015946, US 2009/0143410, WO 2007/123855 A2, US 2011/0118212, U.S. Pat. No. 7,951,828 & U.S. Pat. No. 7,662,972, US 2010/0137372 A1, US 2010/0179194 A2, US 2011/0086886 A2, US 2011/0059988 A1, US 2010/0179195 A1, US 2015/0126523, WO 2010/003923, WO 2010/003877, WO 2010/072602, WO 2014/134236, WO 2017/147352, U.S. Pat. Nos. 7,897,630, and 7,951,828, all of which are incorporated herein by reference in their entirety.

In another embodiment of the description, nodulisporic acid and its derivatives may be added to the compositions of the description. These compounds are used to treat or prevent infections in humans and animals and are described, for example, in U.S. Pat. Nos. 5,399,582, 5,962,499, 6,221,894 and 6,399,786, all of which are hereby incorporated by reference in their entirety. The compositions may include one or more of the known nodulisporic acid derivatives in the art, including all stereoisomers, such as those described in the literature cited above.

In another embodiment, anthelmintic compounds of the amino acetonitrile class (AAD) of compounds such as monepantel (ZOLVIX) and the like may be added to the compositions of the description. These compounds are described, for example, in U.S. Pat. No. 7,084,280 to Ducray et al. (incorporated herein by reference); Sager et al., Veterinary Parasitology, 2009, 159, 49-54; Kaminsky et al., Nature vol. 452, 13 Mar. 2008, 176-181.

The compositions of the description may also include aryloazol-2-yl cyanoethylamino compounds such as those described in U.S. Pat. No. 8,088,801 to Soll et al., which is incorporated herein by reference, and thioamide derivatives of these compounds, as described in U.S. Pat. No. 7,964,621 to Le Hir de Fallois, which is also incorporated herein by reference. Aryloazol-2-yl cyanoethylamino active agents, which are systemically-acting against endoparasites, may be used in combination with the compound in veterinary compositions of the description.

The compositions of the description may also include paraherquamide compounds and derivatives of these compounds, including derquantel (see Ostlind et al., *Research in Veterinary Science*, 1990, 48, 260-61; and Ostlind et al., *Medical and Veterinary Entomology*, 1997, 11, 407-408). The paraherquamide family of compounds is a known class of compounds that include a spirodioxepino indole core with activity against certain parasites (see *Tett. Lett.* 1981, 22, 135; *J. Antibiotics* 1990, 43, 1380, and *J. Antibiotics* 1991, 44, 492). In addition, the structurally related marcfortine family of compounds, such as marcfortines A-C, are also known and may be combined with the compositions of the description (see *J. Chem. Soc.-Chem. Comm.* 1980, 601 and *Tet. Lett.* 1981, 22, 1977). Further references to the paraherquamide derivatives can be found, for example, in WO 91/09961, WO 92/22555, WO 97/03988, WO 01/076370, WO 09/004432 and US 2010/0197624, U.S. Pat. Nos. 5,703,078 and 5,750,695, all of which are hereby incorporated by reference in their entirety.

In another embodiment of the description, the compositions may include a spinosyn active agent produced by the soil actinomycete *Saccharopolyspora spinosa* (see, for example Salgado V. L. and Sparks T. C., "*The Spinosyns: Chemistry, Biochemistry, Mode of Action, and Resistance*," in Comprehensive Molecular Insect Science, vol. 6, pp. 137-173, 2005) or a semi-synthetic spinosoid active agent. The spinosyns are typically referred to as factors or components A, B, C, D, E, F, G, H, J, K, L, M, N, O, P, Q, R, S, T, U, V, W, or Y, and any of these components, or a combination thereof, may be used in the compositions of the description. The spinosyn compound may be a 5,6,5-tricylic ring system, fused to a 12-membered macro cyclic lactone, a neutral sugar (rhamnose), and an amino sugar (forosamine). These and other natural spinosyn compounds, including 21-butenyl spinosyn produced by Saccharopolysporapagona, which may be used in the compositions of the description, may be produced via fermentation by conventional techniques known in the art. Other spinosyn compounds that may be used in the compositions of the description are disclosed in U.S. Pat. Nos. 5,496,931; 5,670,364; 5,591,606; 5,571,901; 5,202,242; 5,767,253; 5,840,861;

5,670,486; 5,631,155 and 6,001,981, all incorporated by reference herein in their entirety. The spinosyn compounds may include, but are not limited to, spinosyn A, spinosyn D, spinosad, spinetoram, or combinations thereof. Spinosad is a combination of spinosyn A and spinosyn D, and spinetoram is a combination of 3'-ethoxy-5,6-dihydro spinosyn J and 3'-ethoxy spinosyn L.

In general, additional active agents (other than the compound of formula (I) described above) is included in the dosage units of the description in an amount of between about 0.1 µg and about 1000 mg. Typically, the active agent may be included in an amount of about 10 µg to about 500 mg, about 10 µg to about 400 mg, about 1 mg to about 300 mg, about 10 mg to about 200 mg or about 10 mg to about 100 mg. More typically the additional active agent will be present in an amount of about 5 mg to about 50 mg in the compositions of the description.

The concentration of the additional active agent in the compositions of the description will typically be from about 0.01% to about 30% (w/w) depending on the potency of the active agent. In certain embodiments for very potent active agents including, but not limited to a macrocyclic lactone active agent, the concentration of the active agent will typically be from about 0.01% to about 10% (w/w), from about 0.01 to about 1% (w/w), from about 0.01% to about 0.5% (w/w), from about 0.1% to about 0.5% (w/w) or from about 0.01% to about 0.1% (w/w). In other embodiments, the concentration of the active agent will typically be from about 0.1% to about 2% (w/w) or about 0.1% to about 1% (w/w).

In other embodiments, the additional active agent will typically be present at higher concentrations to achieve the desired efficacy. In some embodiments, the active agent will be present in a concentration of about 1% to about 30% (w/w), about 1% to about 20% (w/w) or about 1% to about 15% (w/w). In still other embodiments, the active agent will be present in a concentration of about 5% to about 20% (w/w) or about 5% to about 15% (w/w) in the composition.

In various embodiments of the description, an additional active agent may be included in the composition to deliver a dose of about 0.001 mg/kg to about 50 mg/kg or about 0.5 mg/kg to about 50 mg/kg of body weight of the animal. In other embodiments, the active agent will typically be present in an amount sufficient to deliver a dose of about 0.05 mg/kg to about 30 mg/kg, about 0.1 mg/kg to about 20 mg/kg. In other embodiments, the active agent will be present in an amount sufficient to deliver a dose of about 0.1 mg/kg to about 10 mg/kg, about 0.1 mg/kg to about 1 mg/kg or about 0.5 mg/kg to about 50 mg/kg per body weight of the animal.

In certain embodiments of the description where the additional active agent is a very potent compound such as a macrocyclic lactone or other potent compounds, the active agent will be present in a concentration to provide a dose of about 0.001 mg/kg to about 5 mg/kg, about 0.001 mg/kg to about 0.1 mg/kg or about 0.001 mg/kg to about 0.01 mg/kg. In still other embodiments, the active agent is present in an amount sufficient to deliver a dose of about 0.01 mg/kg to about 2 mg/kg or about 0.1 mg/kg to about 1 mg/kg per body weight of the animal. In still other embodiments, the additional active agent may be present in an amount to deliver a dose of about 1 µg/kg to about 200 µg/kg or about 0.1 mg/kg to about 1 mg/kg of weight of animal.

In addition to the other active agents mentioned above, combinations of two or more active agents may be used with the compounds of the description in a composition to treat a desired spectrum of pests and parasites. It would be well within the skill level of the practitioner to decide which individual compound can be used in the inventive composition to treat a particular infection of an insect.

The description will now be further described by way of the following non-limiting examples.

EXAMPLES

Preparation Examples

The compounds of Formula (I) or pharmaceutically or a veterinarily acceptable salts thereof may be prepared by adopting one of the following reaction schemes. The starting materials for their preparation may be commercially available or can be prepared by methods known by persons of skill in the art and as described in the literature. It will be appreciated that the following procedures may be modified by persons of skill in the art to prepare additional compounds according to the invention. For example, a person of skill in the art will understand that replacement of certain starting materials or the use of different intermediates will enable the preparation of different compounds of Formula (I).

List of Abbreviations

ACN acetonitrile
AIBN azobi sisobutyronitrile
BINAP (2,2'-Bis(diphenylphosphino)-1,1'-binaphthyl)
BSA bovine serum albumin
BOC tert-butoxycarbonyl
BOP-Cl Bis(2-oxo-3-oxazolidinyl)phosphinic chloride
DAST Diethylaminosulfur trifluoride
DCC N,N'-Dicyclohexylcarbodiimide solution
DCM dichloromethane
DEAD Diethyl azodicarboxylate
DIEA diisopropylethylamine
DMF N,N-dimethylformamide
DMAP 4-(Dimethylamino)pyridine
DMSO dimethylsulfoxide
EDAC N-(3-Dimethylaminopropyl)-N'-ethylcarbodiimide hydrochloride
ES electrospray
EtOAc or EA ethyl acetate
HATU 1-[bis(dimethylamino)methylene]-1H-1,2,3-triazolo[4,5 b]pyridinium 3-oxide hexafluorophosphate
HOBt or HOBT 1-hydroxybenzotriazole
KHMDS potassium hexamethyldisilazide, more precisely potassium bis(trimethylsilyl)amide
MeOH methanol
m-CPBA m-Chloroperbenzoic acid
NMO N-Methylmorpholine-N-oxide
o/n over night
PE petroleum ether
Pd(dtbpf)Cl2 Dichloro[1,1'-bis (di-tert-butylphosphino) ferrocene] palladium(II)
Pd2dba3 Tris(dibenzylideneacetone)dipalladium(0)
Pd(dppf)Cl2 [1,1'-Bis(diphenylphosphino)ferrocene]dichloropalladium(II), complex with dichloromethane
TBAF tert-butyl ammonium fluoride
TfO triflate
THF tetrahydrofuran
TLC thin-layer chromatography The process depicted in Scheme 5 may be used to prepare the following compounds: 026, 027, 028, 029, 083, 090, 092, 098, 099, 100, 101, 102, 102-1, 123, 124, 125, 126, 127, 128, 129, 130, 218, 219, 302.

In some cases for certain compounds, the process in Scheme 5 may be modified according to methods known to persons of skill in the art to incorporate different functional groups in the core structure. For example, intermediate 026-E may be used to incorporate different groups corresponding to variable $R^1$ in the structure. Similarly, intermediate 026-C may be used to incorporate different groups at the position corresponding to variable $R^3$.

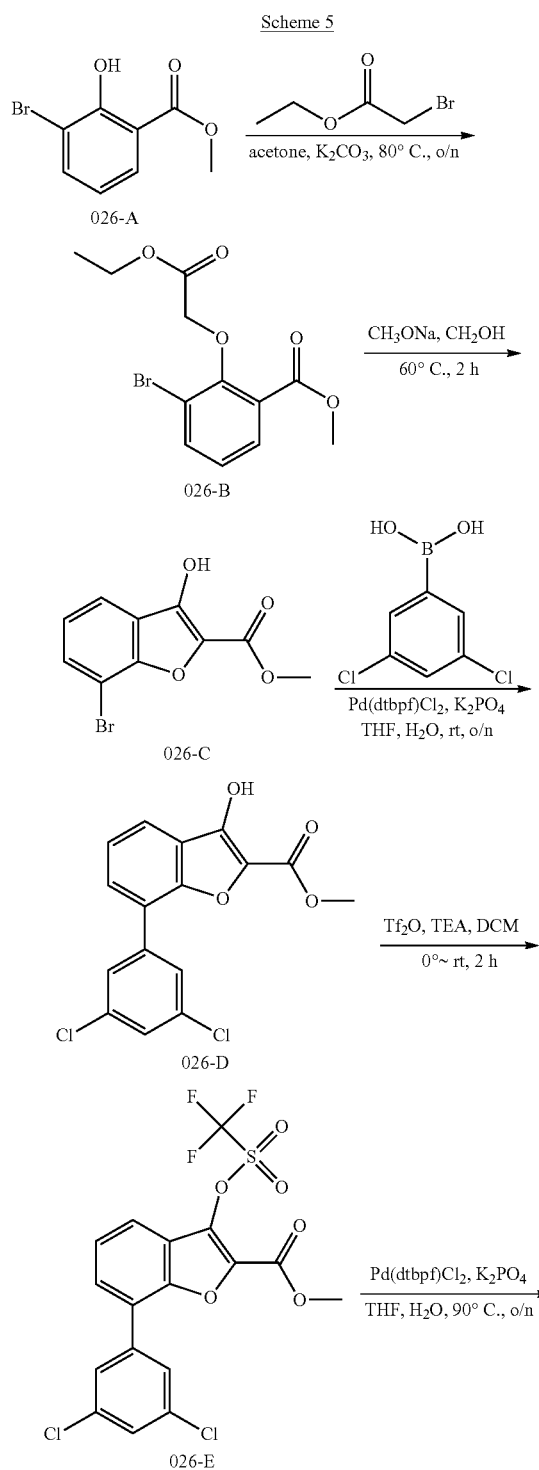

Scheme 5

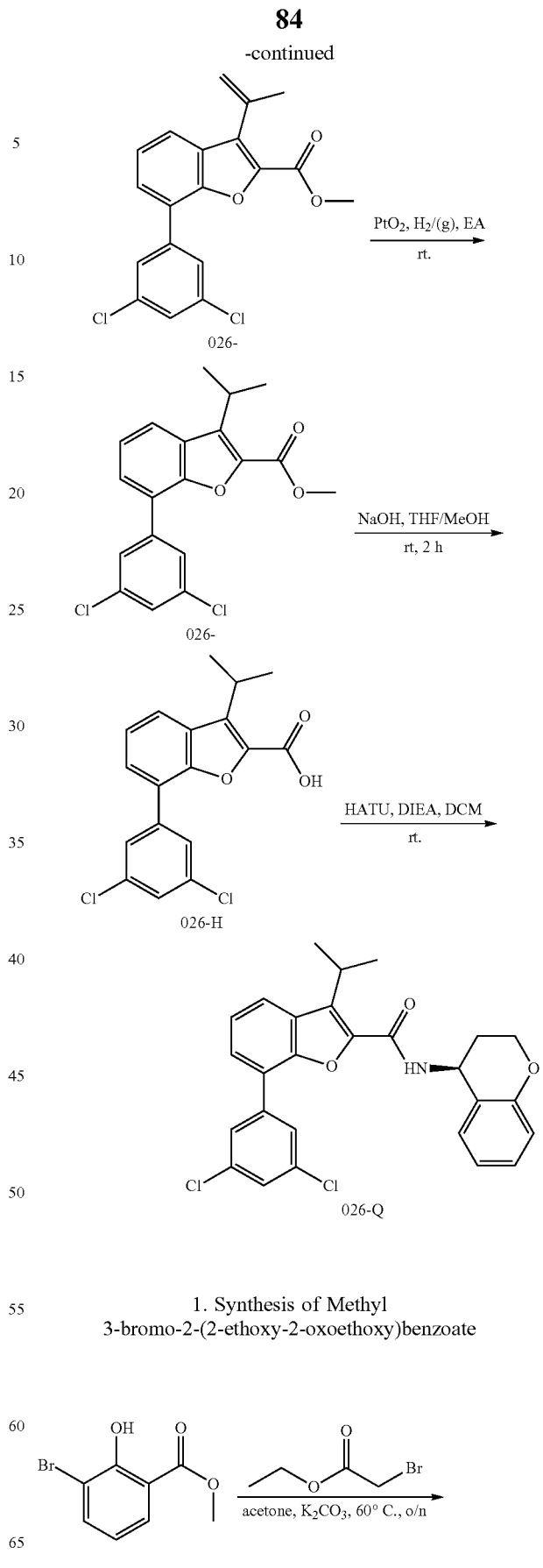

1. Synthesis of Methyl 3-bromo-2-(2-ethoxy-2-oxoethoxy)benzoate

3. Synthesis of Methyl 7-(3,5-dichlorophenyl)-3-hydroxybenzofuran-2-carboxylate

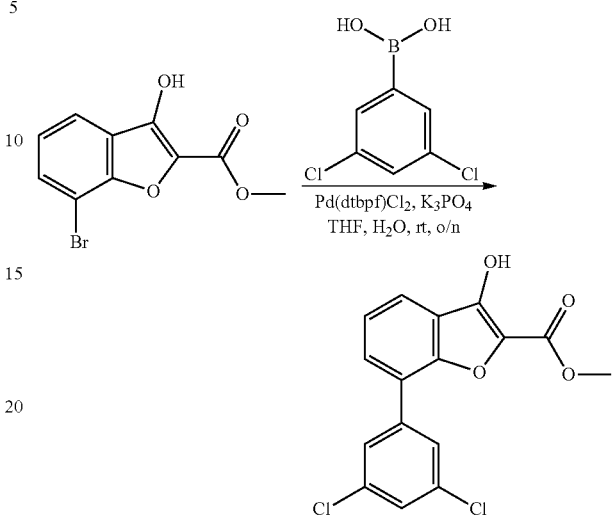

Into a 50-mL round-bottom flask purged and maintained with an inert atmosphere of nitrogen, was placed methyl 7-bromo-3-hydroxy-1-benzofuran-2-carboxylate (1.50 g, 5.53 mmol, 1.00 equiv), 3,5-dichlorophenylboronic acid (1.1 g, 6.1 mmol, 1.1 equiv), Pd(dtbpf)Cl$_2$ (180 mg, 0.28 mmol, 0.05 equiv), H$_2$O (2.0 mL), THF (8.0 mL), K$_3$PO$_4$ (2.3 g, 11.0 mmol, 2.0 equiv). The resulting solution was stirred overnight at room temperature. The resulting mixture was concentrated. The residue was applied onto a silica gel column with ethyl acetate/petroleum ether (1/3). This resulted in 1 g (53.6%) of methyl 7-(3,5-dichlorophenyl)-3-hydroxy-1-benzofuran-2-carboxylate as a white solid.

4. Synthesis of Methyl 7-(3,5-dichlorophenyl)-3-(trifluoromethylsulfonyloxy)benzofuran-2-carboxylate

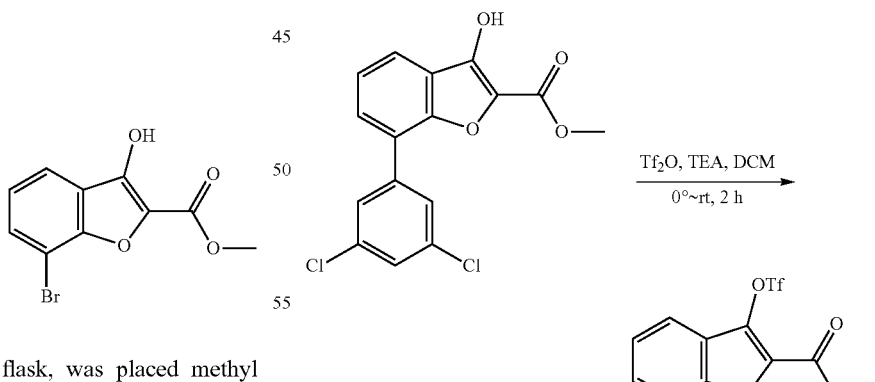

Into a 50-mL 3-necked round-bottom flask purged and maintained with an inert atmosphere of nitrogen, was placed

---

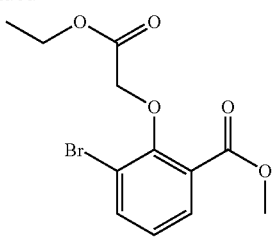

Into a 100-mL round-bottom flask, was placed methyl 3-bromo-2-hydroxybenzoate (5.0 g, 21.6 mmol, 1.0 equiv), ethyl bromoacetate (3.6 g, 21.6 mmol, 1 equiv), acetone (50 mL), K$_2$CO$_3$ (8.97 g, 64.9 mmol, 3.0 equiv). The resulting solution was stirred overnight at 60° C. The reaction mixture was cooled. The solids were filtered out. The resulting mixture was concentrated. The residue was applied onto a silica gel column with ethyl acetate/petroleum ether (1/2). This resulted in 7 g (crude) of methyl 3-bromo-2-(2-ethoxy-2-oxoethoxy)benzoate as a light yellow solid.

2. Synthesis of Methyl 7-bromo-3-hydroxybenzofuran-2-carboxylate

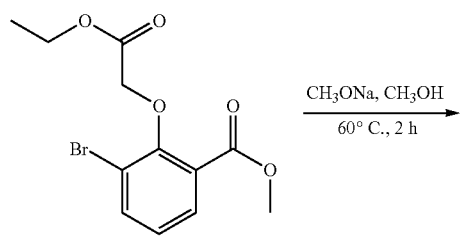

Into a 50-mL round-bottom flask, was placed methyl 3-bromo-2-(2-ethoxy-2-oxoethoxy)benzoate (5.0 g, 15.7 mmol, 1.0 equiv), CH$_3$OH (20.0 mL, 315.3 mmol), CH$_3$ONa (1.7 g, 31.5 mmol, 2.0 equiv). The resulting solution was stirred for 2 hrs at 60° C. The reaction mixture was cooled to room temperature. The resulting mixture was concentrated. The residue was applied onto a silica gel column with ethyl acetate/petroleum ether (1/3). This resulted in 3.5 g (81.9%) of methyl 7-bromo-3-hydroxy-1-benzofuran-2-carboxylate as a white solid.

methyl 7-(3,5-dichlorophenyl)-3-hydroxy-1-benzofuran-2-carboxylate (0.9 g, 2.67 mmol, 1.0 equiv), TEA (0.5 g, 5.3 mmol, 2.0 equiv), DCM (10.0 mL), This was followed by the addition of Tf$_2$O (0.9 g, 3.20 mmol, 1.2 equiv) at 0° C. The resulting solution was stirred for 2 hrs at room temperature. The reaction was then quenched by the addition of 20 mL of water. The resulting solution was extracted with 2×10 mL of dichloromethane and the organic layers combined. The resulting mixture was washed with 1×10 ml of brine. The mixture was dried over anhydrous sodium sulfate and concentrated. This resulted in 1.1 g (87.8%) of methyl 7-(3,5-dichlorophenyl)-3-(trifluoromethanesulfonyloxy)-1-benzofuran-2-carboxylate as a yellow solid.

5. Synthesis of Methyl 7-(3,5-dichlorophenyl)-3-(prop-1-en-2-yl)benzofuran-2-carboxylate

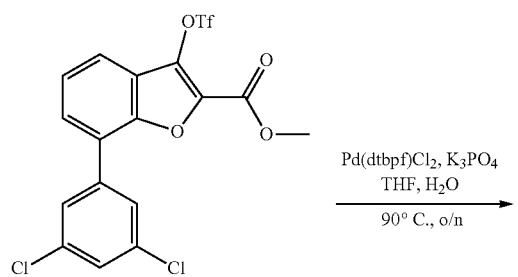

Into a 50-mL round-bottom flask purged and maintained with an inert atmosphere of nitrogen, was placed methyl 7-(3,5-dichlorophenyl)-3-(trifluoromethanesulfonyloxy)-1-benzofuran-2-carboxylate (1.10 g, 2.34 mmol, 1.0 equiv), 4,4,5,5-tetramethyl-2-(prop-1-en-2-yl)-1,3,2-dioxaborolane (0.5 g, 2.8 mmol, 1.2 equiv), Pd(dtbpf)Cl$_2$ (76.4 mg, 0.12 mmol, 0.05 equiv), H$_2$O (2.0 mL), THF (8.0 mL), K$_3$PO$_4$ (1.0 g, 4.7 mmol, 2.0 equiv). The resulting solution was stirred for 2 hr at room temperature. The resulting mixture was concentrated. The residue was applied onto a silica gel column with ethyl acetate/petroleum ether (1/8). This resulted in 400 mg (47.2%) of methyl 7-(3,5-dichlorophenyl)-3-(prop-1-en-2-yl)-1-benzofuran-2-carboxylate as a white solid.

6. Synthesis of Methyl 7-(3,5-dichlorophenyl)-3-isopropylbenzofuran-2-carboxylate

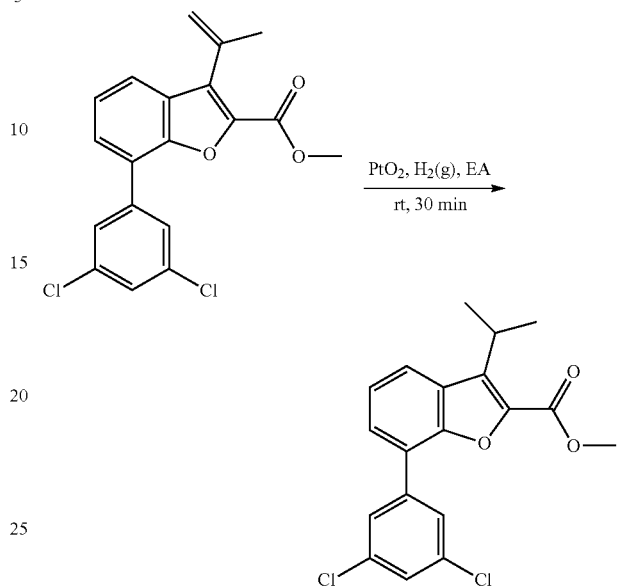

Into a 50-mL round-bottom flask, was placed methyl 7-(3,5-dichlorophenyl)-3-(prop-1-en-2-yl)-1-benzofuran-2-carboxylate (390 mg, 1.1 mmol, 1.0 equiv), PtO$_2$ (37 mg, 0.16 mmol, 0.15 equiv), EA (10 mL), To the above H$_2$ gas (1 atm) was introduced. The resulting solution was stirred for 30 min at room temperature. The solids were filtered out. The resulting mixture was concentrated. This resulted in 370 mg (94.4%) of methyl 7-(3,5-dichlorophenyl)-3-isopropyl-1-benzofuran-2-carboxylate as a grey solid.

7. Synthesis of 7-(3,5-dichlorophenyl)-3-isopropyl-benzofuran-2-carboxylic Acid

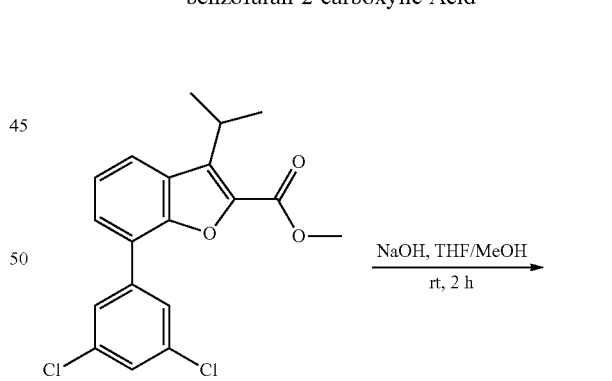

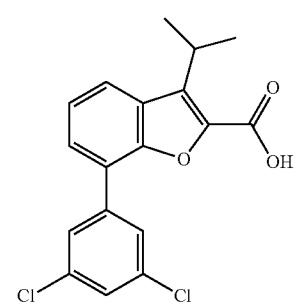

Into a 25-mL round-bottom flask, was placed methyl 7-(3,5-dichlorophenyl)-3-isopropyl-1-benzofuran-2-carboxylate (350 mg, 1.0 mmol, 1.0 equiv), NaOH (385 mg, 9.6 mmol, 10.0 equiv), THF (1.0 mL), MeOH (4.0 mL), H₂O (1.0 mL). The resulting solution was stirred for 2 hr at room temperature. The resulting mixture was concentrated. The pH value of the solution was adjusted to 4 by addition of aqueous solution of HCl (1 mol/L). The solids were collected by filtration. This resulted in 300 mg (89.2%) of 7-(3,5-dichlorophenyl)-3-isopropyl-1-benzofuran-2-carboxylic acid as a white solid.

8. Synthesis of (S)—N-(chroman-4-yl)-7-(3,5-dichlorophenyl)-3-isopropylbenzofuran-2-carboxamide

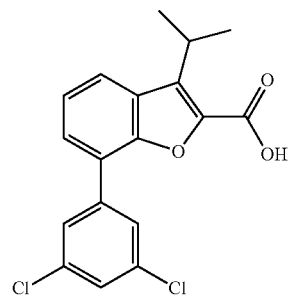

HATU, DIEA, DCM
rt, 2 h

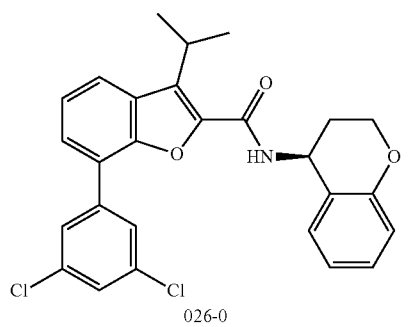

026-0

Into a 25-mL round-bottom flask, was placed 7-(3,5-dichlorophenyl)-3-isopropyl-1-benzofuran-2-carboxylic acid (150 mg, 0.4 mmol, 1.0 equiv), (4S)-3,4-dihydro-2H-1-benzopyran-4-amine (76.9 mg, 0.52 mmol, 1.20 equiv), HATU (196 mg, 0.52 mmol, 1.20 equiv), DIEA (166.6 mg, 1.3 mmol, 3.0 equiv), DCM (5 mL). The resulting solution was stirred for 2 hr at room temperature. The resulting mixture was concentrated. The crude product was further purified by Flash-Prep-HPLC with the following conditions (IntelFlash-1): Column, C18 silica gel; mobile phase, 0.05% FA in water and CH₃CN (40% CH₃CN increasing to 95% within 13 min); Detector, UV 254 &220 nm. This resulted in 120 mg (58.2%) of 7-(3,5-dichlorophenyl)-N-[(4S)-3,4-dihydro-2H-1-benzopyran-4-yl]-3-isopropyl-1-benzofuran-2-carboxamide as a white solid. (ES, m/z): 480 [M+H]⁺;

¹H-NMR (300 MHz, CDCl₃): δ=7.88 (dd, J=7.9, 1.2 Hz, 1H), 7.66 (d, J=1.9 Hz, 2H), 7.51 (dd, J=7.5, 1.2 Hz, 1H), 7.45-7.32 (m, 3H), 7.27-7.18 (m, 1H), 6.96 (td, J=7.5, 1.2 Hz, 1H), 6.89 (dd, J=8.2, 1.2 Hz, 1H), 6.80 (d, J=7.8 Hz, 1H), 5.48-5.31 (m, 1H), 4.47-4.19 (m, 3H), 2.51-2.33 (m, 1H), 2.28-2.13 (m, 1H), 1.53 (dd, J=7.1, 2.1 Hz, 6H) ppm.

The following reaction may be used to prepare methyl 7-(3,5-dichlorophenyl)-3-morpholinobenzofuran-2-carboxylate which may be converted according to Scheme 5 to an alternate compound having a morpholine group at the position corresponding to R³.

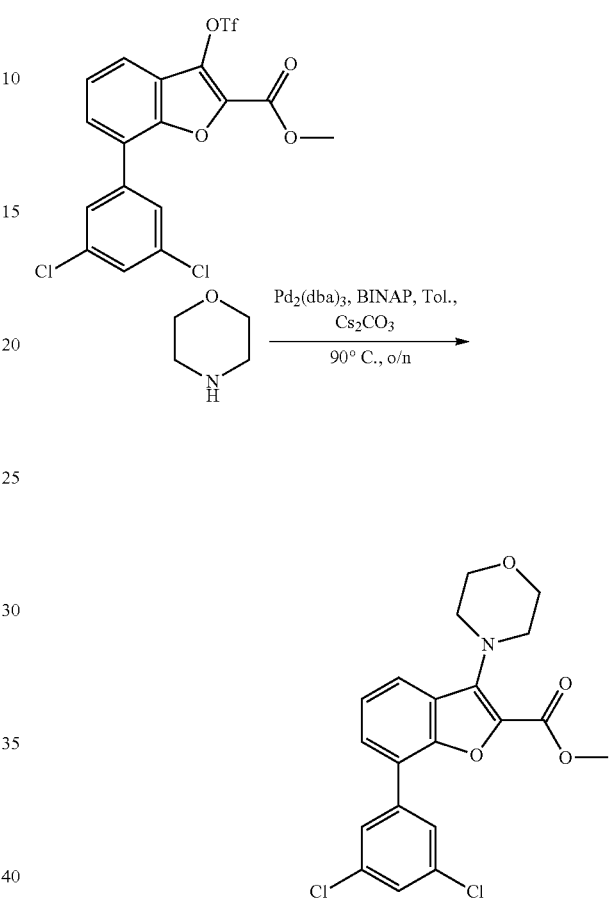

Into a 50-mL round-bottom flask purged and maintained with an inert atmosphere of nitrogen, was placed methyl 7-(3,5-dichlorophenyl)-3-(trifluoromethanesulfonyloxy)-1-benzofuran-2-carboxylate (500.0 mg, 1.07 mmol, 1.0 equiv), morpholine (186 mg, 2.1 mmol, 2.0 equiv), BINAP (133 mg, 0.21 mmol, 0.20 equiv), Pd₂(dba)₃ (97.6 mg, 0.11 mmol, 0.1 equiv), Cs₂CO₃ (0.69 g, 2.13 mmol, 2.0 equiv), toluene (10 mL). The resulting solution was stirred overnight at 90° C. The reaction mixture was cooled to room temperature. The reaction was then quenched by the addition of 20 mL of water. The resulting solution was extracted with 2×15 mL of ethyl acetate and the organic layers combined and dried over anhydrous sodium sulfate and concentrated. The residue was applied onto a silica gel column with ethyl acetate/petroleum ether (1/5). This resulted in 200 mg (46.2%) of methyl 7-(3,5-dichlorophenyl)-3-(morpholin-4-yl)-1-benzofuran-2-carboxylate as a white solid.

The following compounds can be synthesized by adopting Scheme 6 below and the following reaction schemes:

119, 120, 122, 199, 202, 204, 205, 207, 210, 212, 212-0A, 251, 252, 253, 253-0A, 254, 256, 258, 259, 259-5, 260, 261, 262, 263, 263-8, 285, 300, 301, 309, 310, 311, 319, 336, 337, 338.

Scheme 6
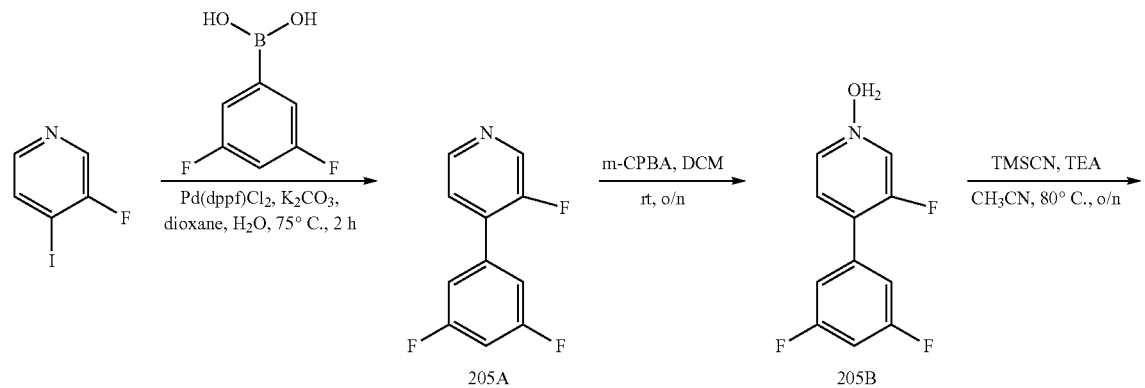
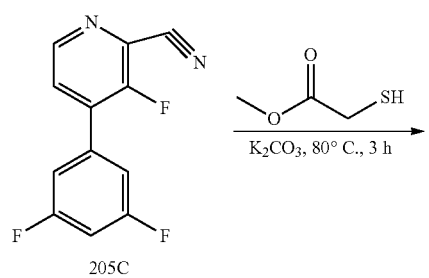
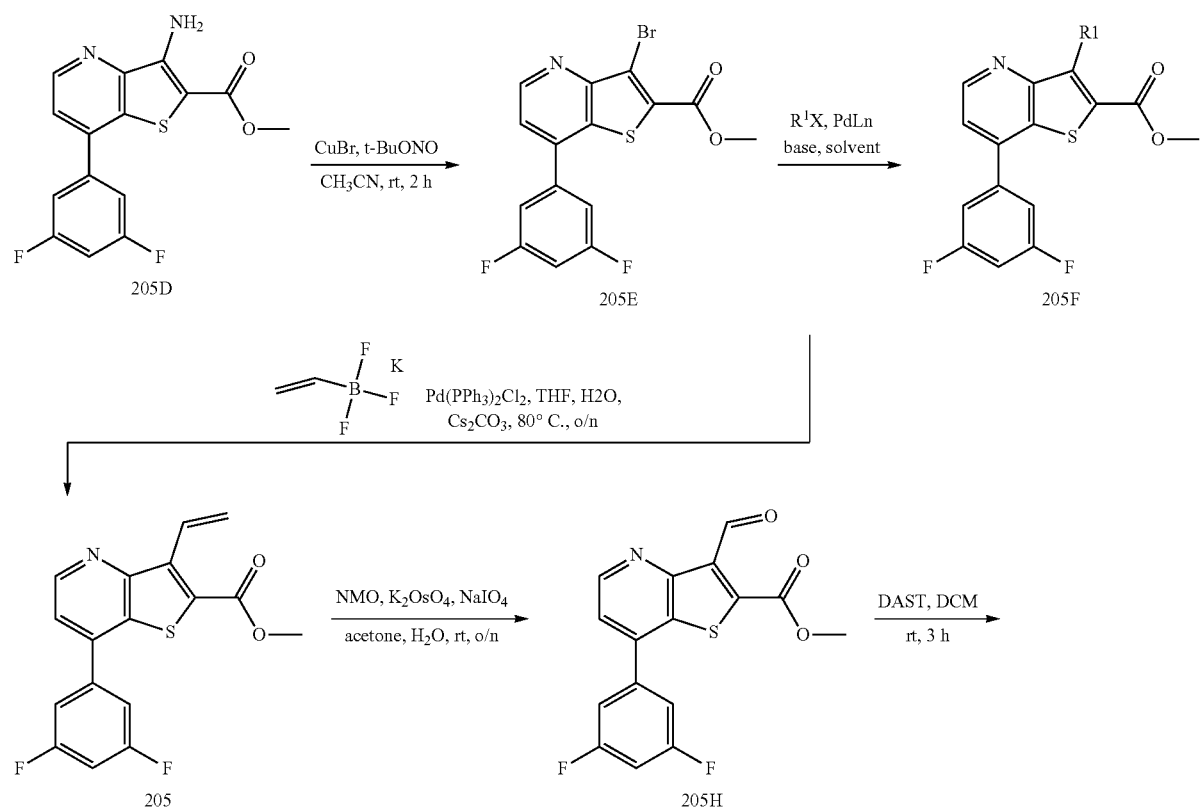

-continued

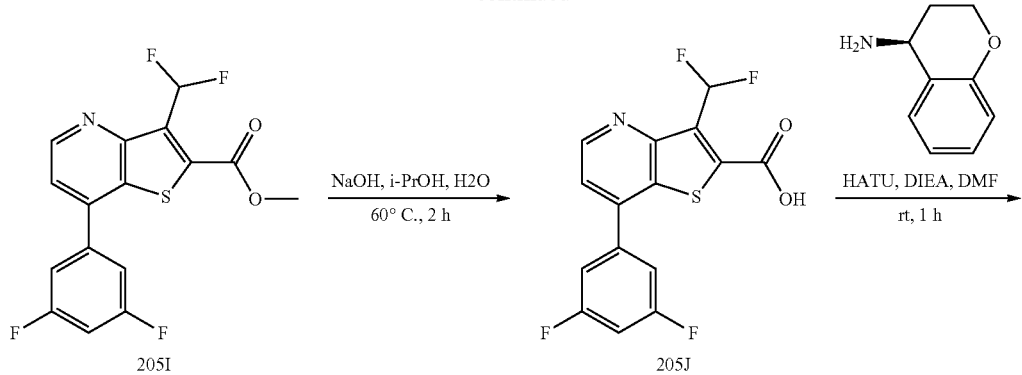

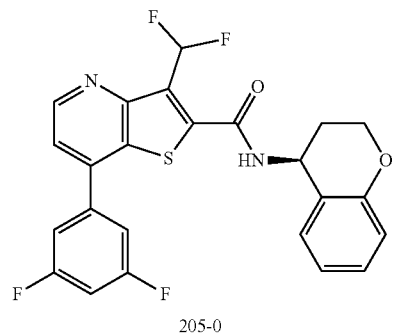

1. Synthesis of 4-(3,5-difluorophenyl)-3-fluoropyridine

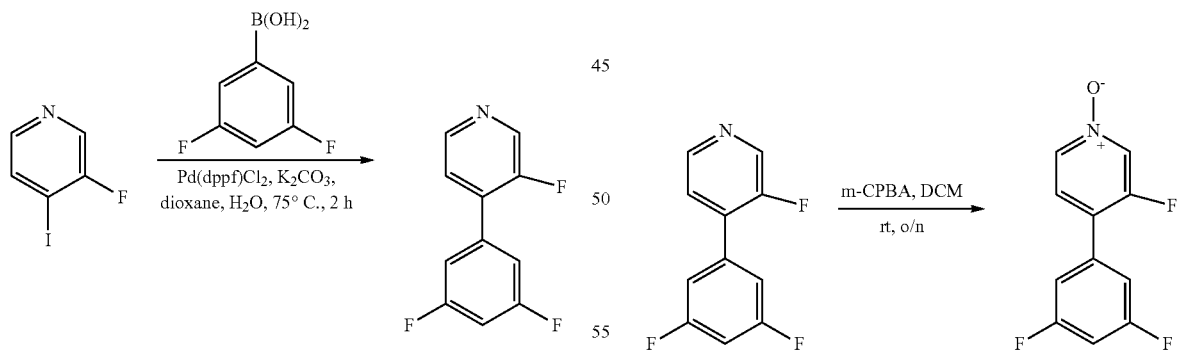

Into a 1000-mL 3-necked round-bottom flask purged and maintained with an inert atmosphere of nitrogen, was placed 3-fluoro-4-iodopyridine (30.0 g, 134.5 mmol, 1.0 equiv), dioxane (20 mL), 3,5-difluorophenylboronic acid (25.5 g, 161.4 mmol, 1.2 equiv), Pd(dppf)Cl$_2$ (4.92 g, 6.7 mmol, 0.05 equiv), K$_2$CO$_3$ (37.2 g, 269.0 mmol, 2.0 equiv), H$_2$O (4 mL). The resulting solution was stirred for 2 hr at ° C. The resulting solution was extracted with 3×500 mL of ethyl acetate concentrated under vacuum. The residue was applied onto a silica gel column with ethyl acetate/petroleum ether (0%~30%). This resulted in 26 g (92.4%) of 4-(3,5-difluorophenyl)-3-fluoropyridine as a white solid.

2. Synthesis of 4-(3,5-difluorophenyl)-3-fluoropyridine 1-oxide

Into a 1000-mL round-bottom flask, was placed 4-(3,5-difluorophenyl)-3-fluoropyridine (26.0 g, 124.3 mmol, 1.0 equiv), DCM (500 mL), m-CPBA (42.9 g, 248.6 mmol, 2.0 equiv). The resulting solution was stirred for 1 overnight at room temperature. The resulting mixture was concentrated under vacuum. The residue was applied onto a silica gel column with ethyl acetate/petroleum ether (EA 0%~100%) ~EA/MeOH(1/2). This resulted in 21 g (75.0%) of 4-(3,5-difluorophenyl)-3-fluoropyridin-1-ium-1-olate as a white solid.

3. Synthesis of 4-(3,5-difluorophenyl)-3-fluoropicolinonitrile

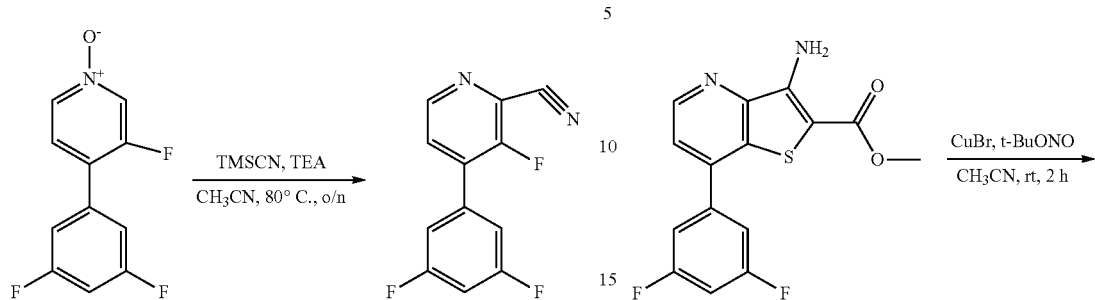

Into a 1000-mL round-bottom flask purged and maintained with an inert atmosphere of nitrogen, was placed 4-(3,5-difluorophenyl)-3-fluoropyridin-1-ium-1-olate (21.0 g, 93.3 mmol, 1.0 equiv), CH₃CN (500 mL), TMSCN (23.1 g, 233.2 mmol, 2.5 equiv), TEA (19.8 g, 195.8 mmol, 2.10 equiv). The resulting solution was stirred overnight at 80° C. The resulting mixture was concentrated under vacuum. The residue was applied onto a silica gel column with ethyl acetate/petroleum ether (EA 0%~30%). This resulted in 10 g (45.8%) of 4-(3,5-difluorophenyl)-3-fluoropyridine-2-carbonitrile as an off-white solid.

4. Synthesis of Methyl 3-amino-7-(3,5-difluorophenyl)thieno[3,2-b]pyridine-2-carboxylate

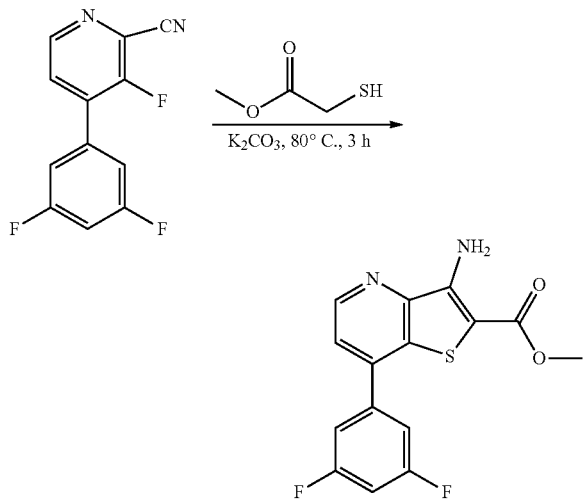

Into a 250-mL round-bottom flask, was placed 4-(3,5-difluorophenyl)-3-fluoropyridine-2-carbonitrile (6.0 g, 25.6 mmol, 1.0 equiv), CH₃CN (100 mL), methyl thioglycolate (8.2 g, 76.9 mmol, 3.0 equiv), K₂CO₃ (10.6 g, 76.86 mmol, 3 equiv). The resulting solution was stirred for 2 hr at 80° C. The reaction mixture was cooled to room temperature. The reaction was then quenched by the addition of 200 mL of water. The solids were collected by filtration and washed with water (3×20 mL). This resulted in 6 g (73.1%) of methyl 3-amino-7-(3,5-difluorophenyl)thieno[3,2-b]pyridine-2-carboxylate as a light yellow solid.

5. Synthesis of Methyl 3-bromo-7-(3,5-difluorophenyl)thieno[3,2-b]pyridine-2-carboxylate

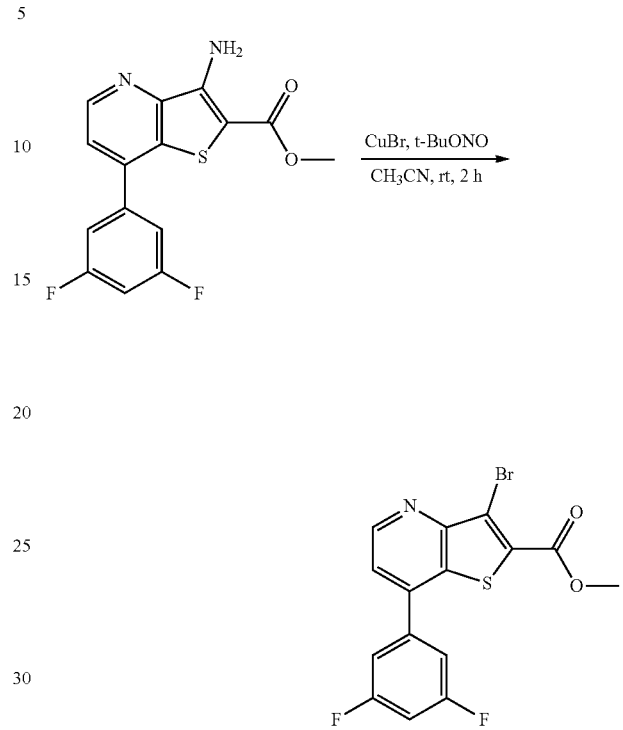

Into a 250-mL 3-necked round-bottom flask purged and maintained with an inert atmosphere of argon, was placed HBr (25.0 mL), CuBr (705.4 mg, 4.9 mmol, 1.0 equiv), methyl 3-amino-7-(3,5-difluorophenyl)thieno[3,2-b]pyridine-2-carboxylate (1.5 g, 4.7 mmol, 1.0 equiv). This was followed by the addition of a solution of NaNO₂ (388 mg, 5.6 mmol, 1.2 equiv) in H₂O (5 mL) dropwise with stirring at 0° C. The resulting solution was stirred for 1 overnight at 20° C. The reaction was poured into 200 mL of ice water. The precipitate was collected by filtration. The solid was dissolved in 100 mL of DCM and washed with 3×100 mL of brine. The mixture was dried over anhydrous sodium sulfate and concentrated under vacuum. This resulted in 1.5 g (83.4%) of methyl 3-bromo-7-(3,5-difluorophenyl)thieno[3,2-b]pyridine-2-carboxylate as a light yellow solid.

6. Synthesis of Methyl 7-(3,5-difluorophenyl)-3-vinylthieno[3,2-b]pyridine-2-carboxylate

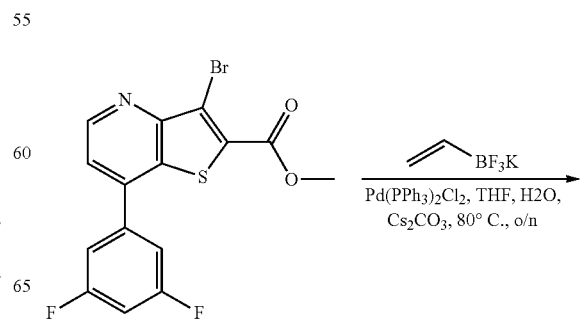

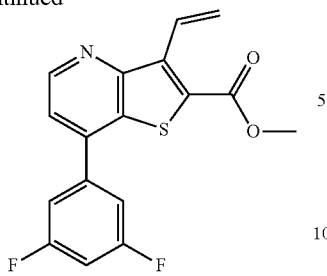

Into a 40-mL vial purged and maintained with an inert atmosphere of nitrogen, was placed methyl 3-bromo-7-(3,5-difluorophenyl)thieno[3,2-b]pyridine-2-carboxylate (500 mg, 1.3 mmol, 1.0 equiv), THF (10 mL), potassium ethenyltrifluoroboranuide (523 mg, 3.9 mmol, 3.0 equiv), H$_2$O (2 mL), Pd(PPh$_3$)$_2$Cl$_2$ (91.4 mg, 0.1 mmol, 0.1 equiv), Cs$_2$CO$_3$ (1.27 g, 3.9 mmol, 3.0 equiv). The resulting solution was stirred overnight at 80° C. The resulting mixture was concentrated under vacuum. The residue was applied onto a silica gel column with ethyl acetate/petroleum ether (EA 0%~30%). This resulted in 350 mg (81.2%) of methyl 7-(3,5-difluorophenyl)-3-ethenylthieno[3,2-b]pyridine-2-carboxylate as a yellow solid.

7. Synthesis of Methyl 7-(3,5-difluorophenyl)-3-formylthieno[3,2-b]pyridine-2-carboxylate

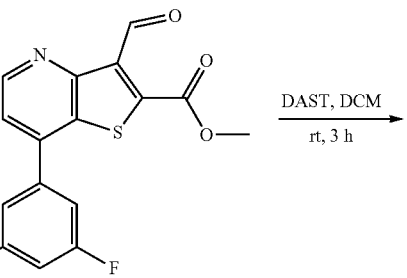

Into a 100-mL round-bottom flask, was placed K$_2$OsO$_4$·2H$_2$O (200.2 mg, 0.5 mmol, 0.6 equiv), acetone (10 mL), H$_2$O (10 mL), NMO (636.4 mg, 5.4 mmol, 6.0 equiv), NaIO$_4$ (1.2 g, 5.4 mmol, 6 equiv), methyl 7-(3,5-difluorophenyl)-3-ethenylthieno[3,2-b]pyridine-2-carboxylate (300 mg, 0.90 mmol, 1.00 equiv). The resulting solution was stirred overnight at room temperature. The resulting solution was extracted with 3×20 mL of ethyl acetate and the organic layers combined. The resulting mixture was washed with 3×20 mL of brine. The resulting mixture was concentrated under vacuum. The residue was applied onto a silica gel column with ethyl acetate/petroleum ether (EA 0%~30%). This resulted in 170 mg (56.3%) of methyl 7-(3,5-difluorophenyl)-3-formylthieno[3,2-b]pyridine-2-carboxylate as a yellow solid.

8. Synthesis of Methyl 3-(difluoromethyl)-7-(3,5-difluorophenyl)thieno[3,2-b]pyridine-2-carboxylate

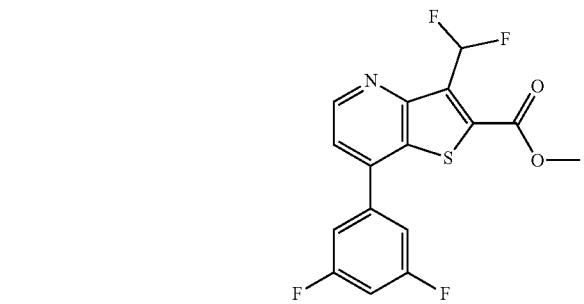

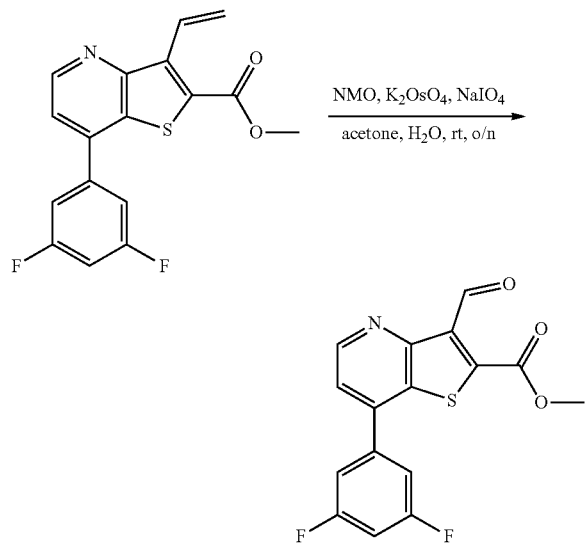

Into a 50-mL round-bottom flask, was placed methyl 7-(3,5-difluorophenyl)-3-formylthieno[3,2-b]pyridine-2-carboxylate (170 mg, 0.5 mmol, 1.0 equiv), DCM (5 mL), DAST (0.5 mL, 0.001 mmol, 0.04 equiv). The resulting solution was stirred for 3 hr at room temperature. The reaction was added by the dropwise into 30 mL of water/ice. The resulting solution was extracted with 3×10 mL of dichloromethane and the organic layers combined. The resulting mixture was washed with 3×20 mL of brine. The resulting mixture was concentrated. The residue was applied onto a silica gel Pre-TLC with ethyl acetate/petroleum ether (1/3). This resulted in 130 mg (71.7%) of methyl 3-(difluoromethyl)-7-(3,5-difluorophenyl)thieno[3,2-b]pyridine-2-carboxylate as a white solid.

9. Synthesis of 3-(difluoromethyl)-7-(3,5-difluorophenyl)thieno[3,2-b]pyridine-2-carboxylic Acid

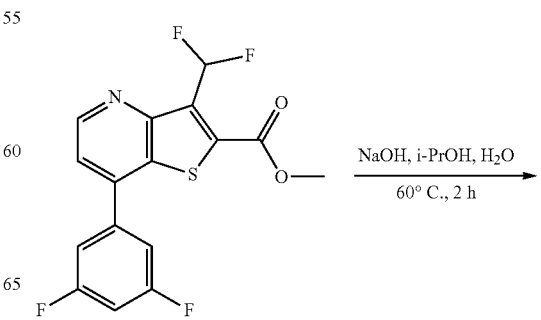

-continued

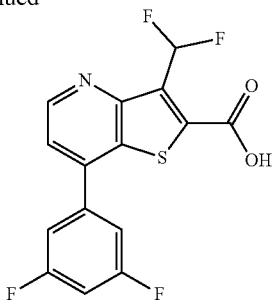

Into a 25-mL round-bottom flask, was placed methyl 3-(difluoromethyl)-7-(3,5-difluorophenyl)thieno[3,2-b]pyridine-2-carboxylate (110 mg, 0.3 mmol, 1.0 equiv), i-PrOH (2.0 mL, 0.1 mmol), NaOH (200 mg, 5.0 mmol, 16.1 equiv), H₂O (2.0 mL, 0.3 mmol). The resulting solution was stirred for 2 hr at 60° C. The reaction mixture was cooled to room temperature. The pH value of the solution was adjusted to 5 by addition of aqueous solution of HCl (2 mol/L). The resulting solution was extracted with 3×10 mL of ethyl acetate and the organic layers combined. The resulting mixture was washed with 3×10 ml of brine. The mixture was dried over anhydrous sodium sulfate and concentrated under vacuum. This resulted in 100 mg (94.6%) of 3-(difluoromethyl)-7-(3,5-difluorophenyl)thieno[3,2-b]pyridine-2-carboxylic acid as a white solid.

10. Synthesis of 3-(difluoromethyl)-7-(3,5-difluorophenyl)-N-[(4S)-3,4-dihydro-2H-1-benzopyran-4-yl]thieno[3,2-b]pyridine-2-carboxamide

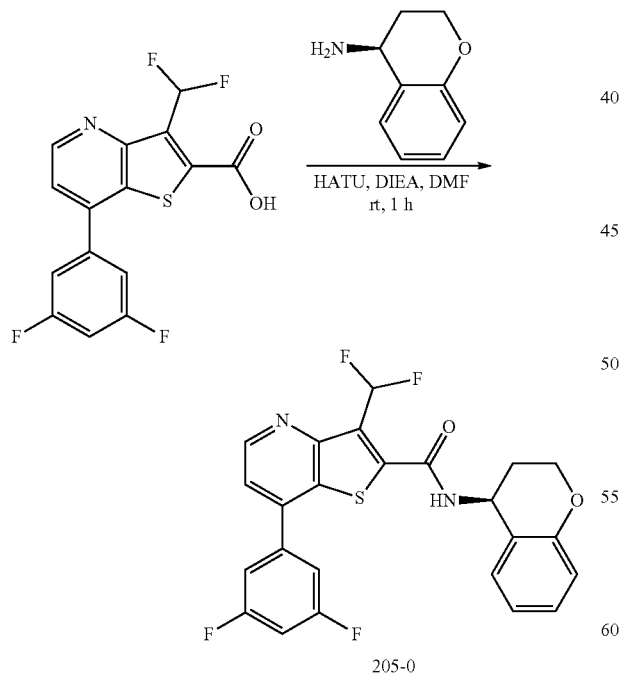

205-0

Into a 50-mL round-bottom flask, was placed 3-(difluoromethyl)-7-(3,5-difluorophenyl)thieno[3,2-b]pyridine-2-carboxylic acid (80 mg, 0.2 mmol, 1.0 equiv), DMF (3 mL), (4S)-3,4-dihydro-2H-1-benzopyran-4-amine (70 mg, 0.5 mmol, 2.0 equiv), DIEA (91 mg, 0.7 mmol, 3.0 equiv), HATU (133.7 mg, 0.3 mmol, 1.5 equiv). The resulting solution was stirred for 1 hr at room temperature. The residue was applied onto a C18 column with 0.05% FA in H₂O and CH₃CN (40% CH₃CN up to 80% in 10 min). This resulted in 82.4 mg (74.4%) of 3-(difluoromethyl)-7-(3,5-difluorophenyl)-N-[(4 S)-3,4-dihydro-2H-1-benzopyran-4-yl]thieno[3,2-b]pyridine-2-carboxamide as an off-white solid. (ES, m/z): 479 [M+H]+; ¹H-NMR (300 MHz, CDCl₃): δ=8.88 (d, J=4.8 Hz, 1H), 7.63 (t, J=54.9 Hz, 1H), 7.45 (d, J=8.0 Hz, 1H), 7.39-7.19 (m, 5H), 7.15 (d, J=8.0 Hz, 1H), 7.09-6.86 (m, 3H), 5.40 (q, J=5.9 Hz, 1H), 4.39-4.22 (m, 2H), 2.43-2.24 (m, 2H) ppm.

Compounds 199-0 and 311-1 can be prepared according to the process decited in Scheme 7 below and the following procedures:

Scheme 7

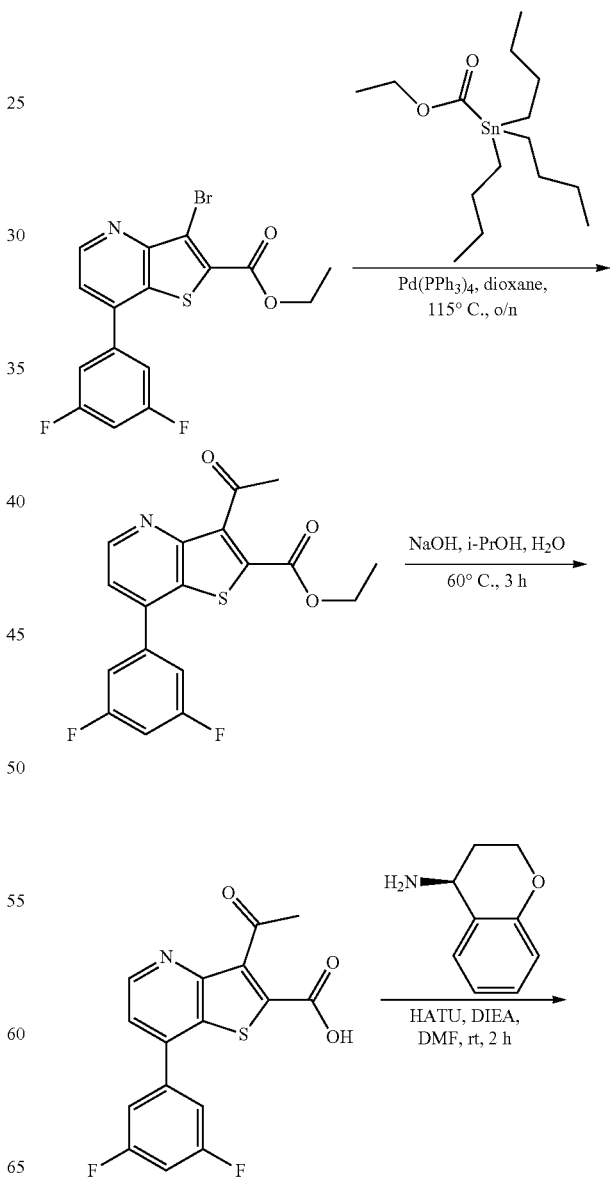

101
-continued

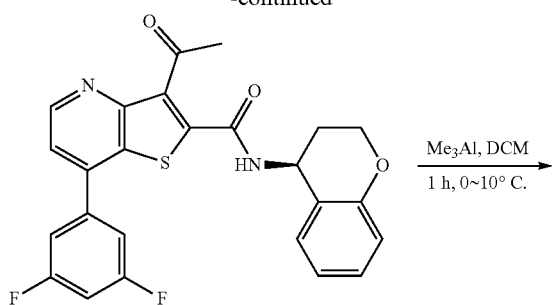

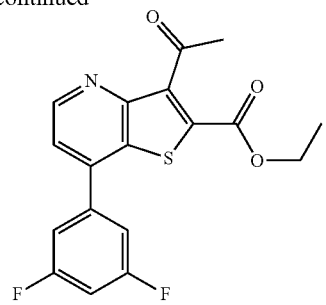

Into a 40-mL vial purged and maintained with an inert atmosphere of nitrogen, was placed ethyl 3-bromo-7-(3,5-difluorophenyl)thieno[3,2-b]pyridine-2-carboxylate (1.0 g, 2.5 mmol, 1.0 equiv), dioxane (20 mL), tributyl(1-ethoxyethenyl)stannane (2.7 g, 7.5 mmol, 3.0 equiv), Pd(PPh₃)₄ (290.2 mg, 0.2 mmol, 0.1 equiv). The resulting solution was stirred overnight at 115° C. The reaction mixture was cooled to room temperature. The reaction was then quenched by the addition of aqueous solution of HCl (10 mL, 2 mol/L). The resulting solution was extracted with 3×20 mL of ethyl acetate concentrated under vacuum. The residue was applied onto a silica gel column with ethyl acetate/petroleum ether (10%-30%). This resulted in 800 mg (88.2%) of ethyl 3-acetyl-7-(3,5-difluorophenyl)thieno[3,2-b]pyridine-2-carboxylate as a light yellow solid.

Synthesis of 3-acetyl-7-(3,5-difluorophenyl)thieno[3,2-b]pyridine-2-carboxylic Acid

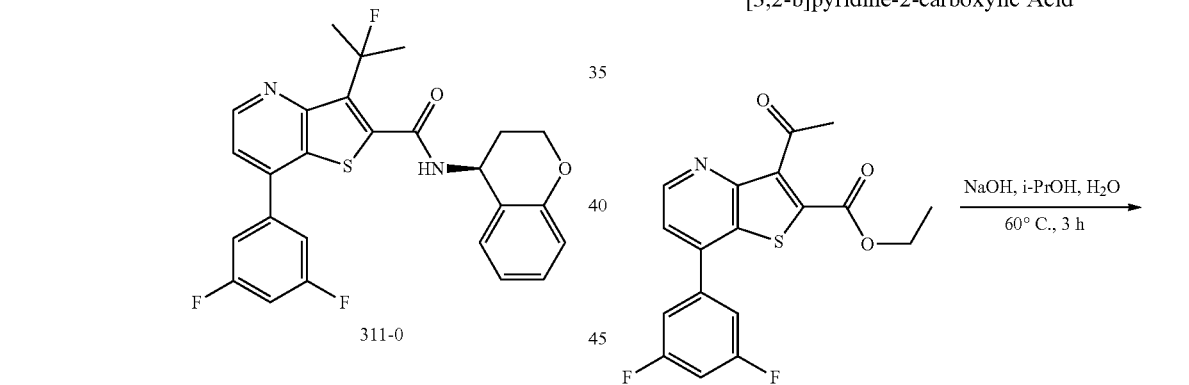

Synthesis of Ethyl 3-acetyl-7-(3,5-difluorophenyl)thieno[3,2-b]pyridine-2-carboxylate

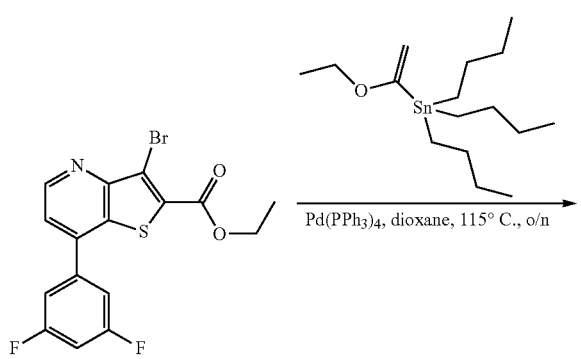

Into a 25-mL round-bottom flask, was placed ethyl 3-acetyl-7-(3,5-difluorophenyl)thieno[3,2-b]pyridine-2-carboxylate (300 mg, 0.8 mmol, 1.0 equiv), i-PrOH (10 mL, 0.2 mmol, 0.2 equiv), H₂O (10 mL), NaOH (300 mg, 7.5 mmol, 9.0 equiv). The resulting solution was stirred for 3 hr at 60° C. The reaction mixture was cooled to room temperature. The pH value of the solution was adjusted to 5 by addition of aqueous solution of HCl (2 mol/L). The resulting solution was extracted with 3×20 mL of ethyl acetate. The resulting mixture was washed with 3×20 ml of brine. The mixture was dried over anhydrous sodium sulfate and concentrated under vacuum. This resulted in 270 mg (97.6%) of 3-acetyl-7-(3,5-difluorophenyl)thieno[3,2-b]pyridine-2-carboxylic acid as yellow oil.

Synthesis of 3-acetyl-7-(3,5-difluorophenyl)-N-[(4S)-3,4-dihydro-2H-1-benzopyran-4-yl]thieno[3,2-b]pyridine-2-carboxamide

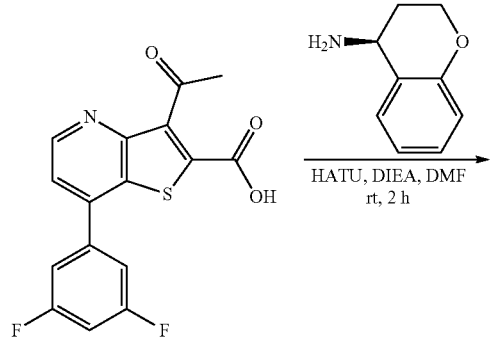

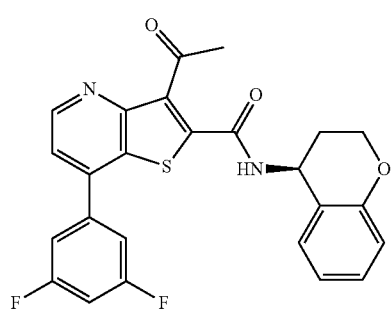

Into a 25-mL round-bottom flask, was placed 3-acetyl-7-(3,5-difluorophenyl)thieno[3,2-b]pyridine-2-carboxylic acid (270 mg, 0.81 mmol, 1.00 equiv), DMF (5 mL), (4S)-3,4-dihydro-2H-1-benzopyran-4-amine (242 mg, 1.62 mmol, 2.00 equiv), DIEA (314 mg, 2.4 mmol, 3.0 equiv), HATU (462 mg, 1.2 mmol, 1.5 equiv). The resulting solution was stirred for 2 hr at room temperature. The residue was applied onto a C18 column with 0.05% FA in H$_2$O and CH$_3$CN (40% CH$_3$CN up to 90% in 10 min). This resulted in 180 mg (47.8%) of 3-acetyl-7-(3,5-difluorophenyl)-N-[(4S)-3,4-dihydro-2H-1-benzopyran-4-yl]thieno[3,2-b]pyridine-2-carboxamide as a white solid.

Synthesis of 7-(3,5-difluorophenyl)-N-[(4S)-3,4-dihydro-2H-1-benzopyran-4-yl]-3-(2-hydroxypropan-2-yl)thieno[3,2-b]pyridine-2-carboxamide

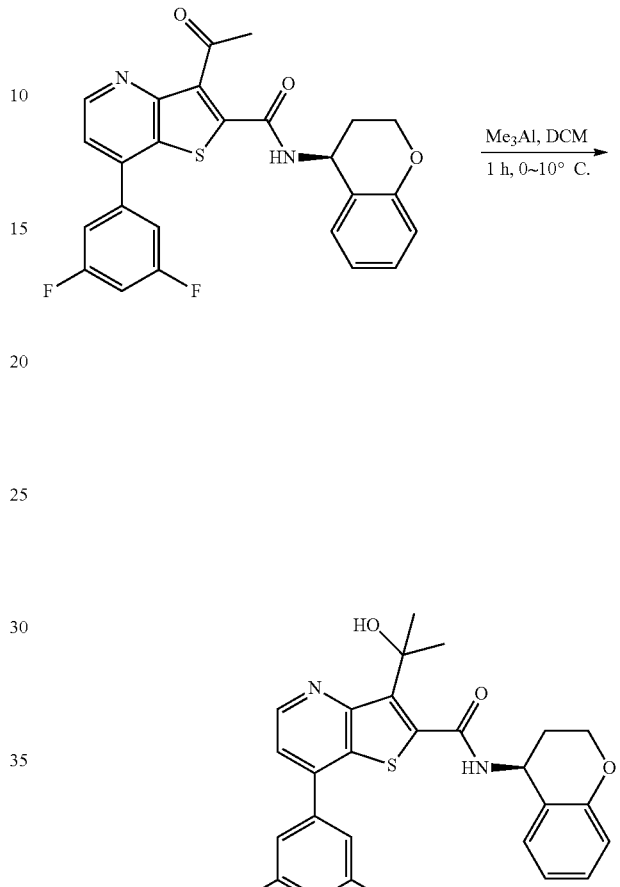

199-0

Into a 40-mL vial purged and maintained with an inert atmosphere of nitrogen, was placed 3-acetyl-7-(3,5-difluorophenyl)-N-[(4S)-3,4-dihydro-2H-1-benzopyran-4-yl]thieno[3,2-b]pyridine-2-carboxamide (160 mg, 0.3 mmol, 1.0 equiv), DCM (10 mL). This was followed by the addition of AlMe$_3$ (0.2 mL, 1.7 mmol, 5.0 equiv) dropwise with stirring at 0° C. The resulting solution was stirred for 1 hr at 0-10° C. The reaction was added by dropwise into 20 mL of ice water. The resulting solution was extracted with 3×10 mL of dichloromethane and the organic layers combined. The resulting mixture was washed with 3×20 mL of brine. The resulting mixture was concentrated under vacuum. The residue was applied onto a silica gel column with ethyl acetate/petroleum ether (1/2). This resulted in 35.3 mg (21.3%) of 7-(3,5-difluorophenyl)-N-[(4S)-3,4-dihydro-2H-1-benzopyran-4-yl]-3-(2-hydroxypropan-2-yl)thieno[3,2-b]pyridine-2-carboxamide as a light yellow solid. (ES, m/z): 447 [M+H]$^+$; $^1$H-NMR (300 MHz, CDCl$_3$): δ=8.79 (d, J=4.8 Hz, 1H), 7.35-7.20 (m, 5H), 7.06-6.92 (m, 2H), 6.88 (dd, J=8.3, 1.2 Hz, 1H), 6.60 (d, J=7.4 Hz, 1H), 6.16 (s, 1H), 5.33 (q, J=5.5 Hz, 1H), 4.38-4.32 (m, 1H), 4.25-4.17 (m, 1H), 2.46-2.16 (m, 2H), 1.89 (d, J=4.2 Hz, 6H) ppm.

Synthesis of 7-(3,5-difluorophenyl)-N-[(4S)-3,4-dihydro-2H-1-benzopyran-4-yl]-3-(2-fluoropropan-2-yl)thieno[3,2-b]pyridine-2-carboxamide

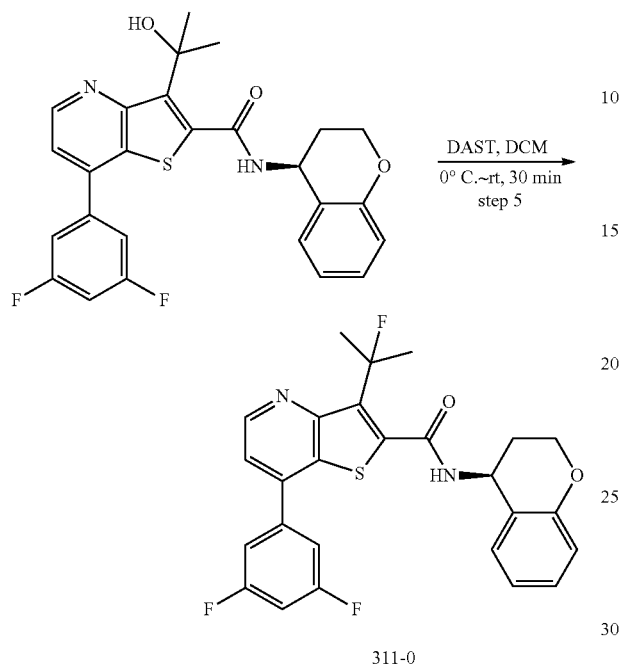

Into a 8-mL vial, was placed 7-(3,5-difluorophenyl)-N-[(4S)-3,4-dihydro-2H-1-benzopyran-4-yl]-3-(2-hydroxypropan-2-yl)thieno[3,2-b]pyridine-2-carboxamide (108 mg, 0.2 mmol, 1.0 equiv), DCM (3 mL). This was followed by the addition of DAST (72.5 mg, 0.4 mmol, 2.0 equiv) dropwise with stirring at 0° C. The resulting solution was stirred for 30 min at room temperature. The reaction was then quenched by the addition of 3 mL of water. The resulting solution was extracted with 3×5 mL of dichloromethane and the organic layers combined and concentrated. The crude product was purified by Prep-HPLC. This resulted in 23.1 mg (21.3%) of 7-(3,5-difluorophenyl)-N-[(4 S)-3,4-dihydro-2H-1-benzopyran-4-yl]-3-(2-fluoropropan-2-yl)thieno[3,2-b]pyridine-2-carboxamide as a yellow solid. (ES, m/z): 483 [M+H]$^+$; $^1$H-NMR (300 MHz, DMSO-d$_6$): δ=9.08 (d, J=8.2 Hz, 1H), 8.87 (d, J=4.8 Hz, 1H), 7.66-7.46 (m, 4H), 7.28 (d, J=7.6 Hz, 1H), 7.21-7.11 (m, 1H), 6.90 (td, J=7.5, 1.3 Hz, 1H), 6.78 (dd, J=8.2, 1.2 Hz, 1H), 5.24-5.13 (m, 1H), 4.29-4.17 (m, 2H), 2.24-2.03 (m, 2H), 1.98 (d, J=9.9 Hz, 3H), 1.90 (d, J=9.8 Hz, 3H) ppm.

Compound 030 can be prepared according to the process depicted in Scheme 8 below and the following procedures:

Scheme 8

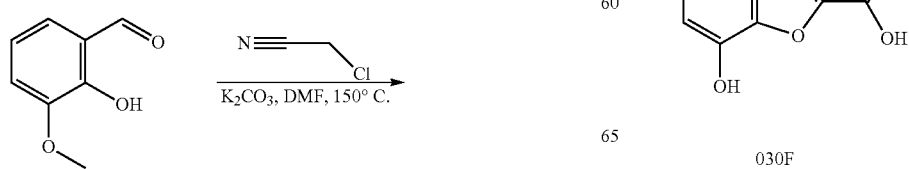

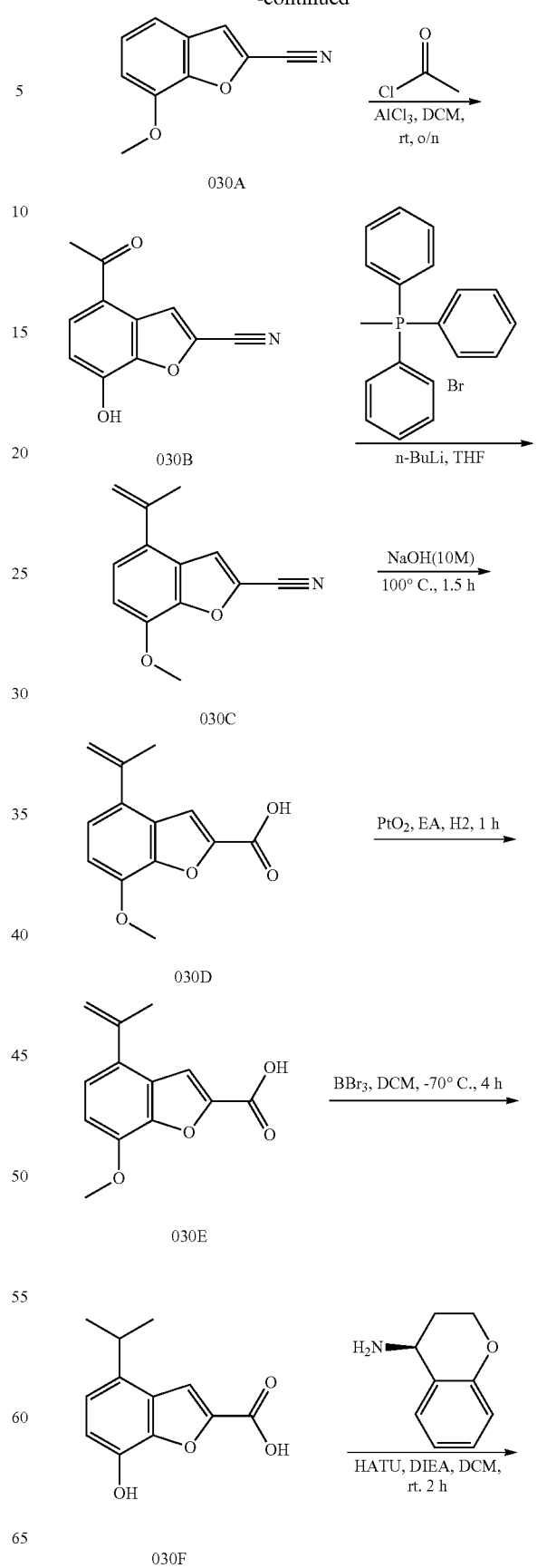

-continued

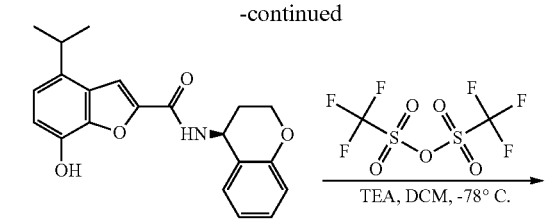

030G

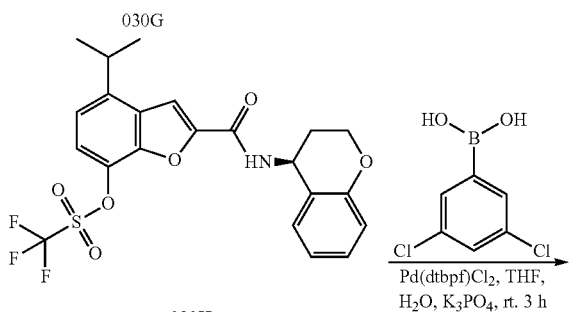

030H

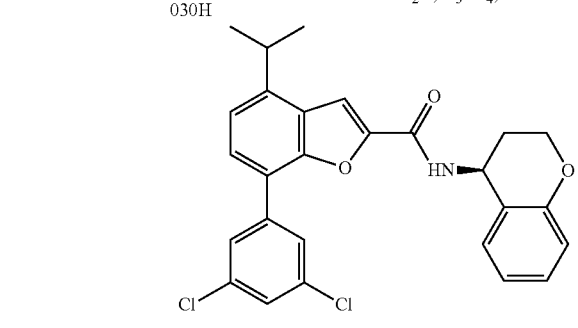

030-O

1. Synthesis of 7-methoxy-1-benzofuran-2-carbonitrile

Into a 500-mL round-bottom flask, was placed O-vanillin (50.0 g, 328.6 mmol, 1.0 equiv), chloroacetonitrile (29.7 g, 394.3 mmol, 1.2 equiv), K$_2$CO$_3$ (49.9 g, 361.5 mmol, 1.1 equiv), DMF (530 mL). The resulting solution was stirred for 1 hr at 150° C. in an oil bath. Then, more K$_2$CO$_3$ (49.9 g, 361.5 mmol, 1.1 equiv), was added and stirred for 20 min. The reaction was then quenched by the addition of 530 mL of water. The resulting solution was extracted with 3×500 mL of ethyl acetate, the organic layer was dried over anhydrous sodium sulfate and concentrated. The residue was applied onto a silica gel column with ethyl acetate/petroleum ether (1:10). This resulted in 14 g (24.6%) of 7-methoxy-1-benzofuran-2-carbonitrile as a white solid.

2. Synthesis of 4-acetyl-7-hydroxy-1-benzofuran-2-carbonitrile

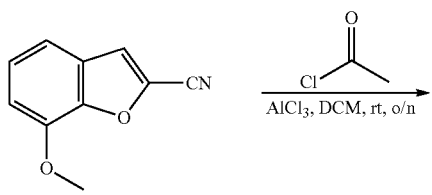

-continued

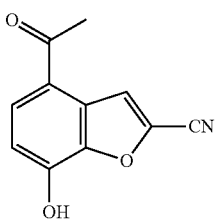

Into a 100-mL round-bottom flask, was placed 7-methoxy-1-benzofuran-2-carbonitrile (14.0 g, 80.8 mmol, 1.00 equiv), acetyl chloride (19.0 g, 242.5 mmol, 3.0 equiv), DCM (300 mL). This was followed by the addition of AlCl$_3$ (43.1 g, 323.3 mmol, 4.0 equiv) in several batches at 0° C. The resulting solution was stirred for 1 overnight at room temperature. The reaction was then quenched by the addition of 500 mL of water/ice. The resulting solution was extracted with 3×400 mL of ethyl acetate, the organic layer was dried over anhydrous sodium sulfate and concentrated. The residue was applied onto a silica gel column with ethyl acetate/petroleum ether (1:10). This resulted in 9 g (51.7%) of 4-acetyl-7-methoxy-1-benzofuran-2-carbonitrile as a white solid.

3. Synthesis of 7-methoxy-4-(prop-1-en-2-yl)-1-benzofuran-2-carbonitrile

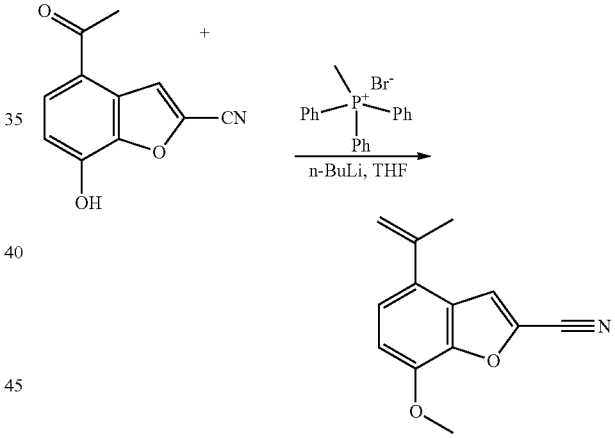

Into a 250-mL 3-necked round-bottom flask purged and maintained with an inert atmosphere of nitrogen, was placed methyltriphenylphosphonium bromide (7.9 g, 22.3 mmol, 1.2 equiv) and THF (50 mL). This was followed by the addition of n-BuLi in hexanes (12.6 mL, 31.6 mmol, 1.7 equiv) dropwise with stirring at 0° C. The resulting solution was stirred for 30 min at 0° C. To this was added 4-acetyl-7-methoxy-1-benzofuran-2-carbonitrile (4.0 g, 18.5 mmol, 1.0 equiv) dropwise with stirring at −78° C. The resulting solution was stirred for 2 hr at room temperature. The reaction was then quenched by the addition of 50 mL of water. The resulting solution was extracted with 3×50 mL of ethyl acetate. The organic phase was washed with 2×50 ml of brine. The mixture was dried over anhydrous sodium sulfate and concentrated. The residue was applied onto a silica gel column and eluted with ethyl acetate/petroleum ether (1:20). This resulted in 1.6 g (40.3%) of 7-methoxy-4-(prop-1-en-2-yl)-1-benzofuran-2-carbonitrile as a white solid.

4. Synthesis of 7-methoxy-4-(prop-1-en-2-yl)-1-benzofuran-2-carboxylic Acid

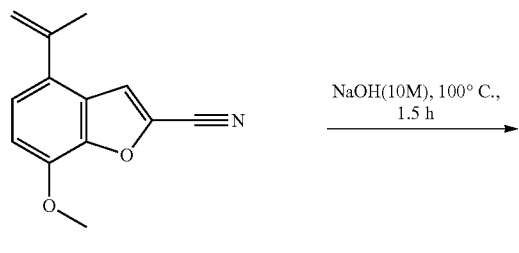

Into a 100-mL round-bottom flask, was placed 7-methoxy-4-(prop-1-en-2-yl)-1-benzofuran-2-carbonitrile (1.6 g, 7.5 mmol, 1.0 equiv) and aqueous NaOH (10 M) (50.0 mL). The resulting solution was stirred for 1.5 hr at 100° C. in an oil bath. The pH value of the solution was adjusted to 3-4 with aqueous HCl (6 M). The solid was collected by filtration. This resulted in 1.4 g (80.3%) of 7-methoxy-4-(prop-1-en-2-yl)-1-benzofuran-2-carboxylic acid as a white solid.

5. Synthesis of 4-isopropyl-7-methoxy-1-benzofuran-2-carboxylic Acid

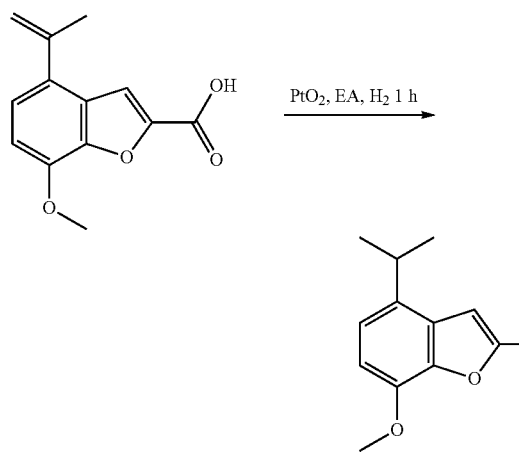

Into a 250-mL round-bottom flask, was placed 7-methoxy-4-(prop-1-en-2-yl)-1-benzofuran-2-carboxylic acid (2.2 g, 9.4 mmol, 1.0 equiv), EA (50.0 mL), PtO$_2$ (0.4 g, 1.8 mmol, 0.2 equiv), To the above H$_2$(g) was introduced in. The resulting solution was stirred for 2 hr at room temperature. The solids were filtered out. The resulting mixture was concentrated. This resulted in 2.2 g (99.1%) of 4-isopropyl-7-methoxy-1-benzofuran-2-carboxylic acid as a yellow solid.

6. Synthesis of 7-hydroxy-4-isopropyl-1-benzofuran-2-carboxylic Acid

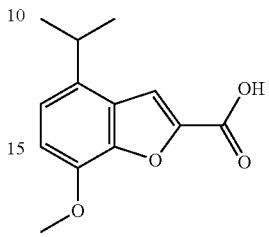

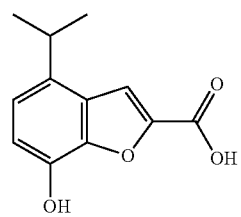

Into a 250-mL round-bottom flask purged and maintained with an inert atmosphere of nitrogen, was placed 4-isopropyl-7-methoxy-1-benzofuran-2-carboxylic acid (500.0 mg, 2.1 mmol, 1.0 equiv), DCM (50 mL). This was followed by the addition of BBr$_3$ (10.6 mL, 10.6 mmol, 5.0 equiv) dropwise with stirring at −70° C. The resulting solution was stirred for 4 hr at 5° C. The reaction was then quenched by the addition of NH$_4$Cl (aq. 50 mL). The resulting solution was extracted with 3×50 mL of DCM concentrated. This resulted in 500 mg (crude) of 7-hydroxy-4-isopropyl-1-benzofuran-2-carboxylic acid as colorless oil.

7. Synthesis of N-[(4S)-3,4-dihydro-2H-1-benzopyran-4-yl]-7-hydroxy-4-isopropyl-1-benzofuran-2-carboxamide

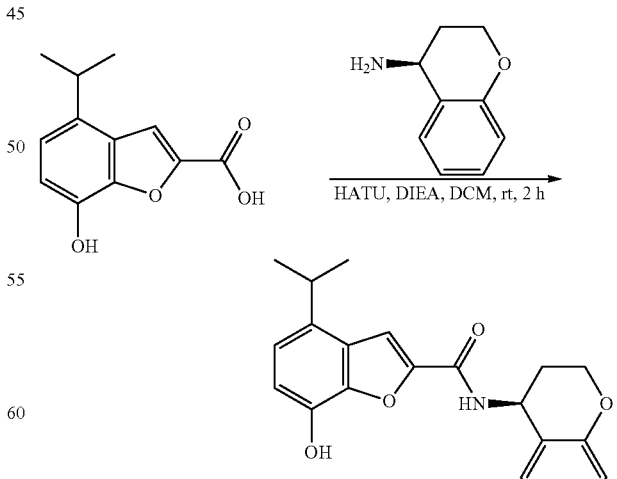

Into a 100-mL round-bottom flask, was placed 7-hydroxy-4-isopropyl-1-benzofuran-2-carboxylic acid (500.00 mg, 2.270 mmol, 1.00 equiv), (4S)-3,4-dihydro-2H-1-benzopyran-4-amine (508.1 mg, 3.4 mmol, 1.5 equiv), HATU (1726.5 mg, 4.5 mmol, 2.0 equiv), DIEA (880.3 mg, 6.8 mmol, 3.0 equiv), DCM (20.0 mL). The resulting solution was stirred for 2 hr at room temperature. The reaction was then quenched by the addition of 20 mL of water. The resulting solution was extracted with 3×30 mL of DCM, the organic layer was concentrated. The residue was applied onto a silica gel column with ethyl acetate/petroleum ether (1:5). This resulted in 250 mg (31.3%) of N-[(4S)-3,4-dihydro-2H-1-benzopyran-4-yl]-7-hydroxy-4-isopropyl-1-benzofuran-2-carboxamide as colorless oil.

8. Synthesis of 2-[[(4S)-3,4-dihydro-2H-1-benzopyran-4-yl]carbamoyl]-4-isopropyl-1-benzofuran-7-yl Trifluoromethanesulfonate

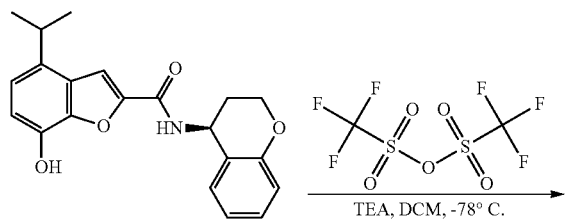

030-7

Into a 50-mL 3-necked round-bottom flask purged and maintained with an inert atmosphere of nitrogen, was placed N-[(4S)-3,4-dihydro-2H-1-benzopyran-4-yl]-7-hydroxy-4-isopropyl-1-benzofuran-2-carboxamide (240.0 mg, 0.6 mmol, 1.0 equiv), DCM (10.0 mL), TEA (138.2 mg, 1.3 mmol, 2.0 equiv). This was followed by the addition of Tf$_2$O (231.2 mg, 0.8 mmol, 1.2 equiv) dropwise with stirring at −70° C. The resulting solution was stirred for 2 hr at room temperature. The reaction was then quenched by the addition of 20 mL of NH$_4$Cl(aq.). The resulting solution was extracted with 3×20 mL of dichloromethane, the organic layer was dried over anhydrous sodium sulfate and concentrated. This resulted in 290 mg (87.8%) of 2-[[(4S)-3,4-dihydro-2H-1-benzopyran-4-yl]carbamoyl]-4-isopropyl-1-benzofuran-7-yl trifluoromethanesulfonate as colorless oil.

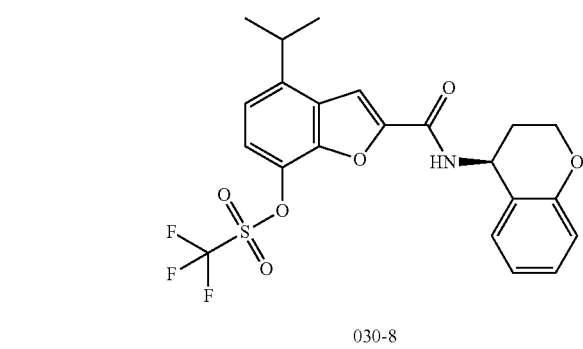

030-8

9. Synthesis of 7-(3,5-dichlorophenyl)-N-[(4S)-3,4-dihydro-2H-1-benzopyran-4-yl]-4-isopropyl-1-benzofuran-2-carboxamide

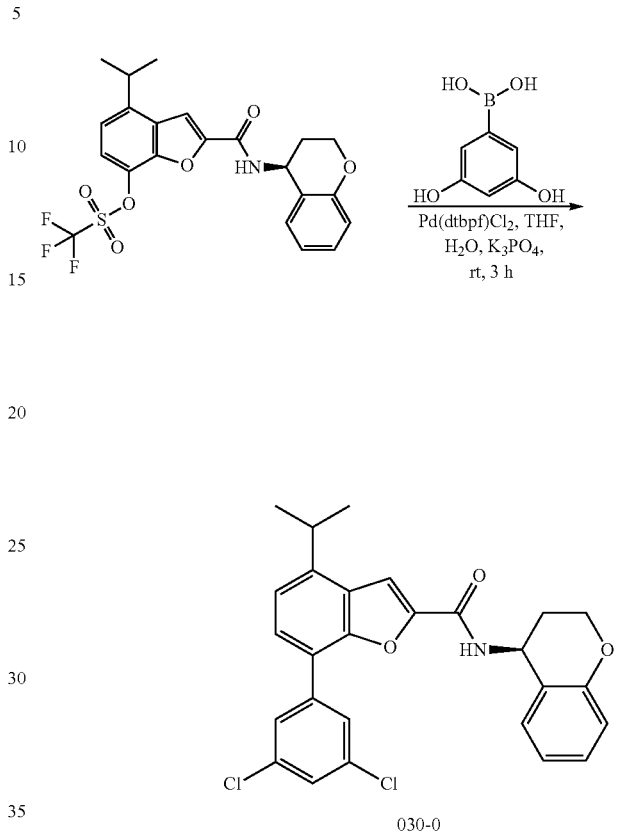

030-0

Into a 50-mL round-bottom flask purged and maintained with an inert atmosphere of nitrogen, was placed 2-[[(4S)-3,4-dihydro-2H-1-benzopyran-4-yl]carbamoyl]-4-isopropyl-1-benzofuran-7-yl trifluoromethanesulfonate (280.0 mg, 0.5 mmol, 1.0 equiv), 3,5-dichlorophenylboronic acid (143.6 mg, 0.7 mmol, 1.3 equiv), Pd(dtbpf)Cl$_2$ (37.7 mg, 0.058 mmol, 0.1 equiv), K$_3$PO$_4$ (245.8 mg, 1.1 mmol, 2.0 equiv), THF (12.00 mL), and water (3.00 mL). The resulting solution was stirred for 3 hr at room temperature. The resulting solution was diluted with 20 mL of water. The resulting solution was extracted with 3×20 mL of ethyl acetate, the organic layer was dried over anhydrous sodium sulfate and concentrated. The crude product was purified by Prep-HPLC with the following conditions (Waters-2767): Column, X-bridge RP18, 5 um, 19*100 mm; mobile phase, 0.03% ammonia in water and CH$_3$CN (50% CH$_3$CN up to 80% in 13 min); Detector, UV 254 nm. This resulted in 87 mg (31.27%) of 7-(3,5-dichlorophenyl)-N-[(4S)-3,4-dihydro-2H-1-benzopyran-4-yl]-4-isopropyl-1-benzofuran-2-carboxamide as a white solid. (ES, m/z): 480[M+H]$^+$; $^1$H-NMR (300 MHz, DMSO-d$_6$): δ=9.08 (d, J=8.2 Hz, 1H), 8.05-7.87 (m, 3H), 7.72 (d, J=7.8 Hz, 1H), 7.67 (t, J=1.9 Hz, 1H), 7.31 (d, J=7.9 Hz, 1H), 7.28-7.14 (m, 2H), 6.96-6.87 (m, 1H), 6.86-6.79 (m, 1H), 5.28 (q, J=6.7 Hz, 1H), 4.30 (dt, J=6.7, 3.8 Hz, 2H), 2.25-1.97 (m, 2H), 1.35 (d, J=6.9 Hz, 6H) ppm.

Compounds 264 and 264-0A can be prepared according to the Scheme 9 below and the following detailed procedures:

Scheme 9
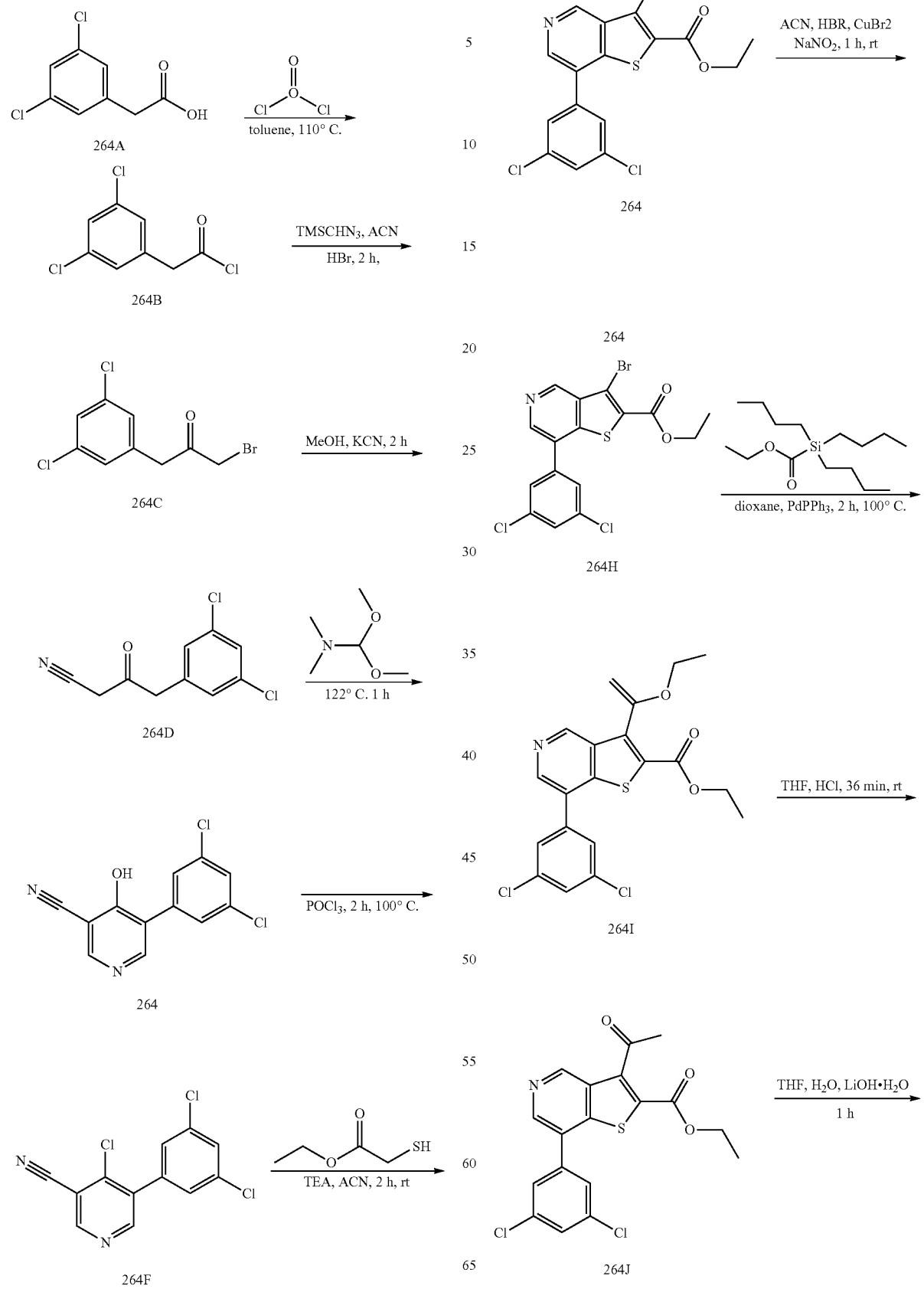

115
-continued

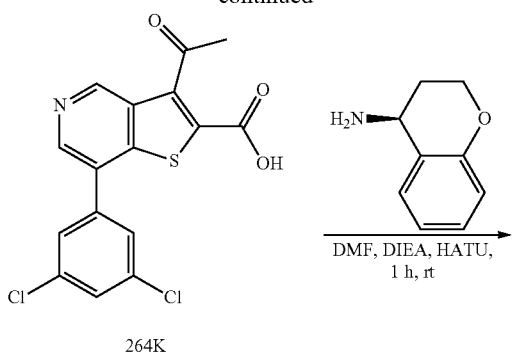

264K

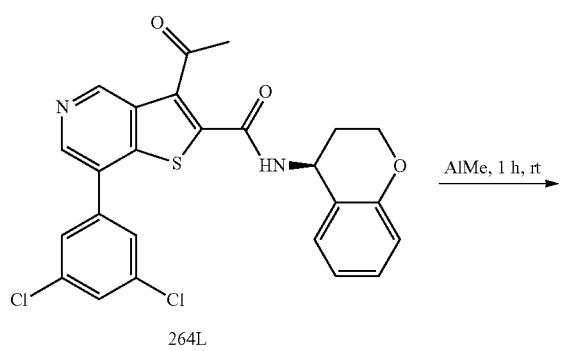

264L

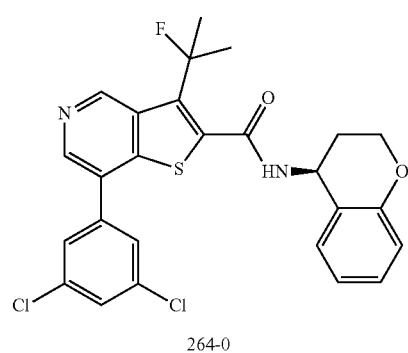

264-A

116

Exemplary Procedure of Compound 264 and 264-0A

1. Synthesis of (3,5-dichlorophenyl)acetyl Chloride

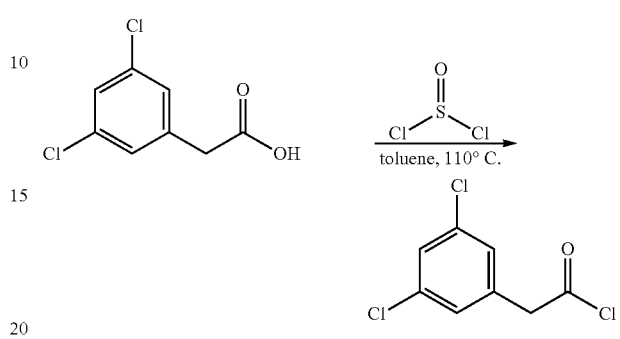

Into a 1-L round-bottom flask, was placed (3,5-dichlorophenyl)acetic acid (20.00 g, 97.547 mmol, 1.0 equiv), toluene (120.0 mL), thionyl chloride (50.0 g, 420.3 mmol, 4.3 equiv). The resulting solution was stirred for 2 hr at 110° C. The reaction mixture was cooled to room temperature. The resulting mixture was concentrated under vacuum. This resulted in 19 g (crude) of (3,5-dichlorophenyl)acetyl chloride as yellow oil.

2. Synthesis of 1-bromo-3-(3,5-dichlorophenyl)propan-2-one

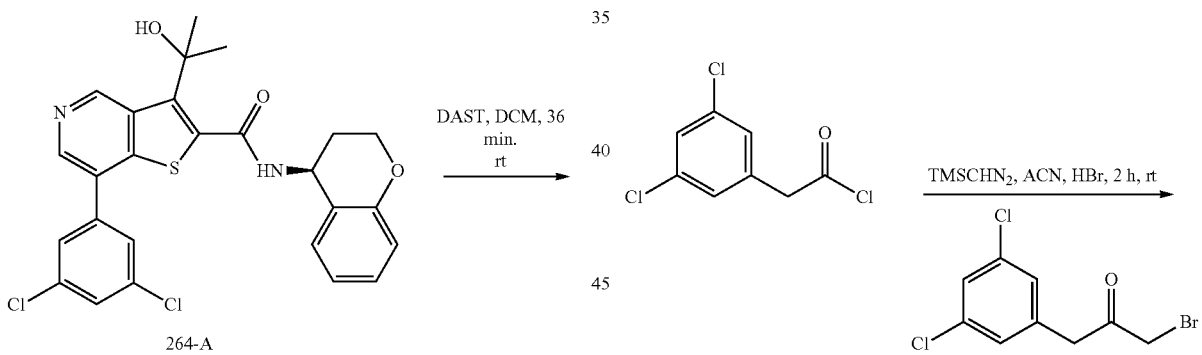

Into a 2-L 3-necked round-bottom flask purged and maintained with an inert atmosphere of nitrogen, was placed (3,5-dichlorophenyl)acetyl chloride (20 g, 89.4 mmol, 1.0 equiv), ACN (400.0 mL). This was followed by the addition of TMSCHN$_2$ (83 mL, 116.3 mmol, 2.0 equiv, 2M) dropwise with stirring at 0° C. The resulting solution was stirred for 1 hr at 0° C. To this was added HBr (40.0 mL, 547.7 mmol, 6.1 equiv, 40%) dropwise with stirring at 0° C. The resulting solution was allowed to react, with stirring, for an additional 2 hr at room temperature. The resulting mixture was concentrated under vacuum. The resulting solution was diluted with 200 mL of ethyl acetate and the resulting mixture was washed with 3×200 mL of water. The mixture was dried over anhydrous sodium sulfate. The filtrate was concentrated under vacuum. The residue was applied onto a silica gel column with ethyl acetate/petroleum ether (1:5). This resulted in 19 g (crude) of 1-bromo-3-(3,5-dichlorophenyl)propan-2-one as yellow oil. MS (ESI, m/z): 281 [M+H].

264-0

3. Synthesis of 4-(3,5-dichlorophenyl)-3-oxobutanenitrile

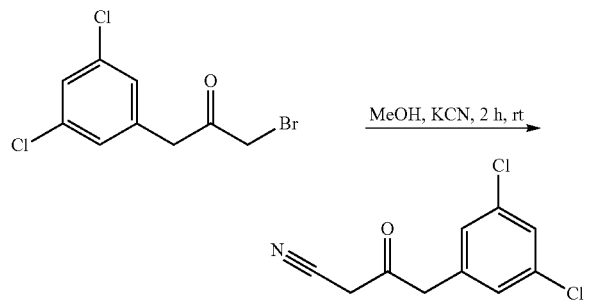

Into a 500-mL round-bottom flask, was placed 1-bromo-3-(3,5-dichlorophenyl)propan-2-one (22.0 g, 78.0 mmol, 1.0 equiv), MeOH (120.0 mL), KCN (10.0 g, 153.5 mmol, 1.9 equiv). The resulting solution was stirred for 2 hr at room temperature. The reaction was then quenched by the addition of 200 mL of water. The resulting solution was extracted with 3×200 mL of ethyl acetate and the organic layers combined and dried over anhydrous sodium sulfate and concentrated under vacuum. This resulted in 5 g (28.1%) of 4-(3,5-dichlorophenyl)-3-oxobutanenitrile as an off-white solid. MS (ESI, m/z): 228 [M+H]+.

4. Synthesis of 5-(3,5-dichlorophenyl)-4-hydroxypyridine-3-carbonitrile

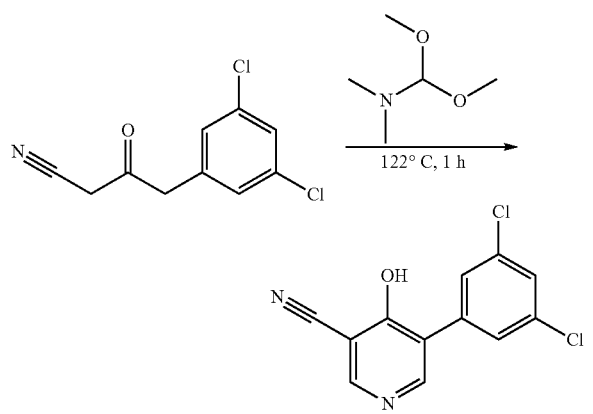

Into a 250-mL round-bottom flask purged and maintained with an inert atmosphere of nitrogen, was placed 4-(3,5-dichlorophenyl)-3-oxobutanenitrile (2.0 g, 8.7 mmol, 1.0 equiv), (dimethoxymethyl) dimethylamine (5.2 g, 43.9 mmol, 5.0 equiv). The resulting solution was stirred for 1 hr at 122° C. This was followed by the addition of CH3COONH4 (5.0 g, 64.9 mmol, 7.4 equiv) and AcOH (50.0 mL). The resulting solution was allowed to react, with stirring, for an additional 1 hr at 80° C. The reaction mixture was cooled to room temperature. The resulting mixture was concentrated under vacuum. The residue was applied onto a silica gel column with MeOH/DCM (1:10). This resulted in 1.6 g (68.8%) of 5-(3,5-dichlorophenyl)-4-hydroxypyridine-3-carbonitrile as a yellow solid. MS (ESI, m/z): 265 [M+H]+.

5. Synthesis of 4-chloro-5-(3,5-dichlorophenyl)pyridine-3-carbonitrile

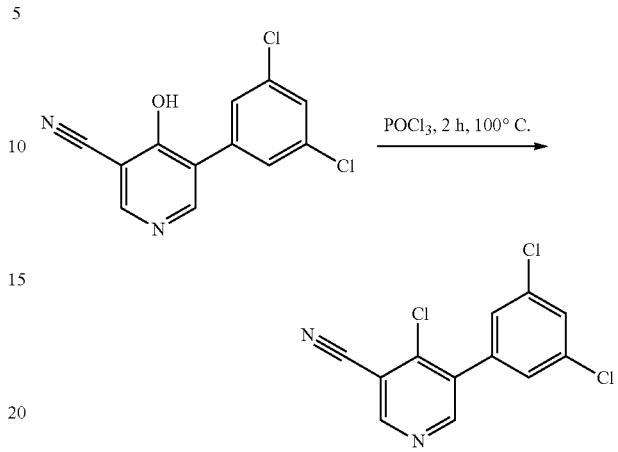

Into a 250-mL round-bottom flask purged and maintained with an inert atmosphere of nitrogen, was placed 5-(3,5-dichlorophenyl)-4-hydroxypyridine-3-carbonitrile (1.6 g, 6.0 mmol, 1.0 equiv) and POCl3 (20.00 mL). The resulting solution was stirred for 2 hr at 100° C. The reaction mixture was cooled to room temperature. The resulting mixture was concentrated under vacuum. This resulted in 1.6 g (93.5%) of 4-chloro-5-(3,5-dichlorophenyl)pyridine-3-carbonitrile as brown oil. MS (ESI, m/z): 283 [M+H]+.

6. Synthesis of 3-amino-7-(3,5-dichlorophenyl)thieno[3,2-c]pyridine-2-carboxylate

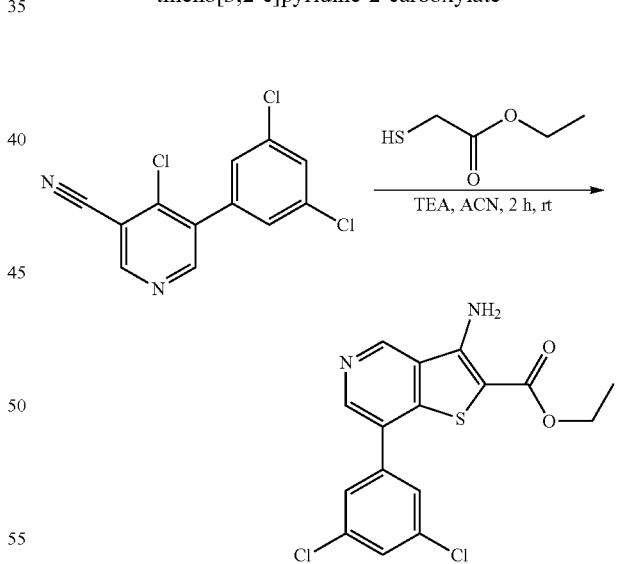

Into a 250-mL round-bottom flask purged and maintained with an inert atmosphere of nitrogen, was placed 4-chloro-5-(3,5-dichlorophenyl)pyridine-3-carbonitrile (1.6 g, 5.6 mmol, 1.0 equiv), ethyl thioglycolate (1.0 g, 8.5 mmol, 1.5 equiv), acetonitrile (20.0 mL), and triethylamine (2.0 g, 19.7 mmol, 3.5 equiv). The resulting solution was stirred for 2 hr at room temperature. The resulting mixture was concentrated under vacuum. The resulting solution was diluted with 100 mL of ethyl acetate and the solids were collected by filtration. This resulted in 660 mg (31.8%) of ethyl 3-amino- 7-(3,5-dichlorophenyl)thieno[3,2-c]pyridine-2-carboxylate as a yellow solid. MS (ESI, m/z): 367 [M+H]+.

7. Synthesis of ethyl 3-bromo-7-(3,5-dichlorophenyl) thieno[3,2-c]pyridine-2-carboxylate

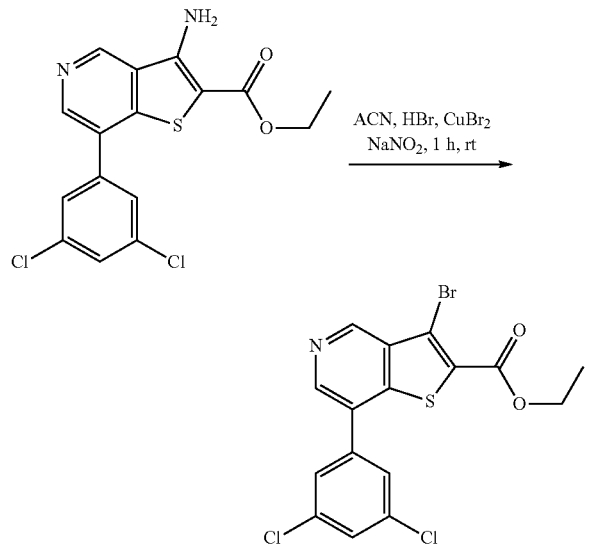

Into a 100-mL round-bottom flask, was placed ethyl 3-amino-7-(3,5-dichlorophenyl)thieno[3,2-c]pyridine-2-carboxylate (300.0 mg, 0.8 mmol, 1.0 equiv), acetonitrile (10.0 mL), and HBr (10.0 mL). This was followed by the addition of CuBr$_2$ (365.6 mg, 1.6 mmol, 2.0 equiv) at 0° C. To this was added NaNO$_2$ (85.0 mg, 1.2 mmol, 1.5 equiv) at 0° C. The resulting solution was stirred for 1 hr at room temperature. The reaction was then quenched by the addition of 100 mL of 1M HCl. The resulting solution was extracted with 3×200 mL of ethyl acetate and the organic layers combined and dried over anhydrous sodium sulfate and then concentrated under vacuum. The residue was applied onto a silica gel column and eluted with ethyl acetate/petroleum ether (1:2). This resulted in 400 mg (crude) of ethyl 3-bromo-7-(3,5-dichlorophenyl) thieno[3,2-c]pyridine-2-carboxylate as a yellow solid. MS (ESI, m/z): 430 [M+H]+.

8. Synthesis of Ethyl 7-(3,5-dichlorophenyl)-3-(1-ethoxyethenyl)thieno[3,2-c]pyridine-2-carboxylate

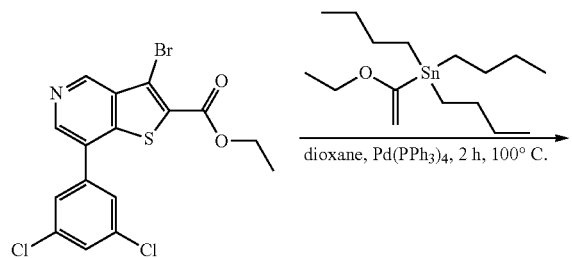

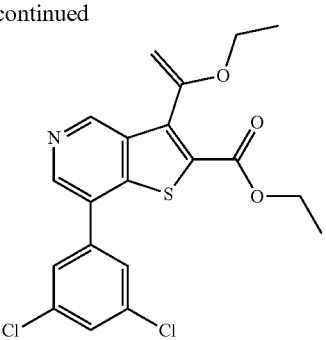

Into a 20-mL vial purged and maintained with an inert atmosphere of nitrogen, was placed ethyl 3-bromo-7-(3,5-dichlorophenyl)thieno[3,2-c]pyridine-2-carboxylate (550.0 mg, 1.2 mmol, 1.0 equiv), tributyl(1-ethoxyethenyl)stannane (1.4 g, 3.8 mmol, 3.0 equiv), dioxane (10.0 mL), and Pd(PPh$_3$)$_4$ (148.0 mg, 0.1 mmol, 0.1 equiv). The resulting solution was stirred for 2 hr at 100° C. The reaction mixture was cooled to room temperature and concentrated under vacuum. The residue was applied onto a silica gel column and eluted with ethyl acetate/petroleum ether (1:3). This resulted in 540 mg (crude) of ethyl 7-(3,5-dichlorophenyl)-3-(1-ethoxyethenyl)thieno[3,2-c]pyridine-2-carboxylate as a yellow solid. MS (ESI, m/z): 422 [M+H]+.

9. Synthesis of Ethyl 3-acetyl-7-(3,5-dichlorophenyl)thieno[3,2-c]pyridine-2-carboxylate

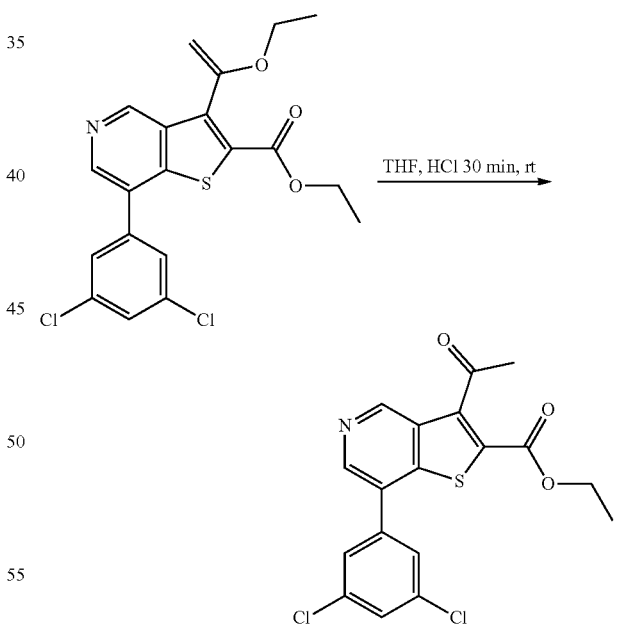

Into a 50-mL round-bottom flask, was placed ethyl 7-(3,5-dichlorophenyl)-3-(1-ethoxyethenyl)thieno[3,2-c] pyridine-2-carboxylate (530.0 mg, 1.2 mmol, 1.0 equiv), THF (6.00 mL), and HCl (0.2 mL, 12 M). The resulting solution was stirred for 30 min at room temperature. The resulting mixture was concentrated under vacuum. The reaction was then quenched by the addition of 50 mL of 2M aqueous NaHCO$_3$. The resulting solution was extracted with 3×50 mL of ethyl acetate and the organic layers combined and

10. Synthesis of 3-acetyl-7-(3,5-dichlorophenyl)thieno[3,2-c]pyridine-2-carboxylic Acid

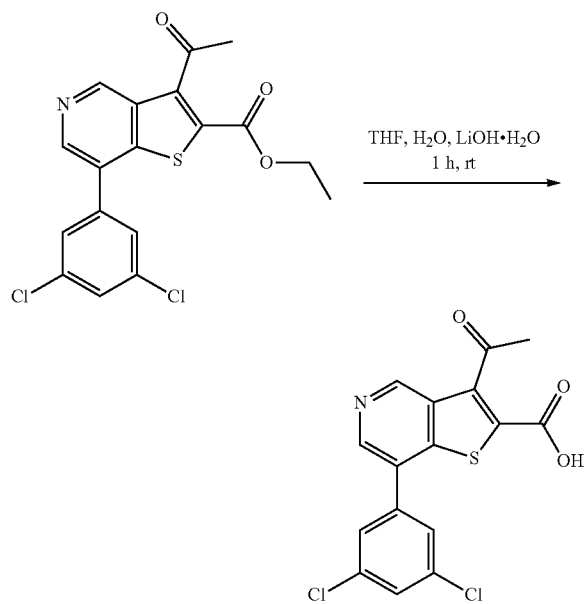

Into a 40-mL vial, was placed ethyl 3-acetyl-7-(3,5-dichlorophenyl)thieno[3,2-c]pyridine-2-carboxylate (500.0 mg, 1.2 mmol, 1.0 equiv), THF (5.0 mL), water (5.0 mL), and LiOH.H₂O (160.0 mg, 3.8 mmol, 3.0 equiv). The resulting solution was stirred for 1 hr at room temperature. The pH value of the solution was adjusted to 3 with aqueous HCl (1M). The resulting solution was extracted with 3×20 mL of ethyl acetate and the organic layers were combined and dried over anhydrous sodium sulfate and concentrated under vacuum. This resulted in 330 mg (71.0%) of 3-acetyl-7-(3,5-dichlorophenyl)thieno[3,2-c]pyridine-2-carboxylic acid as a white solid. MS (ESI, m/z): 366 [M+H]⁺.

11. Synthesis of 3-acetyl-7-(3,5-dichlorophenyl)-N-[(4S)-3,4-dihydro-2H-1-benzopyran-4-yl]thieno[3,2-c]pyridine-2-carboxamide

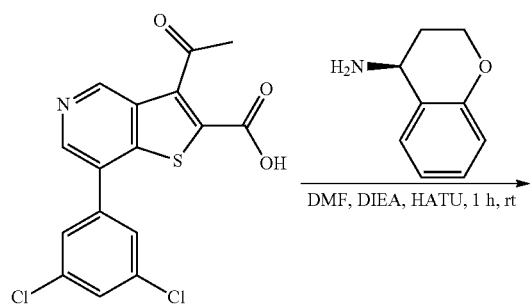

dried over anhydrous sodium sulfate. The filtrate was concentrated under vacuum. This resulted in 500 mg (crude) of ethyl 3-acetyl-7-(3,5-dichlorophenyl)thieno[3,2-c]pyridine-2-carboxylate as a yellow solid. MS (ESI, m/z): 394 [M+H]⁺.

-continued

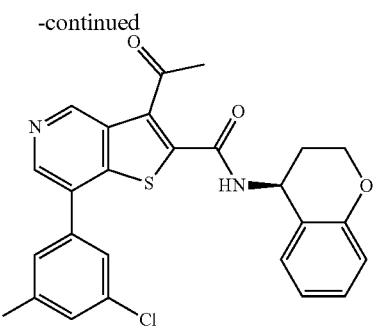

Into a 50-mL round-bottom flask, was placed 3-acetyl-7-(3,5-dichlorophenyl)thieno[3,2-c]pyridine-2-carboxylic acid (330.0 mg, 0.9 mmol, 1.0 equiv), (4S)-3,4-dihydro-2H-1-benzopyran-4-amine (202.0 mg, 1.3 mmol, 1.5 equiv), DMF (3.00 mL), HATU (687.0 mg, 1.8 mmol, 2.0 equiv), DIEA (350.0 mg, 2.7 mmol, 3.0 equiv). The resulting solution was stirred for 1 hr at room temperature. The crude product was purified by Flash-Prep-HPLC with the following conditions (IntelFlash-1): C₁₈; mobile phase, CH₃CN:H₂O=20% increasing to CH₃CN:H₂O=90% within 20 min. This resulted in 320 mg (71.4%) of 3-acetyl-7-(3,5-dichlorophenyl)-N-[(4S)-3,4-dihydro-2H-1-benzopyran-4-yl]thieno[3,2-c]pyridine-2-carboxamide as a yellow solid. MS (ESI, m/z): 497 [M+H]⁺.

12. Synthesis of 7-(3,5-dichlorophenyl)-N-[(4S)-3,4-dihydro-2H-1-benzopyran-4-yl]-3-(2-hydroxypropan-2-yl)thieno[3,2-c]pyridine-2-carboxamide

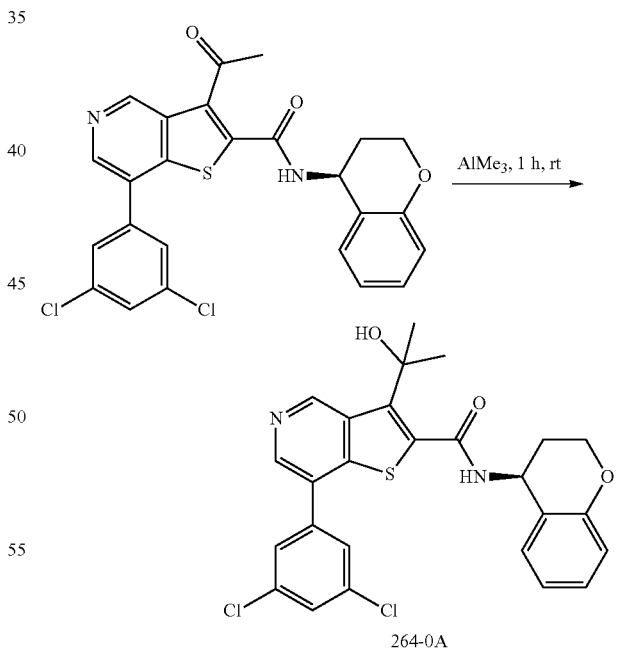

264-0A

Into a 50-mL round-bottom flask purged and maintained with an inert atmosphere of nitrogen, was placed AlMe₃ (5 mL, 2M in hexane). This was followed by the addition of 3-acetyl-7-(3,5-dichlorophenyl)-N-[(4S)-3,4-dihydro-2H-1-benzopyran-4-yl]thieno[3,2-c]pyridine-2-carboxamide (140.0 mg, 0.2 mmol, 1.0 equiv) at 0° C. The resulting solution was stirred for 1 hr at room temperature. The pH value of the solution was adjusted to 2 with aqueous HCl (3 M). The resulting solution was extracted with 3×20 mL of ethyl acetate and the organic layers combined and dried over anhydrous sodium sulfate and concentrated under vacuum. The crude product was purified by Flash-Prep-HPLC with the following conditions (IntelFlash-1): Column, $C_{18}$ silica gel; mobile phase, $CH_3CN:H_2O=20\%$ increasing to $CH_3CN:H_2O=50\%$ within 20 min. This resulted in 5.4 mg (3.7%) of 7-(3,5-dichlorophenyl)-N-[(4S)-3,4-dihydro-2H-1-benzopyran-4-yl]-3-(2-hydroxypropan-2-yl)thieno[3,2-c]pyridine-2-carboxamide as a white solid. MS (ESI, m/z): 513 [M+H]$^+$; $^1$H-NMR (300 MHz, CDCl$_3$): δ=9.58 (s, 1H), 9.40 (d, J=7.8 Hz, 1H), 8.45 (s, 1H), 7.71 (s, 3H), 7.20-7.13 (m, 2H), 6.90-6.86 (m, 1H), 6.76 (d, J=9.0 Hz, 1H), 5.14-5.13 (d, J=1.8 Hz, 1H), 4.18 (s, 2H), 2.11-2.10 (m, 1H), 2.00-1.95 (m, 1H), 1.68 (s, 6H) ppm.

13. Synthesis of 7-(3,5-dichlorophenyl)-N-[(4S)-3,4-dihydro-2H-1-benzopyran-4-yl]-3-(2-fluoropropan-2-yl)thieno[3,2-c]pyridine-2-carboxamide

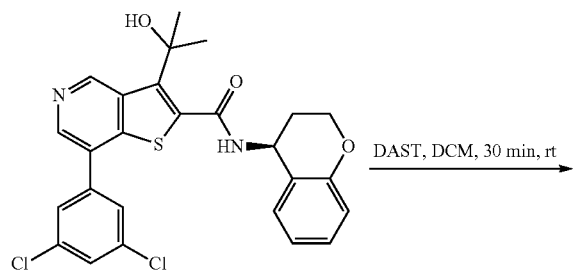

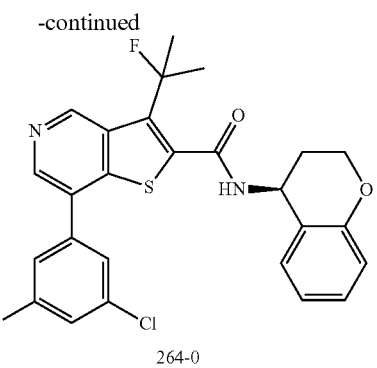

264-0

Into a 50-mL round-bottom flask purged and maintained with an inert atmosphere of nitrogen, was placed 7-(3,5-dichlorophenyl)-N-[(4S)-3,4-dihydro-2H-1-benzopyran-4-yl]-3-(2-hydroxypropan-2-yl)thieno[3,2-c]pyridine-2-carboxamide (35.0 mg, 0.06 mmol, 1.0 equiv), DCM (5.0 mL), DAST (21.0 mg, 0.1 mmol, 1.9 equiv). The resulting solution was stirred for 30 min at room temperature. The reaction was then quenched by the addition of 5 mL of water. The resulting solution was extracted with 3×5 mL of dichloromethane and the organic layers combined and dried over anhydrous sodium sulfate and concentrated under vacuum. The crude product was purified by Flash-Prep-HPLC with the following conditions (IntelFlash-1): Column, $C_{18}$ silica gel; mobile phase, $CH_3CN:H_2O=45\%$ increasing to $CH_3CN:H_2O=65\%$ within 20 min. This resulted in 22.7 mg (64.6%) of 7-(3,5-dichlorophenyl)-N-[(4S)-3,4-dihydro-2H-1-benzopyran-4-yl]-3-(2-fluoropropan-2-yl)thieno[3,2-c]pyridine-2-carboxamide as a white solid. MS (ESI, m/z): 515 [M+H]$^+$; $^1$H-NMR (300 MHz, CDCl$_3$): δ=9.37 (s, 1H), 8.50 (s, 1H), 7.54-7.50 (m, 3H), 7.31 (s, 1H), 7.23 (d, J=7.4 Hz, 1H), 6.99-6.90 (m, 1H), 6.89 (d, J=8.2 Hz, 1H), 6.31 (d, J=7.5 Hz, 1H), 5.33-5.25 (m, 1H), 4.39-4.32 (m, 1H), 4.25-4.17 (m, 1H), 2.37-2.34 (m, 1H), 2.27-2.22 (m, 1H), 2.07 (d, J=7.1 Hz, 3H), 1.99 (d, J=7.1 Hz, 3H) ppm.

The following compounds can be prepared according to Scheme 10 below and the following detailed procedures: 121, 226-3, 215, 227, 224, 225, 228, 225-0A, 230, 226, 234.

Scheme 10

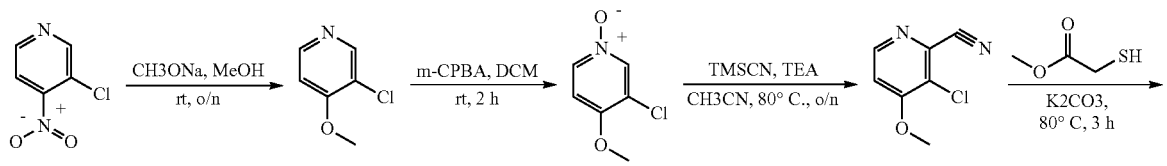

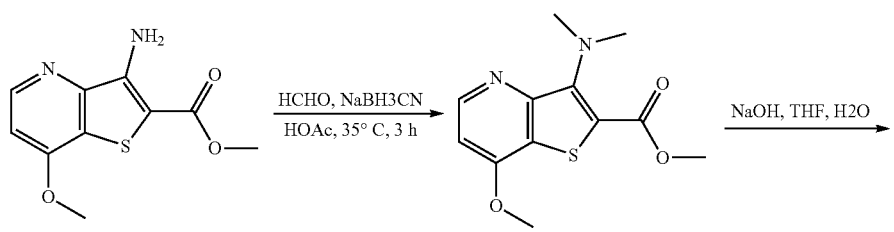

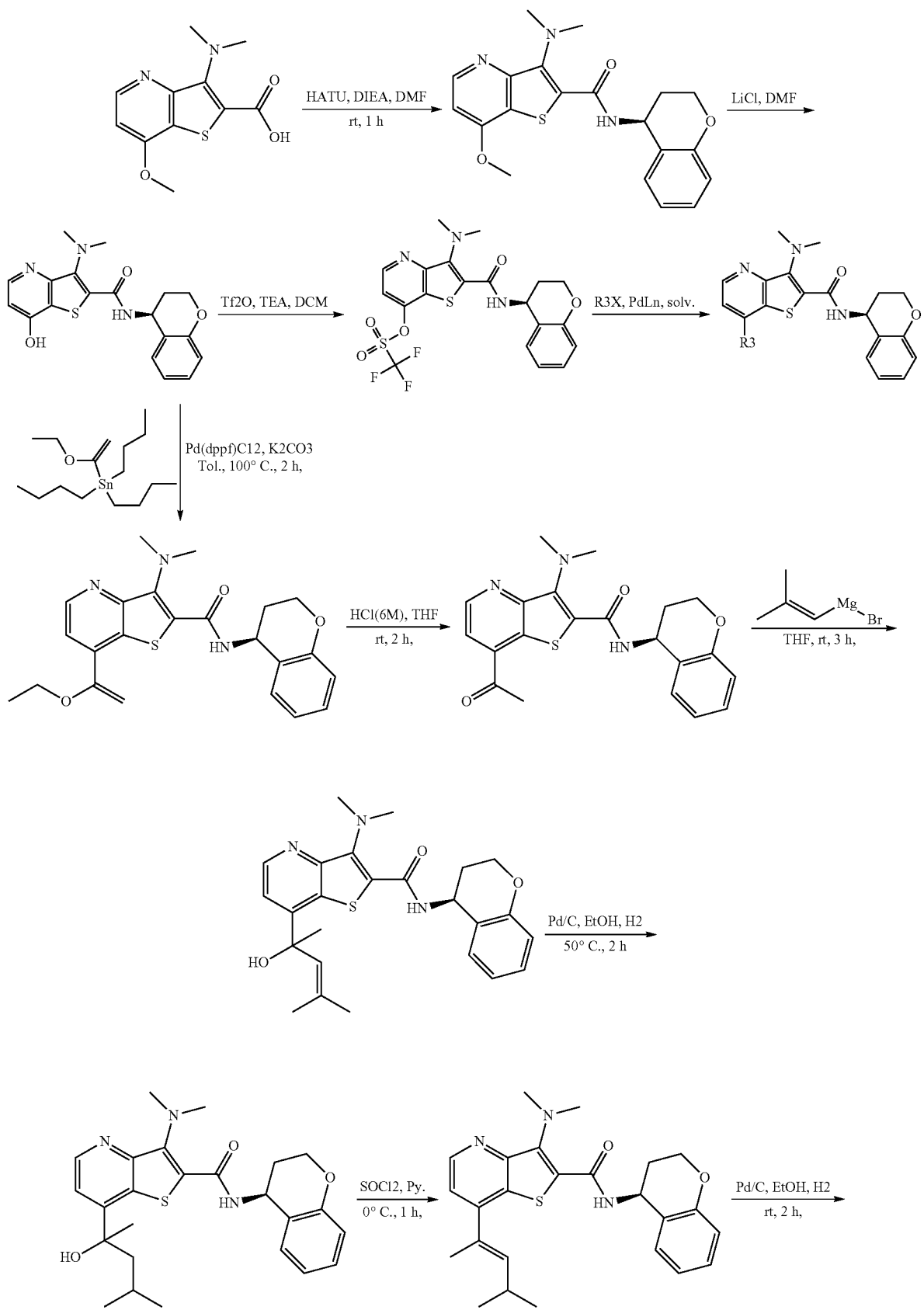

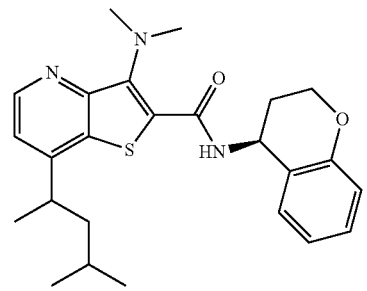

226

Exemplary Procedure of Compound 226-3

1. Synthesis of 3-chloro-4-methoxypyridine

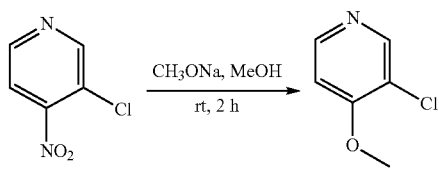

Into a 1000-mL round-bottom flask, was placed 3-chloro-4-nitropyridine (30.00 g, 189.2 mmol, 1.0 equiv), MeOH (400.0 mL), CH$_3$ONa (56.7 mL, 5 mol/L, 1.50 equiv). The resulting solution was stirred for 2 hr at room temperature. The resulting mixture was concentrated under vacuum. The residue was dissolved in 500 mL of EA. The resulting mixture was washed with 3×500 ml of brine. The mixture was dried over anhydrous sodium sulfate and concentrated under vacuum. This resulted in 25 g (92.0%) of 3-chloro-4-methoxypyridine as yellow oil.

2. Synthesis of 3-chloro-4-methoxypyridin-1-ium-1-olate

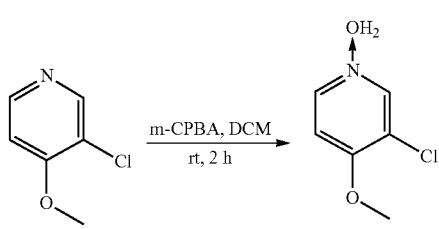

Into a 1000-mL round-bottom flask, was placed 3-chloro-4-methoxypyridine (25.00 g, 174.131 mmol, 1.00 equiv), DCM (500.0 mL), m-CPBA (60.1 g, 348.2 mmol, 2.0 equiv). The resulting solution was stirred for 2 h at room temperature. The resulting mixture was concentrated under vacuum. The residue was applied onto a silica gel column with ethyl acetate/petroleum ether (EA 0%~100%)~EA/MeOH(1/2). This resulted in 30 g (crude) of 3-chloro-4-methoxypyridin-1-ium-1-olate as an off-white solid.

3. Synthesis of 3-chloro-4-methoxypyridine-2-carbonitrile

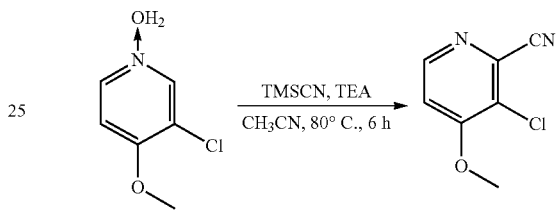

Into a 1000-mL round-bottom flask, was placed 3-chloro-4-methoxypyridin-1-ium-1-olate (30.00 g, 188.0 mmol, 1.0 equiv), CH$_3$CN (600.0 mL), TMSCN (46.6 g, 470.0 mmol, 2.5 equiv), TEA (39.95 g, 394.8 mmol, 2.1 equiv). The resulting solution was stirred for 6 hr at 80° C. The resulting mixture was concentrated under vacuum. This resulted in 35 g (crude) of 3-chloro-4-methoxypyridine-2-carbonitrile as a brown solid.

4. Synthesis of Methyl 3-amino-7-methoxythieno[3,2-b]pyridine-2-carboxylate

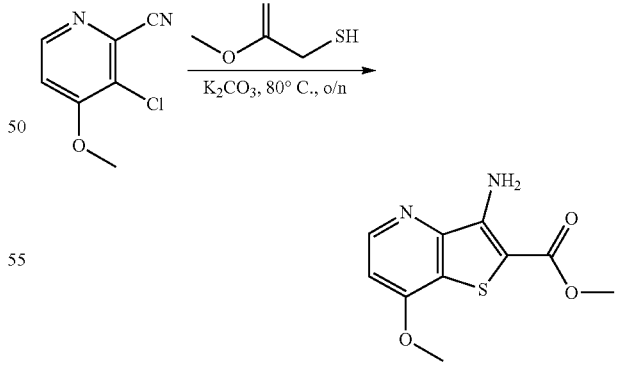

Into a 500-mL round-bottom flask, was placed 3-chloro-4-methoxypyridine-2-carbonitrile (16.00 g, 94.9 mmol, 1.0 equiv), CH$_3$CN (300.0 mL), methyl thioglycolate (40.30 g, 379.6 mmol, 4.0 equiv), K$_2$CO$_3$ (52.47 g, 379.6 mmol, 4.0 equiv). The resulting solution was stirred for 1 overnight at 80° C. The resulting mixture was concentrated under vacuum. The residue was applied onto a silica gel column with ethyl acetate/petroleum ether (EA 0%-70%). This resulted in 2.7 g (11.9%) of methyl 3-amino-7-methoxythieno[3,2-b]pyridine-2-carboxylate as a yellow solid.

5. Synthesis of Methyl 3-(dimethylamino)-7-methoxythieno[3,2-b]pyridine-2-carboxylate

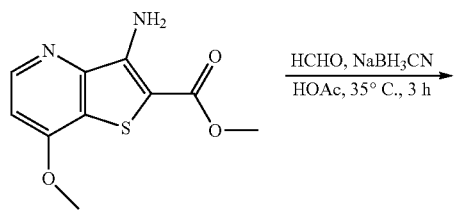

Into a 250-mL round-bottom flask, was placed methyl 3-amino-7-methoxythieno[3,2-b]pyridine-2-carboxylate (1.00 g, 4.1 mmol, 1.0 equiv), HOAc (40.0 mL), HCHO (1260.2 mg, 41.9 mmol, 10.0 equiv), NaBH$_3$CN (2637.5 mg, 41.9 mmol, 10.0 equiv). The resulting solution was stirred for 3 hr at 35° C. The reaction was then quenched by the addition of 50 mL of water. The resulting solution was extracted with 3×50 mL of ethyl acetate and the organic layers combined. The resulting mixture was washed with 3×100 ml of NaHCO$_3$(aq.) and 3×100 mL of brine. The resulting mixture was concentrated under vacuum. The residue was applied onto a silica gel column with ethyl acetate/petroleum ether (EA 0%-50%). This resulted in 1.1 g (98.4%) of methyl 3-(dimethylamino)-7-methoxythieno[3,2-b]pyridine-2-carboxylate as a light yellow solid.

6. Synthesis of 3-(dimethylamino)-7-methoxythieno[3,2-b]pyridine-2-carboxylic Acid

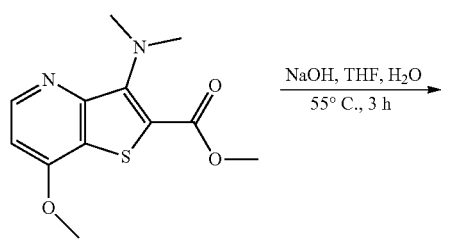

Into a 100-mL round-bottom flask, was placed methyl 3-(dimethylamino)-7-methoxythieno[3,2-b]pyridine-2-carboxylate (130.0 mg, 0.4 mmol, 1.0 equiv), THF (3.0 mL), NaOH (130.00 mg, 3.2 mmol, 6.6 equiv), H$_2$O (3.0 mL). The resulting solution was stirred for 3 hr at 55° C. The resulting mixture was concentrated under vacuum. This resulted in 150 mg (crude) of 3-(dimethylamino)-7-methoxythieno[3,2-b]pyridine-2-carboxylic acid as a yellow solid.

7. Synthesis of N-[(4S)-3,4-dihydro-2H-1-benzopyran-4-yl]-3-(dimethylamino)-7-methoxythieno[3,2-b]pyridine-2-carboxamide

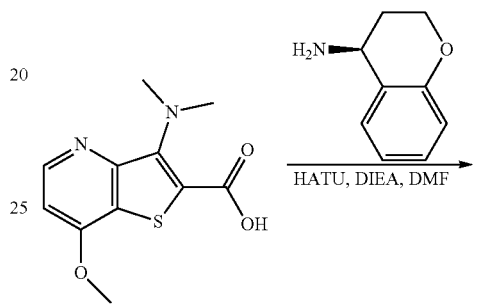

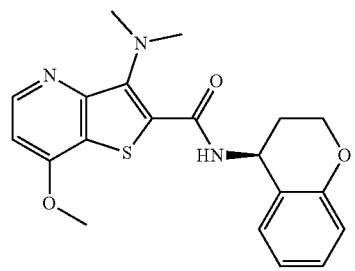

Into a 100-mL round-bottom flask, was placed 3-(dimethylamino)-7-methoxythieno[3,2-b]pyridine-2-carboxylic acid (900.0 mg, 3.5 mmol, 1.0 equiv), DMF (20.0 mL), (4S)-3,4-dihydro-2H-1-benzopyran-4-amine (532.2 mg, 3.5 mmol, 1.0 equiv), DIEA (1383.1 mg, 10.7 mmol, 3.0 equiv), HATU (2034.60 mg, 5.3 mmol, 1.5 equiv). The resulting solution was stirred for 1 hr at room temperature. The reaction was then quenched by the addition of 20 mL of water. The resulting solution was extracted with 3×20 mL of ethyl acetate and the organic layers combined. The resulting mixture was washed with 3×20 ml of brine. The resulting mixture was concentrated under vacuum. The residue was applied onto a silica gel column with ethyl acetate/petroleum ether (0%~50%). This resulted in 530 mg (38.7%) of N-[(4S)-3,4-dihydro-2H-1-benzopyran-4-yl]-3-(dimethylamino)-7-methoxythieno[3,2-b]pyridine-2-carboxamide as a yellow semi-solid.

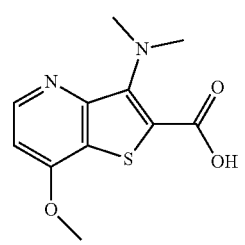

8. Synthesis of N-[(4S)-3,4-dihydro-2H-1-benzopyran-4-yl]-3-(dimethylamino)-7-hydroxythieno[3,2-b]pyridine-2-carboxamide

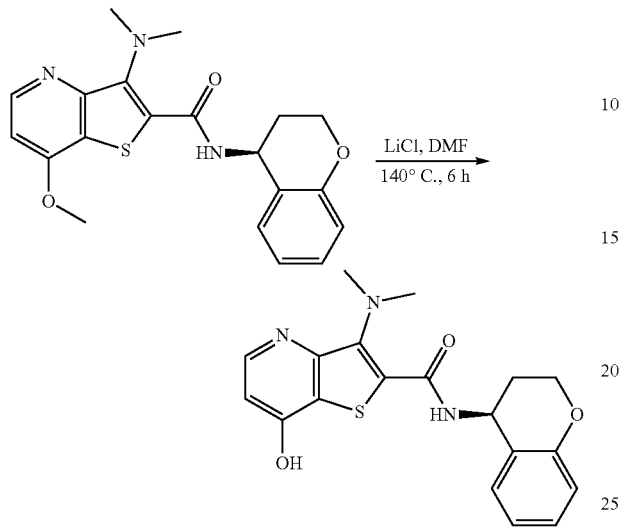

Into a 40-mL vial, was placed N-[(4S)-3,4-dihydro-2H-1-benzopyran-4-yl]-3-(dimethylamino)-7-methoxythieno[3,2-b]pyridine-2-carboxamide (500.0 mg, 1.3 mmol, 1.0 equiv), DMF (10.0 mL, 0.014 mmol), LiCl (300.1 mg, 7.0 mmol, 5.4 equiv). The resulting solution was stirred for 6 hr at 140° C. The reaction mixture was cooled to room temperature. The residue was applied onto a silica C18 column with 0.05% TFA in H₂O and CH₃CN (20% CH₃CN up to 60% in 12 min). This resulted in 200 mg (41.5%) of N-[(4S)-3,4-dihydro-2H-1-benzopyran-4-yl]-3-(dimethylamino)-7-hydroxythieno[3,2-b]pyridine-2-carboxamide as a light yellow solid.

9. Synthesis of 2-[[(4S)-3,4-dihydro-2H-1-benzopyran-4-yl]carbamoyl]-3-(dimethylamino)thieno[3,2-b]pyridin-7-yl Trifluoromethanesulfonate

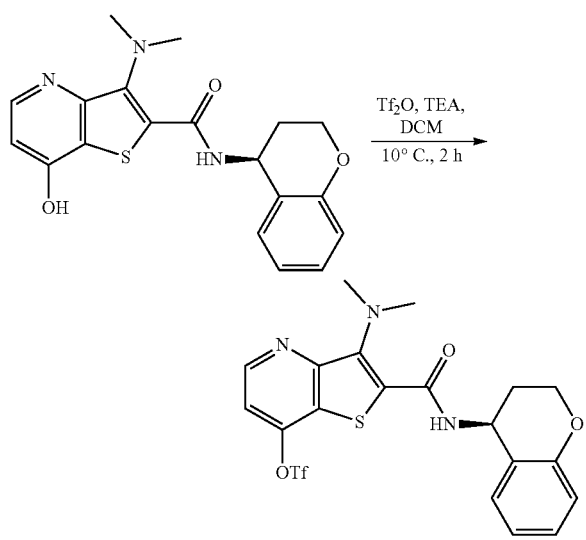

Into a 50-mL 3-necked round-bottom flask purged and maintained with an inert atmosphere of nitrogen, was placed N-[(4S)-3,4-dihydro-2H-1-benzopyran-4-yl]-3-(dimethylamino)-7-hydroxythieno[3,2-b]pyridine-2-carboxamide (180.0 mg, 0.4 mmol, 1.0 equiv), DCM (5.0 mL), TEA (493.0 mg, 4.8 mmol, 10.0 equiv), Tf₂O (687.3 mg, 2.4 mmol, 5.0 equiv). The resulting solution was stirred for 2 hr at 10° C. The reaction was then quenched by the addition of 10 mL of water. The resulting solution was extracted with 3×10 mL of ethyl acetate and the organic layers combined. The resulting mixture was washed with 3×20 mL of brine. The resulting mixture was concentrated under vacuum. The residue was applied onto a silica gel Pre-TLC with ethyl acetate/petroleum ether (1/3). This resulted in 150 mg (61.3%) of 2-[[(4S)-3,4-dihydro-2H-1-benzopyran-4-yl]carbamoyl]-3-(dimethylamino)thieno[3,2-b]pyridin-7-yl trifluoromethanesulfonate as yellow oil.

10. Synthesis of N-[(4S)-3,4-dihydro-2H-1-benzopyran-4-yl]-3-(dimethylamino)-7-(1-ethoxyethenyl)thieno[3,2-b]pyridine-2-carboxamide

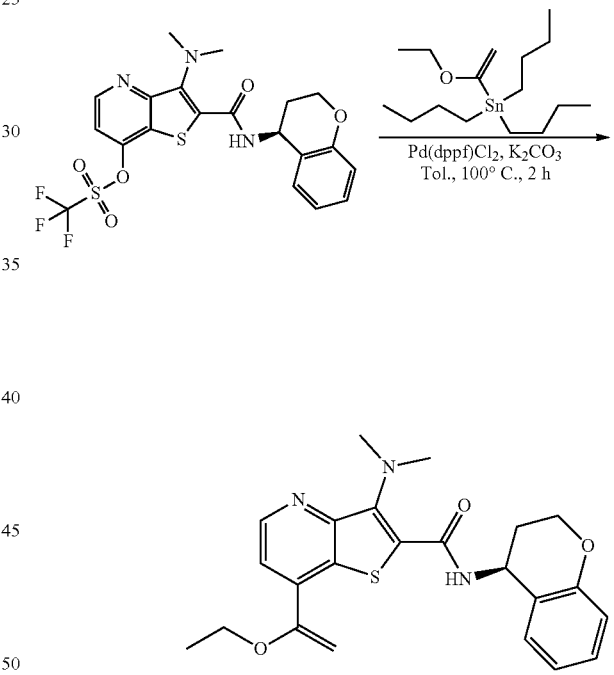

Into a 50-mL round-bottom flask purged and maintained with an inert atmosphere of nitrogen, was placed toluene (20.0 mL), 2-[[(4S)-3,4-dihydro-2H-1-benzopyran-4-yl]carbamoyl]-3-(dimethylamino)thieno[3,2-b]pyridin-7-yl trifluoromethanesulfonate (500.0 mg, 1.0 mmol, 1.0 equiv), tributyl(1-ethoxyethenyl)stannane (1 g, 2.7 mmol, 2.7 eq), Pd(dppf)Cl₂ (160.00 mg, 0.2 mmol, 0.2 equiv), K₂CO₃ (250.0 mg, 1.8 mmol, 1.8 equiv). The resulting solution was stirred for 2 hr at 100° C. The resulting mixture was concentrated under vacuum. The residue was applied onto a silica gel column with ethyl acetate/petroleum ether (1:4). This resulted in 350 mg (82.8%) of N-[(4S)-3,4-dihydro-2H-1-benzopyran-4-yl]-3-(dimethylamino)-7-(1-ethoxyethenyl)thieno[3,2-b]pyridine-2-carboxamide as a brown solid.

133

11. Synthesis of 7-acetyl-N-[(4S)-3,4-dihydro-2H-1-benzopyran-4-yl]-3-(dimethylamino)thieno[3,2-b]pyridine-2-carboxamide

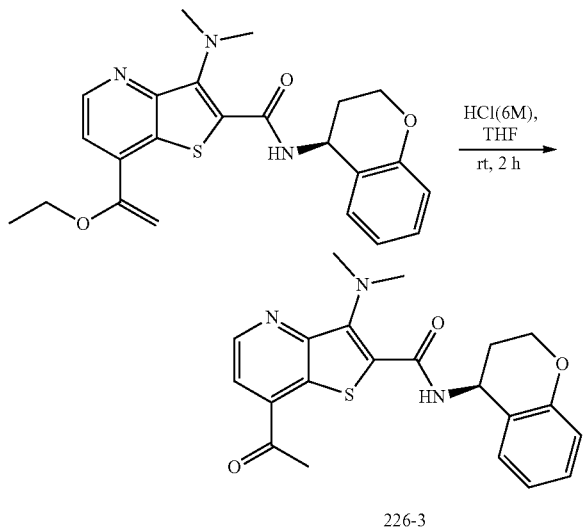

226-3

Into a 50-mL round-bottom flask, was placed THF (5.0 mL), N-[(4S)-3,4-dihydro-2H-1-benzopyran-4-yl]-3-(dimethylamino)-7-(1-ethoxyethenyl)thieno[3,2-b]pyridine-2-carboxamide (350.0 mg, 0.8 mmol, 1.0 equiv), HCl (6M) (5.0 mL). The resulting solution was stirred for 2 hr at room temperature. The reaction was then quenched by the addition of 10 mL of water. The resulting solution was extracted with 3×20 mL of ethyl acetate and the organic layers combined and dried over anhydrous sodium sulfate and concentrated under vacuum. The residue was applied onto a silica gel column with ethyl acetate/petroleum ether (1:3). This resulted in 180 mg (55.0%) of 7-acetyl-N-[(4S)-3,4-dihydro-2H-1-benzopyran-4-yl]-3-(dimethylamino)thieno[3,2-b]pyridine-2-carboxamide as a yellow solid. $^1$H-NMR (300 MHz, CD$_3$OD): δ=8.96 (d, J=4.7 Hz, 1H), 8.04 (d, J=4.8 Hz, 1H), 7.37-7.32 (m, 1H), 7.28-7.16 (m, 1H), 6.97-6.91 (m, 1H), 6.86 (dd, J=8.2, 1.2 Hz, 1H), 5.31 (t, J=5.6 Hz, 1H), 4.39-4.32 (m, 1H), 4.27-4.22 (m, 1H), 2.99 (s, 6H), 2.80 (s, 3H), 2.39-2.33 (m, 1H), 2.21-2.16 (m, 1H) ppm.

12. Synthesis of N-[(4S)-3,4-dihydro-2H-1-benzopyran-4-yl]-3-(dimethylamino)-7-(2-hydroxy-4-methylpent-3-en-2-yl)thieno[3,2-b]pyridine-2-carboxamide

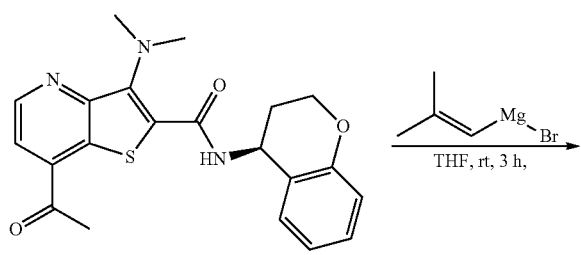

134

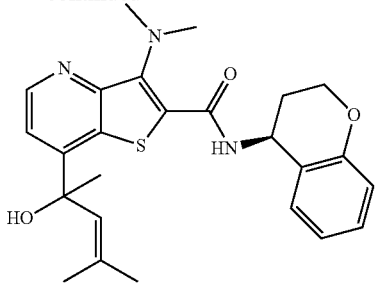

Into a 50-mL 3-necked round-bottom flask, was placed THF (5.0 mL), 7-acetyl-N-[(4S)-3,4-dihydro-2H-1-benzopyran-4-yl]-3-(dimethylamino)thieno[3,2-b]pyridine-2-carboxamide (300.0 mg, 0.7 mmol, 1.0 equiv). This was followed by the addition of bromo(2-methylprop-1-en-1-yl)magnesium (1.0 mL, 0.006 mmol, 0.01 equiv) dropwise with stirring at 0° C. The resulting solution was stirred for 3 hr at room temperature. The reaction was then quenched by the addition of water/ice. The resulting solution was extracted with 3×20 mL of ethyl acetate and the organic layers combined and dried over anhydrous sodium sulfate and concentrated under vacuum. The residue was applied onto a silica gel column with ethyl acetate/petroleum ether (1:4). This resulted in 150 mg (43.7%) of N-[(4S)-3,4-dihydro-2H-1-benzopyran-4-yl]-3-(dimethylamino)-7-(2-hydroxy-4-methylpent-3-en-2-yl)thieno[3,2-b]pyridine-2-carboxamide as a yellow solid.

13. Synthesis of N-[(4S)-3,4-dihydro-2H-1-benzopyran-4-yl]-3-(dimethylamino)-7-(2-hydroxy-4-methylpentan-2-yl)thieno[3,2-b]pyridine-2-carboxamide

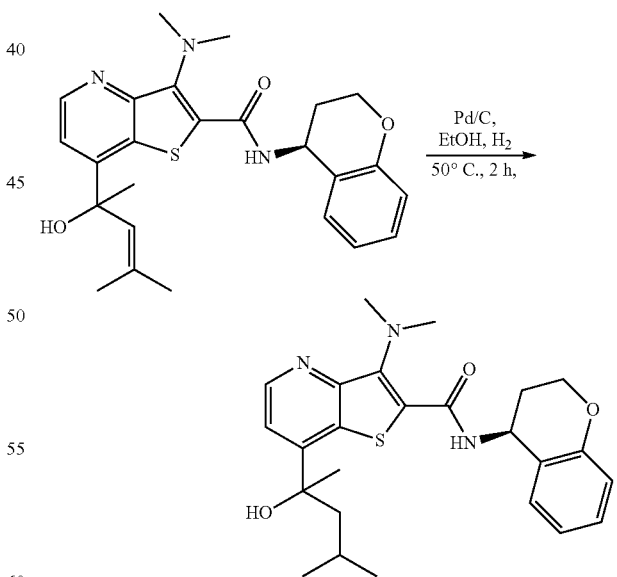

Into a 50-mL round-bottom flask, was placed EtOH (5.0 mL), N-[(4S)-3,4-dihydro-2H-1-benzopyran-4-yl]-3-(dimethylamino)-7-(2-hydroxy-4-methylpent-3-en-2-yl)thieno[3,2-b]pyridine-2-carboxamide (150.0 mg, 0.3 mmol, 1.0 equiv), Pd/C (30.0 mg, 0.2 mmol, 0.8 equiv). To the above H$_2$ (g) was introduced in. The resulting solution was stirred for 2 hr at 50° C. The solids were filtered out. The resulting mixture was concentrated under vacuum. This resulted in 100 mg (66.3%) of N-[(4S)-3,4-dihydro-2H-1-benzopyran-4-yl]-3-(dimethylamino)-7-(2-hydroxy-4-methylpentan-2-yl)thieno[3,2-b]pyridine-2-carboxamide as a white solid.

14. Synthesis of N-[(4S)-3,4-dihydro-2H-1-benzopyran-4-yl]-3-(dimethylamino)-7-[(2E)-4-methylpent-2-en-2-yl]thieno[3,2-b]pyridine-2-carboxamide

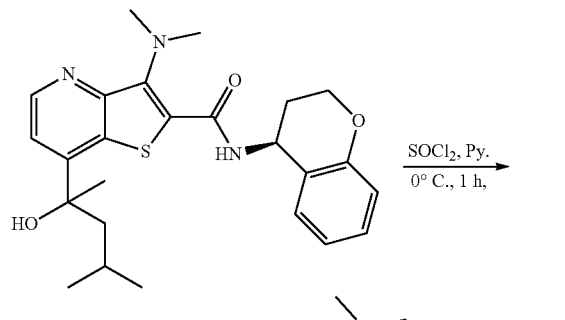

Into a 50-mL round-bottom flask, was placed Pyridine (3.0 mL), N-[(4S)-3,4-dihydro-2H-1-benzopyran-4-yl]-3-(dimethylamino)-7-(2-hydroxy-4-methylpentan-2-yl)thieno[3,2-b]pyridine-2-carboxamide (100.0 mg, 0.2 mmol, 1.0 equiv), SOCl$_2$(0.5 mL). The resulting solution was stirred for 1 hr at 0° C. The reaction was then quenched by the addition of water/ice. The resulting solution was extracted with 3×20 mL of ethyl acetate and the organic layers combined and dried over anhydrous sodium sulfate and concentrated under vacuum. This resulted in 70 mg (72.8%) of N-[(4S)-3,4-dihydro-2H-1-benzopyran-4-yl]-3-(dimethylamino)-7-[(2E)-4-methylpent-2-en-2-yl]thieno[3,2-b]pyridine-2-carboxamide as a yellow solid.

15. Synthesis of N-[(4S)-3,4-dihydro-2H-1-benzopyran-4-yl]-3-(dimethylamino)-7-(4-methylpentan-2-yl)thieno[3,2-b]pyridine-2-carboxamide

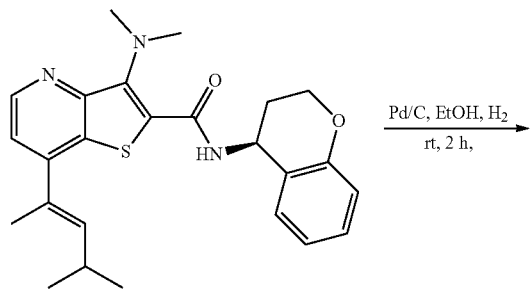

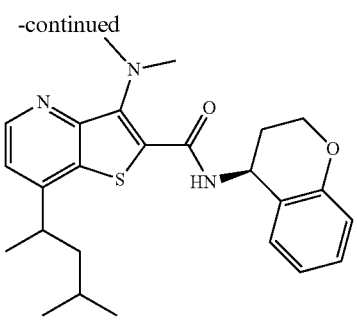

226-0

Into a 50-mL round-bottom flask, was placed EtOH (5.0 mL), N-[(4S)-3,4-dihydro-2H-1-benzopyran-4-yl]-3-(dimethylamino)-7-[(2E)-4-methylpent-2-en-2-yl]thieno[3,2-b]pyridine-2-carboxamide (70.0 mg, 0.16 mmol, 1.0 equiv), Pd/C (20.0 mg, 0.19 mmol, 1.2 equiv). To the above H$_2$(g) was introduced in. The resulting solution was stirred for 2 hr at room temperature. The solids were filtered out. The resulting mixture was concentrated under vacuum. The crude product was purified by Flash-Prep-HPLC with the following conditions (IntelFlash-1): Column, C18 silica gel; mobile phase, H$_2$O and CH$_3$CN (20% CH$_3$CN increasing to 90% within 20 min); Detector, 220 nm. This resulted in 12.2 mg (17.3%) of N-[(4S)-3,4-dihydro-2H-1-benzopyran-4-yl]-3-(dimethylamino)-7-(4-methylpentan-2-yl)thieno[3,2-b]pyridine-2-carboxamide as a white solid. (ES, m/z): 438 [M+H]$^+$; $^1$H-NMR (300 MHz, CDCl$_3$): δ=8.65 (d, J=4.8 Hz, 1H), 7.38-7.29 (m, 2H), 7.28-7.16 (m, 1H), 6.97-6.94 (m, 1H), 6.86 (d, J=8.3 Hz, 1H), 5.31 (t, J=5.6 Hz, 1H), 4.38-4.36 (m, 1H), 4.27-4.24 (m, 1H), 3.24-2.22 (m, 1H), 2.99 (s, 6H), 2.45-2.28 (m, 1H), 2.27-2.11 (m, 1H), 1.90-1.75 (m, 1H), 1.66-1.35 (m, 6H), 0.99-0.90 (m, 6H) ppm.

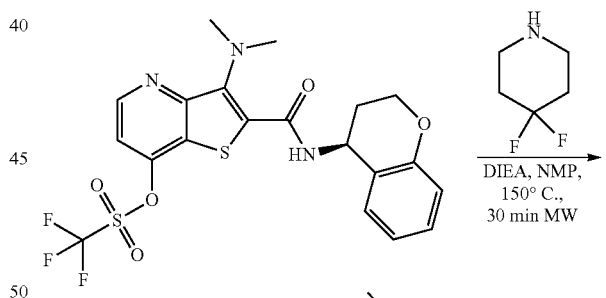

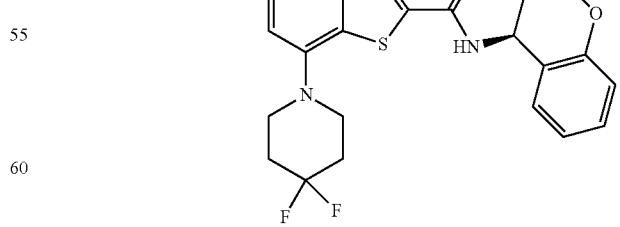

230-0

Into a 8-mL sealed tube, was placed NMP (5.0 mL), 2-[[(4S)-3,4-dihydro-2H-1-benzopyran-4-yl]carbamoyl]-3-

(dimethylamino)thieno[3,2-b]pyridin-7-yl trifluoromethanesulfonate (200.0 mg, 0.4 mmol, 1.0 equiv), 4,4-difluoropiperidine (400.0 mg, 3.3 mmol, 8.3 equiv). The final reaction mixture was irradiated with microwave radiation for 30 min at 150° C. The crude product was purified by Flash-Prep-HPLC with the following conditions (IntelFlash-1): Column, C18 silica gel; mobile phase, H$_2$O and CH$_3$CN (20% CH$_3$CN increasing to 90% within 20 min); Detector, 254 nm. This resulted in 24.9 mg (13.3%) of 7-(4,4-difluoropiperidin-1-yl)-N-[(4S)-3,4-dihydro-2H-1-benzopyran-4-yl]-3-(dimethylamino)thieno[3,2-b]pyridine-2-carboxamideas a light yellow solid. (ES, m/z): 473 [M+H]$^+$; $^1$H-NMR (300 MHz, CD$_3$OD): δ=8.51 (d, J=5.4 Hz, 1H), 7.38-7.28 (m, 1H), 7.28-7.16 (m, 1H), 7.00-6.91 (m, 2H), 6.86 (d, J=8.3 Hz, 1H), 5.30 (t, J=5.6 Hz, 1H), 4.38-4.32 (m, 1H), 4.27-4.23 (m, 1H), 3.67-3.58 (m, 4H), 2.97 (s, 6H), 2.44-2.11 (m, 6H) ppm.

The following compounds can be prepared according to Scheme 11 below: 115, 116, 117, 118, 237, 115-INT-3, 239, 239-INT-1, 237A.

Scheme 11

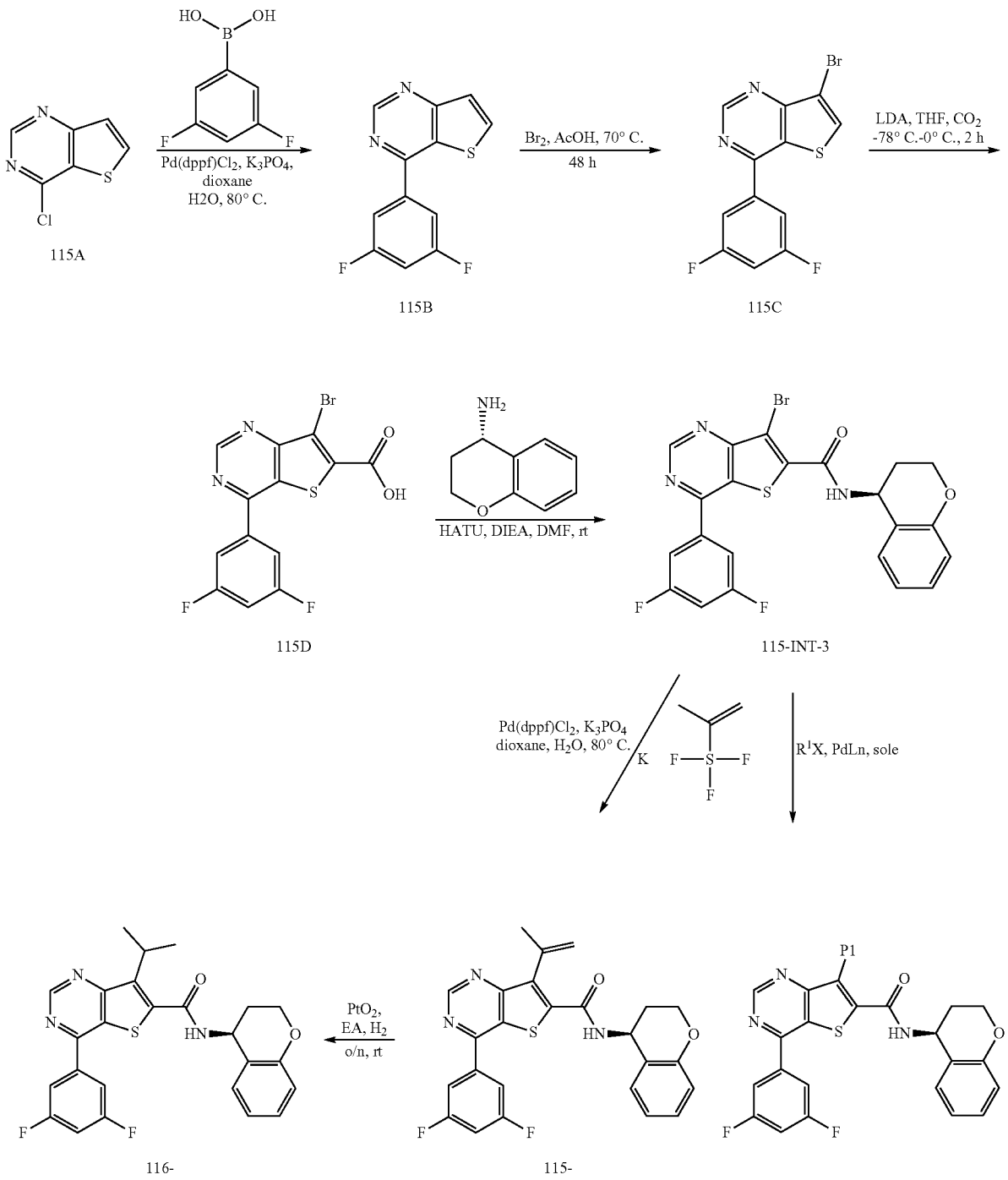

Exemplary Procedure of Compound 115 and 116

Synthesis of 4-(3,5-difluorophenyl)thieno[3,2-d]pyrimidine as a White Solid

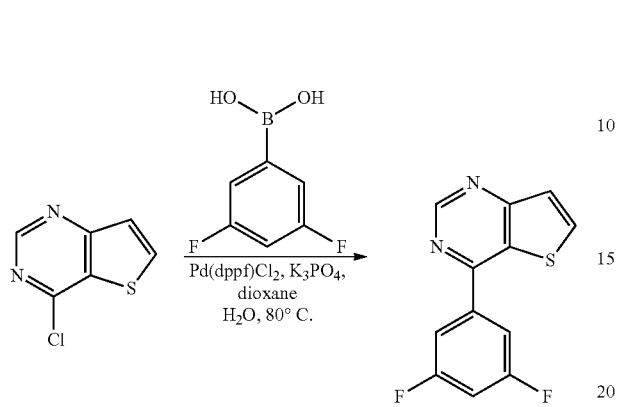

Into a 250-mL round-bottom flask purged and maintained with an inert atmosphere of nitrogen, was placed 4-chlorothieno[3,2-d]pyrimidine (5.0 g, 29.3 mmol, 1.0 equiv), 3,5-difluorophenylboronic acid (6.0 g, 38.0 mmol, 1.3 equiv), Pd(dppf)Cl$_2$ (2.1 g, 3.0 mmol, 0.1 equiv), K$_3$PO$_4$ (12.4 g, 59.0 mmol, 2 equiv), dioxane (100.0 mL), H$_2$O (10.0 mL). The resulting solution was stirred overnight at 80° C. The resulting mixture was concentrated. The residue was applied onto a silica gel column with ethyl acetate/petroleum ether (1/10-1/4). This resulted in 7.8 g (crude) of 4-(3,5-difluorophenyl)thieno[3,2-d]pyrimidine as a white solid. (ES, m/z): 249 [M+H]$^+$.

1. Synthesis of 7-bromo-4-(3,5-difluorophenyl)thieno[3,2-d] pyrimidine

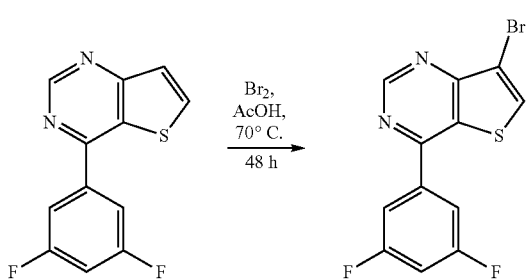 [SMILES: Fc1cc(F)cc(-c2ncnc3ccsc23)c1 ; Fc1cc(F)cc(-c2ncnc3c(Br)csc23)c1]

Into a 250-mL round-bottom flask, was placed 4-(3,5-difluorophenyl)thieno[3,2-d]pyrimidine (3.50 g, 14.1 mmol, 1.0 equiv), Br$_2$ (11.30 g, 70.6 mmol, 5.0 equiv), AcOH (52.0 mL). The resulting solution was stirred for 2 days at 70° C. The reaction was then quenched by pouring into 500 mL of ice aq. NaHCO$_3$. The resulting solution was extracted with 2×500 mL of ethyl acetate. The EA mixture was washed with 2×500 mL of aq. NaCHO$_3$ and 1×500 mL of aq. NaS$_2$SO$_3$. The resulting EA mixture was washed with 1×500 mL of brine. The EA mixture was dried over anhydrous sodium sulfate. The solids were filtered out. The filtrate was concentrated. This resulted in 4 g of 7-bromo-4-(3,5-difluorophenyl)thieno[3,2-d] pyrimidine as a light yellow solid.

2. Synthesis of 7-bromo-4-(3,5-difluorophenyl)thieno[3,2-d]pyrimidine-6-carboxylic Acid

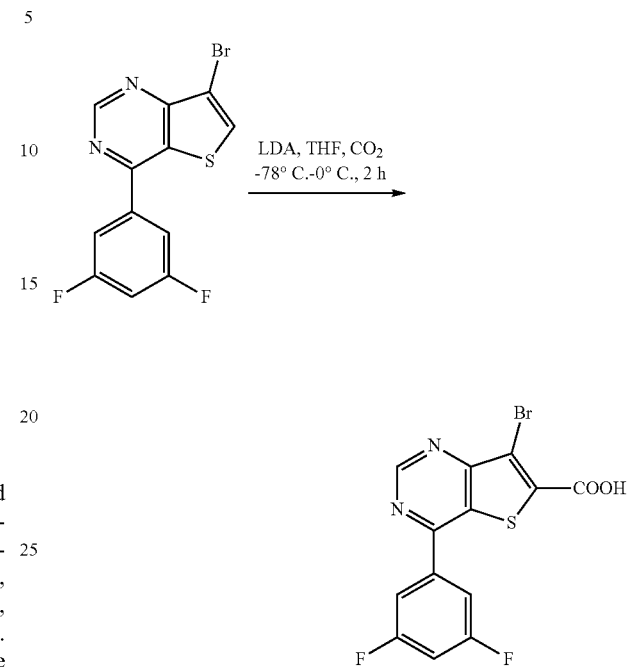

Into a 250-mL 3-necked round-bottom flask purged and maintained with an inert atmosphere of nitrogen, was placed 7-bromo-4-(3,5-difluorophenyl)thieno[3,2-d]pyrimidine (1.3 g, 1.0 equiv), THF (130.0 mL). This was followed by the addition of LDA (4.0 mL, 1.5 equiv) dropwise with stirring at −78° C. The resulting solution was stirred for 30 min at −78° C. To this was flowed CO$_2$ at −50° C. The resulting solution was allowed to react, with stirring, for an additional 2 hr at −50° C. The resulting solution was allowed to react, with stirring, for an additional 2 hr at room temperature. The reaction was then quenched by the addition of 100 mL of water. The solids were collected by filtration. This resulted in 500 mg of 7-bromo-4-(3,5-difluorophenyl)thieno[3,2-d]pyrimidine-6-carboxylic acid as a light yellow solid.

3. Synthesis of 7-bromo-4-(3,5-difluorophenyl)-N-[(4S)-3,4-dihydro-2H-1-benzopyran-4-yl]thieno[3,2-d]pyrimidine-6-carboxamide

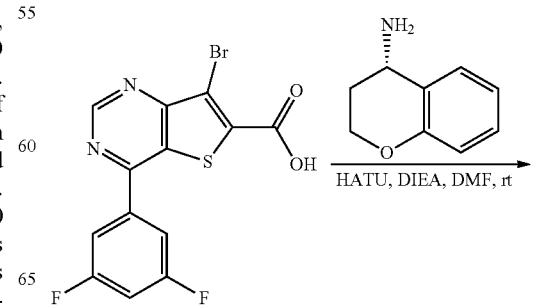

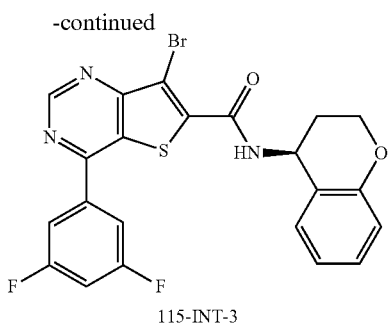

115-INT-3

Into a 250-mL round-bottom flask, was placed 7-bromo-4-(3,5-difluorophenyl)thieno[3,2-d]pyrimidine-6-carboxylic acid (1.6 g, 4.3 mmol, 1.0 equiv), (4S)-3,4-dihydro-2H-1-benzopyran-4-amine (707.4 mg, 4.7 mmol, 1.1 equiv), HATU (3278.2 mg, 8.6 mmol, 2 equiv), DIEA (1392.8 mg, 10.7 mmol, 2.5 equiv), DMF (50.0 mL). The resulting solution was stirred for 3 hr at room temperature. The reaction was then quenched by the addition of 50 mL of water. The solids were collected by filtration. This resulted in 1.1 g (50.8%) of 7-bromo-4-(3,5-difluorophenyl)-N-[(4S)-3,4-dihydro-2H-1-benzopyran-4-yl] thieno[3,2-d]pyrimidine-6-carboxamide as a yellow solid. (ES, m/z): 502 [M+H]$^+$; $^1$H-NMR (300 MHz, DMSO-d$_6$): δ=9.49 (s, 1H), 9.40 (d, J=8.1 Hz, 1H), 7.82 (d, J=6.6 Hz, 2H), 7.65 (t, J=9.0 Hz, 1H), 7.35 (d, J=7.2 Hz, 1H), 7.20 (t, J=6.9 Hz, 1H), 6.94 (t, J=7.2 Hz, 1H), 6.82 (d, J=8.1 Hz, 1H), 5.29 (d, J=6.6 Hz, 1H), 4.29 (s, 2H), 42.25-2.13 (m, 2H) ppm.

4. Synthesis of 4-(3,5-difluorophenyl)-N-[(4S)-3,4-dihydro-2H-1-benzopyran-4-yl]-7-(prop-1-en-2-yl)thieno[3,2-d]pyrimidine-6-carboxamide

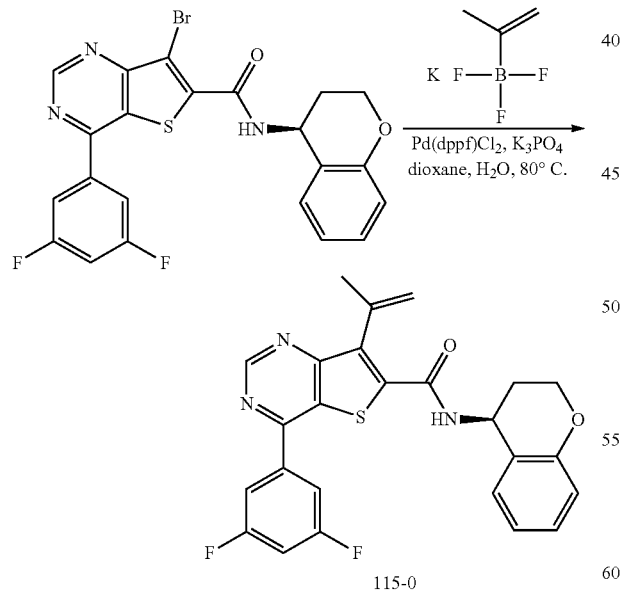

115-0

Into a 50-mL round-bottom flask purged and maintained with an inert atmosphere of nitrogen, was placed 7-bromo-4-(3,5-difluorophenyl)-N-[(4S)-3,4-dihydro-2H-1-benzopyran-4-yl]thieno[3,2-d]pyrimidine-6-carboxamide (57.0 mg, 0.1 mmol, 1.0 equiv), trifluoro(prop-1-en-2-yl)-lambda4-borane potassium (38.0 mg, 0.3 mmol, 2.0 equiv), Pd(dppf)Cl$_2$ (15.0 mg, 0.02 mmol, 0.2 equiv), K$_3$PO$_4$ (48.0 mg, 0.3 mmol, 2.0 equiv), dioxane (3.0 mL), H$_2$O (0.3 mL). The resulting solution was stirred overnight at 80° C. The crude product was purified by Flash-Prep-HPLC with the following conditions (IntelFlash-1): Column, C18 silica gel; mobile phase, ACN/H$_2$O=20/80 increasing to ACN/H$_2$O=100/0 within 15 min; Detector, 254 nm. This resulted in 27.8 mg of 4-(3,5-difluorophenyl)-N-[(4S)-3,4-dihydro-2H-1-benzopyran-4-yl]-7-(prop-1-en-2-yl)thieno[3,2-d]pyrimidine-6-carboxamide as an off-white solid. (ES, m/z): 464 [M+H]$^+$; $^1$H-NMR (300 MHz, CD$_3$OD): δ=9.34 (s, 1H), 7.81-7.78 (m, 2H), 7.49 (d, J=7.2 Hz, 1H), 7.26-7.21 (m, 1H), 7.09-7.02 (m, 1H), 6.97-6.87 (m, 2H), 5.60 (t, J=1.5 Hz, 1H), 5.38-5.35 (m, 1H), 5.27 (s, 1H), 4.34-4.31 (m, 1H), 4.19-4.12 (m, 1H), 2.39-2.36 (m, 1H), 2.22-2.19 (m, 4H) ppm.

5. Synthesis of 4-(3,5-difluorophenyl)-N-[(4S)-3,4-dihydro-2H-1-benzopyran-4-yl]-7-isopropylthieno[3,2-d]pyrimidine-6-carboxamide

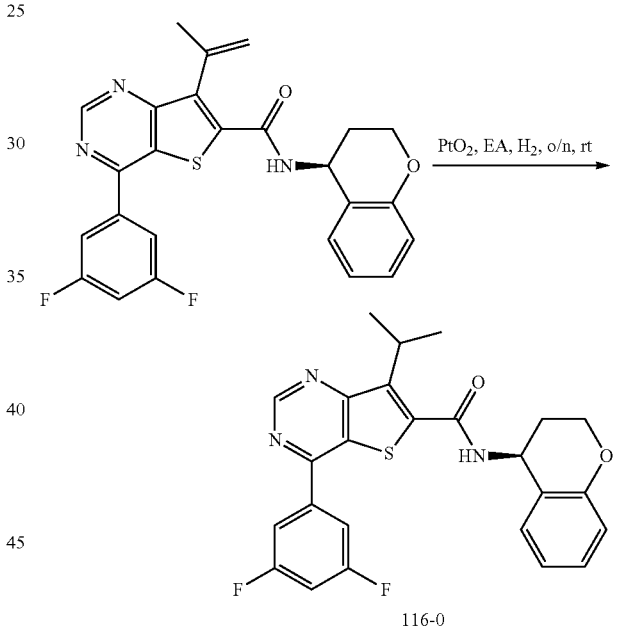

116-0

Into a 50-mL round-bottom flask, was placed 4-(3,5-difluorophenyl)-N-[(4S)-3,4-dihydro-2H-1-benzopyran-4-yl]-7-(prop-1-en-2-yl)thieno[3,2-d]pyrimidine-6-carboxamide (90.0 mg, 0.2 mmol, 1.0 equiv), PtO$_2$ (90.0 mg, 1.0 equiv), EA (20.0 mL). The mixture was flushed with H$_2$ for 6 times. The resulting solution was stirred overnight at room temperature. The solids were filtered out. The filtrate was concentrated. The crude product was purified by Flash-Prep-HPLC with the following conditions (IntelFlash-1): Column, C18 silica gel; mobile phase, ACN/H$_2$O=30/70 increasing to ACN/H$_2$O=80/20 within 15 min; Detector, 254 nm. This resulted in 27.7 mg of 4-(3,5-difluorophenyl)-N-[(4S)-3,4-dihydro-2H-1-benzopyran-4-yl]-7-isopropylthieno[3,2-d]pyrimidine-6-carboxamide as a white solid. (ES, m/z): 466 [M+H]$^+$; $^1$H-NMR (300 MHz, DMSO-d$_6$): δ=9.40 (s, 1H), 9.34 (d, J=6.9 Hz, 1H), 7.79 (d, J=6.0 Hz, 2H), 7.64-7.61 (m, 1H), 7.27-7.16 (m, 2H), 6.96-6.93 (m, 1H), 6.82-6.79 (m, 1H), 5.30 (s, 1H), 4.26 (m, 2H), 3.85-3.81 (m, 1H), 2.30-1.98 (m, 2H), 1.51 (m, 6H) ppm.

6. Synthesis of 4-(3,5-difluorophenyl)-N-[(4S)-3,4-dihydro-2H-1-benzopyran-4-yl]-7-(dimethylamino)thieno[3,2-d]pyrimidine-6-carboxamide

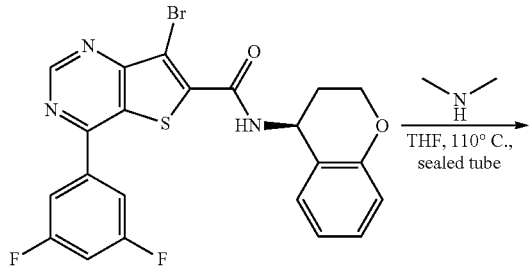

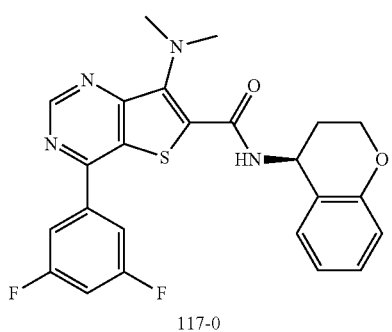

117-0

Into a 50-mL sealed tube, was placed 7-bromo-4-(3,5-difluorophenyl)-N-[(4S)-3,4-dihydro-2H-1-benzopyran-4-yl]thieno[3,2-d]pyrimidine-6-carboxamide (80.0 mg, 0.16 mmol, 1.0 equiv), dimethylamine (2 M in THF, 50.0 mL). The resulting solution was stirred for 4 hr at 110° C. The resulting mixture was concentrated. The crude product was purified by Flash-Prep-HPLC with the following conditions (IntelFlash-1): Column, C18 silica gel; mobile phase, ACN/H$_2$O=20/80 increasing to ACN/H$_2$O=90/10 within 15 min; Detector, 254 nm. This resulted in 5 mg of 4-(3,5-difluorophenyl)-N-[(4S)-3,4-dihydro-2H-1-benzopyran-4-yl]-7-(dimethylamino)thieno[3,2-d]pyrimidine-6-carboxamide as a white solid. (ES, m/z): 467 [M+H]$^+$; $^1$H-NMR (300 MHz, CDCl$_3$): δ=10.36 (d, J=8.1 Hz, 1H), 9.28 (s, 1H), 7.76 (dd, J=8.1, 2.1 Hz, 2H), 7.32 (d, J=7.8 Hz, 1H), 7.26-7.20 (m, 1H), 7.08-7.01 (m, 1H), 6.96-6.88 (m, 2H), 5.42-5.38 (m, 1H), 4.39-4.33 (m, 1H), 4.28-4.20 (m, 1H), 2.99 (s, 6H), 2.44-2.38 (m, 1H), 2.23-2.16 (m, 1H) ppm.

7. Synthesis of 4-(3,5-difluorophenyl)-N-[(4S)-3,4-dihydro-2H-1-benzopyran-4-yl]-7-(morpholin-4-yl)thieno[3,2-d]pyrimidine-6-carboxamide

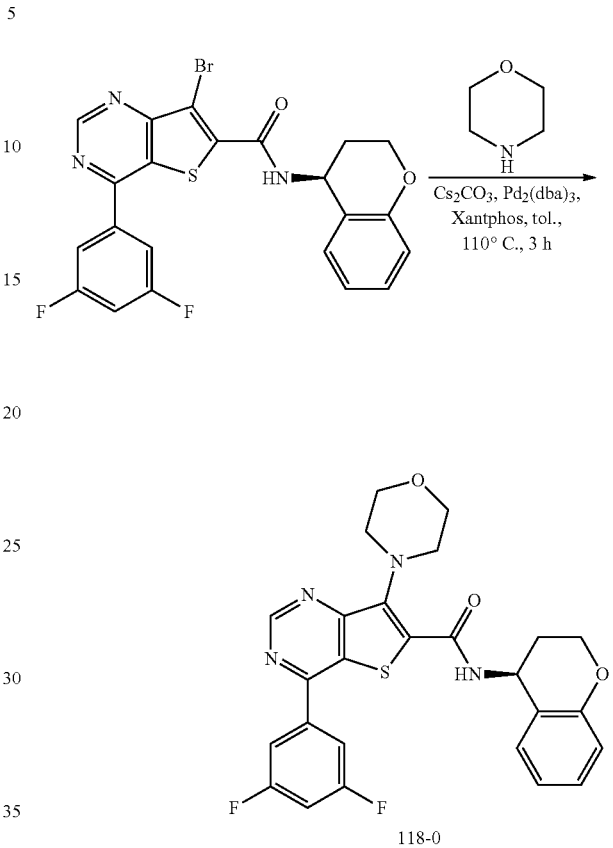

118-0

Into a 50-mL round-bottom flask purged and maintained with an inert atmosphere of nitrogen, was placed 7-bromo-4-(3,5-difluorophenyl)-N-[(4S)-3,4-dihydro-2H-1-benzopyran-4-yl]thieno[3,2-d]pyrimidine-6-carboxamide (100.0 mg, 0.2 mmol, 1.0 equiv), morpholine (174.0 mg, 2.0 mmol, 10.0 equiv), Pd$_2$(dba)$_3$ (20.0 mg, 0.02 mmol, 0.1 equiv), Xantphos (23.0 mg, 0.04 mmol, 0.2 equiv), toluene (10.0 mL), Cs$_2$CO$_3$ (130.0 mg, 0.4 mmol, 2.0 equiv). The resulting solution was stirred for 3 hr at 110° C. The solids were filtered out. The filtrate was concentrated. The crude product was purified by Flash-Prep-HPLC with the following conditions (IntelFlash-1): Column, C18 silica gel; mobile phase, ACN/H$_2$O=10/90 increasing to ACN/H$_2$O=90/10 within 15 min; Detector, 254 nm. This resulted in 47.4 mg of 4-(3,5-difluorophenyl)-N-[(4S)-3,4-dihydro-2H-1-benzopyran-4-yl]-7-(morpholin-4-yl)thieno[3,2-d]pyrimidine-6-carboxamide as a yellow solid. (ES, m/z): 509 [M+H]$^+$; $^1$H-NMR (300 MHz, CDCl$_3$): δ=10.64 (d, J=6.9 Hz, 1H), 9.31 (s, 1H), 7.80 (dd, J=8.1, 2.1 Hz, 2H), 7.31-7.27 (m, 2H), 7.11-7.05 (m, 1H), 6.99-6.93 (m, 2H), 5.35-5.30 (m, 1H), 4.43-4.38 (m, 1H), 4.27-4.19 (m, 1H), 3.52-3.39 (m, 8H), 2.41-2.33 (m, 2H) ppm.

The following compounds can be prepared according to Scheme 12 below and the following detailed procedures: 201, 203, 206, 208, 209, 211, 211-0A, 213, 214, 216, 217, 220, 221, 222, 223, 229, 231, 232, 236, 238, 240, 241, 242, 243, 245, 246, 247, 248, 249, 250, 255, 255-0A, 257, 268, 268-4, 347, 348.

Scheme 12

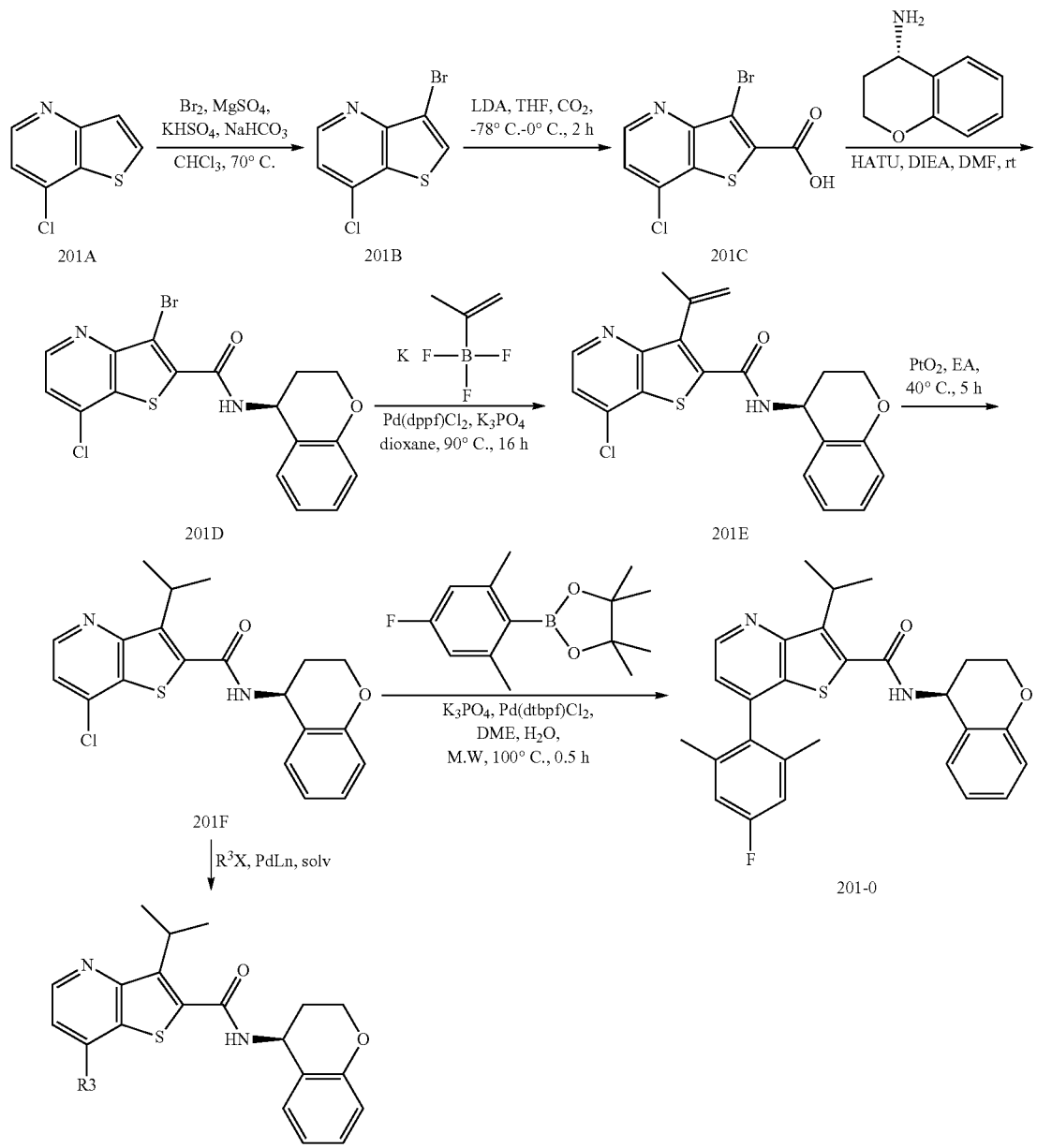

Exemplary Procedure of Compound 201

1. Synthesis of 3-bromo-7-chlorothieno[3,2-b]pyridine

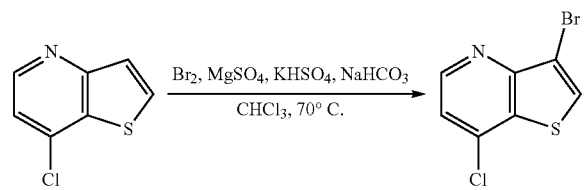 [SMILES: Clc1ccnc2ccsc12 ; Clc1ccnc2c(Br)csc12]

Into a 3000-mL 3-necked round-bottom flask, was placed 7-chlorothieno[3,2-b]pyridine (25.0 g, 147.3 mmol, 1.0 equiv), CHCl₃ (4166.6 mL, 34903.0 mmol, 350.5 equiv), KHSO₄ (30.1 g, 221.0 mmol, 1.5 equiv), NaHCO₃ (12.3 g, 147.4 mmol, 1.0 equiv), MgSO₄ (26.6 g, 221.0 mmol, 1.5 equiv), Br₂ (235.5 g, 1473.8 mmol, 10.0 equiv). The resulting solution was stirred for 16 hr at 70° C. The reaction was cooled to room temperature. The reaction was then quenched by the addition of 500 mL of Na₂S₂O₃ (aq.). The resulting solution was extracted with 2×1 L of DCM. The organic layers were combined, dried and concentrated under vacuum. This resulted in 30 g (81.9%) of 3-bromo-7-chlorothieno[3,2-b]pyridine as a yellow solid.

2. Synthesis of 3-bromo-7-chlorothieno[3,2-b]pyridine-2-carboxylic Acid

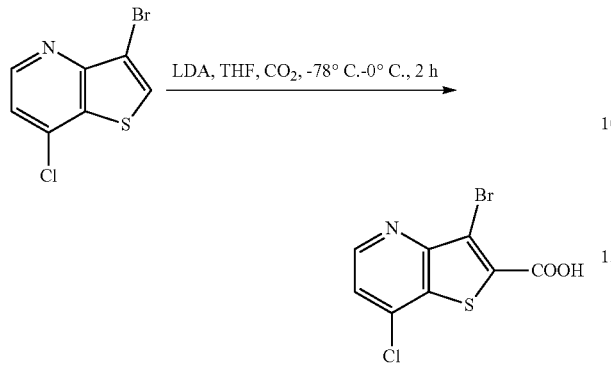

Into a 2000-mL flask, was placed 3-bromo-7-chlorothieno[3,2-b]pyridine (30.0 g, 1.0 equiv), THF (1000.0 mL), LDA (84.0 mL, 1.5 equiv). The resulting solution was stirred for 2 hr at −78° C. To the above CO₂ was introduced for 2 hours at −78 degrees C. The reaction was then quenched by the addition of 500 mL of NH₄Cl. The solids were collected by filtration. This resulted in 18 g (51.1%) of 3-bromo-7-chlorothieno[3,2-b]pyridine-2-carboxylic acid as a yellow solid.

3. Synthesis of 3-bromo-7-chloro-N-[(4S)-3,4-dihydro-2H-1-benzopyran-4-yl]thieno[3,2-b]pyridine-2-carboxamide

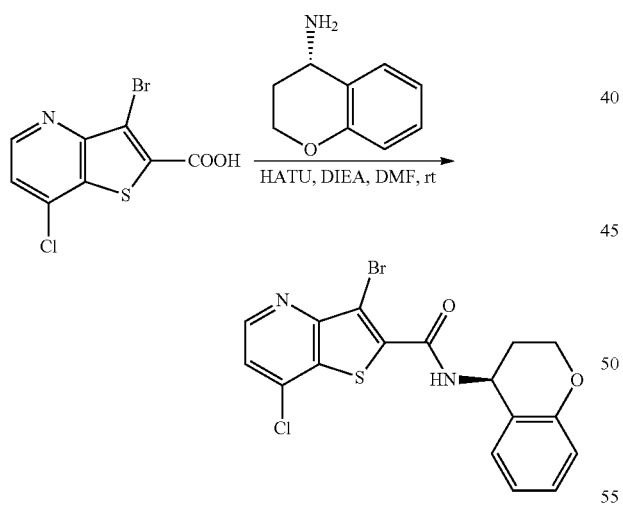

Into a 500-mL round-bottom flask, was placed 3-bromo-7-chlorothieno[3,2-b]pyridine-2-carboxylic acid (25.0 g, 85.4 mmol, 1.0 equiv), HATU (48.7 g, 128.2 mmol, 1.5 equiv), DMF (300.0 mL), DIEA (33.1 g, 256.4 mmol, 3.0 equiv), (4S)-3,4-dihydro-2H-1-benzopyran-4-amine (19.1 g, 128.2 mmol, 1.5 equiv). The resulting solution was stirred for 3 hr at room temperature. The reaction was then quenched by the addition of 500 mL of water. The solids were collected by filtration. This resulted in 30 g (82.8%) of 3-bromo-7-chloro-N-[(4S)-3,4-dihydro-2H-1-benzopyran-4-yl]thieno[3,2-b]pyridine-2-carboxamide as a yellow solid.

4. Synthesis of 7-chloro-N-[(4S)-3,4-dihydro-2H-1-benzopyran-4-yl]-3-(prop-1-en-2-yl)thieno[3,2-b]pyridine-2-carboxamide

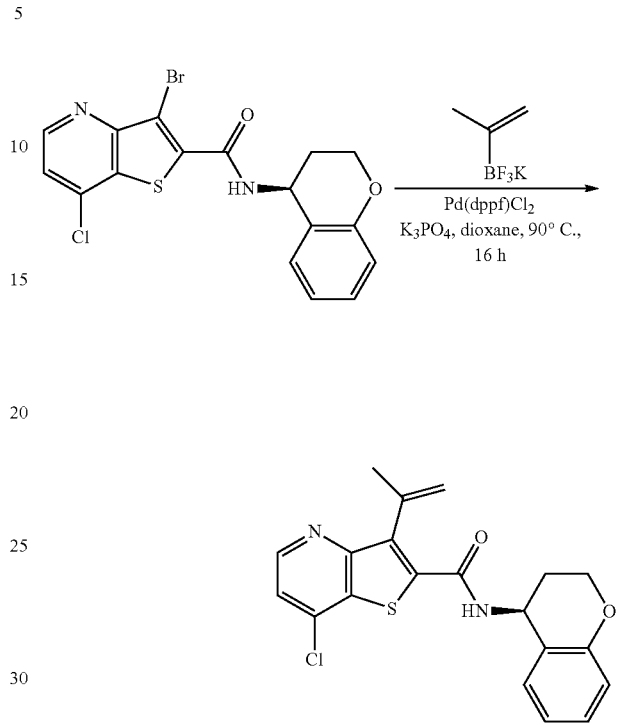

Into a 500-mL round-bottom flask purged and maintained with an inert atmosphere of nitrogen, was placed 3-bromo-7-chloro-N-[(4S)-3,4-dihydro-2H-1-benzopyran-4-yl]thieno[3,2-b]pyridine-2-carboxamide (5.0 g, 11.8 mmol, 1.0 equiv), trifluoro(prop-1-en-2-yl)-lambda4-borane potassium (2.6 g, 17.7 mmol, 1.5 equiv), Pd(dppf)Cl₂ (0.8 g, 1.2 mmol, 0.1 equiv), K₃PO₄ (5.0 g, 23.6 mmol, 2.0 equiv), dioxane (100 mL), H₂O (10 mL). The resulting solution was stirred for 3 hr at 90° C. The resulting mixture was concentrated. The residue was applied onto a silica gel column with ethyl acetate/petroleum ether (1:10). This resulted in 2.8 g (61.6%) of 7-chloro-N-[(4S)-3,4-dihydro-2H-1-benzopyran-4-yl]-3-(prop-1-en-2-yl)thieno[3,2-b]pyridine-2-carboxamide as a yellow solid.

5. Synthesis of 7-chloro-N-[(4S)-3,4-dihydro-2H-1-benzopyran-4-yl]-3-isopropylthieno[3,2-b]pyridine-2-carboxamide

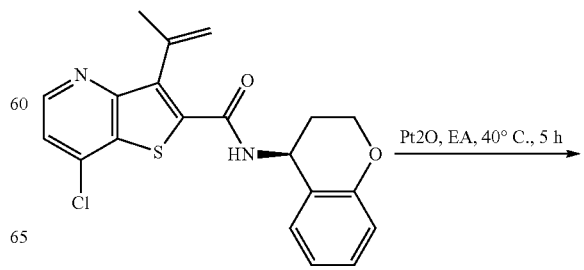

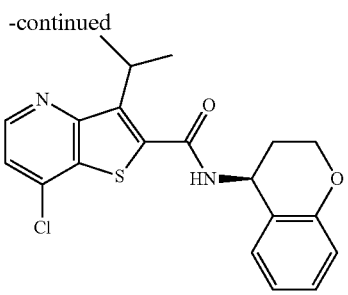

Into a 1000-mL round-bottom flask, was placed 7-chloro-N-[(4S)-3,4-dihydro-2H-1-benzopyran-4-yl]-3-(prop-1-en-2-yl)thieno[3,2-b]pyridine-2-carboxamide as a yellow solid (2.50 g, 6.5 mmol, 1.0 equiv), EA (500.0 mL), Pt₂O (1.5 g). The flask was evacuated and flushed three times with nitrogen, followed by flushing with hydrogen. The mixture was stirred 3 h at 40° C. under an atmosphere of hydrogen (balloon). The reaction mixture was cooled to room temperature. The solids were filtered out. The filtrate was concentrated. This resulted in 1.2 g (59.7%) of 7-chloro-N-[(4S)-3,4-dihydro-2H-1-benzopyran-4-yl]-3-isopropylthieno[3,2-b]pyridine-2-carboxamide as a yellow solid.

6. Synthesis of N-[(4S)-3,4-dihydro-2H-1-benzopyran-4-yl]-7-(4-fluoro-2,6-dimethylphenyl)-3-isopropylthieno[3,2-b]pyridine-2-carboxamide Into a 20-mL microwave tube purged and maintained with an inert atmosphere of nitrogen, was placed 7-chloro-N-[(4S)-3,4-dihydro-2H-1-benzopyran-4-yl]-3-isopropylthieno[3,2-b]pyridine-2-carboxamide (100.0 mg, 0.2 mmol, 1.0 equiv), DME (3.00 mL), 2-(4-fluoro-2,6-dimethylphenyl)-4,4,5,5-tetramethyl-1,3,2-dioxaborolane (162.0 mg, 0.6 mmol, 2.5 equiv), Pd(dtbpf)Cl₂ (17.00 mg, 0.026 mmol, 0.1 equiv), K₃PO₄ (137.0 mg, 0.6 mmol, 2.5 equiv), H₂O (0.50 mL). The final reaction mixture was irradiated with microwave radiation for 0.5 hr at 100° C. The resulting mixture was concentrated. The crude product was purified by Flash-Prep-HPLC with the following conditions (IntelFlash-1): Column, C18 silica gel; mobile phase, CH₃CN/0.05% NH₃.H₂O=100%; Detector, 254&220 nm. This resulted in 38.9 mg (31.7%) of N-[(4 S)-3,4-dihydro-2H-1-benzopyran-4-yl]-7-(4-fluoro-2,6-dimethylphenyl)-3-isopropylthieno[3,2-b]pyridine-2-carboxamide as an off-white solid. (ES, m/z): 475 [M+H]⁺; ¹H-NMR (300 MHz, DMSO-d₆): δ=9.03 (d, J=7.8 Hz, 1H), 8.84 (d, J=3.6 Hz, 1H), 7.30 (d, J=3.9 Hz, 1H), 7.20-7.09 (m, 4H), 6.91-6.77 (m, 2H), 5.24-5.22 (m, 1H), 4.23 (s, 2H), 3.93 (t, J=6.9 Hz, 1H), 2.12-2.04 (m, 8H), 1.53 (s, 6H) ppm.

Exemplary Procedure of Compound 255

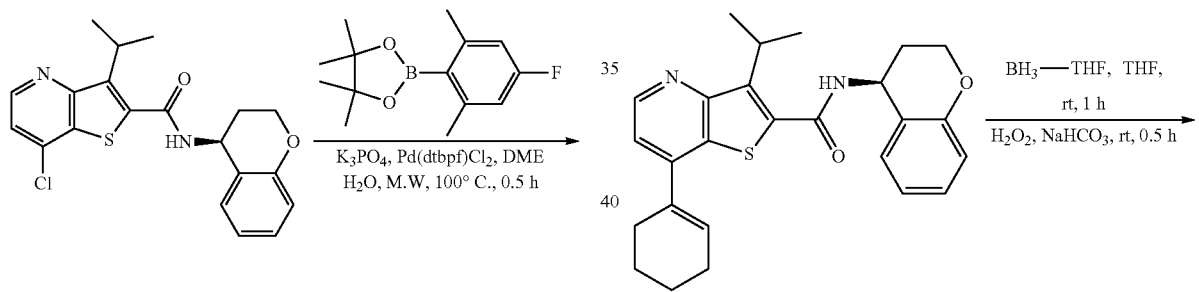

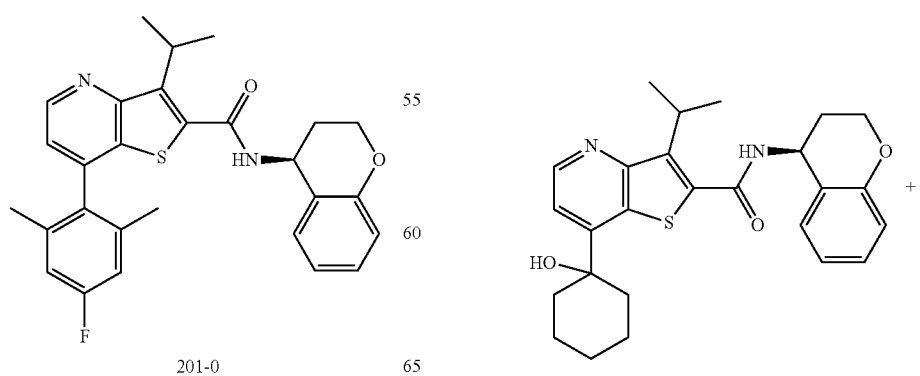

201-0

151

-continued

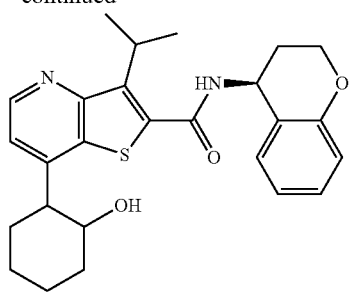

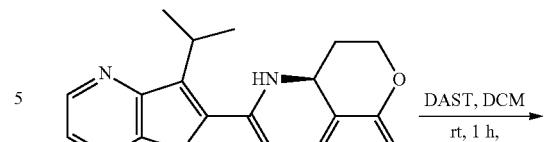

Into a 100-mL round-bottom flask, was placed 7-(cyclohex-1-en-1-yl)-N-[(4S)-3,4-dihydro-2H-1-benzopyran-4-yl]-3-isopropylthieno[3,2-b]pyridine-2-carboxamide (50.0 mg, 0.1 mmol, 1.0 equiv), THF (10.0 mL), BH$_3$-THF (1M in THF) (2.5 mL, 26.1 mmol, 226.0 equiv). The resulting solution was stirred for 1 hr at room temperature. Then H$_2$O$_2$ (30%) (2.50 mL, 107.3 mmol, 928.3 equiv), NaHCO$_3$ (5 mL) was dropped in the flask. The resulting solution was allowed to react, with stirring, for an additional 30 min at room temperature. The resulting solution was diluted with 50 mL of DCM. The organic phase was separated. The organic phase was dried over anhydrous sodium sulfate and concentrated under vacuum. The crude product was purified by Prep-HPLC with the following conditions (2# SHIMADZU (HPLC-01)): Column, SunFire Prep C18 OBD Column, 19*150 mm 5 um 10 nm; mobile phase, Water and ACN (16% PhaseB up to 40% in 7 min); Detector, UV 254 nm. This resulted in 15 mg (28.8%) of N-[(4S)-3,4-dihydro-2H-1-benzopyran-4-yl]-7-(1-hydroxycyclohexyl)-3-isopropylthieno[3,2-b]pyridine-2-carboxamide as a white solid and 20 mg (38.4%) of N—((S)-chroman-4-yl)-7-(2-hydroxycyclohexyl)-3-isopropylthieno[3,2-b]pyridine-2-carboxamide as a white solid.

152

255-O

Into a 50-mL round-bottom flask, was placed N-[(4S)-3,4-dihydro-2H-1-benzopyran-4-yl]-7-(1-hydroxycyclohexyl)-3-isopropylthieno[3,2-b]pyridine-2-carboxamide (15.0 mg, 0.03 mmol, 1.0 equiv), DCM (2.0 mL). This was followed by the addition of DAST (0.1 mL) dropwise with stirring at 0° C. The resulting solution was stirred for 1 hr at 25° C. The reaction was then quenched by the addition of MeOH (0.5 mL). The resulting mixture was concentrated under vacuum. The crude product was purified by Prep-HPLC with the following conditions (2# SHIMADZU (HPLC-01)): Column, SunFire Prep C18 OBD Column, 19*150 mm 5 um 10 nm; mobile phase, Water and ACN (16% CH$_3$CN up to 40% in 7 min); Detector, UV 254 nm. This resulted in 2.0 mg (13.2%) of N-[(4S)-3,4-dihydro-2H-1-benzopyran-4-yl]-7-(1-fluorocyclohexyl)-3-isopropylthieno[3,2-b]pyridine-2-carboxamide as a white solid. $^1$H-NMR (300 MHz, CDCl$_3$): δ=8.81 (s, 1H), 7.61 (s, 1H), 7.46-7.18 (m, 2H), 6.98-6.86 (m, 2H), 6.25 (d, J=6.9 Hz, 1H), 5.35 (d, J=5.7 Hz, 1H), 4.36-4.33 (m, 1H), 4.25-4.10 (m, 2H), 2.37-2.34 (m, 1H), 2.35-1.15 (m, 17H) ppm.

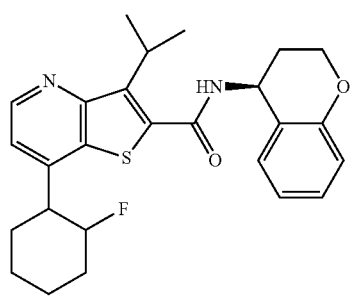

255-OA $^1$H-NMR (300 MHz, CDCl$_3$): δ = 8.75 (s, 1H), 7.41 (s, 1H), 7.32-7.29 (m, 1H), 7.25-7.21 (m, 1H), 6.95 (t, J = 7.2 Hz, 1H), 6.88 (d, J = 8.1 Hz, 1H), 6.21 (s, 1H), 5.36 (s, 1H), 5.00 (d, J = 36.9 Hz, 1H), 4.41-4.33 (m, 1H), 4.29-4.21 (m, 1H), 4.17-4.06 (m, 1H), 2.91 (dd, J = 13.8, 11.7 Hz, 1H), 2.46-2.35 (m, 1H), 2.22-2.10 (m, 3H), 1.97 (d, J = 13.2 Hz, 1H), 1.83 (d, J = 14.4 Hz, 1H), 1.76 (s, 2H), 1.57 (s, 6H), 1.31 (s, 2H) ppm.

The following additional compounds were prepared according to the aforementioned schemes:

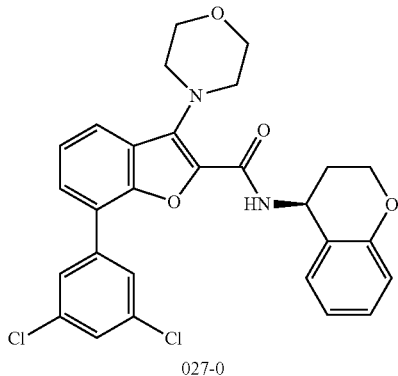 [SMILES: O=C(N[C@H]1CCOc2ccccc21)c1oc2c(-c3cc(Cl)cc(Cl)c3)cccc2c1N1CCOCC1]

027-0

$^1$H-NMR (300 MHz, CDCl$_3$): δ = 8.95 (d, J = 7.2 Hz, 1H), 7.83 (dd, J = 8.0, 1.2 Hz, 1H), 7.74 (d, J = 1.9 Hz, 2H), 7.54 (dd, J = 7.6, 1.2 Hz, 1H), 7.44-7.34 (m, 2H), 7.28-7.21 (m, 2H), 7.02-6.89 (m, 2H), 5.40-5.27 (m, 1H), 4.47-4.32 (m, 1H), 4.29-4.15 (m, 1H), 3.69-3.48 (m, 4H), 3.42-3.24 (m, 4H), 2.47-2.18 (m, 2H) ppm.

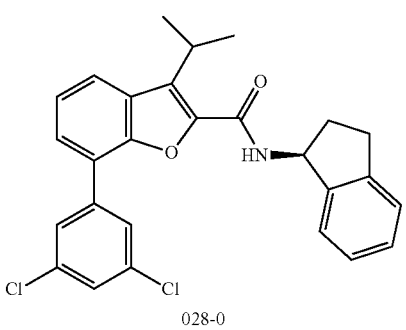 [SMILES: CC(C)c1c(C(=O)N[C@H]2CCc3ccccc32)oc2c(-c3cc(Cl)cc(Cl)c3)cccc12]

028-0

$^1$H-NMR (300 MHz, CDCl$_3$): δ = 7.88 (dd, J = 7.9, 1.2 Hz, 1H), 7.67 (d, J = 1.9 Hz, 2H), 7.50 (dd, J = 7.5, 1.2 Hz, 1H), 7.48-7.41 (m, 1H), 7.41-7.34 (m, 2H), 7.32-7.29 (m, 2H), 7.26 (d, J = 5.7 Hz, 1H), 6.80 (d, J = 8.1 Hz, 1H), 5.77-5.59 (m, 1H), 4.51-4.23 (m, 1H), 3.21-2.86 (m, 2H), 2.85-2.68 (m, 1H), 2.07-1.86 (m, 1H), 1.53 (dd, J = 7.1, 2.8 Hz, 6H) ppm.

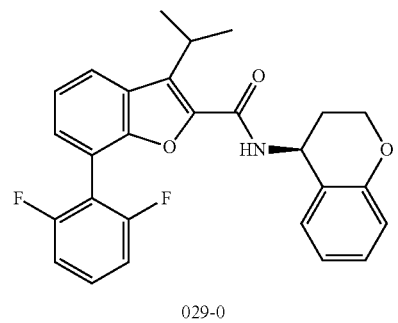 [SMILES: CC(C)c1c(C(=O)N[C@H]2CCOc3ccccc32)oc2c(-c3c(F)cccc3F)cccc12]

029-0

$^1$H-NMR (300 MHz, CDCl$_3$): δ = 7.93 (dd, J = 7.9, 1.3 Hz, 1H), 7.55-7.44 (m, 1H), 7.43-7.33 (m, 2H), 7.32 (d, J = 1.6 Hz, 1H), 7.26-7.17 (m, 1H), 7.07-6.97 (m, 2H), 6.97-6.90 (m, 1H), 6.87 (dd, J = 8.2, 1.2 Hz, 1H), 6.72 (d, J = 8.1 Hz, 1H), 5.49-5.27 (m, 1H), 4.46-4.11 (m, 3H), 2.36 (dddd, J = 16.3, 8.3, 5.4, 3.2 Hz, 1H), 2.14 (dtd, J = 14.0, 7.1, 3.1 Hz, 1H), 1.54 (dd, J = 7.1, 2.9 Hz, 6H) ppm.

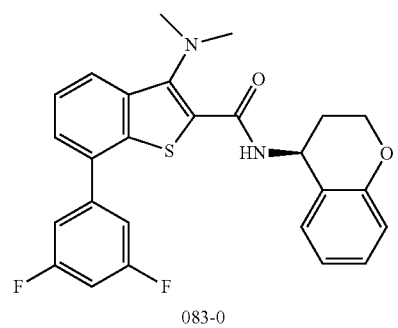 [SMILES: CN(C)c1c(C(=O)N[C@H]2CCOc3ccccc32)sc2c(-c3cc(F)cc(F)c3)cccc12]

083-0

$^1$H-NMR (300 MHz, CD$_3$OD): δ = 8.40 (s, 1H), 8.06 (s, 1H), 7.96 (d, J = 8.7 Hz, 1H), 7.60 (d, J = 8.7 Hz, 1H), 7.39 (d, J = 7.2 Hz, 1H), 7.18 (t, J = 8.4 Hz, 1H), 6.94 (t, J = 8.4 Hz, 1H), 6.82 (d, J = 8.4 Hz, 1H), 5.39 (t, J = 5.7 Hz, 1H), 4.34-4.29 (m, 2H), 3.66-3.61 (m, 1H), 2.33-2.26 (m, 2H), 1.43-1.39 (m, 6H) ppm.

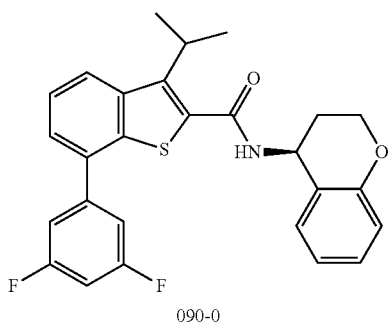 [SMILES: CC(C)c1c(C(=O)N[C@H]2CCOc3ccccc32)sc2c(-c3cc(F)cc(F)c3)cccc12]

090-0

¹H-NMR (300 MHz, CD₃OD): δ = 8.40 (s, 1H), 8.06 (s, 1H), 7.96 (d, J = 8.7 Hz, 1H), 7.60 (d, J = 8.7 Hz, 1H), 7.39 (d, J = 7.2 Hz, 1H), 7.18 (t, J = 8.4 Hz, 1H), 6.94 (t, J = 8.4 Hz, 1H), 6.82 (d, J = 8.4 Hz, 1H), 5.39 (t, J = 5.7 Hz, 1H), 4.34-4.29 (m, 2H), 3.66-3.61 (m, 1H), 2.33-2.26 (m, 2H), 1.43-1.39 (m, 6H) ppm.

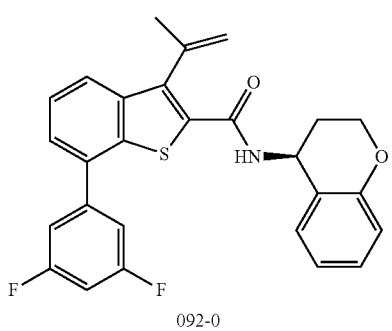

092-0

¹H-NMR (300 MHz, CD₃OD): δ = 8.40 (s, 1H), 8.06 (s, 1H), 7.96 (d, J = 8.7 Hz, 1H), 7.60 (d, J = 8.7 Hz, 1H), 7.39 (d, J = 7.2 Hz, 1H), 7.18 (t, J = 8.4 Hz, 1H), 6.94 (t, J = 8.4 Hz, 1H), 6.82 (d, J = 8.4 Hz, 1H), 5.39 (t, J = 5.7 Hz, 1H), 4.34-4.29 (m, 2H), 3.66-3.61 (m, 1H), 2.33-2.26 (m, 2H), 1.43-1.39 (m, 6H) ppm.

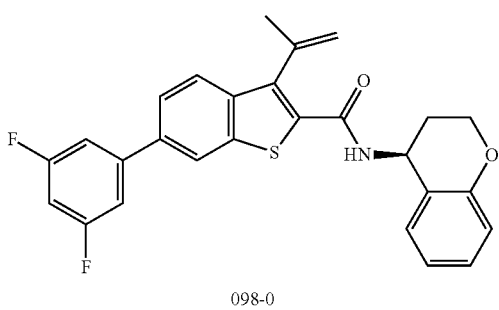 [SMILES: C=C(C)c1c(C(=O)N[C@H]2CCOc3ccccc32)sc2cc(-c3cc(F)cc(F)c3)ccc12]

098-0

¹H-NMR (300 MHz, DMSO-d6): δ = 8.48 (d, J = 8.7 Hz, 2H), 7.87-7.79 (m, 2H), 7.62-7.56 (m, 2H), 7.31-7.15 (m, 3H), 6.95-6.90 (m, 1H), 6.82-6.80 (m, 1H), 5.50 (s, 1H), 5.26-5.19 (m, 1H), 5.13 (s, 1H), 4.27-4.23 (m, 2H), 2.18-2.05 (m, 5H) ppm.

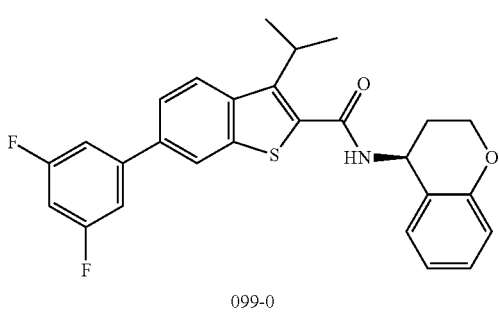 [SMILES: CC(C)c1c(C(=O)N[C@H]2CCOc3ccccc32)sc2cc(-c3cc(F)cc(F)c3)ccc12]

099-0

¹H-NMR (300 MHz, DMSO-d6): δ = 9.04 (d, J = 8.4 Hz, 1H), 8.44 (s, 1H), 8.13 (d, J = 8.7 Hz, 1H), 7.83-7.79 (m, 1H), 7.58-7.55 (m, 2H), 7.29-7.15 (m, 3H), 6.96-6.90 (m, 1H), 6.81-6.78 (m, 1H), 5.28 (d, J = 7.5 Hz, 1H), 4.30-4.25 (m, 2H), 3.81-3.76 (m, 1H), 2.27-1.95 (m, 2H), 1.47-1.43 (m, 6H) ppm.

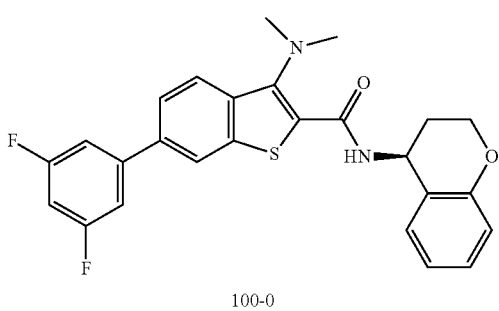 [SMILES: CN(C)c1c(C(=O)N[C@H]2CCOc3ccccc32)sc2cc(-c3cc(F)cc(F)c3)ccc12]

100-0

¹H-NMR (300 MHz, DMSO-d6): δ = 10.06 (d, J = 8.1 Hz, 1H), 8.45 (s, 1H), 8.16 (d, J = 8.7 Hz, 1H), 7.81 (d, J = 7.8 Hz, 1H), 7.59 (d, J = 7.2 Hz, 2H), 7.33-7.17 (m, 3H), 6.95-6.90 (m, 1H), 6.85 (d, J = 8.1 Hz, 1H), 5.26-5.20 (m, 1H), 4.36-4.30 (m, 1H), 4.24-4.19 (m, 1H), 2.90 (s, 6H), 2.28-2.23 (m, 1H), 2.13-2.08 (m, 1H) ppm.

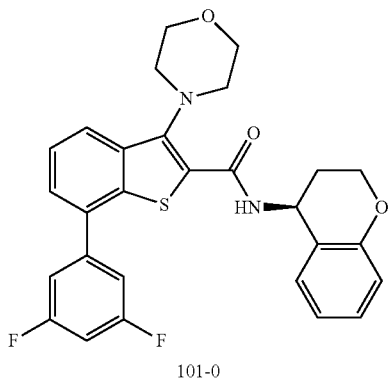 [SMILES: O=C(N[C@H]1CCOc2ccccc21)c1sc2c(-c3cc(F)cc(F)c3)cccc2c1N1CCOCC1]
101-0
¹H-NMR (300 MHz, CDCl₃): δ = 10.44 (s, 1H), 8.04 (dd, J = 8.0, 1.2 Hz, 1H), 7.50 (t, J = 7.7 Hz, 1H), 7.42 (dd, J = 7.3, 1.1 Hz, 1H), 7.28-7.18 (m, 4H), 7.04-6.80 (m, 3H), 5.29 (s, 1H), 4.50-4.29 (m, 1H), 4.22 (dt, J = 12.0, 6.4 Hz, 1H), 3.41 (d, J = 49.1 Hz, 8H), 2.45-2.24 (m, 2H) ppm.
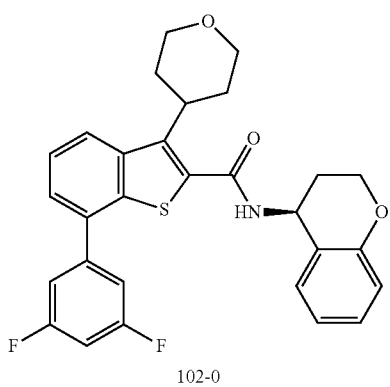 [SMILES: O=C(N[C@H]1CCOc2ccccc21)c1sc2c(-c3cc(F)cc(F)c3)cccc2c1C1CCOCC1]
102-0
¹H-NMR (300 MHz, CDCl₃): δ = 8.22 (d, J = 8.1 Hz, 1H), 7.61-7.49 (m, 1H), 7.42 (dd, J = 7.3, 1.0 Hz, 1H), 7.24 (s, 1H), 7.20-7.17 (m, 2H), 7.09-7.77 (m, 3H), 6.23 (d, J = 7.4 Hz, 1H), 5.36 (q, J = 5.7 Hz, 2H), 4.36-4.33 (m, 1H), 4.26-4.16 (m, 4H), 3.74-3.58 (m, 2H), 2.55 (q, J = 12.6 Hz, 2H), 2.45-2.32 (m, 1H), 2.31-2.13 (m, 1H), 1.79 (d, J = 13.6 Hz, 3H) ppm.
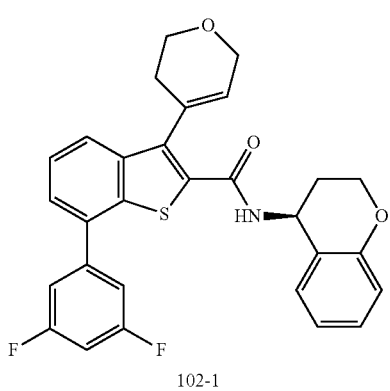 [SMILES: O=C(N[C@H]1CCOc2ccccc21)c1sc2c(-c3cc(F)cc(F)c3)cccc2c1C1=CCOCC1]
102-1
¹H-NMR (300 MHz, CDCl₃): δ = 7.66 (dd, J = 7.8, 1.5 Hz, 1H), 7.53-7.41 (m, 2H), 7.25-7.17 (m, 3H), 7.11 (d, J = 7.2 Hz, 1H), 6.98-6.82 (m, 3H), 5.97-5.96 (m, 1H), 5.32-5.29 (m, 1H), 4.37-4.30 (m, 1H), 4.21-3.96 (m, 3H), 3.81-3.74 (m, 1H), 3.68-3.61 (m, 1H), 2.49-2.27 (m, 3H), 2.26-2.14 (m, 1H) ppm.
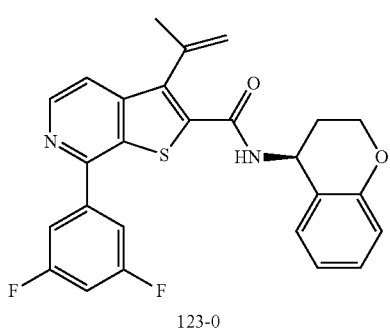 [SMILES: C=C(C)c1c(C(=O)N[C@H]2CCOc3ccccc32)sc2c(-c3cc(F)cc(F)c3)nccc12]
123-0
¹H-NMR (300 MHz, CDCl₃): δ = 8.68 (d, J = 5.7 Hz, 1H), 7.73-7.62 (m, 2H), 7.57 (d, J = 5.5 Hz, 1H), 7.29-7.18 (m, 3H), 7.03-6.87 (m, 3H), 5.60 (s, 1H), 5.59-5.37 (m, 1H), 5.25 (s, 1H), 4.36-4.33 (m, 1H), 4.21-4.13 (m, 1H), 2.40-2.37 (m, 1H), 2.23-2.15 (m, 4H) ppm.

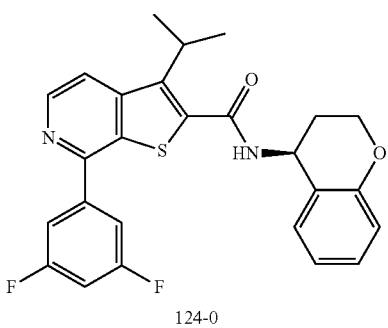 [SMILES: CN(C)c1c(C(=O)N[C@H]2CCOc3ccccc32)sc2c(-c3cc(F)cc(F)c3)nccc12]
124-0
¹H-NMR (300 MHz, CDCl₃): δ = 8.71 (d, J = 5.1 Hz, 1H), 7.96 (d, J = 4.8 Hz, 1H), 7.59-7.57 (m, 2H), 7.31-7.23 (m, 2H), 7.02-6.98 (m, 2H), 6.96-6.89 (m, 1H), 6.29-6.27 (m, 1H), 5.39-5.37 (m, 1H), 4.41-4.35 (m, 1H), 4.26-4.20 (m, 1H), 4.05-4.00 (m, 1H), 2.42-2.38 (m, 4H), 2.36-2.22 (m, 1H), 1.58-1.55 (m, 6H) ppm.
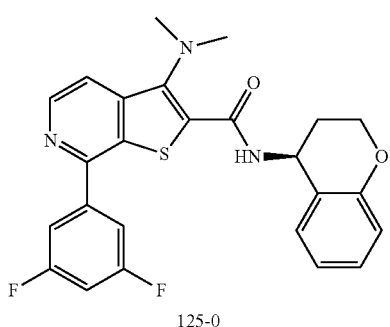
125-0
¹H-NMR (300 MHz, DMSO-d6): δ = 9.87 (d, J = 8.0 Hz, 1H), 8.67 (d, J = 5.5 Hz, 1H), 8.08 (d, J = 5.5 Hz, 1H), 7.74-7.63 (m, 2H), 7.55-7.44 (m, 1H), 7.30 (d, J = 7.6 Hz, 1H), 7.24-7.16 (m, 1H), 6.95-6.90 (m, 1H), 6.84-6.82 (m, 1H), 5.27-5.25 (m, 1H), 4.32-4.22 (m, 2H), 2.92 (s, 6H), 2.27-2.22 (m, 1H), 2.14-2.08 (m, 1H) ppm.
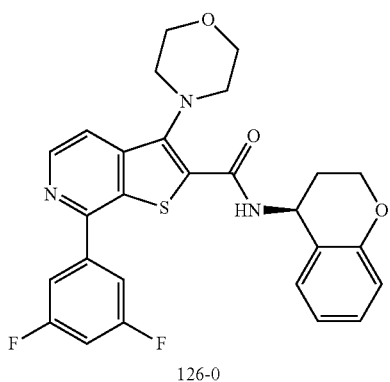 [SMILES: O=C(N[C@H]1CCOc2ccccc21)c1sc2c(-c3cc(F)cc(F)c3)nccc2c1N1CCOCC1]
126-0
¹H-NMR (300 MHz, DMSO-d6): δ 10.20 (d, J = 7.1 Hz, 1H), 8.66 (d, J = 5.5 Hz, 1H), 8.12 (d, J = 5.6 Hz, 1H), 7.69-7.66 (m, 2H), 7.51-7.47 (m, 1H), 7.36-7.34 (m, 1H), 7.28-7.23 (m, 1H), 6.97-6.87 (m, 2H), 5.18-5.16 (m, 1H), 4.32-4.31 (m, 1H), 4.21-4.18 (m, 1H), 3.47-3.38 (m, 4H), 3.36-3.25 (m, 4H), 2.69 (s, 2H), 2.22-2.08 (m, 2H) ppm.
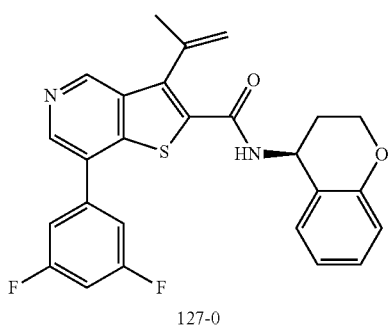 [SMILES: C=C(C)c1c(C(=O)N[C@H]2CCOc3ccccc32)sc2c(-c3cc(F)cc(F)c3)cncc12]
127-0
¹H-NMR (300 MHz, CD₃OD): δ = 8.99 (s, 1H), 8.57 (s, 1H), 7.50-7.38 (m, 2H), 7.34-7.25 (m, 1H), 7.25-7.10 (m, 2H), 6.95-6.91 (m, 1H), 6.83 (d, J = 8.3 Hz, 1H), 5.64 (t, J = 1.6 Hz, 1H), 5.30 (d, J = 2.5 Hz, 2H), 4.29-4.24 (m, 2H), 2.38-2.09 (m, 5H) ppm.

-continued
| | |
|---|---|
| 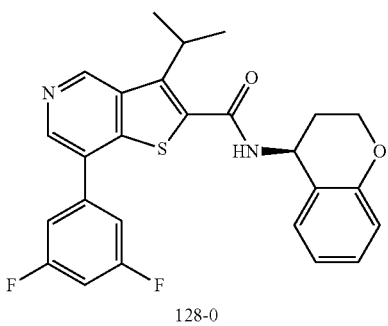<br>128-0 | ¹H-NMR (300 MHz, CD₃OD): δ = 9.30 (s, 1H), 8.52 (s, 1H), 7.40 (d, J = 6.5 Hz, 2H), 7.30 (d, J = 7.7 Hz, 1H), 7.16 (m, 2H), 6.94 (t, J = 7.4 Hz, 1H), 6.81 (d, J = 8.2 Hz, 1H), 5.33 (t, J = 5.6 Hz, 1H), 4.32-4.28 (m, 2H), 3.94-3.81 (m, 1H), 2.28 (s, 1H), 1.58 (d, J = 7.1 Hz, 6H) ppm. |
| 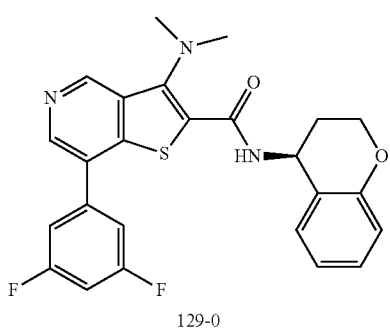 [SMILES: CC(C)c1c(C(=O)N[C@H]2CCOc3ccccc32)sc2c(-c3cc(F)cc(F)c3)cncc12]<br>129-0 | ¹H-NMR (300 MHz, CD₃OD): δ = 9.36 (s, 1H), 8.54 (s, 1H), 7.42-7.38 (m, 2H), 7.35-7.29 (m, 1H), 7.28-7.11 (m, 2H), 6.97-6.64 (m, 1H), 6.86 (d, J = 8.3 Hz, 1H), 5.30 (t, J = 5.6 Hz, 1H), 4.38-4.34 (m, 1H), 4.27-4.24 (m, 1H), 3.00 (s, 5H), 2.37-2.34 (m, 1H), 2.27-2.12 (m, 1H), 1.43-1.21 (m, 2H) ppm. |
| 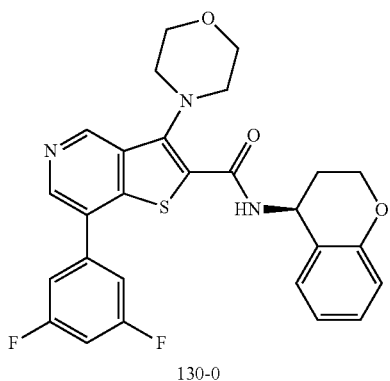 [SMILES: O=C(N[C@H]1CCOc2ccccc21)c1sc2c(-c3cc(F)cc(F)c3)cncc2c1N1CCOCC1]<br>130-0 | ¹H-NMR (300 MHz, CD₃OD): δ = 9.43 (s, 1H), 8.55 (s, 1H), 7.47-7.12 (m, 5H), 7.04-6.89 (m, 2H), 5.22 (t, J = 4.5 Hz, 1H), 4.43-4.32 (m, 1H), 4.32-4.17 (m, 1H), 3.57-3.45 (m, 2H), 3.43-3.36 (m, 2H), 2.31-2.28 (m, 2H) ppm. |
| 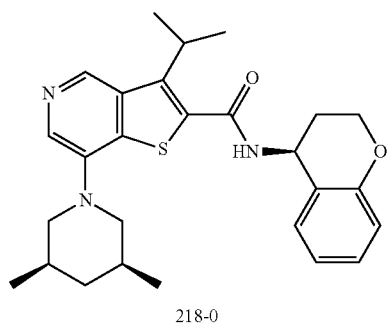 [SMILES: CC(C)c1c(C(=O)N[C@H]2CCOc3ccccc32)sc2c(N3C[C@H](C)C[C@H](C)C3)cncc12]<br>218-0 | ¹H-NMR (300 MHz, CD₃OD) δ = 8.88 (s, 1H), 8.05 (s, 1H), 7.31 (d, J = 7.5 Hz, 1H), 7.24-7.13 (m, 1H), 6.95 (td, J = 7.5, 1.2 Hz, 1H), 6.82 (d, J = 8.3 Hz, 1H), 5.34 (t, J = 5.7 Hz, 1H), 4.31-4.27 (m, 2H), 3.79 (p, J = 7.1 Hz, 1H), 3.59 (d, J = 11.6 Hz, 2H), 2.47-2.30 (m, 2H), 2.30-2.10 (m, 2H), 1.92 (d, J = 11.1 Hz, 3H), 1.53 (dd, J = 7.2, 2.0 Hz, 6H), 0.98 (dd, J = 6.4, 3.4 Hz, 6H), 0.95-0.71 (m, 2H) ppm. |

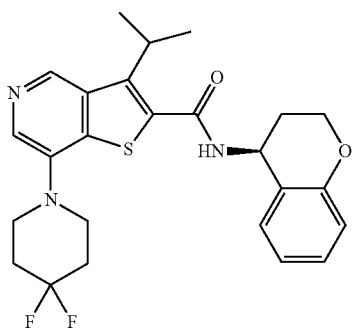
219-0
¹H-NMR (300 MHz, CD₃OD): δ = 8.96 (s, 1H), 8.18-8.12 (m, 1H), 7.31 (d, J = 7.6 Hz, 1H), 7.25-7.13 (m, 1H), 6.99-6.95 (m, 1H), 6.82 (d, J = 8.4 Hz, 1H), 5.34 (t, J = 5.7 Hz, 1H), 4.37-4.22 (m, 2H), 3.80 (p, J = 7.2 Hz, 1H), 3.41 (t, J = 5.7 Hz, 5H), 2.26-2.24 (m, 6H), 1.53 (d, J = 7.2 Hz, 6H) ppm.
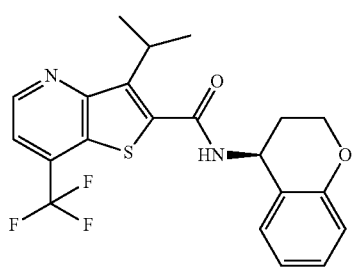
302-0
¹H-NMR (300 MHz, CDCl₃): δ = 8.92 (d, J = 4.8 Hz, 1H), 7.56 (d, J = 4.5 Hz, 1H), 7.25-7.23 (m, 1H), 7.02-7.01 (m, 1H), 7.01-6.92 (m, 1H), 6.92-6.89 (m, 1H), 6.26 (d, J = 6.9 Hz, 1H), 5.40-5.37 (m, 1H), 4.37-4.34 (m, 1H), 4.28-4.21 (m, 1H), 4.11-4.07 (m, 1H), 2.41-2.37 (m, 1H), 2.29-2.25 (m, 1H), 1.61-1.54 (m, 6H) ppm.
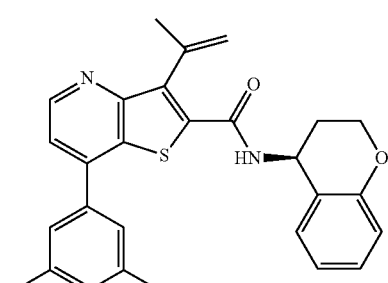
119
¹H-NMR (300 MHz, CD₃OD): δ = 8.80 (d, J = 4.8 Hz, 1H), 7.58 (d, J = 4.8 Hz, 1H), 7.53-7.43 (m, 2H), 7.30 (dd, J = 7.6, 1.2 Hz, 1H), 7.26-7.15 (m, 2H), 6.94 (td, J = 7.5, 1.2 Hz, 1H), 6.83 (dd, J = 8.3, 1.2 Hz, 1H), 5.52 (t, J = 1.7 Hz, 1H), 5.36-5.21 (m, 2H), 4.36-4.15 (m, 2H), 2.35-2.23 (m, 4H), 2.23-2.08 (m, 1H) ppm.
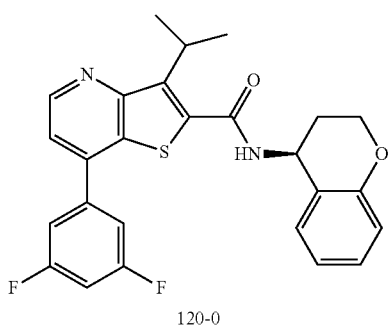
120-0
¹H-NMR (300 MHz, DMSO-d₆): δ = 9.08 (d, J = 8.4 Hz, 1H), 8.86 (d, J = 4.8 Hz, 1H), 7.61-7.46 (m, 4H), 7.24-7.14 (m, 2H), 6.94-6.89 (m, 1H), 6.80 (d, J = 8.1 Hz, 1H), 5.27 (q, J = 7.1 Hz, 1H), 4.36-4.07 (m, 2H), 3.96-3.91 (m, 1H), 2.28-2.04 (m, 2H), 1.52 (dd, J = 7.0, 4.7 Hz, 6H) ppm.

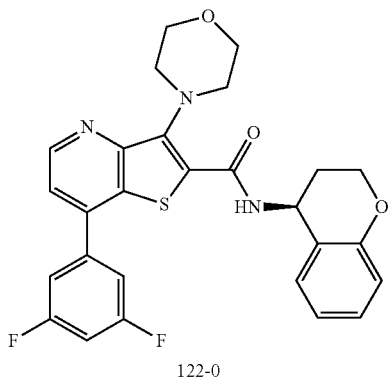 [SMILES: O=C(N[C@H]1CCOc2ccccc21)c1sc2c(-c3cc(F)cc(F)c3)ccnc2c1N1CCOCC1]
122-0
¹H-NMR (300 MHz, CD₃OD): δ = 8.82 (d, J = 4.7 Hz, 1H), 7.53 (d, J = 4.8 Hz, 1H), 7.50-7.38 (m, 2H), 7.38-7.14 (m, 3H), 7.04-6.89 (m, 2H), 5.22 (t, J = 4.4 Hz, 1H), 4.45-4.32 (m, 1H), 4.30-4.19 (m, 1H), 3.61-3.39 (m, 6H), 3.39-3.34 (m, 2H), 2.31 (p, J = 4.2 Hz, 2H) ppm.
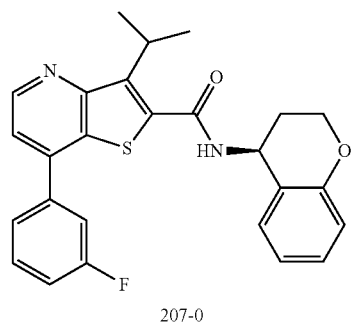 [SMILES: CC(C)c1c(C(=O)N[C@H]2CCOc3ccccc32)sc2c(-c3cccc(F)c3)ccnc12]
207-0
¹H-NMR (300 MHz, CDCl₃): δ = 8.84 (d, J = 4.7 Hz, 1H), 7.61-7.48 (m, 2H), 7.47-7.16 (m, 8H), 7.02-6.85 (m, 2H), 6.24 (d, J = 7.6 Hz, 1H), 5.37 (q, J = 5.9 Hz, 1H), 4.42-4.06 (m, 3H), 2.45-2.18 (m, 2H), 1.65-1.62 (m, 6H) ppm.
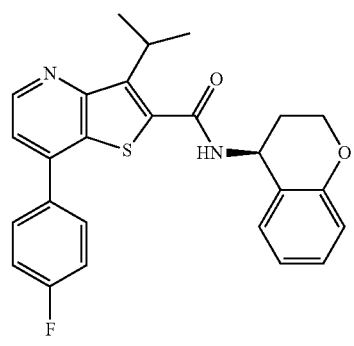
202-0
¹H-NMR (300 MHz, CD₃OD): δ = 8.76 (d, J = 4.8 Hz, 1H), 7.89-7.78 (m, 2H), 7.45 (d, J = 4.8 Hz, 1H), 7.33-7.28 (m, 3H), 7.17 (td, J = 7.9, 1.7 Hz, 1H), 6.93 (td, J = 7.5, 1.2 Hz, 1H), 6.81 (dd, J = 8.2, 1.3 Hz, 1H), 5.33 (t, J = 5.7 Hz, 1H), 4.35-4.24 (m, 2H), 3.88 (p, J = 7.1 Hz, 1H), 2.38-2.08 (m, 2H), 1.58 (dd, J = 7.1, 2.5 Hz, 6H) ppm.
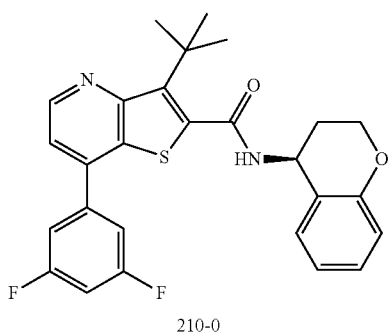 [SMILES: CC(C)(C)c1c(C(=O)N[C@H]2CCOc3ccccc32)sc2c(-c3cc(F)cc(F)c3)ccnc12]
210-0
¹H-NMR (300 MHz, CD₃OD): δ = 8.81 (d, J = 4.7 Hz, 1H), 7.43-7.30 (m, 3H), 7.29 (d, J = 7.6 Hz, 1H), 7.20-7.12 (m, 2H), 6.96-6.91 (m, 1H), 6.81 (dd, J = 8.3, 1.2 Hz, 1H), 5.28 (t, J = 5.2 Hz, 1H), 4.33-7.24 (m, 2H), 2.30-2.13 (m, 2H), 1.70 (s, 9H) ppm.

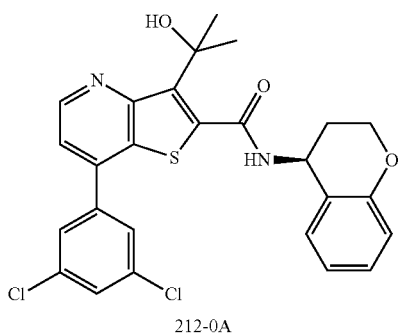 [SMILES: CC(C)(O)c1c(C(=O)N[C@H]2CCOc3ccccc32)sc2c(-c3cc(Cl)cc(Cl)c3)ccnc12]
212-0A
¹H-NMR (300 MHz, CDCl₃): δ = 8.79 (d, J = 4.8 Hz, 1H), 7.56 (dd, J = 11.1, 1.8 Hz, 3H), 7.37-7.29 (m, 2H), 7.29-7.18 (m, 3H), 6.99-6.96 (m, 1H), 6.88 (dd, J = 8.3, 1.2 Hz, 1H), 6.60 (d, J = 7.5 Hz, 1H), 5.33 (q, J = 5.8 Hz, 1H), 4.39-4.33 (m, 1H), 4.25-4.20 (m, 1H), 2.46-2.17 (m, 2H), 1.89 (d, J = 4.2 Hz, 6H) ppm.
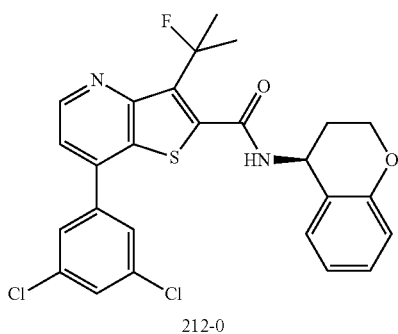 [SMILES: CC(C)(F)c1c(C(=O)N[C@H]2CCOc3ccccc32)sc2c(-c3cc(Cl)cc(Cl)c3)ccnc12]
212-0
¹H-NMR (300 MHz, CDCl₃): δ = 8.79 (d, J = 4.8 Hz, 1H), 7.56 (d, J = 11.1 Hz, 3H), 7.37-7.29 (m, 2H), 7.29-7.18 (m, 3H), 6.97 (d, J = 7.5 Hz, 1H), 6.88 (dd, J = 8.3, 1.2 Hz, 1H), 6.60 (d, J = 7.4 Hz, 1H), 5.33 (q, J = 5.7 Hz, 1H), 4.42-4.29 (m, 1H), 4.25-4.20 (m, 1H), 2.46-2.18 (m, 2H), 1.89 (d, J = 4.2 Hz, 6H), 1.28 (s, 1H), 1.08 (d, J = 1.3 Hz, 1H) ppm.
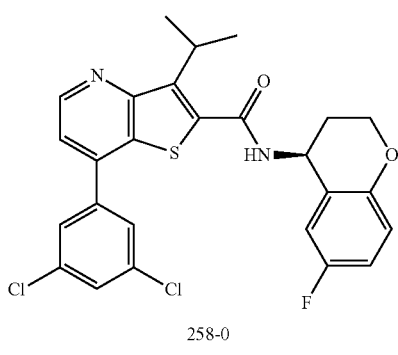 [SMILES: CC(C)c1c(C(=O)N[C@H]2CCOc3ccc(F)cc32)sc2c(-c3cc(Cl)cc(Cl)c3)ccnc12]
258-0
¹H-NMR (300 MHz, CD₃OD): δ = 8.82 (d, J = 4.8 Hz, 1H), 7.78 (d, J = 1.9 Hz, 2H), 7.66 (t, J = 1.9 Hz, 1H), 7.50 (d, J = 4.8 Hz, 1H), 7.04 (d, J = 9.1 Hz, 1H), 6.99-6.87 (m, 1H), 6.81 (d, J = 9.0 Hz, 1H), 5.34 (t, J = 6.1 Hz, 1H), 4.28 (t, J = 5.4 Hz, 2H), 3.94-3.91 (m, 1H), 2.37-2.09 (m, 3H), 1.58 (d, J = 7.1 Hz, 6H) ppm.
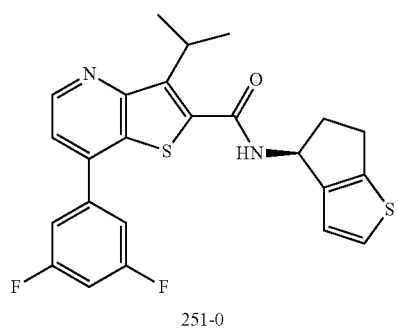 [SMILES: CC(C)c1c(C(=O)N[C@H]2CCc3sccc32)sc2c(-c3cc(F)cc(F)c3)ccnc12]
251-0
¹H-NMR (300 MHz, DMSO-d₆): δ = 8.92 (d, J = 7.2 Hz, 1H), 8.85 (d, J = 4.8 Hz, 1H), 7.61-7.46 (m, 4H), 7.40 (d, J = 4.8 Hz, 1H), 6.91 (d, J = 4.8 Hz, 1H), 5.36 (d, J = 6.6 Hz, 1H), 3.91 (t, J = 7.2 Hz, 1H), 3.05-2.91 (m, 1H), 2.90-2.82 (m, 2H), 2.40-2.34 (m, 1H), 1.50 (dd, J = 1.8, 3.0 Hz, 6H) ppm.

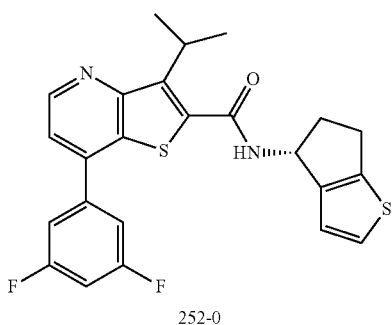 [SMILES: CC(C)c1c(C(=O)N[C@@H]2CCc3sccc32)sc2c(-c3cc(F)cc(F)c3)ccnc12]
252-0
¹H-NMR (300 MHz, DMSO-d₆): δ = 8.92 (d, J = 7.8 Hz, 1H), 8.85 (d, J = 4.8 Hz, 1H), 7.61-7.46 (m, 4H), 7.40 (d, J = 4.8 Hz, 1H), 6.91 (d, J = 5.1 Hz, 1H), 5.36 (d, J = 6.0 Hz, 1H), 3.91 (t, J = 6.9 Hz, 1H), 3.05-2.98 (m, 1H), 2.90-2.82 (m, 2H), 2.40-2.34 (m, 1H), 1.50 (dd, J = 2.1, 2.1 Hz, 6H) ppm.
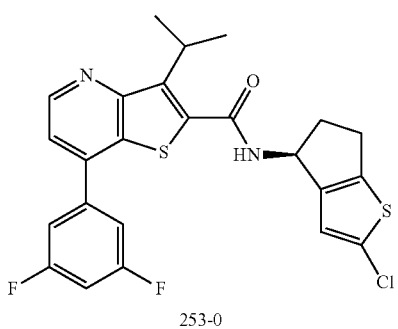 [SMILES: CC(C)c1c(C(=O)N[C@H]2CCc3sc(Cl)cc32)sc2c(-c3cc(F)cc(F)c3)ccnc12]
253-0
¹H-NMR (300 MHz, CDCl₃): δ = 8.85 (d, J = 4.8 Hz, 1H), 7.34 (d, J = 4.8 Hz, 1H), 729-7.25 (m, 2H), 7.01-6.95 (m, 1H), 6.86 (s, 1H), 6.12 (d, J = 7.8 Hz, 1H), 5.53 (d, J = 4.8 Hz, 1H), 4.15-4.06 (m, 1H), 3.08-2.93 (m, 3H), 2.35-2.25 (m, 1H), 1.61 (d, J = 6.9 Hz, 6H) ppm.
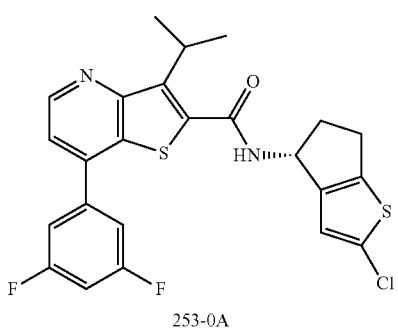 [SMILES: CC(C)c1c(C(=O)N[C@@H]2CCc3sc(Cl)cc32)sc2c(-c3cc(F)cc(F)c3)ccnc12]
253-0A
¹H-NMR (300 MHz, CDCl₃): δ = 8.85 (d, J = 4.5 Hz, 1H), 7.35-7.26 (m, 3H), 7.01-6.93 (m, 1H), 6.86 (s, 1H), 6.12 (d, J = 8.1 Hz, 1H), 5.53 (d, J = 5.7 Hz, 1H), 4.15-4.06 (m, 1H), 3.11-2.93 (m, 3H), 2.35-2.25 (m, 1H), 1.61 (d, J = 6.6 Hz, 6H) ppm.
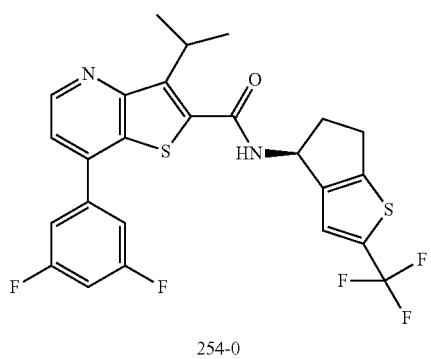 [SMILES: CC(C)c1c(C(=O)N[C@H]2CCc3sc(C(F)(F)F)cc32)sc2c(-c3cc(F)cc(F)c3)ccnc12]
254-0
¹H-NMR (300 MHz, DMSO-d6): δ = 9.01 (d, J = 7.8 Hz, 1H), 8.85 (d, J = 4.8 Hz, 1H), 7.61-7.49 (m, 5H), 5.37 (t, J = 6.3 Hz, 1H), 3.92 (t, J = 6.6 Hz, 1H), 3.14-2.83 (m, 3H), 2.50-2.32 (m, 1H), 1.48 (d, J = 7.2 Hz, 6H) ppm.

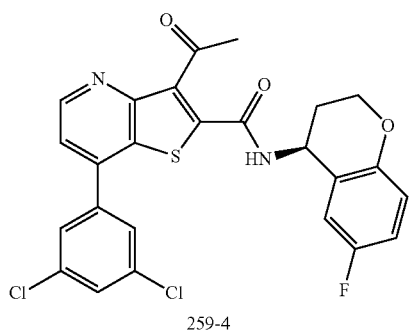 [SMILES: CC(=O)c1c(C(=O)N[C@H]2CCOc3ccc(F)cc32)sc2c(-c3cc(Cl)cc(Cl)c3)ccnc12]
259-4
¹H-NMR (300 MHz, CD₃OD): δ = 8.92 (d, J = 4.7 Hz, 1H), 7.81 (d, J = 1.9 Hz, 2H), 7.73-7.64 (m, 1H), 7.59 (dd, J = 11.8, 4.9 Hz, 1H), 7.13 (dd, J = 9.0, 3.1 Hz, 1H), 6.97-6.74 (m, 1H), 6.82 (dd, J = 9.1, 4.7 Hz, 1H), 5.29 (t, J = 5.8 Hz, 1H), 4.29-4.24 (m, 2H), 2.93 (s, 2H), 2.26-2.21 (m, 2H), 2.05 (d, J = 5.8 Hz, 1H) ppm.
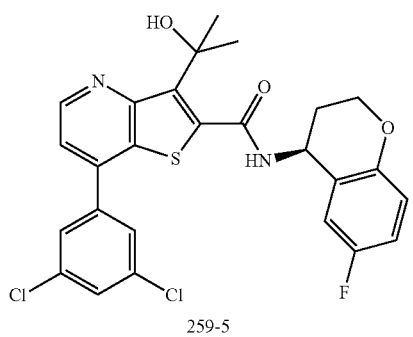 [SMILES: CC(C)(O)c1c(C(=O)N[C@H]2CCOc3ccc(F)cc32)sc2c(-c3cc(Cl)cc(Cl)c3)ccnc12]
259-5
¹H-NMR (300 MHz, CD₃OD): δ = 8.82 (d, J = 4.9 Hz, 1H), 7.78 (d, J = 1.9 Hz, 2H), 7.68 (t, J = 1.9 Hz, 1H), 7.54 (d, J = 4.9 Hz, 1H), 7.18-7.08 (m, 1H), 6.96-6.92 (m, 1H), 6.80 (dd, J = 9.0, 4.8 Hz, 1H), 5.27 (t, J = 5.6 Hz, 1H), 4.36-4.12 (m, 2H), 2.35-2.09 (m, 2H), 1.86 (d, J = 3.2 Hz, 6H) ppm.
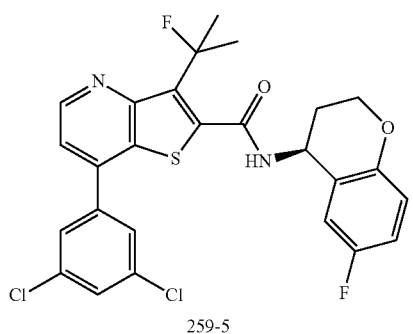 [SMILES: CC(C)(F)c1c(C(=O)N[C@H]2CCOc3ccc(F)cc32)sc2c(-c3cc(Cl)cc(Cl)c3)ccnc12]
259-5
¹H-NMR (300 MHz, CD₃OD): δ = 8.83 (d, J = 4.8 Hz, 1H), 7.77 (d, J = 1.9 Hz, 2H), 7.67 (t, J = 1.9 Hz, 1H), 7.50 (d, J = 4.8 Hz, 1H), 7.12 (d, J = 9.2 Hz, 1H), 6.94-6.90 (m, 1H), 6.79 (d, J = 9.0 Hz, 1H), 5.27 (t, J = 5.8 Hz, 1H), 4.34-4.18 (m, 2H), 2.01 (d, J = 23.5 Hz, 6H) ppm.
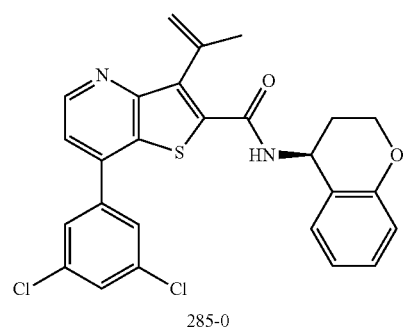 [SMILES: C=C(C)c1c(C(=O)N[C@H]2CCOc3ccccc32)sc2c(-c3cc(Cl)cc(Cl)c3)ccnc12]
285-0
¹H-NMR (300 MHz, CDCl₃): δ = 8.85 (d, J = 4.8 Hz, 1H), 7.66 (d, J = 1.9 Hz, 2H), 7.55 (d, J = 1.9 Hz, 1H), 7.53 (d, J = 5.7 Hz, 1H), 7.36 (d, J = 4.7 Hz, 1H), 7.28-7.24 (m, 3H), 7.01-6.86 (m, 2H), 5.63-5.56 (m, 1H), 5.39-5.36 (m, 1H), 5.31-5.24 (m, 1H), 4.38-4.34 (m, 1H), 4.19-4.16 (m, 1H), 2.48-2.31 (m, 1H), 2.27-2.11 (m, 4H) ppm.

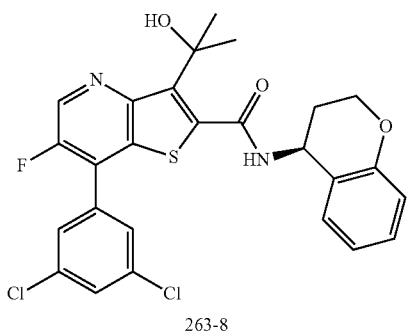
263-8
¹H-NMR (300 MHz, DMSO-d₆): δ = 9.52 (d, J = 8.0 Hz, 1H), 8.90 (d, J = 1.7 Hz, 1H), 7.91-7.79 (m, 3H), 7.36-7.11 (m, 2H), 6.95-6.75 (m, 2H), 5.89 (s, 1H), 5.17 (t, J = 6.7 Hz, 1H), 4.34-4.14 (m, 2H), 2.16-2.00 (m, 2H), 1.76 (d, J = 3.1 Hz, 6H) ppm.
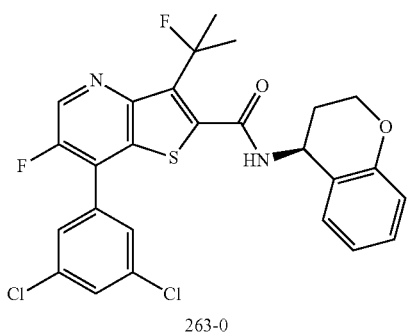 [SMILES: CC(C)(F)c1c(C(=O)N[C@H]2CCOc3ccccc32)sc2c(-c3cc(Cl)cc(Cl)c3)c(F)cnc12]
263-0
¹H-NMR (300 MHz, DMSO-d₆): δ = 9.08 (d, J = 8.2 Hz, 1H), 8.93 (d, J = 1.8 Hz, 1H), 7.90 (t, J = 1.9 Hz, 1H), 7.85-7.80 (m, 2H), 7.30-7.22 (m, 1H), 7.21-7.12 (m, 1H), 6.96-6.84 (m, 1H), 6.82-6.74 (m, 1H), 5.16 (q, J = 6.2 Hz, 1H), 4.21 (d, J = 8.4 Hz, 2H), 2.10 (s, 2H), 1.98-1.86 (m, 6H) ppm.
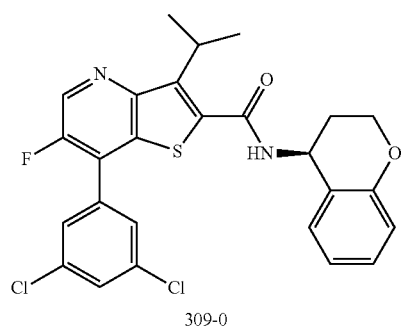 [SMILES: CC(C)c1c(C(=O)N[C@H]2CCOc3ccccc32)sc2c(-c3cc(Cl)cc(Cl)c3)c(F)cnc12]
309-0
¹H-NMR (300 MHz, DMSO-d₆): δ = 9.08 (d, J = 8.2 Hz, 1H), 8.91 (d, J = 1.8 Hz, 1H), 7.87 (t, J = 1.9 Hz, 1H), 7.81 (dd, J = 2.0, 0.8 Hz, 2H), 7.25-7.11 (m, 2H), 6.90 (t, J = 7.4, 1H), 6.79 (dd, J = 8.2, 1.2 Hz, 1H), 5.24 (q, J = 6.8 Hz, 1H), 4.25 (q, J = 5.3, 4.5 Hz, 2H), 4.00-3.84 (m, 1H), 2.19-1.99 (m, 2H), 1.50 (dd, J = 7.0, 4.7 Hz, 6H) ppm.
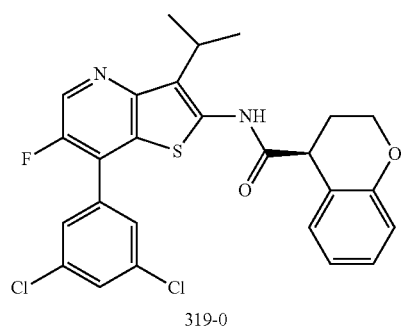 [SMILES: CC(C)c1c(NC(=O)[C@H]2CCOc3ccccc32)sc2c(-c3cc(Cl)cc(Cl)c3)c(F)cnc12]
319-0
¹H-NMR (300 MHz, CDCl₃): δ = 8.63 (s, 1H), 8.40 (s, 1H), 7.54 (d, J = 6.4 Hz, 3H), 7.37 (t, J = 7.6 Hz, 1H), 7.23 (d, J = 7.5 Hz, 1H), 7.13-6.98 (m, 2H), 4.39 (d, J = 11.3 Hz, 1H), 4.10-3.92 (m, 2H), 3.87-3.70 (m, 1H), 2.67-2.56 (m, 1H), 2.34 (d, J = 13.6 Hz, 1H), 1.11 (d, J = 5.6 Hz, 3H), 1.01 (d, J = 5.6 Hz, 3H) ppm.

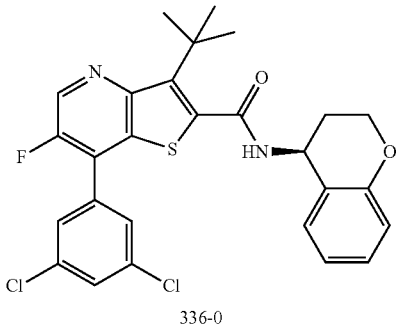 [SMILES: CC(C)(C)c1c(C(=O)N[C@H]2CCOc3ccccc32)sc2c(-c3cc(Cl)cc(Cl)c3)c(F)cnc12]
336-0
¹H-NMR (300 MHz, DMSO-d₆): δ = 9.36 (d, J = 8.1 Hz, 1H), 8.90 (d, J = 1.6 Hz, 1H), 7.88 (t, J = 1.9 Hz, 1H), 7.79 (d, J = 2.0 Hz, 2H), 7.26-7.11 (m, 2H), 6.90 (t, J = 7.5, 1H), 6.79 (dd, J = 8.2,1.2 Hz, 1H), 5.18 (q, J = 5.9 Hz, 1H), 4.32-4.14 (m, 2H), 2.20-2.10 (m, 1H), 2.03-1.93 (m, 1H), 1.60 (s, 9H) ppm.
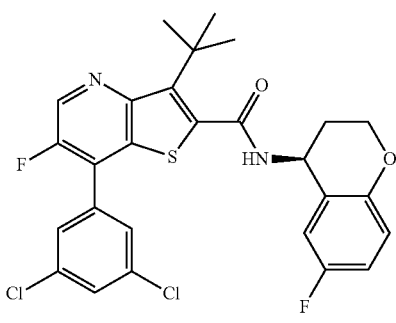
338-0
¹H-NMR (300 MHz, DMSO-d₆): δ = 9.39 (d, J = 8.0 Hz, 1H), 8.91 (d, J = 1.6 Hz, 1H), 7.88 (t, J = 1.9 Hz, 1H), 7.79 (dd, J = 1.9, 0.9 Hz, 2H), 7.09-6.96 (m, 2H), 6.87-6.76 (m, 1H), 5.24-5.12 (m, 1H), 4.29-4.13 (m, 2H), 2.18-2.09 (m, 1H), 2.00 (d, J = 2.9 Hz, 1H), 1.60 (s, 9H) ppm.
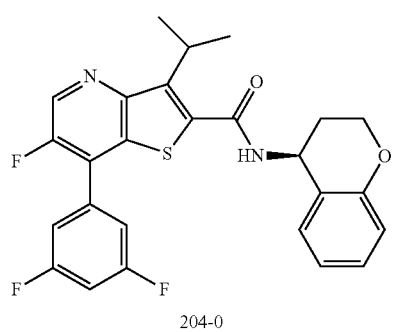 [SMILES: CC(C)c1c(C(=O)N[C@H]2CCOc3ccccc32)sc2c(-c3cc(F)cc(F)c3)c(F)cnc12]
204-0
¹H-NMR (300 MHz, DMSO-d₆): δ = 9.06 (d, J = 8.3 Hz, 1H), 8.91 (d, J = 1.9 Hz, 1H), 7.51 (dd, J = 7.1, 3.0 Hz, 3H), 7.25-7.12 (m, 2H), 6.90 (t, J = 7.5, 1H), 6.79 (dd, J = 8.2, 1.2 Hz, 1H), 5.24 (q, J = 6.7 Hz, 1H), 4.33-4.16 (m, 2H), 4.00-3.85 (m, 1H), 2.19-2.01 (m, 2H), 1.55-1.46 (m, 6H) ppm.
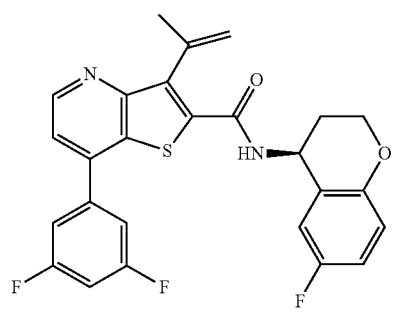
256-0
¹H-NMR (300 MHz, CDCl₃): δ = 8.83 (d, J = 4.8 Hz, 1H), 7.49 (d, J = 7.2 Hz, 1H), 7.37-7.26 (m, 2H), 7.00-6.90 (m, 3H), 6.856.80 (m, 1H), 5.61 (s, 1H), 5.36 (t, J = 6.6 Hz, 1H ), 5.27 (s, 1H), 4.33-4.27 (m, 1H), 4.18-4.11 (m, 1H), 2.38-2.31 (m, 1H), 2.24 (s, 3H), 2.14-2.09 (m, 1H), 1.52 (d, J = 8.7 Hz, 1H) ppm.

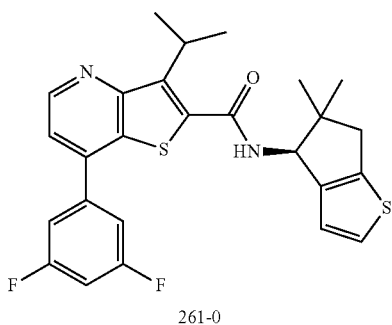 [SMILES: CC(C)c1c(C(=O)N[C@@H]2c3ccsc3CC2(C)C)sc2c(-c3cc(F)cc(F)c3)ccnc12]
261-0
¹H-NMR (300 MHz, DMSO-d₆): δ = 8.85 (d, J = 4.5 Hz, 1H), 8.76 (d, J = 9.3 Hz, 1H), 7.60-7.46 (m, 4H), 7.40 (d, J = 5.1 Hz, 1H), 6.91 (d, J = 5.1 Hz, 1H), 5.04 (d, J = 9.0 Hz, 1H), 3.88 (t, J = 6.9 Hz, 1H), 2.86 (d, J = 15.3 Hz, 1H), 2.66 (d, J = 15.3 Hz, 1H), 1.50 (d, J = 6.9 Hz, 6H), 1.28 (s, 3H), 1.14 (s, 3H) ppm.
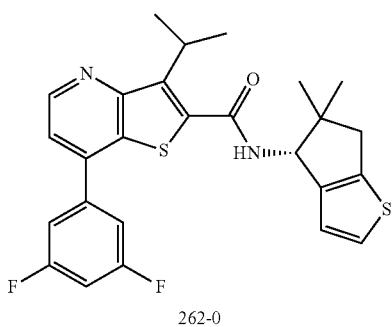 [SMILES: CC(C)c1c(C(=O)N[C@H]2c3ccsc3CC2(C)C)sc2c(-c3cc(F)cc(F)c3)ccnc12]
262-0
¹H-NMR (300 MHz, DMSO-d6): δ = 8.84 (d, J = 4.8 Hz, 1H), 8.76 (d, J = 9.3 Hz, 1H), 7.60-7.46 (m, 4H), 7.40 (d, J = 5.1 Hz, 1H), 6.90 (d, J = 4.8 Hz, 1H), 5.03 (d, J = 9.0 Hz, 1H), 3.87 (t, J = 6.9 Hz, 1H), 2.86 (d, J = 15.3 Hz, 1H), 2.65 (d, J = 15.3 Hz, 1H), 1.50 (d, J = 6.9 Hz, 6H), 1.28 (s, 3H), 1.14 (s, 3H) ppm.
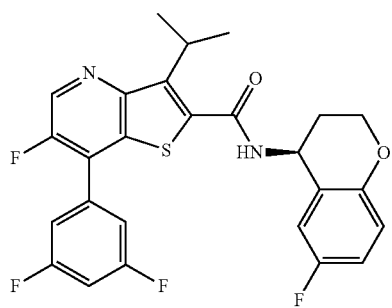
260-0
¹H-NMR (300 MHz, DMSO-d₆): δ = 9.09 (d, J = 8.1 Hz, 1H), 8.92 (d, J = 1.8 Hz, 1H), 7.59-7.48 (m, 3H), 7.09-6.95 (m, 2H), 6.88-6.78 (m, 1H), 5.23 (q, J = 6.7 Hz, 1H), 4.30-4.15 (m, 2H), 4.03-3.86 (m, 1H), 2.20-2.00 (m, 2H), 1.58-1.40 (m, 6H) ppm.
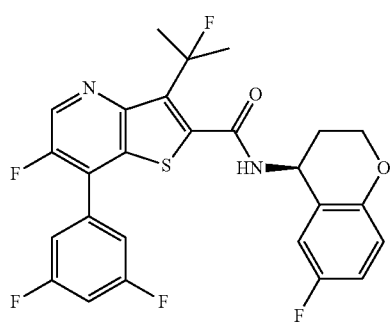
300-0
¹H-NMR (300 MHz, DMSO-d₆): δ = 9.10 (d, J = 8.2 Hz, 1H), 9.00-8.86 (m, 1H), 7.52 (d, J = 7.4 Hz, 3H), 7.14-6.94 (m, 2H), 6.80 (dd, J = 9.1, 4.8 Hz, 1H), 5.16 (d, J = 6.3 Hz, 1H), 4.21 (s, 2H), 2.10 (s, 1H), 1.93 (dd, J = 23.2, 7.3 Hz, 7H) ppm.

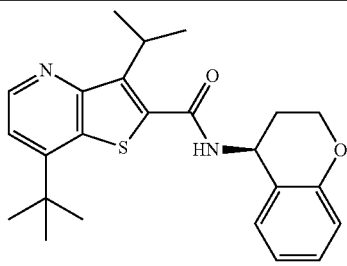
301-0
¹H-NMR (300 MHz, CDCl₃): δ = 8.71 (d, J = 4.8 Hz, 1H), 7.36-7.29 (m, 1H), 7.26-7.23 (m, 1H), 7.02-6.96 (m, 1H), 6.92-6.90 (m, 1H), 6.27 (d, J = 7.8 Hz, 1H), 5.00 (d, J = 6.9 Hz, 1H), 4.38-4.34 (m, 1H), 4.29-4.25 (m, 1H), 4.14-4.09 (m, 1H), 2.41-2.36 (m, 1H), 2.31-2.27 (m, 1H), 1.61-1.56 (m, 6H), 1.55 (s, 9H) ppm.
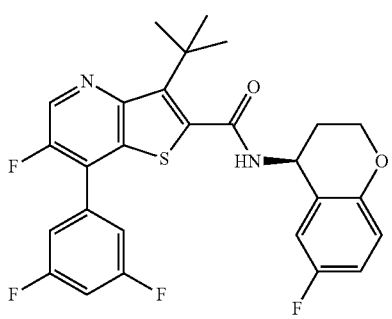
337-0
¹H-NMR (300 MHz, DMSO-d₆): δ = 9.39 (d, J = 8.0 Hz, 1H), 8.91 (d, J = 1.6 Hz, 1H), 7.59-7.43 (m, 3H), 7.11-6.98 (m, 2H), 6.88-6.78 (m, 1H), 5.17 (d, J = 7.3 Hz, 1H), 4.31-4.13 (m, 2H), 2.22-2.07 (m, 1H), 2.05-1.91 (m, 1H), 1.60 (s, 9H) ppm.
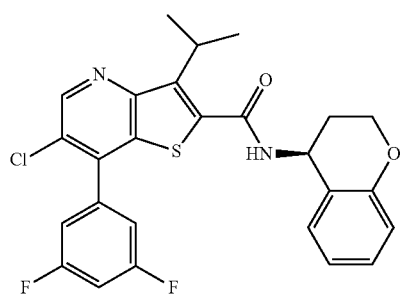
310
¹H-NMR (300 MHz, CDCl₃): δ = 8.78 (s, 1H), 7.26-7.17 (m, 2H), 7.06-6.83 (m, 5H), 6.14 (d, J = 7.5 Hz, 1H), 5.31 (q, J = 5.9 Hz, 1H), 4.35-4.28 (m, 1H), 4.21-4.13 (m, 1H), 4.08-3.99 (m, 1H), 2.42-2.27 (m, 1H), 2.23-2.15 (m, 1H), 1.57 (dd, J = 7.1, 2.6 Hz, 6H) ppm.
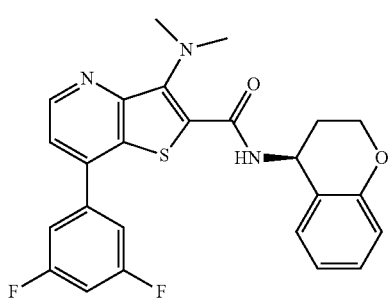
121-0
¹H-NMR (300 MHz, CDCl₃): δ = 10.50 (d, J = 7.7 Hz, 1H), 8.80 (d, J = 4.7 Hz, 1H), 7.40-7.28 (m, 5H), 7.26-7.21 (m, 2H), 7.05-6.86 (m, 3H), 6.50-6.33 (m, 1H), 5.40 (q, J = 6.4 Hz, 1H), 4.38-4.34 (m, 1H), 4.30-4.27 (m, 1H), 3.03 (s, 6H), 2.51-2.35 (m, 1H), 2.23-2.20 (m, 1H), 1.41-1.16 (m, 1H) ppm.
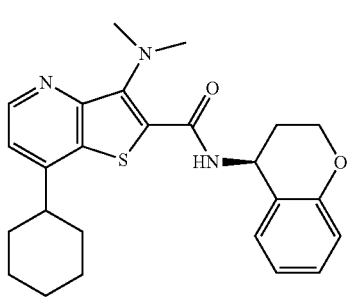
224-0
¹H-NMR (300 MHz, CD₃OD): δ = 8.63 (d, J = 4.8 Hz, 1H), 7.38-7.27 (m, 2H), 7.27-7.16 (m, 1H), 6.96-6.93 (m, 1H), 6.86 (d, J = 8.3 Hz, 1H), 5.30 (t, J = 5.6 Hz, 1H), 4.43-4.30 (m, 1H), 4.27-4.22 (m, 1H), 2.98 (s, 6H), 2.96-2.83 (m, 1H), 2.39-2.32 (m, 1H), 2.21-2.17 (m, 1H), 2.05 (s, 1H), 2.00 (s, 3H), 1.93 (s, 1H), 1.86 (d, J = 12.5 Hz, 1H), 1.77-1.56 (m, 3H) ppm.

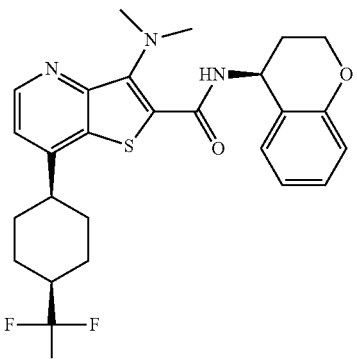
225-0
¹H-NMR (300 MHz, CD₃OD): δ = 8.66 (d, J = 4.8 Hz, 1H), 7.38-7.29 (m, 2H), 7.28-7.16 (m, 1H), 6.97-6.91 (m, 1H), 6.86 (d, J = 8.2 Hz, 1H), 5.30 (t, J = 5.6 Hz, 1H), 4.39-4.35 (m, 1H), 4.28-4.23 (m, 1H), 3.09 (d, J = 9.3 Hz, 1H), 2.99 (s, 6H), 2.56-2.50 (m, 1H), 2.45-2.28 (m, 1H), 2.27-1.95 (m, 8H) ppm.
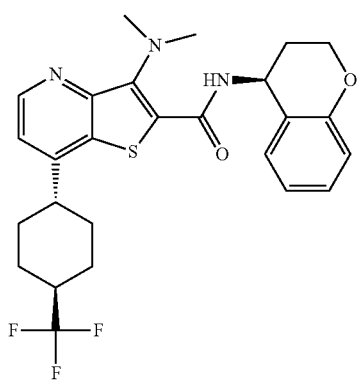
225-0A
¹H-NMR (300 MHz, CD₃OD): δ = 8.66 (d, J = 4.8 Hz, 1H), 7.38-7.29 (m, 2H), 7.28-7.16 (m, 1H), 6.97-6.92(M, 1H), 6.86 (dd, J = 8.2, 1.2 Hz, 1H), 5.30 (t, J = 5.6 Hz, 1H), 4.38-4.33 (m, 1H), 4.27-4.23 (m, 1H), 2.98 (s, 7H), 2.45-2.28 (m, 2H), 2.27-2.11 (m, 5H), 1.74-1.62 (m, 4H) ppm.
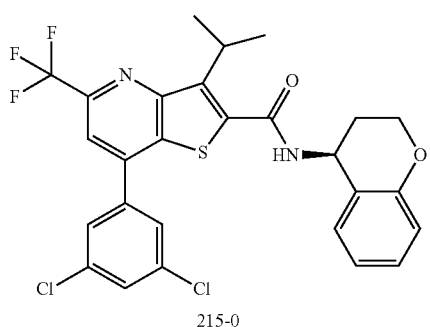 [SMILES: CC(C)c1c(C(=O)N[C@H]2CCOc3ccccc32)sc2c(-c3cc(Cl)cc(Cl)c3)cc(C(F)(F)F)nc12]
215-0
¹H-NMR (300 MHz, CD₃OD): δ = 7.89-7.77 (m, 3H), 7.70 (t, J = 1.9 Hz, 1H), 7.35-7.26 (m, 1H), 7.24-7.12 (m, 1H), 6.94 (td, J = 7.5, 1.3 Hz, 1H), 6.82 (d, J = 8.2 Hz, 1H), 5.34 (t, J = 5.6 Hz, 1H), 4.37-4.20 (m, 2H), 3.88 (p, J = 7.0 Hz, 1H), 2.39-2.11 (m, 2H), 2.05 (s, 2H), 1.59 (d, J = 7.1 Hz, 6H) ppm.
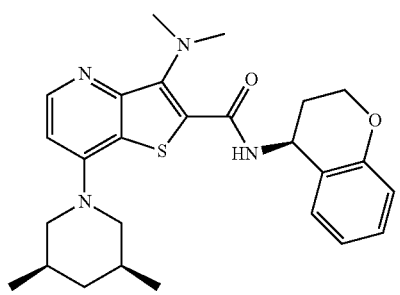
227-0
¹H-NMR (300 MHz, CD₃OD): δ = 8.42 (d, J = 5.5 Hz, 1H), 7.33 (d, J = 7.7 Hz, 1H), 7.27-7.15 (m, 1H), 6.96-6.93 (m, 1H), 6.88-6.78 (m, 2H), 5.29 (t, J = 5.6 Hz, 1H), 4.38-4.32 (m, 1H), 4.27-4.22 (m, 1H), 3.98 (d, J = 12.2 Hz, 2H), 2.95 (s, 6H), 2.52 (t, J = 11.9 Hz, 2H), 2.44-2.28 (m, 1H), 2.19-2.16 (m, 1H), 1.31 (s, 2H), 1.01 (d, J = 6.4 Hz, 6H), 0.94-0.79 (m, 2H) ppm.

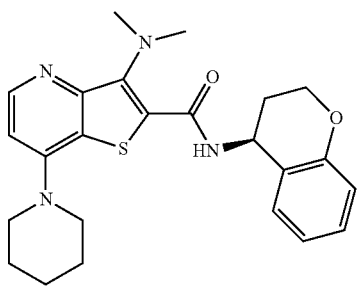
228-0
¹H-NMR (300 MHz, CD₃OD): δ = 8.43 (d, J = 5.5 Hz, 1H), 7.33 (d, J = 7.6, 1.6 Hz, 1H), 7.27-7.16 (m, 1H), 6.96-6.92 (m, 1H), 6.89-6.80 (m, 2H), 5.29 (t, J = 5.6 Hz, 1H), 4.38-4.32 (m, 1H), 4.26-4.24 (m, 1H), 3.49 (t, J = 5.1 Hz, 4H), 2.95 (s, 6H), 2.44-2.28 (m, 1H), 2.26-2.10 (m, 1H), 1.82 (s, 2H), 1.80 (s, 3H) ppm.
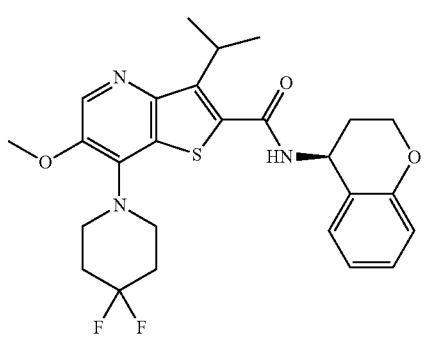
234
¹H-NMR (300 MHz, DMSO-d₆): δ = 8.93 (d, J = 8.4 Hz, 1H), 8.55 (s, 1H), 7.24-7.15 (m, 2H), 6.92 (t, J = 7.5 Hz, 1H), 6.80 (d, J = 7.2 Hz, 1H), 5.24 (m, 1H), 4.29-4.24 (m, 2H), 3.99 (s, 3H), 3.89-3.84 (m, 1H), 3.40-3.23 (m, 4H), 2.16-2.05 (m, 6H), 1.48-1.45 (m, 6H) ppm.
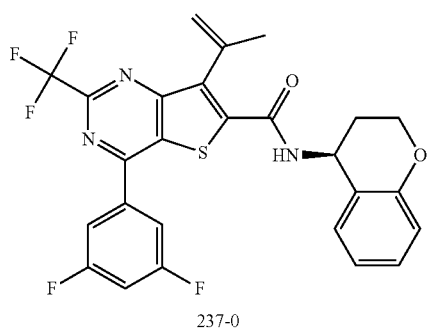 [SMILES: C=C(C)c1c(C(=O)N[C@H]2CCOc3ccccc32)sc2c(-c3cc(F)cc(F)c3)nc(C(F)(F)F)nc12]
237-0
¹H-NMR (300 MHz, DMSO-d₆): δ = 9.20 (d, J = 7.8 Hz, 1H), 7.84-7.82 (m, 2H), 7.72-7.66 (m, 1H), 7.27 (d, J = 7.5 Hz, 1H), 7.19 (t, J = 7.2 Hz, 1H), 6.93 (t, J = 7.2 Hz, 1H), 6.81 (d, J = 7.8 Hz, 1H), 5.50 (s, 1H), 5.30-5.25 (m, 2H), 4.30-4.22 (m, 2H), 2.29 (s, 3H), 2.19-2.17 (m, 1H), 2.07-2.00 (m, 1H) ppm.
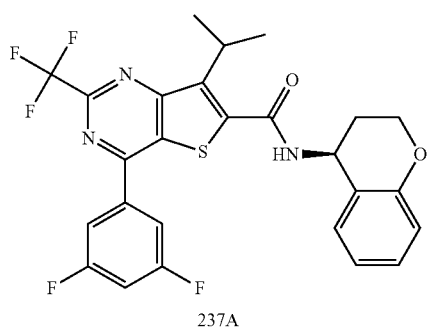 [SMILES: CC(C)c1c(C(=O)N[C@H]2CCOc3ccccc32)sc2c(-c3cc(F)cc(F)c3)nc(C(F)(F)F)nc12]
237A
¹H-NMR (300 MHz, DMSO-d₆): δ = 9.46 (d, J = 8.1 Hz, 1H), 7.80 (d, J = 7.8 Hz, 2H), 7.79-7.65 (m, 1H), 7.28 (d, J = 7.8 Hz, 1H), 7.22-7.17 (m, 1H), 6.94 (t, J = 7.2 Hz, 1H), 6.82 (d, J = 8.1 Hz, 1H), 5.30 (q, J = 6.6 Hz, 1H), 4.27 (t, J = 4.8 Hz, 2H), 3.89-3.80 (m, 1H), 2.22-2.02 (m, 2H), 1.51 (dd, J = 7.0, 5.0 Hz, 6H) ppm.

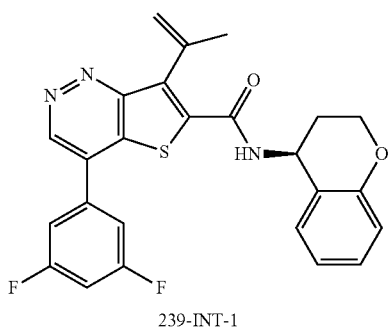 [SMILES: C=C(C)c1c(C(=O)N[C@H]2CCOc3ccccc32)sc2c(-c3cc(F)cc(F)c3)cnnc12]
239-INT-1
$^1$H-NMR (300 MHz, CD$_3$OD): δ = 9.33 (s, 1H), 7.59-7.56 (m, 2H), 7.32-7.18 (m, 3H), 6.95 (t, J = 7.5 Hz, 1H), 6.83 (d, J = 8.1 Hz, 1H), 5.83 (s, 1H), 5.38 (s, 1H), 5.30 (t, J = 5.1 Hz, 1H), 4.32-4.23 (m, 2H), 2.37 (s, 3H), 2.31-2.21 (m, 2H), 2.20-2.15 (m, 1H) ppm.
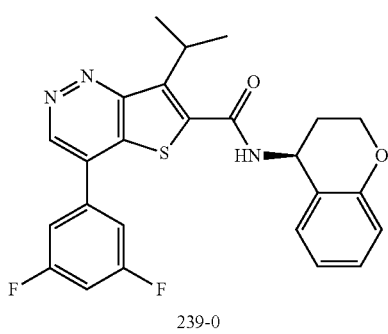 [SMILES: CC(C)c1c(C(=O)N[C@H]2CCOc3ccccc32)sc2c(-c3cc(F)cc(F)c3)cnnc12]
239-0
$^1$H-NMR (300 MHz, CD$_3$OD): δ = 9.29 (s, 1H), 7.57-7.54 (m, 2H), 7.33-7.16 (m, 3H), 6.98-6.93 (m, 1H), 6.83 (dd, J = 8.1, 0.9 Hz, 1H), 5.36 (t, J = 5.4 Hz, 1H), 4.33-4.27 (m, 2H), 4.00-3.95 (m, 1H), 2.34-2.30 (m, 1H), 2.22-2.16 (m, 1H), 1.65 (dd, J = 6.9, 3.0 Hz, 6H) ppm.
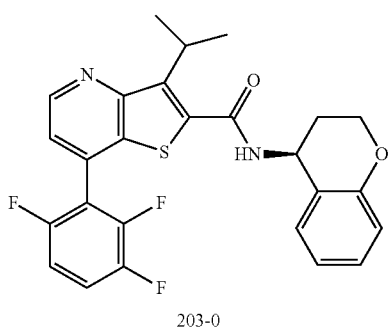 [SMILES: CC(C)c1c(C(=O)N[C@H]2CCOc3ccccc32)sc2c(-c3c(F)ccc(F)c3F)ccnc12]
203-0
$^1$H-NMR (300 MHz, DMSO-d$_6$): δ = 9.11 (d, J = 8.4 Hz, 1H), 8.90 (d, J = 4.5 Hz, 1H), 7.80-7.74 (m, 1H), 7.62 (d, J = 4.5 Hz, 1H), 7.46-7.40 (m, 1H), 7.22-7.13 (m, 2H), 6.90 (t, J = 7.5 Hz, 1H), 6.78 (d, J = 8.1 Hz, 1H), 5.27-5.21 (m, 1H), 4.24 (t, J = 5.1 Hz, 2H), 3.99-3.85 (m, 1H), 2.18-2.00 (m, 2H), 1.54-1.50 (m, 6H) ppm.
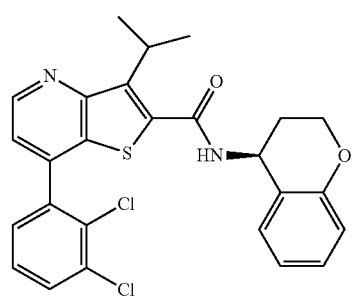
206-0
$^1$H-NMR (300 MHz, DMSO-d$_6$): δ = 9.05 (d, J = 8.4 Hz, 1H), 8.87 (d, J = 4.8 Hz, 1H), 7.84 (dd, J = 6.3, 3.6 Hz, 1H), 7.57-7.55 (m, 2H), 7.48 (d, J = 4.8 Hz, 1H), 7.20-7.13 (m, 2H), 6.89 (t, J = 6.6 Hz, 1H), 6.78 (d, J = 8.1 Hz, 1H), 5.26-5.20 (m, 1H), 4.23 (s, 2H), 3.98-3.88 (m, 1H), 2.17-1.99 (m, 2H), 1.52 (dd, J = 6.9, 4.8 Hz, 6H) ppm.

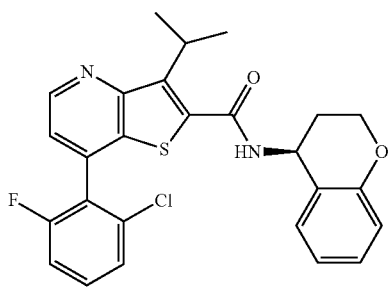

208-0

¹H-NMR (300 MHz, DMSO-d₆): δ = 9.10 (d, J = 8.1 Hz, 1H), 8.89 (d, J = 4.5 Hz, 1H), 7.67-7.57 (m, 2H), 7.52-7.47 (m, 2H), 7.21-7.13 (m, 2H), 6.89 (t, J = 6.9 Hz, 1H), 6.78 (d, J = 8.1 Hz, 1H), 5.27-5.20 (m, 1H), 4.23 (s, 2H), 3.93-3.89 (m, 1H), 2.15-2.04 (m, 2H), 1.56-1.51 (m, 6H) ppm.

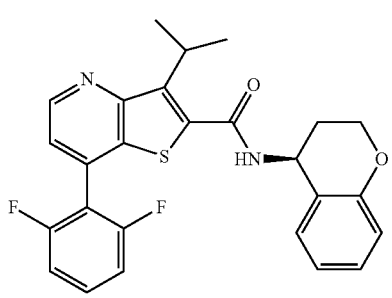

209-0

¹H-NMR (300 MHz, DMSO-d₆): δ = 9.09 (d, J = 8.1 Hz, 1H), 8.88 (d, J = 4.8 Hz, 1H), 7.72-7.66 (m, 1H), 7.57 (d, J = 4.5 Hz, 1H), 7.37 (t, J = 8.4 Hz, 2H), 7.22-7.13(m, 2H), 6.90 (td, J = 7.5, 0.9 Hz, 1H), 6.78 (d, J = 8.4 Hz, 1H), 5.25-5.23 (m, 1H), 4.26-4.22 (m, 2H), 3.93-3.89 (m, 1H), 2.16-2.03 (m, 2H), 1.55-1.51 (m, 6H) ppm.

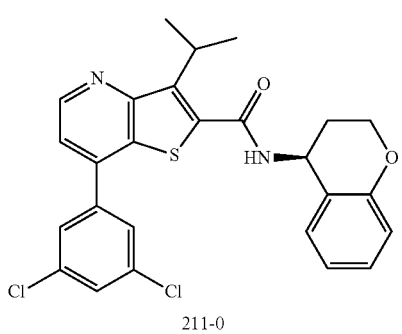 [SMILES: CC(C)c1c(C(=O)N[C@H]2CCOc3ccccc32)sc2c(-c3cc(Cl)cc(Cl)c3)ccnc12]

211-0

¹H-NMR (300 MHz, CDCl₃): δ = 9.11 (d, J = 8.3 Hz, 1H), 8.85 (d, J = 4.8 Hz, 1H), 7.84 (q, J = 1.3 Hz, 3H), 7.61 (d, J = 4.8 Hz, 1H), 7.28-7.20 (m, 1H), 7.20-7.11 (m, 1H), 6.95-6.91 (m, 1H), 6.80 (d, J = 8.2 Hz, 1H), 5.27 (q, J = 6.7 Hz, 1H), 4.28-4.25 (m, 2H), 3.96-3.92 (m, 1H), 2.20-1.99 (m, 2H), 1.51 (dd, J = 7.1, 5.0 Hz, 6H) ppm.

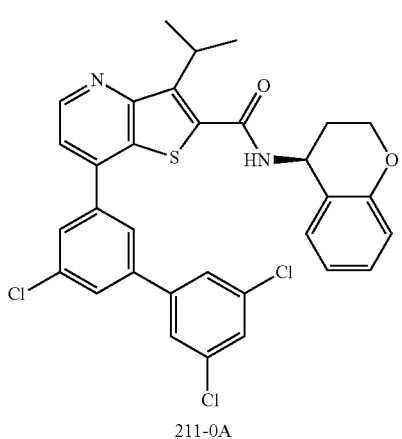 [SMILES: CC(C)c1c(C(=O)N[C@H]2CCOc3ccccc32)sc2c(-c3cc(Cl)cc(-c4cc(Cl)cc(Cl)c4)c3)ccnc12]

211-0A

¹H-NMR (300 MHz, CDCl₃): δ = 8.86 (d, J = 4.7 Hz, 1H), 7.74 (t, J = 1.6 Hz, 1H), 7.70 (t, J = 1.7 Hz, 1H), 7.67 (t, J = 1.8 Hz, 1H), 7.49 (d, J = 1.9 Hz, 2H), 7.43 (t, J = 1.8 Hz, 1H), 7.38 (d, J = 4.7 Hz, 1H), 7.32 (d, J = 7.7 Hz, 1H), 7.27-7.19 (m, 1H), 7.02-6.84 (m, 2H), 6.25 (d, J = 7.5 Hz, 1H), 5.38 (q, J = 5.8 Hz, 1H), 4.36 (ddd, J = 9.8, 6.2, 3.4 Hz, 1H), 4.23 (ddd, J = 11.6, 8.9, 2.9 Hz, 1H), 4.12 (p, J = 7.0 Hz, 1H), 2.48-2.32 (m, 1H), 2.31-2.17 (m, 1H), 1.63 (dd, J = 7.1, 3.2 Hz, 6H) ppm.

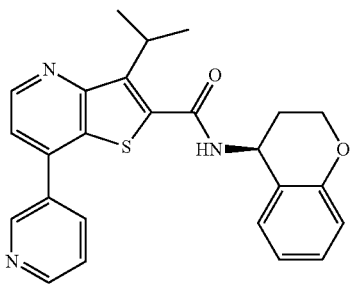

213-0

¹H-NMR (300 MHz, DMSO-d₆): δ = 9.07 (d, J = 8.4 Hz, 1H), 8.98 (d, J = 2.1 Hz, 1H), 8.87 (d, J = 4.8 Hz, 1H), 8.76 (dd, J = 4.8, 3.3 Hz, 1H), 8.23-8.19 (m, 1H), 7.67-7.62 (m, 2H), 7.24-7.14 (m, 2H), 6.91 (t, J = 7.5 Hz, 1H), 6.79 (d, J = 8.4 Hz, 1H), 5.30-5.23 (m, 1H), 4.26 (s, 2H), 3.98-3.91 (m, 1H), 2.18-2.04 (m, 2H), 1.54-1.50 (m, 6H) ppm.

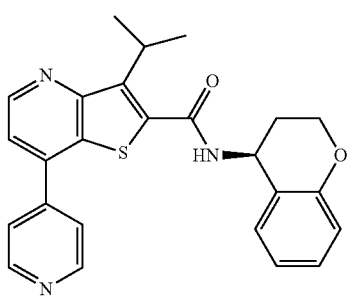

214-0

¹H-NMR (300 MHz, DMSO-d₆): δ = 9.09 (d, J = 8.4 Hz, 1H), 8.89 (d, J = 4.8 Hz, 1H), 8.82 (d, J = 4.5 Hz, 2H), 7.80 (d, J = 4.5 Hz, 2H), 7.65 (d, J = 4.8 Hz, 1H), 7.25-7.14 (m, 2H), 6.91 (t, J = 7.2 Hz, 1H), 6.79 (d, J = 8.1 Hz, 1H), 5.30-5.23 (m, 1H), 4.26 (s, 2H), 3.97-3.86 (m, 1H), 2.22-2.03 (m, 2H), 1.53-1.50 (m, 6H) ppm.

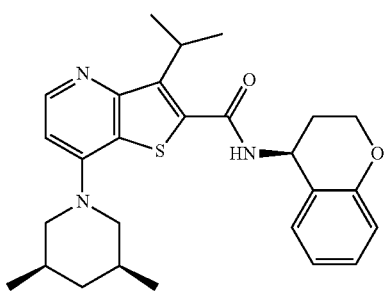

220-0

1H-NMR (300 MHz, DMSO-d6): δ = 9.01 (d, J = 8.4 Hz, 1H), 8.42 (d, J = 4.8 Hz, 1H), 7.25 (d, J = 4.5 Hz, 1H), 7.15 (t, J = 6.8 Hz, 1H), 5.25-5.15 (m, 1H), 4.25-4.35 (m, 2H), 3.75-3.85 (m, 3H), 2.51 (s, 2H), 2.05-2.20 (m, 2H), 1.90-1.75 (m, 3H), 1.55 (t, J = 4.5 Hz, 6H), 1.40 (t, J = 4.5 Hz, 6H), 1.80 (dd, J = 4.5 Hz, J = 4.2 Hz, 1H) ppm.

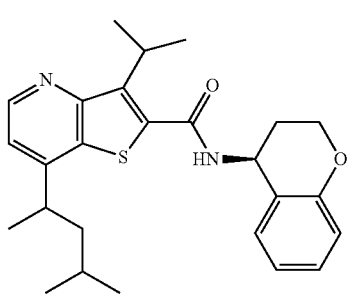

221-0

¹H-NMR (300 MHz, CDCl₃): δ = 8.70 (d, J = 4.8 Hz, 1H), 7.35 (d, J = 7.8 Hz, 1H), 7.24 (d, J = 7.2 Hz, 1H), 7.18 (d, J = 4.5 Hz, 1H), 6.99 (t, J = 7.5 Hz, 1H), 6.91 (d, J = 8.1 Hz, 1H), 6.26 (d, J = 6.9 Hz, 1H), 5.40-5.38 (m, 1H), 4.37-4.34 (m, 1H), 4.29-4.25 (m, 1H), 4.11-4.07 (m, 1H), 3.10-3.07 (m, 1H), 2.40-2.36 (m, 1H), 2.29-2.26 (m, 1H), 1.80-1.75 (m, 1H), 1.60 (dd, J = 6.9, 3.0 Hz, 6H), 1.56-1.49 (m, 2H), 1.35 (d, J = 6.9 Hz, 3H), 0.92 (d, J = 5.7 Hz, 6H) ppm.

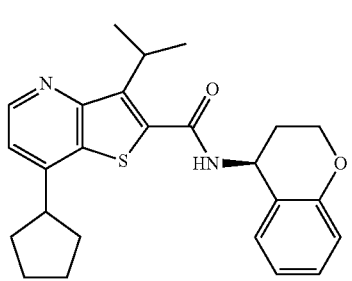

222-0

¹H-NMR (300 MHz, DMSO-d₆): δ = 9.05 (d, J = 8.4 Hz, 1H), 8.65 (d, J = 4.8 Hz, 1H), 7.34 (d, J = 4.8 Hz, 1H), 7.26 (d, J = 7.5 Hz, 1H), 7.18 (t, J = 7.8 Hz, 1H), 6.93 (t, J = 7.5 Hz, 1H), 6.81 (d, J = 8.1 Hz, 1H), 5.31-5.24 (m, 1H), 4.33-4.23 (m, 2H), 3.90-3.81 (m, 1H), 3.27-3.22 (m, 1H), 2.18-2.02 (m, 4H), 1.84-1.75 (m, 6H), 1.50-1.46 (m, 6H) ppm.

| | |
|---|---|
| 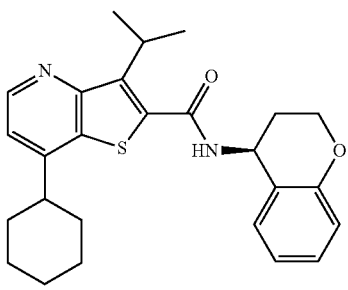<br>223 | ¹H-NMR (300 MHz, DMSO-d₆): δ = 8.65 (d, J = 8.4 Hz, 1H), 7.35-7.25 (m, 2H), 7.21-7.16 (m, 1H), 6.90-6.85 (m, 1H), 6.81 (d, J = 8.1 Hz, 1H), 5.35-5.29 (m, 1H), 4.33-4.23 (m, 2H), 3.90-3.81 (m, 1H), 3.90-2.75 (m, 1H), 2.35-2.05 (m, 2H), 2.01-1.80 (m, 5H), 1.80-1.3 (m, 11H) ppm. |
| 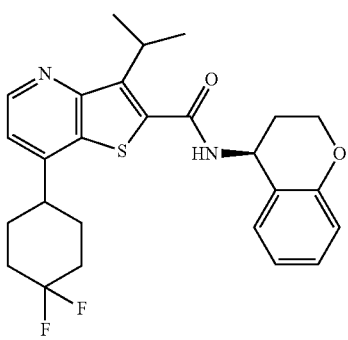<br>246-0 | ¹H-NMR (300 MHz, CDCl₃): δ = 8.69 (d, J = 4.7 Hz, 1H), 7.31 (d, J = 7.8 Hz, 1H), 7.19 (dd, J = 19.3, 6.3 Hz, 2H), 7.02-6.81 (m, 2H), 6.23 (d, J = 7.5 Hz, 1H), 5.35 (q, J = 6.1 Hz, 1H), 4.44-4.29 (m, 1H), 4.22 (t, J = 9.9 Hz, 1H), 4.06 (p, J = 7.3 Hz, 1H), 2.83 (s, 1H), 2.48-2.16 (m, 4H), 2.15-1.77 (m, 7H), 1.57 (dd, J = 7.4, 3.2 Hz, 6H) ppm. |
| 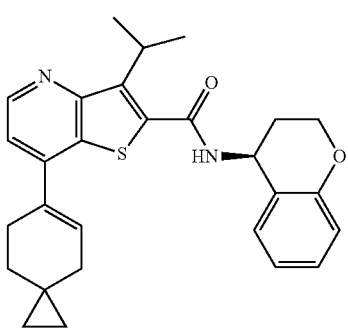<br>247-0 | ¹H-NMR (300 MHz, DMSO-d₆): δ = 9.04 (d, J = 8.3 Hz, 1H), 8.69 (d, J = 4.8 Hz, 1H), 7.36 (d, J = 4.8 Hz, 1H), 7.30-7.13 (m, 2H), 7.00-6.88 (m, 1H), 6.87-6.76 (m, 1H), 6.50-6.42 (m, 1H), 5.34-5.20 (m, 1H), 4.34-4.20 (m, 2H), 3.98-3.78 (m, 1H), 2.64-2.53 (m, 2H), 2.23-2.00 (m, 4H), 1.63-1.53 (m, 2H), 1.53-1.43 (m, 6H), 0.45-0.35 (m, 4H) ppm. |
| 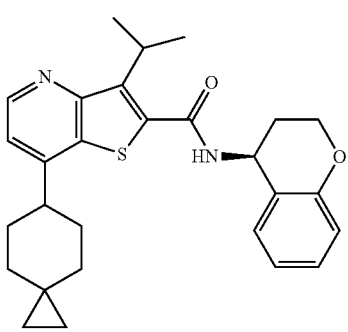<br>248-0 | ¹H-NMR (300 MHz, DMSO-d₆): δ = 9.05 (d, J = 8.2 Hz, 1H), 8.66 (d, J = 4.8 Hz, 1H), 7.46-7.12 (m, 3H), 7.03-6.87 (m, 1H), 6.80 (d, J = 8.2 Hz, 1H), 5.27 (d, J = 6.4 Hz, 1H), 4.27 (s, 2H), 3.99-3.76 (m, 1H), 2.92-2.71 (m, 1H), 2.30-2.04 (m, 2H), 2.02-1.68 (m, 6H), 1.48 (s, 6H), 0.99 (d, J = 12.6 Hz, 2H), 0.31 (d, J = 14.6 Hz, 4H) ppm. |

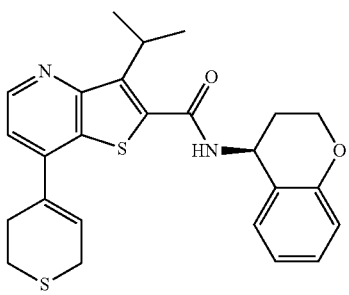

249-0

¹H-NMR (300 MHz, CDCl₃): δ = 7.26 (dt, J = 17.8, 7.8 Hz, 2H), 7.12 (s, 1H), 7.02-6.82 (m, 2H), 6.44 (s, 1H), 6.24 (s, 1H), 5.36 (s, 1H), 4.34 (q, J = 6.3, 4.5 Hz, 1H), 4.22 (t, J = 9.6 Hz, 1H), 4.07 (q, J = 7.3 Hz, 1H), 3.39 (s, 2H), 2.92 (s, 2H), 2.72 (s, 2H), 2.30 (d, J = 33.9 Hz, 2H), 1.57 (s, 6H) ppm.

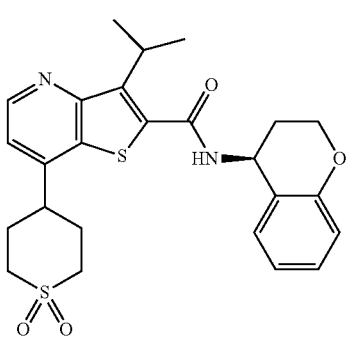

250-0

¹H-NMR (300 MHz, CDCl₃): δ = 7.30 (d, J = 7.6 Hz, 1H), 7.25-7.15 (m, 2H), 7.03-6.76 (m, 2H), 6.21 (d, J = 7.5 Hz, 1H), 5.36 (d, J = 6.6 Hz, 1H), 4.44-4.29 (m, 1H), 4.22 (dd, J = 11.2, 8.2 Hz, 1H), 4.04 (p, J = 7.0 Hz, 1H), 3.33-3.11 (m, 4H), 3.00 (t, J = 12.2 Hz, 1H), 2.55 (s, 2H), 2.45-2.15 (m, 4H), 1.56 (d, J = 7.1 Hz, 6H) ppm.

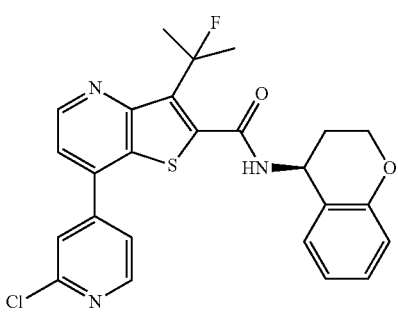

268-0

¹H-NMR (300 MHz, CDCl₃): δ = 8.81 (dd, J = 5.0, 1.6 Hz, 1H), 8.59 (d, J = 5.2 Hz, 1H), 7.72-7.49 (m, 2H), 7.34 (dd, J = 4.7, 1.7 Hz, 1H), 7.26 (d, J = 1.7 Hz, 1H), 7.20 (t, J = 7.9 Hz, 1H), 7.00-6.79 (m, 2H), 5.30 (q, J = 6.0 Hz, 1H), 4.41-4.28 (m, 1H), 4.20 (dd, J = 11.4, 8.0 Hz, 1H), 2.42-2.17 (m, 2H), 2.01 (dd, J = 24.1, 4.8 Hz, 6H) ppm.

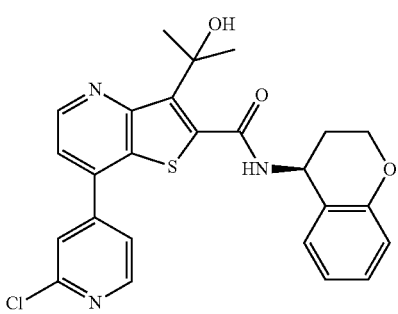

268-4

¹H-NMR (300 MHz, CDCl₃): δ = 8.82 (d, J = 4.8 Hz, 1H), 8.59 (d, J = 5.1 Hz, 1H), 7.62 (d, J = 1.3 Hz, 1H), 7.54 (dd, J = 5.1, 1.6 Hz, 1H), 7.37 (d, J = 4.7 Hz, 1H), 7.30 (d, J = 7.7 Hz, 1H), 7.21 (d, J = 7.2 Hz, 1H), 6.95 (t, J = 7.5 Hz, 1H), 6.87 (d, J = 8.2 Hz, 1H), 6.59 (d, J = 7.4 Hz, 1H), 5.31 (d, J = 7.1 Hz, 1H), 4.40-4.29 (m, 1H), 4.26-4.13 (m, 1H), 2.34 (dd, J = 9.8, 4.5 Hz, 1H), 2.27-2.13 (m, 1H), 1.88 (d, J = 3.9 Hz, 5H) ppm.

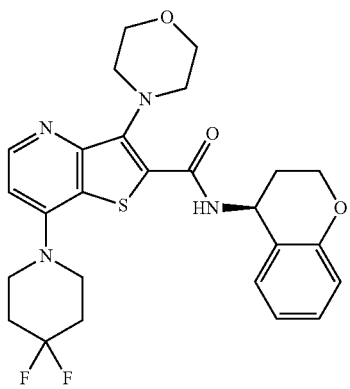
216-0
¹H-NMR (300 MHz, CDCl₃): δ = 10.59 (d, J = 4.0 Hz, 1H), 8.56 (d, J = 5.4 Hz, 1H), 7.26-7.22 (m, 2H), 6.95-6.88 (m, 2H), 6.76 (d, J = 5.4 Hz, 1H), 5.31-5.28 (m, 1H), 4.39-4.11 (m, 2H), 3.80-3.67 (m, 4H), 3.45-3.37 (m, 8H), 2.40-2.20 (m, 6H) ppm.
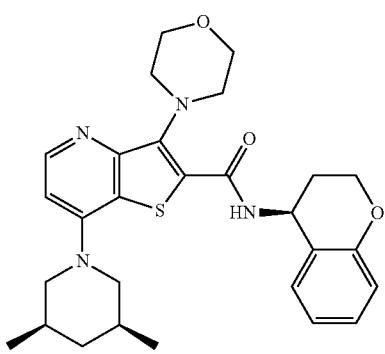
217
1H-NMR (300 MHz, DMSO-d6): δ = 10.56 (d, J = 8.4 Hz, 1H), 8.42 (d, J = 4.8 Hz, 1H), 7.35 (d, J = 4.4 Hz, 1H), 7.25-7.19 (m, 1H), 7.00-6.81 (m, 3H), 5.15 (m, 1H), 4.35-4.25 (m, 1H), 4.15-4.10 (m, 1H), 3.92-3.85 (m, 2H), 3.45-3.10 (m, 6H), 2.55-2.50 (b, 2H), 2.25-2.15 (m, 2H), 1.90-1.75 (m, 3H), 1.90 (d, J = 4.5 Hz, 6H), 1.85 (dd, J = 4.4 Hz, J = 4.1 Hz, 1H) ppm.
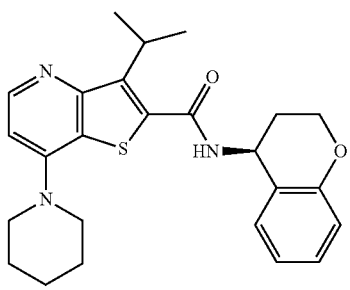
229-0
¹H-NMR (300 MHz, DMSO-d₆): δ = 8.99 (d, J = 8.1 Hz, 1H), 8.86 (d, J = 5.4 Hz, 1H), 7.25 (d, J = 8.1 Hz, 1H), 7.18 (t, J = 6.6 Hz, 1H), 6.93 (t, J = 7.2 Hz, 1H), 6.85 (d, J = 5.4 Hz, 1H), 6.80 (d, J = 8.1 Hz, 1H), 5.29-5.23 (m, 1H), 4.32-4.22 (m, 2H), 3.89-3.80 (m, 1H), 3.38 (d, J = 4.8 Hz, 4H), 2.17-2.06 (m, 2H), 1.68 (s, 6H), 1.41-1.49 (m, 6H) ppm.
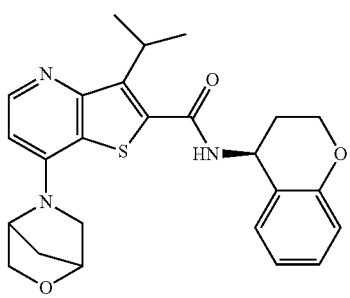
231-0
¹H-NMR (300 MHz, CDCl₃): δ = 8.38 (d, J = 5.4 Hz, 1H), 7.30 (d, J = 7.8 Hz, 1H), 7.21 (d, J = 7.5 Hz, 1H), 6.95 (t, J = 7.2 Hz, 1H), 6.88 (d, J = 8.1 Hz, 1H), 6.34 (d, J = 5.1 Hz, 1H), 6.23 (d, J = 6.3 Hz, 1H), 5.36-5.32 (m, 1H), 4.85 (s, 1H), 4.73 (s, 1H), 4.38-4.31 (m, 1H), 4.24-4.17 (m, 1H), 4.07-3.92 (m, 3H), 3.84 (d, J = 9.3 Hz, 1H), 3.66 (d, J = 8.7 Hz, 1H), 2.39-2.31 (m, 1H), 2.25-2.20 (m, 1H), 2.07 (s, 2H), 1.54 (dd, J = 6.6, 4.8 Hz, 6H) ppm.

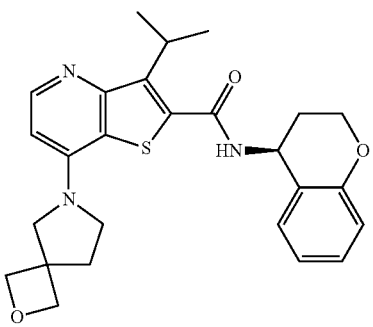

232-0

¹H-NMR (300 MHz, CDCl₃): δ = 8.38 (d, J = 5.7 Hz, 1H), 7.34 (d, J = 7.5 Hz, 1H), 7.24 (d, J = 6.9 Hz, 1H), 6.99 (td, J = 7.2, 1.2 Hz, 1H), 6.91 (d, J = 8.4 Hz, 1H), 6.29 (d, J = 5.7 Hz, 1H), 6.24 (d, J = 6.3 Hz, 1H), 5.38-5.36 (m, 1H), 4.75 (d, J = 6.3 Hz, 2H), 4.69 (d, J = 6.3 Hz, 2H), 4.37-4.34 (m, 1H), 4.28-4.24 (m, 1H), 4.08-4.01 (m, 3H), 3.79-3.75 (m, 2H), 2.42-2.36 (m, 3H), 2.29-2.26 (m, 1H), 1.56 (dd, J = 6.9, 3.9 Hz, 6H) ppm.

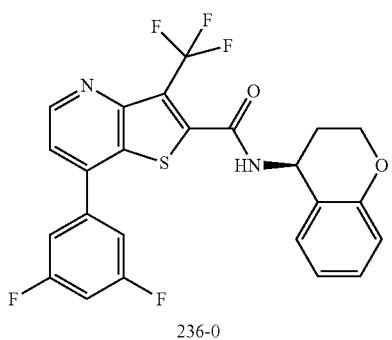 [SMILES: O=C(N[C@H]1CCOc2ccccc21)c1sc2c(-c3cc(F)cc(F)c3)ccnc2c1C(F)(F)F]

236-0

¹H-NMR: (300 MHz, DMSO-d₆): δ = 9.62 (d, J = 8.1 Hz, 1H), 8.97 (d, J = 4.8 Hz, 1H), 7.78 (d, J = 4.8 Hz, 1H), 7.67-7.50 (m, 3H), 7.25 (d, J = 7.5 Hz, 1H), 7.22-7.13 (td, J = 7.5, 1.2 Hz, 1H), 6.93 (td, J = 7.5, 1.2 Hz, 1H), 6.81 (dd, J = 8.1, 1.2 Hz, 1H), 5.23 (q, J = 6.0 Hz, 1H), 4.24 (m, 2H), 2.19 (m, 1H), 2.07-2.00 (m, 1H) ppm.

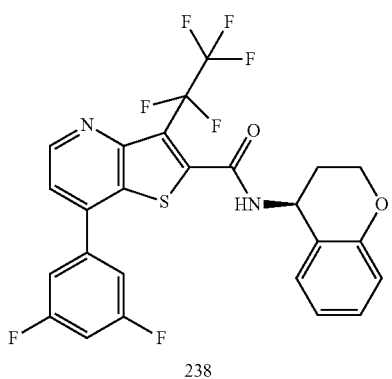 [SMILES: O=C(N[C@H]1CCOc2ccccc21)c1sc2c(-c3cc(F)cc(F)c3)ccnc2c1C(F)(F)C(F)(F)F]

238

¹H-NMR (300 MHz, DMSO-d₆): δ = 9.52 (d, J = 8.1 Hz, 1H), 8.96 (d, J = 4.8 Hz, 1H), 7.75 (d, J = 4.8 Hz, 1H), 7.62 (m, 3H), 7.26-7.15 (m, 2H), 6.92 (td, J = 7.5 Hz, 0.9 Hz, 1H), 6.80 (d, J = 7.2 Hz, 1H), 5.22 (d, J = 7.8 Hz, 1H), 4.27-4.18 (m, 2H), 2.19-2.16 (m, 1H), 2.08-1.98 (m, 1H) ppm.

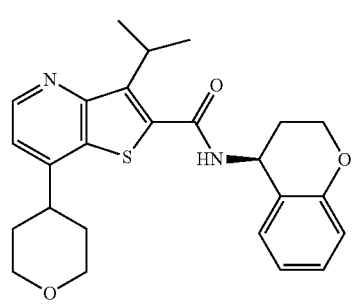

240-0

¹H-NMR (300 MHz, CDCl₃): δ = 8.70 (d, J = 4.5 Hz, 1H), 7.32 (d, J = 6.6 Hz, 1H), 7.24-7.21 (m, 1H), 7.16 (d, J = 4.8 Hz, 1H), 6.99-6.94 (m, 1H), 6.88 (d, J = 8.1 Hz, 1H), 6.22 (d, J = 6.6 Hz, 1H), 5.37-5.35 (m, 1H), 4.35-4.32 (m, 1H), 4.26-4.16 (m, 1H), 4.12-4.05 (m, 3H), 3.63-3.56 (m, 2H), 3.01-2.96 (m, 1H), 2.38-2.35 (m, 1H), 2.26-2.23 (m, 1H), 2.03-1.87 (m, 4H), 1.59-1.54 (m, 6H) ppm.

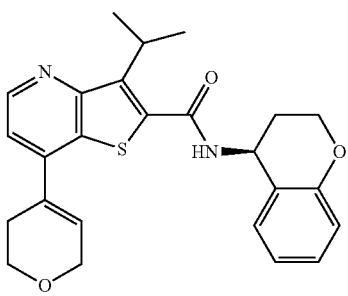

241-0

¹H-NMR (300 MHz, CDCl₃): δ = 8.71 (d, J = 4.8 Hz, 1H), 7.31 (d, J = 7.2 Hz, 1H), 7.26-7.21 (m, 1H), 7.16 (d, J = 4.8 Hz, 1H), 6.98-6.93 (m, 1H), 6.88 (d, J = 8.1 Hz, 1H), 6.46 (s, 1H), 6.22 (d, J = 7.2 Hz, 1H), 5.38-5.35 (m, 1H), 4.40-4.31 (m, 3H), 4.26-4.18 (m, 1H), 4.10-4.06 (m, 1H), 3.98 (t, J = 5.4 Hz, 2H), 2.60-2.58 (m, 2H), 2.38-2.31 (m, 1H), 2.28-2.22 (m, 1H), 1.59-1.52 (m, 6H) ppm.

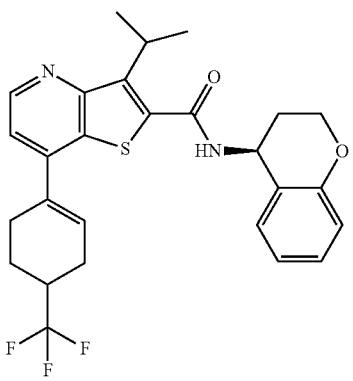

242-0

¹H-NMR (300 MHz, CDCl₃): δ = 8.70 (d, J = 4.8 Hz, 1H), 7.30 (d, J = 7.8 Hz, 1H), 7.24 (d, J = 8.7 Hz, 1H), 7.17 (d, J = 4.5 Hz, 1H), 6.96 (t, J = 7.5 Hz, 1H), 6.88 (d, J = 8.1 Hz, 1H), 6.36 (s, 1H), 6.21 (d, J = 6.6 Hz, 1H), 5.41-5.34 (m, 1H), 4.36-4.31 (m, 1H), 4.26-4.22 (m, 1H), 4.19-4.06 (m, 1H), 2.58-2.33 (m, 6H), 2.27-2.19 (m, 2H), 1.86-1.72 (m, 1H), 1.57 (dd, J = 6.9, 3.0 Hz, 6H) ppm.

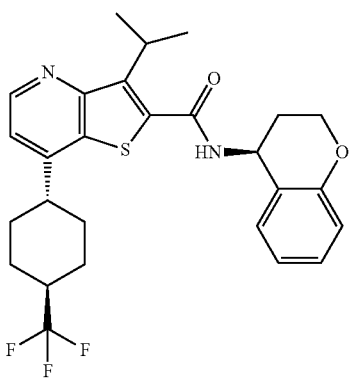

243-0

¹H-NMR (300 MHz, CDCl₃): δ = 8.69 (d, J = 4.8 Hz, 1H), 7.32 (d, J = 7.2 Hz, 1H), 7.25 (d, J = 8.1 Hz, 1H), 7.20 (d, J = 5.7 Hz, 1H), 6.99 (t, J = 8.4 Hz, 1H), 6.88 (d, J = 8.1 Hz, 1H), 6.21 (d, J = 7.5 Hz, 1H), 5.37-5.34 (m, 1H), 4.35-4.32 (m, 1H), 4.26-4.22 (m, 1H), 4.08-4.04 (m, 1H), 2.89-2.87 (m, 1H), 2.40-2.27 (m, 2H), 2.26-2.13 (m, 1H), 2.12-2.06 (m, 2H), 2.01-1.79 (m, 6H), 1.57 (dd, J = 7.2, 3.3 Hz, 6H) ppm.

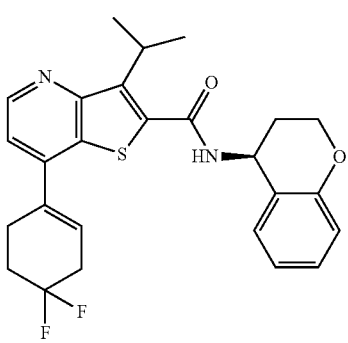

245-0

¹H-NMR (300 MHz, CDCl₃): δ = 8.70 (d, J = 4.8 Hz, 1H), 7.32-7.22 (m, 2H), 7.14 (d, J = 4.8 Hz, 1H), 6.96 (t, J = 7.4 Hz, 1H), 6.88 (d, J = 8.3 Hz, 1H), 6.21 (s, 2H), 5.35 (q, J = 5.9 Hz, 1H), 4.40-4.33 (m, 1H), 4.58-4.20 (m, 1H), 4.14-4.05 (m, 1H), 2.90-2.69 (m, 4H), 2.43-2.14 (m, 4H), 1.58 (dd, J = 6.1, 3.0 Hz, 6H) ppm.

-continued

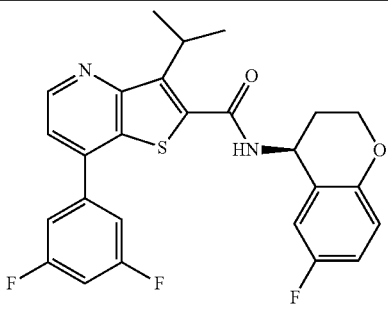

257-0

¹H-NMR (300 MHz, DMSO-d₆): δ = 9.12 (d, J = 8.1 Hz, 1H), 8.86 (d, J = 4.5 Hz, 1H), 7.62-7.46 (m, 4H), 7.06-7.00 (m, 2H), 6.85-6.80 (m, 1H), 5.27-5.24 (m, 1H), 4.26-4.23 (m, 2H), 3.97-3.92 (m, 1H), 2.14-2.04 (m, 2H), 1.51 (dd, J = 7.0, 4.7 Hz, 6H) ppm.

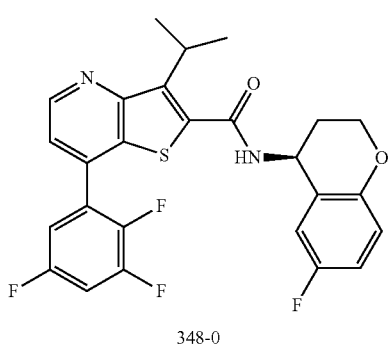 [SMILES: CC(C)c1c(C(=O)N[C@H]2CCOc3ccc(F)cc32)sc2c(-c3cc(F)cc(F)c3F)ccnc12]

348-0

¹H-NMR (300 MHz, DMSO-d₆): δ = 9.12 (d, J = 8.1 Hz, 1H), 8.89 (d, J = 4.8 Hz, 1H), 7.83-7.78 (m, 1H), 7.59 (d, J = 4.8 Hz, 1H), 7.54-7.50 (m, 1H), 7.06-6.99 (m, 2H), 6.84-6.80 (m, 1H), 5.25 (q, J = 6.6 Hz, 1H), 4.25-4.22 (m, 2H), 3.95-3.90 (m, 1H), 2.14-2.02 (m, 2H), 1.52 (dd, J = 6.9, 4.8 Hz, 6H) ppm.

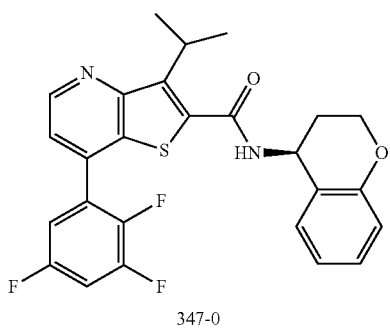 [SMILES: CC(C)c1c(C(=O)N[C@H]2CCOc3ccccc32)sc2c(-c3cc(F)cc(F)c3F)ccnc12]

347-0

¹H-NMR (300 MHz, DMSO-d₆): δ = 9.10 (d, J = 8.4 Hz, 1H), 8.88 (d, J = 4.8 Hz, 1H), 7.82-7.78 (m, 1H), 7.57 (d, J = 4.5 Hz, 1H), 7.52-7.48 (m, 1H), 7.22-7.13 (m, 2H), 6.90 (td, J = 7.5, 1.2 Hz, 1H), 6.79 (d, J = 8.4 Hz, 1H), 5.25 (q, J = 6.6 Hz, 1H), 4.24-4.22 (m, 2H), 3.94-3.89 (m, 1H), 2.14-2.06 (m, 2H), 1.52 (dd, J = 7.0, 4.8 Hz, 6H) ppm.

Biological Examples

The disclosure is further illustrated by the following biological examples, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Example 1: Screening Method to Test Activity of Compounds Against Microfilaria of *Dirofilaria immitis*

Four hundred to six hundred microfilariae of *Dirofilaria immitis* were added to wells of a microtiter plate containing RPMI media and the test compound formulated in 100% DMSO. Plates were held for three days at 37° C. and 5% $CO_2$. The efficacy of a compound was determined based on the motility of the microfilaria as compared to average motility of control wells containing DMSO only. A dose response assay was conducted to determine an $EC_{50}$ value. Compounds 310, 228, 217, 301, 205 and 259-4 exhibited $EC_{50}$ values of between 100 nM and 10 μM. Compounds 259-5, 260, 258, 220, 222, 203, 213, 199, 229, 224, 221, 247 and 214 exhibited $EC_{50}$ values between 10 nM and 100 nM. Compounds 236, 243, 238, 256, 253, 252, 337, 212-0, 207, 120, 102, 259, 264, 211, 210, 263, 263-8, 204, 311, 309, 212, 209, 206 and 223 exhibited $EC_{50}$ values of less than 10 nM.

Example 2: Screening Method to Test Activity of Compounds Against *Haemonchus contortus*

Twenty L1 *Haemonchus contortus* larvae were added to wells of a microtitre plate containing a nutrient medium and the test compound in DMSO. An analysis was conducted at 4 days to determine the extent of development of the larvae from L1 to L3. Larvae exposed to DMSO alone served as controls. A dose response assay was conducted to determine an $EC_{50}$ value. Compounds 124, 090, 205, 236, 238, 256, 246, 337, 128, 207, 119, 260, 102, 338, 268-4, 268, 220, 222, 255, 255-0, 243, 213, 201, 229, 223, 115, 126, 127, 129, 102-1, 101, 130, 121, 092, 239-INT-1, 239, 240, 241, 249, 245, 242 and 123 were found to be active with $EC_{50}$ values of 15 between 100 nM and 10 µM. Compounds 263-8, 263, 210, 204, 211, 336, 259-5, 264, 309, 264-0, 259, 285, 212, 120, 258, 212-0, 310, 252, 209, 253, 206, 203 and 199 exhibited $EC_{50}$ values of less than 100 nM.

Example 3: In Vivo Efficacy Against *Dirofilaria immitis* in Immunodeficient NSG Mice The following in vivo studies to evaluate the effectiveness of the compounds of the invention for preventing infection by *Dirofilaria immitis* in mammals were conducted according to the procedure described in WO 2018/148392 A1 (incorporated herein by reference). For the following studies, *D. immitis* were obtained from Filariasis Research Reagent Resource Center at the University of Georgia Vet School (referred to as "FR3" herein) and from an internal insectary. In general, worms were recovered from mosquitos and shipped overnight in media and antibiotics. Worms were washed and counted for use in mice. Immunodeficient NSG mice susceptible to *D. immitis* infection were injected subcutaneously or via intraperitoneal injection with 50 L3 *D. immitis* (2005 Missouri isolate or JYD-34) on day 0. NSG mice were dosed orally with the compounds of the invention at the dose level indicated in the study at Days 1, 15, and 30 post-infection.

For the recovery of parasites, mice were exsanguinated for serum collection at 6 weeks post-infection, skinned and the fascia scored, the viscera (pluck) removed, and the muscle fascia scored. All pieces were left to soak overnight room temperature in RPMI media supplemented with 10% FBS and Pen/strep antibiotics. The following morning, approximately 18 hours later, worms were counted and fixed in 95% ethanol/5% glycerol. Worms were mounted in glycerine jelly and then measured using cellSens software.

Study #1

Four groups of six Immunodeficient NSG mice were set up. One untreated group served as a control and the other three groups were dosed with Compounds 211, 204 and 212 at dose levels of 25 mg/kg body weight, 50 mg/kg and 25 mg/kg, respectively. The compounds were formulated in a Labrasol/Labrifil® M 1944 CS (70:30) carrier at a concentration of 2.5 mg/mL and dosed orally to the mice at the dose indicated in the tables below. The efficacy of the compounds was evaluated against the undosed control group of mice. Table 6 below shows percent reduction of live worms recovered from the treated groups compared with the control group.

TABLE 6

| Compound # | Dose (mg/kg) | % Reduction worms | P value |
|---|---|---|---|
| 211 | 25 | 61 | 0.002 |
| 204 | 50 | 65 | 0.002 |
| 212 | 23 | 13 | 0.501 |

Study #2

Using a protocol similar to that of Study #1, the efficacy of compounds 119 and 120 at two different dose levels was studied. A control group of 6 NSG mice was allocated. Four groups of 5 NSG mice each was allocated for administration of compounds 119 and 120 at dose levels of 25 mg/kg and 50 mg/kg body weight was studied. The compounds were formulated in a Labrasol/Labrifil® M 1944 CS (70:30) carrier at a concentration of 2.5 mg/mL as in Study #1 and dosed orally to the mice at the dose indicated in Table 7 below.

TABLE 7

| Compound # | Dose (mg/kg) | % Reduction worms | P value |
|---|---|---|---|
| 119 | 25 | 67 | 0.000 |
| 119 | 50 | 37 | 0.005 |
| 120 | 25 | 47 | 0.003 |
| 120 | 50 | 33 | 0.009 |

Study #3

Using a protocol similar to that of Study #1, the efficacy of compounds 210, 257, 207 and 102 was studied. A control group of 7 NSG mice was allocated. Four additional test groups were allocated for administration of compounds 210, 257, 207 and 102. The group for compound 210 contained 7 NSG mice and the groups for compounds 257, 207 and 102 contained 6 NSG mice each. The compounds were formulated in a Labrasol/Labrifil® M 1944 CS (70:30) carrier at a concentration of 2.5 mg/mL as in Study #1 and dosed orally to the mice at a level of 25 mg/kg body weight. The results of the study is shown in Table 8 below.

TABLE 8

| Compound # | % Reduction worms | P value |
|---|---|---|
| 210 | 55 | 0.008 |
| 257 | 45 | 0.028 |
| 207 | 55 | 0.010 |
| 102 | 50 | 0.018 |

Accordingly, the compounds of the invention were found to be active against *Dirofilaria immitis* in the NSG mouse model.

Example 4: In Vivo Efficacy Against *Haemonchus contortus* and *Trichostrongylus colubriformis* in Mongolian Jird (*Meriones unguiculatus*)

Several in vivo studies were conducted to test the efficacy of the compounds of the present invention against *Haemonchus contortus* and *Trichostrongylus colubriformis* in Mongolian jirds. Groups of 5 animals each were allotted for each treatment group, a non-treated control group and positive control groups. Jirds in the non-treated control group were administered the Labrasol/Labrifil® M 1944 CS (70:30) vehicle. Animals in the positive control groups were treated with levamisole (10 mg/kg in water vehicle) and/or ivermectin (0.1 mg/kg in DMSO/Corn Oil (50%/50% v/v)). On Day 0, Mongolian jirds that have been immunosuppressed were artificially infected with approximately 1,000 infective ensheathed *H. contortus* third instar larvae. After at least 4 hours the jirds were also infected with approximately 1,000 ensheathed *T. columbriformis* third instar larvae. Six days after infection, the jirds were treated by oral gavage with the test compounds, dissolved in a mixture of Labrasol/Labrifil® M 1944 CS (70:30), at the dose level indicated in Tables 9-12 below. On day 9 (3 days after treatment) the jirds were euthanized and necropsied for recovery of parasites from the stomach and small intestine. Efficacy was calculated as the average % reduction in the number of worms in each test group compared with the average number of worms from the control group. The efficacy of the compounds tested is presented in Tables 9 to 12 below.

Study 1:

TABLE 9

| Compound # | Dose (mg/kg) | % Reduction H. contortus | % Reduction T. columbriformis |
| --- | --- | --- | --- |
| 263 | 25 | 100.0 | 100.0 |
| 285 | 25 | 100.0 | 100.0 |
| Levamisole | 10 | 98.4 | 89.1 |
| Ivermectin | 0.1 | 66.1 | 92.9 |

Study 2:

TABLE 10

| Compound # | Dose (mg/kg) | % Reduction H. contortus | % Reduction T. columbriformis |
| --- | --- | --- | --- |
| 263-8 | 25 | 99.8 | 100.0 |
| Levamisole | 10 | 100.0 | 96.4 |

Study 3:

TABLE 11

| Compound # | Dose (mg/kg) | % Reduction H. contortus | % Reduction T. columbriformis |
| --- | --- | --- | --- |
| 211 | 25 | 100.0 | 100.0 |
| 204 | 25 | 100.0 | 100.0 |
| 210 | 25 | 100.0 | 100.0 |
| Levamisole | 10 | 100.0 | 100.0 |

Study 4:

TABLE 12

| Compound # | Dose (mg/kg) | % Reduction H. contortus | % Reduction T. columbriformis |
| --- | --- | --- | --- |
| 204 | 5 | 50.1 | 22.2 |
| 259 | 25 | 100.0 | 99.5 |
| 260 | 25 | 23.5 | 45.8 |
| 263-8 | 5 | 99.8 | 99.9 |
| Levamisole | 10 | 99.8 | 72.2 |

Thus, the compounds of the invention were found to be highly effective against *Haemonchus contortus* and *Trichostrongylus colubriformis* in the Mongolian Jird model.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A compound of Formula I:

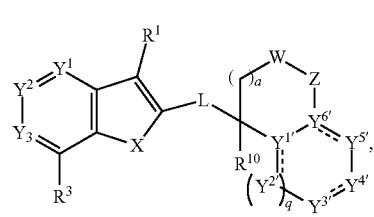

or salt thereof,
wherein:
L is L1 or L2:

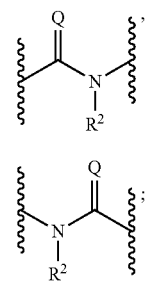

is optionally substituted alkyl, optionally substituted alkoxy, optionally substituted alkenyl, optionally substituted alkynyl, optionally substituted aryl, optionally substituted aryloxy, optionally substituted heteroaryl, optionally substituted cycloalkyl, optionally substituted cycloalkyloxy, optionally substituted heterocyclyl, optionally substituted alkylcarbonyl, optionally substituted alkoxycarbonyl, aminocarbonyl, optionally substituted alkylaminocarbonyl, optionally substituted dialkylaminocarbonyl, —SO$_p$(optionally substituted alkyl or haloalkyl), —SF$_5$, or —NR$^a$R$^b$ wherein R$^a$ and R$^b$ are independently H or optionally substituted alkyl; or R$^a$ and R$^b$ may form, with the nitrogen to which they are attached, a 3-, 4-, 6-, 7-, or 8-membered-heterocyclyl group, which may include one to three additional heteroatoms selected from the group consisting of N, O and S and may be optionally substituted;

R$_2$ is hydrogen, optionally substituted alkyl, optionally substituted cycloalkyl, or optionally substituted aryl;

R$^{2'}$ is optionally substituted alkyl, optionally substituted cycloalkyl, or optionally substituted aryl;

R$^3$ is optionally substituted alkyl, optionally substituted cycloalkyl, optionally substituted alkylcarbonyl, optionally substituted alkoxycarbonyl, aminocarbonyl, optionally substituted alkylaminocarbonyl, optionally substituted dialkylaminocarbonyl, —S(O)$_p$(optionally substituted alkyl), —SF$_5$, optionally substituted heterocyclyl, optionally substituted 6- to 10-membered aryl, optionally substituted 5- to 10-membered heteroaryl, a spirocyclic heterocyclyl-carbocyclyl group, a spirocyclic heterocyclyl-heterocyclyl group, a spirocyclic carbocyclyl-carbocyclyl group, a spirocyclic carbocycyclyl-heterocyclyl group, or —NR$^a$Rb wherein R$^a$ and R$^b$ are independently H or optionally substituted alkyl; or R$^a$ and R$^b$ may form, with the nitrogen to which they are attached, a 3-, 4-, 5-, 6-, 7-, or 8-membered-heterocyclyl group, which may include one to three additional heteroatoms selected from the group consisting of N, O and S and may be optionally substituted;

$R^4$ is independently in each occurrence hydrogen, cyano, halogen, hydroxyl, optionally substituted alkyl, optionally substituted alkoxy, optionally substituted alkenyl, optionally substituted alkynyl, optionally substituted aryl; optionally substituted aryloxy, optionally substituted heteroaryl, optionally substituted cycloalkyl, optionally substituted cycloalkyloxy, optionally substituted heterocyclyl, optionally substituted alkylcarbonyl, optionally substituted alkoxycarbonyl, optionally substituted aminocarbonyl, optionally substituted alkylaminocarbonyl, optionally substituted dialkylaminocarbonyl, —SO$_p$(optionally substituted alkyl or haloalkyl), —SF$_5$, or —NR$^a$Rb wherein R$^a$ and R$^b$ are independently H or optionally substituted alkyl; or R$^a$ and R$^b$ may form, with the nitrogen to which they are attached, a 3-, 4-, 5-, 6-, 7-, or 8-membered-heterocyclyl group, which may include one to three additional heteroatoms selected from the group consisting of N, O and S and may be optionally substituted;

$R^5$ and $R^{5'}$ are independently in each occurrence, hydrogen, halogen, cyano, nitro, hydroxyl, optionally substituted alkyl, optionally substituted alkoxy, optionally substituted cycloalkyl, optionally substituted cycloalkyloxy, optionally substituted aryl, optionally substituted heteroaryl, —SF$_5$, —SO$_p$(optionally substituted alkyl or haloalkyl), or —NR$^c$R$^d$ wherein R$^c$ and R$^d$ are independently H or optionally substituted alkyl; or R$^c$ and R$^d$ may form, with the nitrogen to which they are attached, a 3-, 4-, 5-, 6-, 7-, or 8-membered-heterocyclyl group, which may include one to three additional heteroatoms selected from the group consisting of N, O and S and may be optionally substituted;

$R^{10}$ is hydrogen, halogen, alkyl, haloalkyl, cycloalkyl, alkenyl or alkynyl;

X is S;

Q is O, S or NR$^{2'}$;

$Y^1$ is N;

$Y^2$ —N— or —CR$^4$—;

$Y^3$ is C-halogen;

$Y^1$ and $Y^{6'}$ are each independently N, C, or —CR$^5$—;

$Y^{2'}$ $Y^{3'}$, $Y^4$, $Y^{5'}$ are each independently N, NR$^2$, S, O, —CR$^5$— or CR$^5$R$^{5'}$;

W is CR$^6$R$^7$, O, S, or N—R$^8$,

Z is CR$^6$R$^7$, O, S, or N—R$^8$, wherein $R^6$ and $R^7$ are independently in each occurrence hydrogen, halogen, C$_1$-C$_4$-alkyl, C$_1$-C$_4$-haloalkyl, C$_1$-C$_4$-alkoxy, C$_1$-C$_4$-haloalkoxy or C$_3$-C$_8$-cycloalkoxy;

$R^8$ is hydrogen or C$_1$-C$_4$-alkyl;

and wherein at most three of $Y^{1'}$, $Y^{2'}$, $Y^{3'}$, $Y^{4'}$, $Y^{5'}$ and $Y^{6'}$ are heteroatoms;

a is 0 or 1;

q is 0 or 1;

p is independently in each occurrence is 0, 1, or 2; and the dashed bonds ( ) signify a single or double bond.

2. The compound of Formula (I) of claim 1, wherein:

is C$_1$-C$_6$-alkyl, C$_1$-C$_6$-haloalkyl, hydroxy-C$_1$-C$_6$-alkyl, hydroxy-C$_1$-C$_6$-haloalkyl, C$_1$-C$_6$-alkoxy-C$_1$-C$_6$-alkyl, C$_1$-C$_6$-haloalkoxy-C$_1$-C$_6$-alkyl, amino-C$_1$-C$_6$-alkyl, C$_1$-C$_6$-alkoxy, C$_1$-C$_6$-haloalkoxy, C$_2$-C$_6$-alkenyl, C$_2$-C$_6$-haloalkenyl, optionally substituted aryl, optionally substituted aryloxy, optionally substituted heteroaryl, optionally substituted C$_3$-C$_8$-cycloalkyl, optionally substituted C$_3$-C$_8$-cycloalkyloxy, optionally substituted 3- to 7-membered heterocyclyl, C$_1$-C$_6$-alkylcarbonyl, C$_1$-C$_6$-haloalkylcarbonyl, C$_1$-C$_6$-alkoxycarbonyl, C$_1$-C$_6$-haloalkoxycarbonyl, aminocarbonyl, C$_1$-C$_6$-alkylaminocarbonyl, C$_1$-C$_6$-haloalkylaminocarbonyl, di-C$_1$-C$_6$-alkylaminocarbonyl, di-C$_1$-C$_6$-haloalkylaminocarbonyl, —SF$_5$, —SO$_p$(optionally substituted C$_1$-C$_6$-alkyl or C$_1$-C$_6$-haloalkyl), or —NR$^a$R$^b$ wherein R$^a$ and R$^b$ are independently H or optionally substituted C$_1$-C$_6$-alkyl; or R$^a$ and R$^b$ may form, with the nitrogen to which they are attached, a 3-, 4-, 5-, 6-, 7-, or 8-membered-heterocyclyl group, which may include one to three additional heteroatoms selected from the group consisting of N, O and S and may be optionally substituted;

$R^2$ is hydrogen, C$_1$-C$_6$-alkyl, C$_1$-C$_6$-haloalkyl, optionally substituted C$_3$-C$_8$-cycloalkyl, or optionally substituted phenyl;

$R^{2'}$ is C$_1$-C$_6$-alkyl, C$_1$-C$_6$-haloalkyl, optionally substituted C$_3$-C$_8$-cycloalkyl, or optionally substituted phenyl;

$R^3$ is C$_1$-C$_6$-alkyl, C$_1$-C$_6$-haloalkyl, C$_1$-C$_6$-alkoxy-C$_1$-C$_6$-alkyl, C$_1$-C$_6$-haloalkoxy-C$_1$-C$_6$-alkyl, optionally substituted C$_3$-C$_8$-cycloalkyl, C$_1$-C$_6$-alkylcarbonyl, C$_1$-C$_6$-haloalkylcarbonyl, C$_1$-C$_6$-alkoxycarbonyl, C$_1$-C$_6$-haloalkoxycarbonyl, aminocarbonyl, C$_1$-C$_6$-alkylaminocarbonyl, C$_1$-C$_6$-haloalkylaminocarbonyl, di-C$_1$-C$_6$-alkylaminocarbonyl, di-C$_1$-C$_6$-haloalkylaminocarbonyl, —SF$_5$, —S(O)$_p$(C$_1$-C$_6$-alkyl or C$_1$-C$_6$-haloalkyl), optionally substituted 3- to 7-membered heterocyclyl containing from one to three heteroatoms selected from the group consisting of N, O and S; optionally substituted phenyl, optionally substituted 5- to 10-membered heteroaryl, a 5- to 11-membered spirocyclic heterocyclyl-carbocyclyl group, a 5- to 11-membered spirocyclic heterocyclyl-heterocyclyl group, a 5-to 11-membered spirocyclic carbocyclyl-carbocyclyl group, a 5- to 11-membered spirocyclic carbocyclyl-heterocyclyl group, or —NR$^a$R$^b$ wherein R$^a$ and R$^b$ are independently H, C$_1$-C$_6$-alkyl or C$_1$-C$_6$-haloalkyl; or R$^a$ and R$^b$ may form, with the nitrogen to which they are attached, a 3-, 4-, 5-, 6-, 7-, or 8-membered-heterocyclyl group, which may include one to three additional heteroatoms selected from the group consisting of N, O and S and may be optionally substituted;

$R^4$ is independently in each occurrence hydrogen, cyano, halogen, hydroxyl, C$_1$-C$_6$-alkyl, C$_1$-C$_6$-haloalkyl, C$_1$-C$_6$-alkoxy, C$_1$-C$_6$-haloalkoxy, C$_2$-C$_6$-alkenyl, C$_2$-C$_6$-haloalkenyl, C$_2$-C$_6$-alkynyl, C$_2$-C$_6$-haloalkynyl, C$_1$-C$_6$-alkoxy-C$_1$-C$_6$-alkyl, C$_1$-C$_6$-haloalkoxy-C$_1$-C$_6$-alkyl, optionally substituted phenyl; optionally substituted phenyloxy, optionally substituted 5-or 6-membered heteroaryl, optionally substituted C$_3$-C$_8$-cycloalkyl, optionally substituted C$_3$-C$_8$-cycloalkyloxy, optionally substituted 3- to 7-membered heterocyclyl containing from one to three heteroatoms selected from the group consisting of N, O and S, C$_1$-C$_6$-alkylcarbonyl, C$_1$-C$_6$-haloalkylcarbonyl, C$_1$-C$_6$-alkoxycarbonyl, C$_1$-C$_6$-haloalkoxycarbonyl, aminocarbonyl, C$_1$-C$_6$-alkylaminocarbonyl, C$_1$-C$_6$-haloalkylaminocarbonyl, di-C$_1$-C$_6$-alkylaminocarbonyl, di-C$_1$-C$_6$-haloalkylaminocarbonyl, —SO$_p$(optionally substituted C$_1$-C$_6$-alkyl or C$_1$-C$_6$-haloalkyl), SF$_5$, or —NR$^a$R$^b$ wherein R$^a$ and R$^b$ are independently H, C$_1$-C$_6$-alkyl or C$_1$-C$_6$-haloalkyl; or R$^a$ and R$^b$ may form, with the nitrogen to which they are attached, a 3-, 4-, 5-, 6-, 7-, or 8-membered-heterocyclyl group, which may include one to three additional heteroatoms selected from the group consisting of N, O and S and may be optionally substituted;

$R^5$ and $R^{5'}$ are independently in each occurrence, hydrogen, halogen, cyano, nitro, hydroxyl, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxy-$C_1$-$C_6$-alkyl, $C_1$-$C_6$-haloalkoxy-$C_1$-$C_6$-alkyl, optionally substituted $C_3$-$C_8$-cycloalkyl, optionally substituted $C_3$-$C_8$-cycloalkyloxy, optionally substituted phenyl, optionally substituted 5- or 6-membered heteroaryl, —$SF_5$, —$SO_p$(optionally substituted $C_1$-$C_6$-alkyl or $C_1$-$C_6$-haloalkyl), or —$NR^cR^d$ wherein $R^c$ and $R^d$ are independently H, $C_1$-$C_6$-alkyl or $C_1$-$C_6$-haloalkyl; or $R^c$ and $R^d$ may form, with the nitrogen to which they are attached, a 3-, 4-, 5 or 6 membered-heterocyclyl group, which may include one to three additional heteroatoms selected from the group consisting of N, O and S and may be optionally substituted; and $R^{10}$ is hydrogen, halogen, $C_1$-$C_6$-alkyl, $C_1$-$C_6$-haloalkyl, $C_3$-$C_8$-cycloalkyl, $C_2$-$C_6$-alkenyl or $C_2$-$C_6$-alkynyl.

3. The compound of Formula (I) according to claim 2, wherein $R^1$ is $C_1$-$C_4$-alkyl, $C_1$-$C_4$-haloalkyl, hydroxy- $C_1$-$C_4$-alkyl, $C_1$-$C_4$-alkoxy, halo-$C_1$-$C_4$-alkoxy, halo-$C_1$-$C_4$-alkoxy, $C_2$-$C_4$-alkenyl, halo $C_2$-$C_4$-alkenyl, $C_2$-$C_4$-alkynyl, halo-$C_1$-$C_4$-alkynyl, $C_3$-$C_6$-cycloalkyl, halo-$C_3$-$C_6$-cycloalkyl, optionally substituted, saturated or unsaturated 5-, 6-, or 7-membered heterocyclyl, optionally substituted phenyl, optionally substituted 5-, or 6-membered heteroaryl, —$NR^aR^b$ wherein $R^a$ and $R^b$ are independently optionally substituted alkyl; or $R^a$ and $R^b$ may form, with nitrogen to which they are attached, a 3-, 4-, 5-, or 6-membered-heterocyclyl group, which may be optionally substituted;

$R^2$ is hydrogen, $C_1$-$C_4$-alkyl, $R^3$ is optionally substituted $C_3$-$C_8$-cycloalkyl or phenyl, which may be optionally substituted with 1, 2, or 3 substituents;

$R^4$ is independently hydrogen, halogen, $C_1$-$C_4$, halo-$C_1$-$C_4$-alkyl, $C_1$-$C_4$-alkoxy, or halo-$C_1$-$C_4$-alkoxy; and $R^5$ and $R^{5'}$ are independently hydrogen, halogen, cyano, nitro, —OH, $C_1$-$C_4$-alkyl, halo-$C_1$-$C_4$-alkyl, $C_1$-$C_4$-alkoxy,-halo-$C_1$-$C_4$-alkoxy or —$NR^cR^d$ wherein $R^c$ and $R^d$ are independently $C_1$-$C_4$-alkyl or halo-$C_1$-$C_4$-alkyl; or $R^c$ and $R^d$ may form, with the nitrogen to which they are attached, a 3-, 4-, 5- or 6-membered-heterocyclyl ring, which may optionally substituted.

4. The compound of Formula (I) according to claim 1, wherein a is 1 and q is 1.

5. The compound of Formula (I) according to claim 1, wherein a is 0 and q is 0.

6. The compound of Formula (I) according to claim 1, wherein a is 1 and q is 0.

7. The compound of Formula (I) according to claim 1, wherein:

L is $L^1$;

$R^1$ is $C_1$-$C_4$-alkyl, $C_1$-$C_4$-haloalkyl, hydroxy-$C_1$-$C_4$-alkyl, hydroxy-$C_1$-$C_4$-haloalkyl, alkoxy-$C_1$-$C_4$-alkyl, alkoxy-$C_1$-$C_4$-haloalkyl, $C_2$-$C_4$-alkenyl, $C_2$-$C_4$-haloalkenyl, optionally substituted 5- or 6-membered heterocyclyl containing 1 to 3 N, S or O heteroatoms or —$NR^aR^b$ wherein $R^a$ and $R^b$ are independently H, $C_1$-$C_4$-alkyl or $C_1$-$C_4$-haloalkyl; or $R^a$ and $R^b$ may form, with the nitrogen to which they are attached, a 3-, 4-, 5- or 6-membered-heterocyclyl group, which may include one or two additional heteroatoms selected from the group consisting of N, O and S and may be optionally substituted;

$R^2$ is hydrogen or $C_1$-$C_4$-alkyl;

$R^3$ is optionally substituted $C_3$-$C_8$- cycloalkyl, optionally substituted 3- to 7-membered heterocyclyl containing from one to three heteroatoms selected from the group consisting of N, O and S; phenyl, which may be substituted by 1 to 3 substituents; optionally substituted 5- or 6-membered heteroaryl, or —$NR^aR^b$ wherein $R^a$ and $R^b$ may form, with the nitrogen to which they are attached, a 3-, 4-, 5- or 6-membered-heterocyclyl group, which may include one or two additional heteroatoms selected from the group consisting of N, O and S and may be optionally substituted;

$R^4$ is independently in each occurrence hydrogen, halogen, C1-$C_4$-alkyl, or $C_1$-$C_4$-haloalkyl;

$R^5$ and $R^{5'}$ independently in each occurrence, hydrogen, halogen, $C_1$-$C_6$-alkyl, $C_1$-$C_4$-haloalkyl, $C_1$-$C_4$-alkoxy or $C_1$-$C_4$-haloalkoxy;

$R^{10}$ is hydrogen, halogen, $C_1$-$C_4$-alkyl or $C_1$-$C_4$-haloalkyl;

Q is O

Z is O; and

W is $CR^6R^7$.

8. The compound of Formula (I) according to claim 7, wherein a is 1 and q is 1.

9. The compound of Formula (I) according to claim 7, wherein a is 0 or 1 and q is 0.

10. The compound of Formula (I) according to claim 7, which is represented by the following structure of Formula (IC):

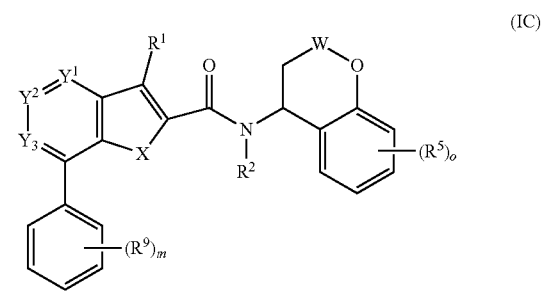

wherein $R^9$ is halogen, $C_1$-$C_4$-alkyl or $C_1$-$C_4$-haloalkyl;

$R^1$ is $C_1$-$C_4$-alkyl, $C_1$-$C_4$-haloalkyl, hydroxy-$C_1$-$C_4$-alkoxy, $C_1$-$C_4$-alkyl, $C_2$-$C_4$-alkenyl, $C_2$-$C_4$-haloalkoxy, optionally substituted 5- or 6-membered heterocyclyl containing 1 to 3 N, S or O heteroatoms or —$NR^aR^b$ wherein $R^a$ and $R^b$ are independently H, $C_1$-$C_4$-alkyl or $C_1$-$C_6$-haloalkyl; or $R^a$ and $R^b$ may form, with the nitrogen to which they are attached, a 3-, 4-, 5- or 6-membered-heterocyclyl group, which may include one or two additional heteroatoms selected from the group consisting of N, O and S and may be optionally substituted;

$Y^2$ is CH or C-halogen;

$R^5$ is halogen, $C_1$-$C_4$-alkyl, $C_1$-$C_4$-haloalkyl, $C_1$-$C_4$-alkoxy, $C_1$-$C_4$-haloalkoxy;

W is $CR^6R^7$ $R^2$ is hydrogen or $C_1$-$C_3$-alkyl;

$R^{10}$ is hydrogen;

is 0, 1 or 2; and m is 0, 1, 2, or 3.

11. The compound of Formula (I) according to claim 7, which is represented by the following structure:

211

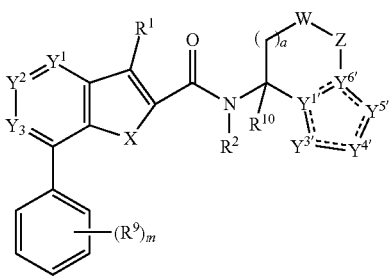

wherein
$R^9$ is halogen, $C_1$-$C_4$-alkyl or $C_1$-$C_4$-haloalkyl;
$R^1$ is $C_1$-$C_4$-alkyl, $C_1$-$C_4$-haloalkyl, hydroxy-$C_1$-$C_4$-alkoxy, $C_1$-$C_4$-alkyl, $C_2$-$C_4$-alkenyl, $C_2$-$C_4$-haloalkoxy, optionally substituted 5- or 6-membered heterocyclyl containing 1 to 3 N, S or O heteroatoms or —NR$^a$R$^b$ wherein R$^a$ and R$^b$ are independently H, $C_1$-$C_4$-alkyl or $C_1$-$C_6$-haloalkyl; or R$^a$ and R$^b$ may form, with the nitrogen to which they are attached, a 3-, 4-, 5- or 6-membered-heterocyclyl group, which may include one or two additional heteroatoms selected from the group consisting of N, O and S and may be optionally substituted;
$Y^2$ is CH or C-halogen;
$R^5$ and $R^{5'}$ are independently in each occurrence hydrogen, halogen, $C_1$-$C_4$-alkyl, $C_1$-$C_4$-haloalkyl, $C_1$-$C_4$-alkoxy, $C_1$-$C_4$-haloalkoxy;
$R^2$ is hydrogen or $C_1$-$C_3$-alkyl;
$R^{10}$ is hydrogen;
Z is CR$^6$R$^7$ or O;
$Y^{1'}$ and $Y^{6'}$ are each independently C, N or CR$^5$;
$Y^{3'}$, $Y^{4'}$, $Y^{5'}$ are each independently CR$^5$, CR$^5$R$^{5'}$, N, NR$^2$, O or S; the dash bonds ( - - - - ) signify a single or double bond;
a is 0, or 1; and
m is 0, 1, 2, or 3.

12. The compound according to claim 11, wherein $Y^{1'}$ and $Y^{6'}$ are each C;
$Y^{3'}$ and $Y^{4'}$ are independently CR$^5$; and
$Y^{5'}$ is S.

13. The compound according to claim 11, wherein $Y^{3'}$ and $Y^{6'}$ are N;
$Y^{1'}$ is C; and
$Y^{4'}$ and $Y^{5'}$ are independently CR$^5$.

14. The compound according to claim 11, wherein $Y^{1'}$ and $Y^{5'}$ are N;
$Y^{6'}$ is C; and
$Y^{3'}$ and $Y^{4'}$ are independently CR$^5$.

15. The compound according to claim 1, which is represented by the following structure:

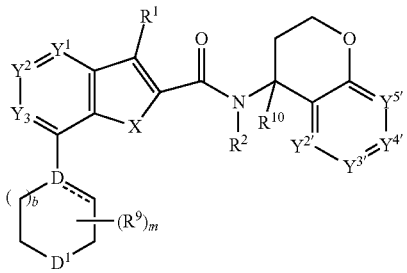

212 wherein
$R^9$ is independently halogen, $C_1$-$C_4$-alkyl, $C_1$-$C_4$-haloalkyl, $C_1$-$C_4$-alkoxy, $C_1$-$C_4$-haloalkoxy, or —NR$^a$R$^b$ wherein R$^a$ and R$^b$ are independently H, $C_1$-$C_4$-alkyl or $C_1$-$C_4$-haloalkyl;
$R^1$ is $C_1$-$C_4$-alkyl, $C_1$-$C_4$-haloalkyl, hydroxy-$C_1$-$C_4$-alkyl, alkoxy-$C_1$-$C_4$alkyl, $C_2$-$C_4$-alkenyl, $C_2$-$C_4$ haloalkenyl, optionally substituted 5- or 6-membered heterocyclyl containing 1 to 3 N, S or O heteroatoms or —NR$^a$R$^b$ wherein R$^a$ and R$^b$ are independently H, $C_1$-$C_6$-alkyl or $C_1$-$C_6$-haloalkyl; or R$^a$ and R$^b$ may form, with the nitrogen to which they are attached, a 3-, 4-, 5- or 6-membered-heterocyclyl group, which may include one or two additional heteroatoms selected from the group consisting of N, O and S and may be optionally substituted;
$R^5$ is halogen, $C_1$-$C_6$-alkyl, $C_1$-$C_6$-haloalkyl, $C_1$-$C_6$-alkoxy or $C_1$-$C_6$-haloalkoxy;
$R^2$ is hydrogen or $C_1$-$C_3$-alkyl;
$R^{10}$ is hydrogen;
D is —N— or —CH$_2$—; or
D$^1$ is —NH—, —O—, —CH$_2$—; or
D$^1$ is bonded to a 2- to 5-membered chain, optionally containing an N, O or S heteroatom, to form a spirocyclic heterocyclyl-heterocyclyl group, a spirocyclic heterocyclyl-carbocyclyl group, a spirocyclic carbocyclyl-carbocyclyl group or a spirocyclic carbocyclyl-heterocyclyl group;
m is 0, 1, 2, or 3; and
b is 0 or 1.

16. The compound according to claim 10, wherein
$R^1$ $C_1$-$C_4$-alkyl, halo-$C_1$-$C_4$, -alkyl $C_2$-$C_4$ alkenyl, hydroxy-$C_1$-$C_4$-alkyl, di($C_1$-$C_4$-alkyl)amino, morpholino, pyranyl, tetrahydropyranyl, or dihydropyranyl;
$Y^2$ is CH;
$Y^3$ is C—Cl or C—F; and
$R^5$ is independently in each occurrence is halogen, $C_1$-$C_4$-alkyl or $C_1$-$C_4$.

17. The compound according to claim 11, wherein
$R^1$ $C_1$-$C_4$-alkyl, halo-$C_1$-$C_4$-alkyl $C_2$-$C_4$ alkenyl, hydroxy-$C_1$-$C_4$-alkyl di($C_1$-$C_4$-alkyl)amino, morpholino, pyranyl, tetrahydropyranyl, or dihydropyranyl;
$Y^2$ is CH;
$Y^3$ is C—Cl or C—F; and
$R^5$ is independently in each occurrence is halogen, $C_1$-$C_4$-alkyl or $C_1$-$C_4$ haloalkyl.

18. The compound according to claim 16, wherein
$R^1$ is isopropyl, tert-butyl, —C(CH$_3$)=CH$_2$, —CF$_3$, —CF(CH$_3$)$_2$, —CF$_2$CF$_3$, —COH(CH$_3$)$_2$, morpholino, pyranyl, tetrahydropyranyl, or dihydropyranyl;
$R^5$ is independently in each occurrence chloro or fluoro; and m is 2 or 3.

19. The compound of claim 18, wherein m is 2.

20. The compound of claim 18, wherein m is 3.

21. The compound of claim 19, wherein $R^9$ is located at the 3.5-positions, the 2.6-positions of the phenyl ring.

22. The compound of claim 1, wherein $Y^2$ is —CR$^4$.

23. The compound of claim 1, wherein $Y^2$ is N.

24. A compound of Formula I,
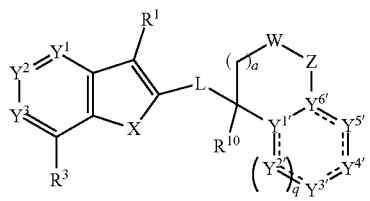
wherein the compound has the structure presented in the table below, wherein L is L1 or L2:
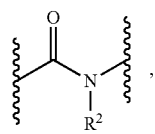 (L1)
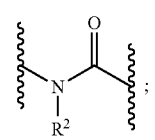 (L2)
hydrogen; Q is oxygen; and
  the group
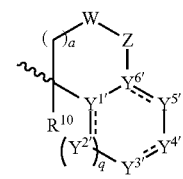
is abbreviated "Ring System" in the table and represents the following groups:
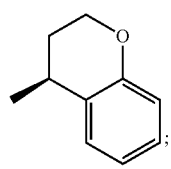 Ring System A
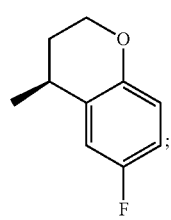 Ring System B
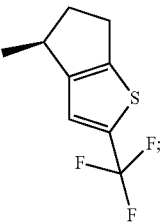 Ring System C
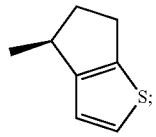 Ring System D
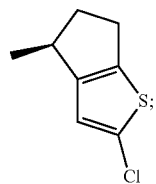 Ring System E
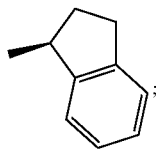 Ring System F
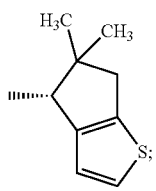 Ring System G
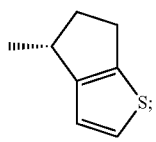 Ring System H
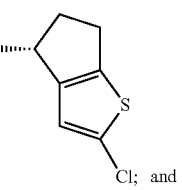 Ring System I
and
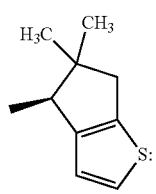 Ring System K

| Cmpd. # | Y¹ | Y² | Y³ | L | X | R¹ | R³ | Ring System |
|---|---|---|---|---|---|---|---|---|
| 309 | N | CH | CF | L1 | S | i-Pr | 3,5-di-Cl-Ph | A |
| 264-0 | CH | N | CH | L1 | S | 2-OH-prop-2-yl | 3,5-di-Cl-Ph | A |
| 310 | N | CH | CCl | L1 | S | i-Pr | 3,5-di-F-Ph | A |
| 347 | N | CH | CH | L1 | S | i-Pr | 2,3,5-tri-F-Ph | A |
| 348 | N | CH | CH | L1 | S | i-Pr | 2,3,5-tri-F-Ph | B |
| 338 | N | CH | CF | L1 | S | t-Bu | 3,5-di-Cl-Ph | B |
| 336 | N | CH | CF | L1 | S | t-Bu | 3,5-di-Cl-Ph | B |
| 122 | N | CH | CH | L1 | S | 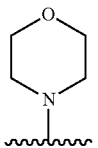 | 3,5-di-F-Ph | B |
| 263-8 | N | CH | CF | L1 | S | 2-OH-prop-2-yl | 3,5-di-Cl-Ph | A |
| 263 | N | CH | CF | L1 | S | 2-F-prop-2-yl | 3,5-di-Cl-Ph | A |
| 210 | N | CH | CH | L1 | S | t-Bu | 3,5-di-F-Ph | A |
| 204 | N | CH | CF | L1 | S | i-Pr | 3,5-di-F-Ph | A |
| 211 | N | CH | CH | L1 | S | i-Pr | 3,5-di-Cl-Ph | B |
| 311 | N | CH | CH | L1 | S | 2-F-prop-2-yl | 3,5-di-Cl-Ph | A |
| 259-5 | N | CH | CH | L1 | S | 2-OH-prop-2-yl | 3,5-di-Cl-Ph | B |
| 257 | N | CH | CH | L1 | S | i-Pr | 3,5-di-F-Ph | B |
| 300 | N | CH | CF | L1 | S | 2-F-prop-2-yl | 3,5-di-F-Ph | B |
| 264 | CH | N | CH | L1 | S | 2-F-prop-2-yl | 3,5-di-Cl-Ph | A |
| 309 | N | CH | CF | L1 | S | i-Pr | 3,5-di-Cl-Ph | A |
| 259 | N | CH | CH | L1 | S | 2-F-prop-2-yl | 3,5-di-Cl-Ph | B |
| 285 | N | CH | CH | L1 | S | prop-1-en-2-yl | 3,5-di-Cl-Ph | A |
| 260 | N | CH | CF | L1 | S | i-Pr | 3,5-di-F-Ph | B |
| 212 | N | CH | CH | L1 | S | 2-F-prop-2-yl | 3,5-di-Cl-Ph | A |
| 119 | N | CH | CH | L1 | S | prop-1-en-2-yl | 3,5-di-F-Ph | A |
| 120 | N | CH | CH | L1 | S | i-Pr | 3,5-di-F-Ph | A |
| 207 | N | CH | CH | L1 | S | i-Pr | 3-F-Ph | A |
| 258 | N | CH | CH | L1 | S | i-Pr | 3,5-di-Cl-Ph | B |
| 212-0 | N | CH | CH | L1 | S | 2-OH-prop-2-yl | 3,5-di-Cl-Ph | A |
| 128 | CH | N | CH | L1 | S | i-Pr | 3,5-di-F-Ph | A |
| 337 | N | CH | CF | L1 | S | t-Bu | 3,5-di-F-Ph | B |
| 268-4 | N | CH | CH | L1 | S | 2-OH-prop-2-yl | 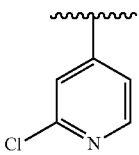 [SMILES: *c1ccnc(Cl)c1] | A |
| 234 | N | CH | C—OMe | L1 | S | i-Pr | 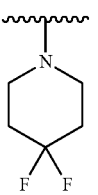 | A |
| 254 | N | CH | CH | L1 | S | i-Pr | 3,5-di-F-Ph | C |
| 268 | N | CH | CH | L1 | S | 2-F-prop-2-yl | 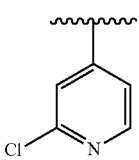 | A |
| 218 | CH | N | CH | L1 | S | i-Pr | 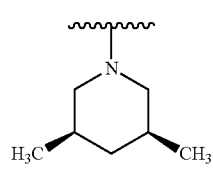 | A |

-continued

| Cmpd. # | Y¹ | Y² | Y³ | L | X | R¹ | R³ | Ring System |
|---|---|---|---|---|---|---|---|---|
| 220 | N | CH | CH | L1 | S | i-Pr | 3,5-dimethylpiperidin-1-yl | A |
| 252 | N | CH | CH | L1 | S | i-Pr | 3,5-di-F-Ph | D |
| 209 | N | CH | CH | L1 | S | i-Pr | 2,6-di-F-Ph | A |
| 253 | N | CH | CH | L1 | S | i-Pr | 3,5-di-F-Ph | E |
| 246 | N | CH | CH | L1 | S | i-Pr | 4,4-difluoropiperidin-1-yl | A |
| 222 | N | CH | CH | L1 | S | i-Pr | Cyclopentyl | A |
| 206 | N | CH | CH | L1 | S | i-Pr | 2,3-di-Cl-Ph | A |
| 255 | N | CH | CH | L1 | S | i-Pr | 1-fluorocyclohexyl | A |
| 255-0 | N | CH | CH | L1 | S | i-Pr | 2-fluorocyclohexyl | A |
| 203 | N | CH | CH | L1 | S | i-Pr | 2,3,6-tri-F-Ph | A |
| 256 | N | CH | CH | L1 | S | prop-1-en-2-yl | 3,5-di-F-Ph | B |
| 302 | N | CH | CH | L1 | S | i-Pr | —CF₃ | A |
| 301 | N | CH | CH | L1 | S | i-Pr | t-Bu | A |
| 238 | N | CH | CH | L1 | S | —CF₂CF₃ | 3,5-di-F-Ph | A |
| 243 | N | CH | CH | L1 | S | i-Pr | 4-(trifluoromethyl)cyclohexyl | A |
| 213 | N | CH | CH | L1 | S | i-Pr | pyridin-3-yl | A |
| 236 | N | CH | CH | L1 | S | —CF₃ | 3,5-di-F-Ph | A |
| 201 | N | CH | CH | L1 | S | i-Pr | 4-F-2,6-di-Me-Ph | A |
| 199 | N | CH | CH | L1 | S | 2-OH-prop-2-yl | 3,5-di-F-Ph | A |
| 205 | N | CH | CH | L1 | S | —CHF₂ | 3,5-di-F-Ph | A |
| 229 | N | CH | CH | L1 | S | i-Pr | piperidin-1-yl | A |

-continued

| Cmpd. # | Y¹ | Y² | Y³ | L | X | R¹ | R³ | Ring System |
|---|---|---|---|---|---|---|---|---|
| 223 | N | CH | CH | L1 | S | i-Pr | cyclohexyl | A |
| 224 | N | CH | CH | L1 | S | —N(CH₃)₂ | cyclohexyl | A |
| 115 | N | CH | N | L1 | S | prop-1-en-2-yl | 3,5-di-F-Ph | A |
| 116 | N | CH | N | L1 | S | i-Pr | 3,5-di-F-Ph | A |
| 127 | CH | N | CH | L1 | S | prop-1-en-2-yl | 3,5-di-F-Ph | A |
| 129 | CH | N | CH | L1 | S | —N(CH₃)₂ | 3,5-di-F-Ph | A |
| 130 | CH | N | CH | L1 | S | 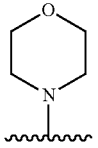 | 3,5-di-F-Ph | A |
| 121 | N | CH | CH | L1 | S | —N(CH₃)₂ | 3,5-di-F-Ph | A |
| 026 | CH | CH | CH | L1 | O | i-Pr | 3,5-di-Cl-Ph | A |
| 029 | CH | CH | CH | L1 | O | i-Pr | 2,6-di-F-Ph | A |
| 030 | C-i-Pr | CH | CH | L1 | O | H | 3,5-di-Cl-Ph | A |
| 027 | CH | CH | CH | L1 | O | 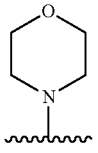 | 3,5-di-Cl-Ph | A |
| 28 | CH | CH | CH | L1 | O | i-Pr | 3,5-di-Cl-Ph | F |
| 239-INT | N | N | CH | L1 | S | prop-1-en-2-yl | 3,5-di-F-Ph | A |
| 239 | N | N | CH | L1 | S | i-Pr | 3,5-di-F-Ph | A |
| 117 | N | CH | N | L1 | S | —N(CH₃)₂ | 3,5-di-F-Ph | A |
| 226-3 | N | CH | CH | L1 | S | —N(CH₃)₂ | —C(O)CH₃ | A |
| 259-4 | N | CH | CH | L1 | S | —C(O)CH₃ | 3,5-di-Cl-Ph | B |
| 221 | N | CH | CH | L1 | S | i-Pr | —CH(CH₃)CH₂—CH(CH₃)₂ | A |
| 319 | N | CH | CF | L1 | S | i-Pr | 3,5-di-Cl-Ph | A |
| 309 | N | CH | CF | L1 | S | i-Pr | 3,5-di-Cl-Ph | A |
| 115-INT-3 | N | CH | N | L1 | S | Br | 3,5-di-F-Ph | A |
| 237 | N | C—CF₃ | N | L1 | S | i-Pr | 3,5-di-F-Ph | A |
| 225-0 | N | CH | CH | L1 | S | —N(CH₃)₂ | 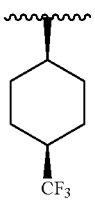 | A |
| 226 | N | CH | CH | L1 | S | —N(CH₃)₂ | —CH(CH₃)CH₂—CH(CH₃)₂ | A |
| 240 | N | CH | CH | L1 | S | i-Pr | 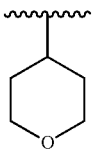 | A |
| 241 | N | CH | CH | L1 | S | i-Pr | 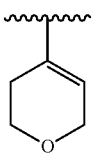 | A |

-continued
| Cmpd. # | Y¹ | Y² | Y³ | L | X | R¹ | R³ | Ring System |
|---|---|---|---|---|---|---|---|---|
| 216 | N | CH | CH | L1 | S | 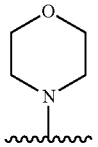 | 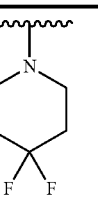 | A |
| 208 | N | CH | CH | L1 | S | i-Pr | 2-Cl-6-F-Ph | A |
| 230 | N | CH | CH | L1 | S | —N(CH$_3$)$_2$ | 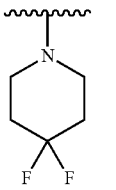 | A |
| 232 | N | CH | CH | L1 | S | i-Pr | 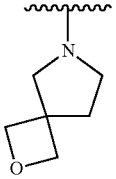 [SMILES: *N1CCC2(COC2)C1] | A |
| 228 | N | CH | CH | L1 | S | —N(CH$_3$)$_2$ | 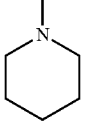 | A |
| 250 | N | CH | CH | L1 | S | i-Pr | 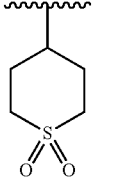 | A |
| 219 | CH | CH | CH | L1 | S | i-Pr | 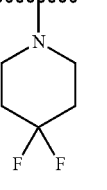 | A |
| 262 | N | CH | CH | L1 | S | i-Pr | 3,5-di-F-Ph | G |
| 249 | N | CH | CH | L1 | S | i-Pr | 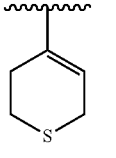 | A |
| 247 | N | CH | CH | L1 | S | i-Pr | 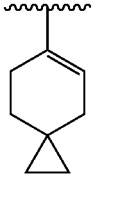 | A |

-continued
| Cmpd. # | Y¹ | Y² | Y³ | L | X | R¹ | R³ | Ring System |
|---|---|---|---|---|---|---|---|---|
| 237 | N | C—CF₃ | N | L1 | S | prop-1-en-2-yl | 3,5-di-F-Ph | A |
| 251 | N | CH | CH | L1 | S | i-Pr | 3,5-di-F-Ph | H |
| 215 | N | C—CF₃ | CH | L1 | S | i-Pr | 3,5-di-Cl-Ph | A |
| 231 | N | CH | CH | L1 | S | i-Pr | 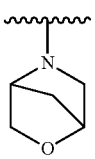 | A |
| 225 | N | CH | CH | L1 | S | —N(CH₃)₂ | 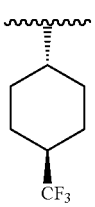 | A |
| 253-0 | N | CH | CH | L1 | S | i-Pr | 3,5-di-F-Ph | I |
| 245 | N | CH | CH | L1 | S | i-Pr | 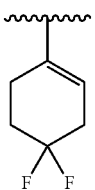 | A |
| 214 | N | CH | CH | L1 | S | i-Pr | 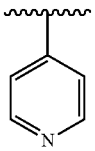 | A |
| 211-0 | N | CH | CH | L1 | S | i-Pr | 3-Cl-5-(3,5-di-Cl-Ph)-Ph | A |
| 248 | N | CH | CH | L1 | S | i-Pr | 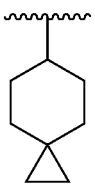 | A |
| 118 | N | CH | N | L1 | S | 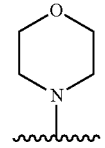 | 3,5-di-F-Ph | A |
| 202 | N | CH | CH | L1 | S | i-Pr | 4-F-Ph | A |
| 242 | N | CH | CH | L1 | S | i-Pr | 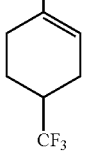 | A |
| 261 | N | CH | CH | L1 | S | i-Pr | 3,5-di-F-Ph | K |

-continued

| Cmpd. # | Y¹ | Y² | Y³ | L | X | R¹ | R³ | Ring System |
|---|---|---|---|---|---|---|---|---|
| 217 | N | CH | CH | L1 | S | 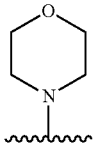 | 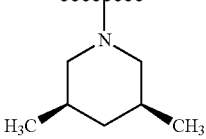 | A |
| 227 | N | CH | CH | L1 | S | —N(CH$_3$)$_2$ | 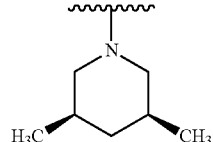 | A. |

25. A veterinary composition comprising the compound of claim 1 or a pharmaceutically or a veterinarily acceptable salt thereof and a veterinarily acceptable carrier.

26. A veterinary composition comprising the compound of claim 1 or a pharmaceutically or a veterinarily acceptable salt thereof, one or more additional active agent(s), and a veterinarily acceptable carrier.

27. A method for the treatment, control or prevention of a parasitic infestation or infection in an animal in need thereof, which comprises administering to said animal an effective amount of the compound of claim 1 or a pharmaceutically acceptable salt thereof.

* * * * *